(12) United States Patent
Ghosh et al.

(10) Patent No.: US 8,241,860 B2
(45) Date of Patent: Aug. 14, 2012

(54) CELL FREE METHODS FOR DETECTING PROTEIN-LIGAND BINDING

(75) Inventors: Indraneel Ghosh, Tucson, AZ (US);
Cliff I. Stains, Melrose, MA (US);
Jason R. Porter, Tucson, AZ (US);
Benjamin Jester, Tucson, AZ (US);
Jennifer Furman, Tucson, AZ (US)

(73) Assignee: The Arizona Board of Regents of Behalf of the University of Arizona, Tucson, AZ (US)

( * ) Notice: Subject to any disclaimer, the term of this patent is extended or adjusted under 35 U.S.C. 154(b) by 754 days.

(21) Appl. No.: 12/290,778

(22) Filed: Nov. 3, 2008

(65) Prior Publication Data
US 2009/0170069 A1 Jul. 2, 2009

Related U.S. Application Data

(60) Provisional application No. 61/001,370, filed on Nov. 1, 2007, provisional application No. 61/072,581, filed on Apr. 1, 2008, provisional application No. 61/072,616, filed on Apr. 1, 2008.

(51) Int. Cl.
*G01N 33/53* (2006.01)
(52) U.S. Cl. ............ 435/7.21; 435/7.1; 436/1; 436/501; 436/518; 424/9.1; 424/520; 422/1; 422/50; 530/300; 530/350
(58) Field of Classification Search .................. None
See application file for complete search history.

(56) References Cited

U.S. PATENT DOCUMENTS

| | | | |
|---|---|---|---|
| 6,054,299 A | 4/2000 | Conrad | |
| 6,294,330 B1 | 9/2001 | Michnick et al. | |
| 6,428,951 B1 | 8/2002 | Michnick et al. | |
| 6,770,451 B2 | 8/2004 | Rouhani et al. | |
| 6,780,599 B2 * | 8/2004 | Hamilton et al. | 435/7.1 |
| 6,828,099 B2 | 12/2004 | Michnick et al. | |
| 6,872,871 B2 | 3/2005 | Brisson et al. | |
| 6,897,017 B1 | 5/2005 | Michnick et al. | |
| 6,929,916 B2 | 8/2005 | Michnick et al. | |
| 7,062,219 B2 | 6/2006 | Michnick et al. | |
| 7,160,691 B2 | 1/2007 | Michnick et al. | |
| 7,166,424 B2 | 1/2007 | Michnick et al. | |
| 7,176,287 B2 * | 2/2007 | Hamilton et al. | 530/350 |
| 2004/0170970 A1 | 9/2004 | Varshavsky et al. | |
| 2004/0229240 A1 | 11/2004 | Watson Michnick et al. | |
| 2004/0235064 A1 | 11/2004 | Hamilton et al. | |
| 2004/0265902 A1 | 12/2004 | Fricker et al. | |
| 2005/0048580 A1 | 3/2005 | Labaer et al. | |
| 2005/0142581 A1 | 6/2005 | Griffey et al. | |
| 2005/0144661 A1 | 6/2005 | Piwnica-Worms et al. | |
| 2006/0224331 A1 | 10/2006 | Watson Michnick et al. | |
| 2006/0257887 A1 | 11/2006 | Waldo et al. | |
| 2007/0161067 A1 | 7/2007 | Gambhir et al. | |
| 2008/0124806 A1 | 5/2008 | Noda et al. | |

FOREIGN PATENT DOCUMENTS

| | | |
|---|---|---|
| WO | 03/079024 | 9/2003 |
| WO | 2006/062882 | 6/2006 |
| WO | 2008/0055313 | 5/2008 |

OTHER PUBLICATIONS

Search Report and Written Opinion corresponding to International Application No. PCT/US2008/12375, parent of the present application.
Applied Biosystems (downloaded Oct. 9, 2008) "In Vitro Translation: The Basics" http://www.ambion.com/techlib/basics/translation/index.html, 7 pp.
Adams et al. (2006) "Humanization of a recombinant monoclonal antibody to produce a therapeutic HER dimerization inhibitor, pertuzumab," Cancer Immunol. Immunother. 55:717-727, published online Sep. 3, 2005.
Ahel et al. (Jan. 3, 2008) "Poly(ADP-ribose)-binding zinc finger motifs in DNA repair/checkpoint proteins," Nature 451:81-85.
Arndt, H.-D. (Jul. 10, 2006) "Small Molecule Modulators of Transcription," Angew. Chem. Int. Ed. 45:4552-4560.
Badran et al. (2011) "Evaluating the Global CpG Methylation Status of Native DNA Utilizing a Bipartite Split-Luciferase Sensor," Anal Chem 83:7151-7157.
Beerli et al. (1998) "Toward controlling gene expression at will: Specific regulation of the *erbB-2/HER-2* promoter by using polydactyl zinc finger proteins constructed from modular building blocks,"Proc Natl Acad Sci USA 95:14628-14633.
Bekker-Jensen et al. (May 16, 2007) "Human Xip1 (C2orf13) is a novel regulator of cellular responses to DNA strand breaks," J. Biol. Chem. 282(27):19638-19643.
Berg et al. (2002) "Small-molecule antagonists of Myc/Max dimerization inhitib Myc-induced transformation of chicken embryo fibroblasts,"Proc Natl Acad Sci USA 99(6):3830-3835.
Berger et al. (2006) "Compact, universal DNA microarrays to comprehensively determine transcription-factor binding site specificities," Nat Biotech 24(11):1429-1435, published online Sep. 24, 2006.
Bird, A. (2002) "DNA methylation patterns and epigenetic memory," Genes Dev. 16:6-21.
Blancafort et al. (2004) "Designing transcription factor architectures for drug discovery," Mol. Pharmacol. 66(6):1361-1371.
Boulikas, T. (1991) "Relation between Carcinogenesis, Chromatin Structure and Poly(ADP-ribosylation) (*Review*)," Anticancer Res. 11:489-527.

(Continued)

*Primary Examiner* — Lisa Cook
(74) *Attorney, Agent, or Firm* — Greenlee Sullivan P.C.

(57) ABSTRACT

Provided are rapid and sensitive cell-free assay methods for detecting and/or measuring specific bimolecular or higher order interactions via reassembly of a split monomeric reporter protein, and methods of detecting or identifying modulators of such interactions by the effect on the signal provided by the reassembled split reporter protein. This methodology is adaptable to protein-protein, protein-peptide, protein-nucleic acid, protein-methylated or nonmethylated nucleic acid and other small or large molecule ligands and binding proteins.

24 Claims, 23 Drawing Sheets
(23 of 23 Drawing Sheet(s) Filed in Color)

OTHER PUBLICATIONS

Braisted et al. (2003) "Discovery of a potent small molecule IL-2 inhibitor through fragment assembly," J Am Chem Soc 125:3714-3715.
Brown et al. (1994) "A mammalian protein targeted by G1-arresting rapamycin-receptor complex," Nature 369:756-758.
Bulyk et al. (2001) "Exploring the DNA-binding specificities of zinc fingers with DNA microarrays," Proc Natl Acad Sci USA 98(13):7158-7163.
Carter et al. (1992) "Humanization of an anti-p185$^{HER2}$ antibody for human cancer therapy,"Proc Natl Acad Sci USA 89:4285-4289.
Chan et al. (1997) "Triplex DNA: fundamentals, advances, and potential applications for gene therapy," J. Mol. Med. 75:267-282.
Chen et al. (1995) "Identification of an 11-kDa FKBP12-rapamycin-binding domain within the 289-kDa FKBP12-rapamycin-associated protein and characterization of a critical serine residue," Proc Natl Acad Sci USA 92:4947-4951.
Chenoweth et al. (2007) "Fluorescent sequence-specific dsDNA binding oligomers," J. Am. Chem. Soc. 129:2216-2217, published online Feb. 6, 2007.
Cheong et al. (Sep. 12, 2006) "Engineering RNA sequence specificity of Pumilio repeats," Proc Natl Acad Sci USA 103(37):13635-13639.
Chin et al. (2001) "Design and Evolution of a Miniature Bcl-2 Binding Protein," Angew. Chem. Int. Ed. 40(20):3806-3809.
Cho et al. (2003) "Structure of the extracellular region of HER2 alone and in complex with the Herceptin Fab," Nature 421:756-760.
Cregan et al. (2004) "Role of AIF in caspase-dependent and caspase-independent cell death," Oncogene 23:2785-2796.
Daugherty et al. (1999) "A fluorescence assay for leucine zipper dimerization: avoiding unintended consequences of fluorophore attachment," J. Am. Chem. Soc. 121:4325-4333.
Demidov et al. (Feb. 14, 2006) "Fast complementation of split fluorescent protein triggered by DNA hybridization," Proc Natl Acad Sci USA 103(7):2052-2056.
Dervan, P.B. (2001) "Molecular recognition of DNA by small molecules," Bioorg. Med. Chem. 9:2215-2235.
Ding et al. (2005) "Structure-based design of potent non-peptide MDM2 inhibitors," J Am Chem Soc 127:10130-10131.
Dreier et al. (2001) "Development of zinc finger domains for recognition of the 5'ANN-3' family of DNA sequences and their use in the construction of artificial transcription factors," J. Biol. Chem. 276(31):29466-29478.
Esteller et al. (2001) "A gene hypermethylation profile of human cancer," Cancer Research 61:3225-3229.
Fechter et al. (2005) "Sequence-specific fluorescence detection of DNA by polyamide-thiazole orange conjugates," J. Am. Chem. Soc. 127:16685-16691.
Feinberg et al. (1983) "Hypomethylation distinguishes genes of some human cancers from their normal counterparts," Nature 301:89-92.
Feinberg et al. (1988) "Reduced genomic 5-methylcytosine content in human colonic neoplasia," Cancer Res. 48:1159-1161.
Fields et al. (1989) "A novel genetic system to detect protein-protein interactions," Nature 340:245-246.
Fields, S. (2005) "High-throughput two-hybrid analysis," FEBS Journal 272:5391-5399.
Forster et al. (2003) "Programming peptidomimetic syntheses by translating genetic codes designed de novo," Proc Natl Acad Sci USA 100(11):6353-6357.
Fraga et al. (2003) "The affinity of different MBD proteins for a specific methylated locus depends on their intrinsic binding properties," Nucl Acids Res 31(6):1765-1774.
Franklin et al. (2004) "Insights Into ErbB Signaling from the Structure of the ErbB2-pertuzumab Complex," Cancer Cell 5:317-328.
Freedman et al. (2002) "Structural Basis for Recruitment of CBP/p300 by Hypoxia-Inducible Factor-1α," Proc Natl Acad Sci USA 99(8):5367-5372.
Furman et al. (2009) "Systematic evaluation of split-fluorescent proteins for the direct detection of native and methylated DNA," Bioorganic & Med Chem Let 19:3748-3751, published online May 5, 2009.
Furman et al. (2010) "A turn-on split-luciferase sensor for the direct detection of poly(ADP-ribose) as a marker for DNA repair and cell death," Chem Commun 47:397-399.
Furman et al. (2010) "Toward a General Approach for RNA-Templated Hierarchical Assembly of Split-Proteins," J Am Chem Soc 132:11692-11701.
Furman et al. (2011) "Turn-On DNA Damage Sensors for the Direct Detection of 8-Oxoguanine and Photoproducts in Native DNA," J Am Chem Soc 133:12518-12527.
Galarneau et al. (2002) "β-Lactamase Protein Fragment Complementation Assays As In Vivo and In Vitro Sensors of Protein-Protein Interactions," Nat Biotechnol 20:619-622.
Gallagher et al. (2007) "An Orthogonal Dexamethasone—Trimethoprim Yeast Three-Hybrid System," Anal. Biochem. 363:160-162, published online Dec. 28, 2006.
Gerstel et al. (1992) "The effects of 5'-capping, 3'-polyadenylation and leader composition upon the translation and stability of mRNA in a cell-free extract derived from the yeast *Saccharomyces cerevisiae*," Molecular Microbiology 6(16):2339-2348.
Ghosh et al. (2000) "Antiparallel Leucine Zipper-Directed Protein Reassembly: Application to the Green Fluorescent Protein," J. Am. Chem. Soc. 122:5658-5659.
Ghosh et al. (2006) "Direct Detection of Double-Stranded DNA: Molecular Methods and Applications for DNA Diagnostics," Molecular Biosystems 2:551-560, published online Sep. 28, 2006.
Gore, S.D. (2005) "Combination Therapy with DNA Methyltransferase Inhibitors in Hematologic Malignancies," Nat. Clin. Pract. Oncol. 2(Suppl1):S30-S35.
Hassa et al. (2002) "The Functional Role of Poly(ADP-Ribose)Polymerase 1 as Novel Coactivator of NF-κB in Inflammatory Disorders," Cell. Mol. Life Sci. 59:1534-1553.
Hassa et al. (2003) "Transcriptional Coactivation of Nuclear Factor-κB-Dependent Gene Expression by p300 Is Regulated by Poly(ADP)-Ribose Polymerase-1*," J. Biol. Chem. 278(46):45145-45153.
Hatakeyama et al. (1986) "Purification and Characterization of Poly(ADP-Ribose) Glycohydrolase," J. Biol. Chem. 261(32):14902-14911.
Herceg et al. (2001) "Functions of Poly(ADP-Ribose) Polymerase (PARP) in DNA Repair, Genomic Integrity and Cell Death," Mutat. Res. 477:97-110.
Hu et al. (2003) "Simultaneous Visualization of Multiple Protein Interactions in Living Cells Using Multicolor Fluorescence Complementation Analysis," Nat Biotechnol 21:539-545.
Hurley, L. H. (2002) "DNA and Its Associated Processes as Targets for Cancer Therapy," Nature Reviews Cancer 2:188-200.
Iles et al. (2007) "APLF (C2orf13) Is a Novel Human Protein Involved in the Cellular Response to Chromosomal DNA Strand Breaks$^\nabla$," Mol. Cell. Biol. 27(10):3793-3803, published online Mar. 12, 2007.
Jester et al. (2010) "A Coiled-Coil Enabled Split-Luciferase Three-Hybrid System: Applied Toward Profiling Inhibitors of Protein Kinases" J Am Chem Soc 132:11727-11735.
Johnsson et al. (1994) "Split Ubiquitin as a Sensor of Protein Interactions in vivo," Proc Natl Acad Sci USA 91:10340-10344.
Johnsson et al. (2007) "Chemical Tools for Biomolecular Imaging," ACS Chem. Biol. 2(1):31-38, published online Jan. 19, 2007.
Jones et al. (2002) "The Fundamental Role of Epigenetic Events in Cancer," Nat. Rev. Genet. 3:415-428.
Kanno et al. (2007) "A Novel Human AP Endonuclease with Conserved Zinc-Finger-Like Motifs Involved in DNA Strand Break Responses," EMBO J. 26:2094-2103, published online Mar. 29, 2007.
Kerppola, T. K. (Jun. 2006) "Visualization of Molecular Interactions by Fluorescence Complementation," Nat. Rev. Mol. Cell. Biol. 7:449-456.
Kim et al. (Jul. 2007) "Bioluminescent Indicator for Determining Protein-Protein Interactions Using Intramolecular Complementation of Split Click Beetle Luciferase," Anal. Chem. 79:4820-4826.
Kim et al. (2006) "A High-Throughput Screen for Compounds That Inhibit Aggregation of the Alzheimer's Peptide," ACS Chem. Biol. 1(7):461-469, published online Aug. 4, 2006.
Kiziltepe et al. (Jun. 2007) "5-Azacytidine, a DNA Methyltransferase Inhibitor, Induces ATR-Mediated DNA Double-Strand Break Responses, Apoptosis, and Synergistic Cytotoxicity with Doxorubicin and Bortezomib Against Multiple Myeloma Cells," Mol. Cancer Ther. 6(6):1718-1727.

Knighton et al. (1991) "Structure of a Peptide Inhibitor Bound to the Catalytic Subunit of Cyclic Adenosine Monophosphate-Dependent Protein Kinase," Science 253:414-420.

Kolpashchikov, D. M. (2008) "Split DNA Enzyme for Visual Single Nucleotide Polymorphism Typing," J. Am. Chem. Soc. 130:2934-2935, published online Feb. 19, 2008.

Kozak, M. (1986) "Point Mutations Define a Sequence Flanking the AUG Initiator Codon That Modulates Translation by Eukaryotic Ribosomes," Cell 44:283-292.

Kubetzko et al. (2006) "PEGylation and Multimerization of the Anti-p185$^{HER-2}$ Single Chain Fv Fragment 4D5," J. Biol. Chem. 281(46):35186-35201, published online Sep. 8, 2006.

Kung et al. (2004) "Small Molecule Blockade of Transcriptional Coactivation of the Hypoxia-Inducible Factor Pathway," Cancer Cell 6:33-43.

Kung et al. (2000) "Suppression of Tumor Growth Through Disruption of Hypoxia-Inducible Transcription," Nat Med 6(12):1335-1340.

Kwon et al. (2004) "Small Molecule Transcription Factor Mimic," J. Am. Chem. Soc. 126:15940-15941.

Kwong et al. (1998) "Structure of an HIVgp120 Envelope Glycoprotein in Complex with the CD4 Receptor and a Neutralizing Human Antibody," Nature 393:648-659.

Levsky et al. (2003) "Fluorescence in situ Hybridization: Past, Present and Future," J. Cell Sci. 116(14):2833-2838.

Lin et al. (2003) "Small-Molecule Switches for Zinc Finger Transcription Factors," J. Am. Chem. Soc. 125:612-613.

Lindahl et al. (1995) "Post-Translational Modification of Poly(ADP-Ribose) Polymerase Induced by DNA Strand Breaks," Trends Biochem. Sci. 20:405-411.

Liu et al. (2002) "Toward Synthetic transcription Activators: Recruitment of Transcription Factors to DNA by a PNA-Peptide Chimera," J. Am. Chem. Soc. 124(9):1838-1839.

Luker et al. (Aug. 17, 2004) "Kinetics of Regulated Protein-Protein Interactions Revealed with Firefly Luciferase Complementation Imaging in Cells and Living Animals," Proc Natl Acad Sci USA 101(33):12288-12293.

Lum et al. (2006) "Converting Inactive Peptides into Potent Transcriptional Activators," ACS Chem. Biol. 1(10):639-643, published online Nov. 10, 2006.

Ma et al. (2004) "Structural Basis for Overhang-Specific Small Interfering RNA Recognition by the PAZ Domain," Nature 429:318-322.

MacDonald et al. (2006) "Identifying off-target effects and hidden phenotypes of drugs in human cells," Nat Chem Biol 2(6):329-337, published online May 7, 2006.

Meister et al. (2004) "Human Argonaute2 Mediates RNA Cleavage Targeted by miRNAs and siRNAs," Mol. Cell 15:185-197.

Mendel et al. (1995) "Site-Directed Mutagenesis with an Expanded Genetic Code," Ann Rev Biophys Biomol Struct 24:435-462.

Meyer et al. (2007) "Tethering Small Molecules to a Phage Display Library: Discovery of a Selective Bivalent Inhibitor of Protein Kinase A," J. Am. Chem. Soc. 129:13812-13813, published online Oct. 18, 2007.

Michnick, S. W. (2003) "Protein Fragment Complementation Strategies for Biochemical Network Mapping," Curr. Opin. Biotechnol. 14:610-617.

Michnick et al. (Jun. 2007) "Universal Strategies in Research and Drug Discovery Based on Protein-Fragment Complementation Assays," Nat Rev Drug Discov 6:569-582.

Narayana et al. (1997) "Crystal Structure of a Polyhistidine-Tagged Recombinant Catalytic Subunit of cAMP-Dependent Protein Kinase Complexed with the Peptide Inhibitor PKI(5-24) and Adenosine," Biochemistry 36:4438-4448.

Nickols et al. (2007) "Modulating Hypoxia-Inducible Transcription by Disrupting the HIF-1-DNA Interface," ACS Chem. Biol. 2(8):561-571, published online Aug. 17, 2007.

Nomura et al. (2007) "In Vivo Site-Specific DNA Methylation with a Designed Sequence-Enabled DNA Methylase," J. Am. Chem. Soc. 129:8676-8677, published online Jun. 21, 2007.

Ohki et al. (2001) "Solution Structure of the Methyl-CpG Binding Domain of Human MBD1 in Complex with Methylated DNA," Cell 105:487-497.

Olshevsky et al. (1990) "Identification of Individual Human Immunodeficiency Virus Type 1 gp120 Amino Acids Important for CD4 Receptor Binding," J. Virol. 64(12):5701-5707.

Ooi et al. (2006) "Sequence-Enabled Reassembly of β-Lactamase (SEER-LAC): A Sensitive Method for the Detection of Double-Stranded DNA," Biochemistry 45:3620-3625, published online Feb. 28, 2006.

Orner et al. (2001) "Toward Proteomimetics: Terphenyl Derivatives as Structural and Functional Mimics of Extended Regions of an α-Helix," J Am Chem Soc 123:5382-5383.

O'Shea et al. (1989) "Preferential Heterodimer Formation by Isolated Leucine Zippers from Fox and Jun," Science 245:646-648.

O'Shea et al. (1992) "Mechanism of Specificity in the Fos-Jun Oncoprotein Heterodimer," Cell 68:699-708.

Ozawa et al. (2007) "Imaging Dynamics of Endogenous Mitochondrial RNA in Single Living Cells," Nat Methods 4(5):413-419, published online Apr. 1, 2007.

Paulmurugan et al. (2002) "Noninvasive Imaging of Protein-Protein Interactions in Living Subjects by Using Reporter Protein Complementation and Reconstitution Strategies," Proc Natl Acad Sci USA 99:15608-15613.

Paulmurugan et al. (2003) "Monitoring Protein-Protein Interactions Using Synthetic Renilla Luciferase Protein-Fragment-Assisted Complementation," Anal. Chem. 75(7):1584-1589.

Paulmurugan et al. (2005) "Firefly Luciferase Enzyme Fragment Complementation for Imaging in Cells and Living Animals," Anal. Chem. 77(5):1295-1302.

Paulmurugan et al. (Aug. 15, 2005) "Novel Fusion Protein Approach for Efficient High-Throughput Screening of Small Molecular-Mediating Protein-Protein Interactions in Cells and Living Animals," Cancer Res 65(16):7413-7420.

Paulmurugan et al. (Oct. 24, 2006) "An Intramolecular Folding Sensor for Imaging Estrogen Receptor-Ligand Interactions," Proc Natl Acad Sci USA 103(43):15883-15888.

Paulmurugan et al. (Mar. 2007) "Combinatorial Library Screening for Developing an Improved Split-Firefly Luciferase Fragment-Assisted Complementation System for Studying Protein-Protein Interactions," Anal. Chem. 79(6):2346-2353.

Pelletier et al. (1998) "Oligomerization Domain-Directed Reassembly of Active Dihydrofolate Reductase from Rationally Designed Fragments," Proc Natl Acad Sci USA 95:12141-12146.

Plate et al. (1992) "Vascular Endothelial Growth Factor is a Potential Tumour Angiogenesis Factor in Human Gliomas in vivo," Nature 359:845-848.

Porter et al. (Sep. 1, 2007) "Split β-Lactamase Sensor for the Sequence-Specific Detection of DNA Methylation," Anal. Chem. 79(17):6702-6708.

Porter et al. (2008) "A General and Rapid Cell-Free Approach for the Interrogation of Protein-Protein, Protein-DNA, and Protein-RNA Interactions and Their Antagonists Utilizing Split-Protein Reporters," J. Am. Chem. Soc. 130:6488-6497, published online Apr. 29, 2008.

Porter et al. (2010) "Profiling small molecule inhibitors against helix—receptor interactions: the Bcl-2 family inhibitor BH3I-1 potently inhibits p53/hDM2," Chem Comm 46:8020-8022.

Prang et al. (2005) "Cellular and Complement-Dependent Cytotoxicity of Ep-CAM-Specific Monoclonal Antibody MT201 Against Breast Cancer Cell Lines," British J. Cancer 92:342-349.

Putt et al. (2004) "An Enzymatic Assay for Poly(ADP-Ribose) Polymerase-1 (PARP-1) via the Chemical Quantitation of NAD$^+$: Application to the High-Throughput Screening of Small Molecules as Potential Inhibitors," Anal. Biochem. 326:78-86.

Putt et al. (2004) "A nonradiometric, high-throughput assay for poly(ADP-ribose) glycohydrolase (PARG): application to inhibitor identification and evaluation," Anal. Biochem. 333:256-264.

Rackham et al. (2005) "A network of orthogonal ribosome•mRNA pairs," Nat Chem Biol 1(3):159-166.

Rajagopal et al. (2006) "A Minimalist Approach Toward Protein Recognition by Epitope Transfer from Functionally Evolved β-Sheet Surfaces," J Am Chem Soc 128:14356-14363, published online Oct. 14, 2006.
Remy et al. (2006) "A highly sensitive protein-protein interaction assay based on *Gaussia* luciferase," Nature Methods 3(12):977-979, published online Nov. 12, 2007.
Remy et al. (2007) "Detection of Protein-Protein Interactions Using a Simple Survival Protein-Fragment Complementation Assay Based on the Enzyme Dihydrofolate Reductase," Nat. Protocols 2(9):2120-2125, published online Aug. 30, 2007.
Reynolds et al. (1992) "Parameters Affecting Transcription Termination by *Escherichia coli* RNA Polymerase," J. Mol. Biol. 224:31-51.
Rossi et al. (1997) "Monitoring Protein-Protein Interactions in Intact Eukaryotic Cells by β-Galactosidase Complementation," Proc Natl Acad Sci USA 94:8405-8410.
Rucker et al. (2003) "Sequence Specific Fluorescence Detection of Double Strand DNA," J. Am. Chem. Soc. 125:1195-1202.
Ryabova et al. (1997) "Functional Antibody Production Using Cell-Free Translation: Effects of Protein Disulfide Isomerase and Chaperones," Nat. Biotechnol. 15:79-84.
Ryu et al. (1990) "Crystal Structure of an HIV-Binding Recombinant Fragment of Human CD4," Nature 348:419-426.
Seebeck et al. "Ribosomal Synthesis of Dehydroalanine-Containing Peptides," J Am Chem Soc 2006, 128:7150-7151, published online May 13, 2006.
Segal et al. (2001) "Custom DNA-Binding Proteins Come of Age: Polydactyl Zinc-Finger Proteins," Curr. Opin. Biotechnol. 12:632-637.
Segal et al. (2003) "Evaluation of a Modular Strategy for the Construction of Novel Polydactyl Zinc Finger DNA-Binding Proteins," Biochemistry 42:2137-2148.
Segal et al. (2006) "Structure of Aart, a Designed Six-Finger Zinc Finger Peptide, Bound to DNA," J. Mol. Biol. 363:405-421, published online Aug. 11, 2006.
Shekhawat et al. (2009) "An Autoinhibited Coiled-Coil Design Strategy for Split-Protein Protease Sensors," J Am Chem Soc 131:15284-15290.
Shimizu et al. (2001) "Cell-Free Translation Reconstituted with Purified Components," Nat Biotech 19:751-755.
Slamon et al. (1987) "Human Breast Cancer: Correlation of Relapse and Survival with Amplification of the HER-2/*neu* Oncogene," Science 235:177-182.
Spencer et al. (1993) "Controlling Signal Transduction with Synthetic Ligands," Science 262:1019-1024.
Stains et al. (2005) "DNA Sequence-Enabled Reassembly of the Green Fluorescent Protein," J. Am. Chem. Soc. 127:10782-10783.
Stains et al. (2006) "Site-Specific Detection of DNA Methylation Utilizing mCpG-SEER," J Am Chem Soc 128:9761-9765, published online Jul. 12, 2006.
Stains et al. (Dec. 2007) "Molecules that Target beta-Amyloid," ChemMedChem 2:1674-1692.
Stains et al. (2010) "A General Approach for Receptor and Antibody-Targeted Detection of Native Proteins Utilizing Split-Luciferase Reassembly," ACS Chemical Biology 5(10):943-952.
Takeda et al. (2008) "Covalent split protein fragment-DNA hybrids generated through N-terminus-specific modification of proteins by oligonucleotides," Org. Biomol. Chem. 6:2187-2194, published online Apr. 23, 2008.
Tan et al. (2004) "Molecular Beacons," Curr. Opin. Chem. Biol. 8:547-553.
Tawfik et al. (1998) "Man-Made Cell-Like Compartments for Molecular Evolution," Nat Biotech 16:652-656.
Taylor et al. (1990) "cAMP-Dependent Protein Kinease: Framework for a Diverse Family of Regulatory Enzymes," Annu Rev Biochem 59:971-1005.
Thali et al. (1993) "Characterization of Conserved Human Immunodeficiency Virus Type 1 gp120 Neutralization Epitopes Exposed Upon gp120-CD4 Binding," J. Virol. 67(7):3978-3988.
Van Duyne et al. (1991) "Atomic Structure of the Rapamycin Human Immunophilin FKBP-12 Complex," J Am Chem Soc 113:7433-7434.
Varshavsky, A. (Sep. 18, 2007) "Targeting the Absence: Homozygous DNA Deletions as Immutable Signposts for Cancer Therapy," Proc Natl Acad Sci USA 104(38):14935-14940.
Vidal et al. (1999) "Yeast Forward and Reverse 'n'-Hybrid Systems," Nucleic Acids Research 27(4):919-929.
Wells et al. (Dec. 13, 2007) "Reaching for high-hanging fruit in drug discovery at protein-protein interfaces," Nature 450:1001-1009.
White et al. (1998) "Recognition of the Four Watson-Crick Base Pairs in the DNA Minor Groove by Synthetic Ligands," Nature 391:468-471.
Wiesmann et al. (1997) "Crystal Structure at 1.7 Å Resolution of VEGF in Complex with Domain 2 of the Flt-1 Receptor," Cell 91:695-704.
Wolfe et al. (1999) "DNA Recognition by $Cys_2His_2$ Zinc Finger Proteins," Ann Rev Biophys Biomol Struct 29:183-212.
Yu et al. (2002) "Mediation of Poly(ADP-Ribose) Polymerase-1-Dependent Cell Death by Apoptosis-Inducing Factor," Science 297:259-263.
Zhou et al. (2004) "Noncovalent Multivalent Assembly of Jun Peptides on a Leucine Zipper Dendrimer Displaying Fos Peptides," Organic Letters 6(20):3561-3564.
Search Report, dated Jan. 24, 2011, corresponding to European Application No. 08844465.8, a related application, 10 pp.
EP First Office Action, dated Feb. 1, 2012, in European Patent Application No. 08844465.8, a related application, 8 pp.
Betton, J.M. (Jan. 2003) "Chapter 17: Using Maltose-Binding Protein Fragment Complementation to Probe Protein-Protein Interactions by Co Expression in the RTS System," Cell-Free Protein Expression, Springer, Berlin, DE, pp. 143-149.
Betton, J.M. (Feb. 2003) "Rapid translation System (RTS): A Promising Alternative for Recombinant Protein Production," Current Protein and Peptide Science 4(1):73-80.
Hoffman et al. (2004) "Rapid Translation System: a Novel Cell-Free Way from Gene to Protein," Biotechnology Annual Review 10:1-30.
Lorenz et al. (2003) "Chapter 18: In Vitro Translation of KRAB Zinc Finger Transcriptional Repressor Proteins and Their Interaction with Their TIF1β Co-Repressor," Cell-Free Protein Expression, Springer, Berlin, DE, pp. 151-157.
Ozawa, T. (2006) "Designing Split Reporter Proteins for Analytical Tools," Analytica Chimica Acta 556:58-68.

* cited by examiner

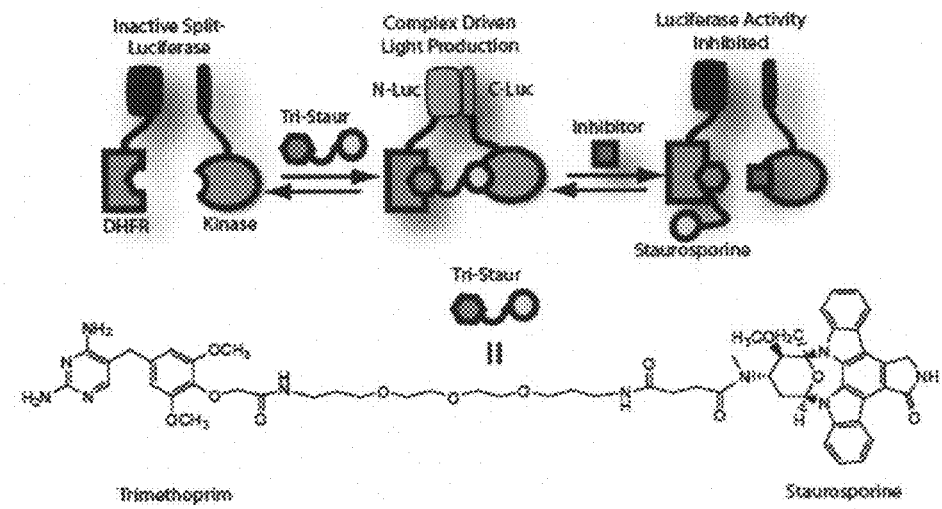

SEQUENCE LISTING

```
<160> NUMBER OF SEQ ID NOS: 99

<210> SEQ ID NO 1
<211> LENGTH: 18
<212> TYPE: DNA
<213> ORGANISM: Artificial Sequence
<220> FEATURE:
<223> OTHER INFORMATION: Synthetic construct:  oligonucleotide

<400> SEQUENCE: 1
atgtagggaa aagcccgg                                                       18

<210> SEQ ID NO 2
<211> LENGTH: 18
<212> TYPE: DNA
<213> ORGANISM: Artificial Sequence
<220> FEATURE:
<223> OTHER INFORMATION: Synthetic construct:  oligonucleotide

<400> SEQUENCE: 2
ggggccggag ccgcagtg                                                       18

<210> SEQ ID NO 3
<211> LENGTH: 11
<212> TYPE: DNA
<213> ORGANISM: Artificial Sequence
<220> FEATURE:
<223> OTHER INFORMATION: Synthetic construct:  Shine-Delgarno sequence

<400> SEQUENCE: 3
taaggaggtg a                                                              11

<210> SEQ ID NO 4
<211> LENGTH: 10
<212> TYPE: DNA
<213> ORGANISM: Artificial Sequence
<220> FEATURE:
<223> OTHER INFORMATION: Synthetic construct:  Kozak sequence

<400> SEQUENCE: 4
gccaccatgg                                                                10

<210> SEQ ID NO 5
<211> LENGTH: 17
<212> TYPE: DNA
<213> ORGANISM: Artificial Sequence
<220> FEATURE:
<223> OTHER INFORMATION: Synthetic construct:  T7 promoter sequence

<400> SEQUENCE: 5
```

```
<210> SEQ ID NO 6
<211> LENGTH: 17
<212> TYPE: DNA
<213> ORGANISM: Artificial Sequence
<220> FEATURE:
<223> OTHER INFORMATION: Synthetic construct:  T3 promoter sequence

<400> SEQUENCE: 6
aattaaccct cactaaa                                                    17

<210> SEQ ID NO 7
<211> LENGTH: 17
<212> TYPE: DNA
<213> ORGANISM: Artificial Sequence
<220> FEATURE:
<223> OTHER INFORMATION: Synthetic construct:  Sp6 promoter sequence

<400> SEQUENCE: 7
atttaggtga cactata                                                    17

<210> SEQ ID NO 8
<211> LENGTH: 1347
<212> TYPE: DNA
<213> ORGANISM: Artificial Sequence
<220> FEATURE:
<223> OTHER INFORMATION: Synthetic construct:  CFluc-17b coding
      sequence
<220> FEATURE:
<221> NAME/KEY: CDS
<222> LOCATION: (1)..(1344)

<400> SEQUENCE: 8
```

| | | | | | | | | | | | | | | | | |
|---|---|---|---|---|---|---|---|---|---|---|---|---|---|---|---|---|
| atg | atg | tcc | ggt | tat | gta | aac | aat | ccg | gaa | gcg | acc | aac | gcc | ttg | att | 48 |
| Met | Met | Ser | Gly | Tyr | Val | Asn | Asn | Pro | Glu | Ala | Thr | Asn | Ala | Leu | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | aag | gat | gga | tgg | cta | cat | tct | gga | gac | ata | gct | tac | tgg | gac | gaa | 96 |
| Asp | Lys | Asp | Gly | Trp | Leu | His | Ser | Gly | Asp | Ile | Ala | Tyr | Trp | Asp | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| gac | gaa | cac | ttc | ttc | ata | gtt | gac | cgc | ttg | aag | tct | tta | att | aaa | tac | 144 |
| Asp | Glu | His | Phe | Phe | Ile | Val | Asp | Arg | Leu | Lys | Ser | Leu | Ile | Lys | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| aaa | gga | tat | cag | gtg | gcc | ccc | gct | gaa | ttg | gaa | tcg | ata | ttg | tta | caa | 192 |
| Lys | Gly | Tyr | Gln | Val | Ala | Pro | Ala | Glu | Leu | Glu | Ser | Ile | Leu | Leu | Gln | |
| 50 | | | | | 55 | | | | | 60 | | | | | | |

| | | | | | | | | | | | | | | | | |
|---|---|---|---|---|---|---|---|---|---|---|---|---|---|---|---|---|
| cac | ccc | aac | atc | ttc | gac | gcg | ggc | gtg | gca | ggt | ctt | ccc | gac | gat | gac | 240 |
| His | Pro | Asn | Ile | Phe | Asp | Ala | Gly | Val | Ala | Gly | Leu | Pro | Asp | Asp | Asp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gcc | ggt | gaa | ctt | ccc | gcc | gcc | gtt | gtt | gtt | ttg | gag | cac | gga | aag | acg | 288 |
| Ala | Gly | Glu | Leu | Pro | Ala | Ala | Val | Val | Val | Leu | Glu | His | Gly | Lys | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| atg | acg | gaa | aaa | gag | atc | gtg | gat | tac | gtc | gcc | agt | caa | gta | aca | acc | 336 |
| Met | Thr | Glu | Lys | Glu | Ile | Val | Asp | Tyr | Val | Ala | Ser | Gln | Val | Thr | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| gcg | aaa | aag | ttg | cgc | gga | gga | gtt | gtg | ttt | gtg | gac | gaa | gta | ccg | aaa | 384 |
| Ala | Lys | Lys | Leu | Arg | Gly | Gly | Val | Val | Phe | Val | Asp | Glu | Val | Pro | Lys | |
| | | 115 | | | | | 120 | | | | | 125 | | | | |

| | | | | | | | | | | | | | | | | |
|---|---|---|---|---|---|---|---|---|---|---|---|---|---|---|---|---|
| ggt | ctt | acc | gga | aaa | ctc | gac | gca | aga | aaa | atc | aga | gag | atc | ctc | ata | 432 |
| Gly | Leu | Thr | Gly | Lys | Leu | Asp | Ala | Arg | Lys | Ile | Arg | Glu | Ile | Leu | Ile | |
| 130 | | | | | 135 | | | | | 140 | | | | | | |

| | | | | | | | | | | | | | | | | |
|---|---|---|---|---|---|---|---|---|---|---|---|---|---|---|---|---|
| aag | gcc | aag | aag | ggc | gga | aag | tcc | aaa | ttg | ggc | ctg | cag | ggc | ggt | tca | 480 |
| Lys | Ala | Lys | Lys | Gly | Gly | Lys | Ser | Lys | Leu | Gly | Leu | Gln | Gly | Gly | Ser | |
| 145 | | | | | 150 | | | | | 155 | | | | | 160 | |

|  |  |
|---|---:|
| ggc ggt ggg ggt tct ggc ggg ggt ggg agc ccc ggg cag gtg cag ctg<br>Gly Gly Gly Gly Ser Gly Gly Gly Gly Ser Pro Gly Gln Val Gln Leu<br>                165                       170                     175 | 528 |
| ctc gag tct ggg gct gag gtg aag aag cct ggg tcc tcg gtg aag gtc<br>Leu Glu Ser Gly Ala Glu Val Lys Lys Pro Gly Ser Ser Val Lys Val<br>            180                       185                     190 | 576 |
| tcc tgc aag gcc tct gga gac acc ttc atc aga tat agt ttt acc tgg<br>Ser Cys Lys Ala Ser Gly Asp Thr Phe Ile Arg Tyr Ser Phe Thr Trp<br>        195                       200                     205 | 624 |
| gtg cga cag gcc cct gga caa ggc ctt gag tgg atg gga agg atc atc<br>Val Arg Gln Ala Pro Gly Gln Gly Leu Glu Trp Met Gly Arg Ile Ile<br>           210                       215                    220 | 672 |
| act atc ctt gat gta gca cac tac gca ccg cac ctc cag ggc aga gtc<br>Thr Ile Leu Asp Val Ala His Tyr Ala Pro His Leu Gln Gly Arg Val<br>225                    230                     235                   240 | 720 |
| acg att acc gcg gac aag tcc acg agc aca gtc tac ctg gag ctg cgg<br>Thr Ile Thr Ala Asp Lys Ser Thr Ser Thr Val Tyr Leu Glu Leu Arg<br>                       245                     250                     255 | 768 |
| aat cta aga tct gac gat acg gcc gta tat ttc tgt gcg gga gtg tac<br>Asn Leu Arg Ser Asp Asp Thr Ala Val Tyr Phe Cys Ala Gly Val Tyr<br>                260                       265                     270 | 816 |
| gag gga gag gcg gac gag ggg gaa tat gat aat aat ggg ttt ctg aaa<br>Glu Gly Glu Ala Asp Glu Gly Glu Tyr Asp Asn Asn Gly Phe Leu Lys<br>        275                       280                     285 | 864 |
| cat tgg ggc cag gga acc ctg gtc acg gtc acc tca ggt ggc ggt ggc<br>His Trp Gly Gln Gly Thr Leu Val Thr Val Thr Ser Gly Gly Gly Gly<br>           290                       295                    300 | 912 |
| tcc gga ggt ggt ggg agc ggt ggc ggc gga tct gag ctc gag ttg acg<br>Ser Gly Gly Gly Gly Ser Gly Gly Gly Gly Ser Glu Leu Glu Leu Thr<br>305                    310                     315                   320 | 960 |
| cag tct cca gcc acc ctg tct gtg tct cca ggg gaa aga gcc acc ctc<br>Gln Ser Pro Ala Thr Leu Ser Val Ser Pro Gly Glu Arg Ala Thr Leu<br>                  325                     330                   335 | 1008 |
| tcc tgc agg gcc agt gag agt gtt agt agc gac tta gcc tgg tac cag<br>Ser Cys Arg Ala Ser Glu Ser Val Ser Ser Asp Leu Ala Trp Tyr Gln<br>              340                     345                   350 | 1056 |
| cag aaa cct ggc cag gct ccc agg ctc ctc ata tat ggt gca tcc acc<br>Gln Lys Pro Gly Gln Ala Pro Arg Leu Leu Ile Tyr Gly Ala Ser Thr<br>            355                     360                   365 | 1104 |
| agg gcc acc ggt gtc cca gcc agg ttc agt ggc agt ggg tct ggg gca<br>Arg Ala Thr Gly Val Pro Ala Arg Phe Ser Gly Ser Gly Ser Gly Ala<br>        370                       375                     380 | 1152 |
| gaa ttc act ctc acc atc agc agc ctg cag tct gaa gat ttt gca gtt<br>Glu Phe Thr Leu Thr Ile Ser Ser Leu Gln Ser Glu Asp Phe Ala Val<br>385                    390                     395                   400 | 1200 |
| tat tac tgt cag cag tac aat aac tgg cct ccg agg tac act ttt ggc<br>Tyr Tyr Cys Gln Gln Tyr Asn Asn Trp Pro Pro Arg Tyr Thr Phe Gly<br>                  405                     410                   415 | 1248 |
| cag ggg acc agg ctg gag atc aaa gtc gag tct ggt aaa gaa acc gct<br>Gln Gly Thr Arg Leu Glu Ile Lys Val Glu Ser Gly Lys Glu Thr Ala<br>                    420                     425                   430 | 1296 |
| gct gcg aaa ttt gaa cgc cag cac atg gac tcg tct act agc gca gct<br>Ala Ala Lys Phe Glu Arg Gln His Met Asp Ser Ser Thr Ser Ala Ala<br>                     435                     440                   445 | 1344 |
| taa | 1347 |

<210> SEQ ID NO 9
<211> LENGTH: 448
<212> TYPE: PRT
<213> ORGANISM: Artificial Sequence

```
<220> FEATURE:
<223> OTHER INFORMATION: Synthetic Construct

<400> SEQUENCE: 9

Met Met Ser Gly Tyr Val Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
            35                  40                  45

Lys Gly Tyr Gln Val Ala Pro Ala Glu Leu Glu Ser Ile Leu Leu Gln
            50                  55                  60

His Pro Asn Ile Phe Asp Ala Gly Val Ala Gly Leu Pro Asp Asp Asp
65                  70                  75                  80

Ala Gly Glu Leu Pro Ala Ala Val Val Leu Glu His Gly Lys Thr
                85                  90                  95

Met Thr Glu Lys Glu Ile Val Asp Tyr Val Ala Ser Gln Val Thr Thr
                100                 105                 110

Ala Lys Lys Leu Arg Gly Gly Val Val Phe Val Asp Glu Val Pro Lys
                115                 120                 125

Gly Leu Thr Gly Lys Leu Asp Ala Arg Lys Ile Arg Glu Ile Leu Ile
    130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Ser Pro Gly Gln Val Gln Leu
                165                 170                 175

Leu Glu Ser Gly Ala Glu Val Lys Lys Pro Gly Ser Ser Val Lys Val
                180                 185                 190

Ser Cys Lys Ala Ser Gly Asp Thr Phe Ile Arg Tyr Ser Phe Thr Trp
            195                 200                 205

Val Arg Gln Ala Pro Gly Gln Gly Leu Glu Trp Met Gly Arg Ile Ile
            210                 215                 220

Thr Ile Leu Asp Val Ala His Tyr Ala Pro His Leu Gln Gly Arg Val
225                 230                 235                 240

Thr Ile Thr Ala Asp Lys Ser Thr Ser Thr Val Tyr Leu Glu Leu Arg
                245                 250                 255

Asn Leu Arg Ser Asp Asp Thr Ala Val Tyr Phe Cys Ala Gly Val Tyr
                260                 265                 270

Glu Gly Glu Ala Asp Glu Gly Glu Tyr Asp Asn Asn Gly Phe Leu Lys
                275                 280                 285

His Trp Gly Gln Gly Thr Leu Val Thr Val Thr Ser Gly Gly Gly Gly
    290                 295                 300

Ser Gly Gly Gly Gly Ser Gly Gly Gly Gly Ser Glu Leu Glu Leu Thr
305                 310                 315                 320

Gln Ser Pro Ala Thr Leu Ser Val Ser Pro Gly Glu Arg Ala Thr Leu
                325                 330                 335

Ser Cys Arg Ala Ser Glu Ser Val Ser Ser Asp Leu Ala Trp Tyr Gln
                340                 345                 350

Gln Lys Pro Gly Gln Ala Pro Arg Leu Leu Ile Tyr Gly Ala Ser Thr
            355                 360                 365

Arg Ala Thr Gly Val Pro Ala Arg Phe Ser Gly Ser Gly Ser Gly Ala
    370                 375                 380

Glu Phe Thr Leu Thr Ile Ser Ser Leu Gln Ser Glu Asp Phe Ala Val
385                 390                 395                 400
```

```
                        Tyr Tyr Cys Gln Gln Tyr Asn Asn Trp Pro Pro Arg Tyr Thr Phe Gly
                                    405                 410                 415

Gln Gly Thr Arg Leu Glu Ile Lys Val Glu Ser Gly Lys Glu Thr Ala
                                420                 425                 430

Ala Ala Lys Phe Glu Arg Gln His Met Asp Ser Ser Thr Ser Ala Ala
                            435                 440                 445

<210> SEQ ID NO 10
<211> LENGTH: 1887
<212> TYPE: DNA
<213> ORGANISM: Artificial Sequence
<220> FEATURE:
<223> OTHER INFORMATION: Synthetic construct: CD4-Nfluc coding
      sequence
<220> FEATURE:
<221> NAME/KEY: CDS
<222> LOCATION: (1)..(1884)

<400> SEQUENCE: 10 atg ggc agc agc cat cac cat cat cac cac agc cag gat ccg aaa gtg       48
Met Gly Ser Ser His His His His His His Ser Gln Asp Pro Lys Val
1               5                   10                  15 gtg ctg ggc aaa aaa ggg gat aca gtg gaa ctg acc tgt aca gct tcc       96
Val Leu Gly Lys Lys Gly Asp Thr Val Glu Leu Thr Cys Thr Ala Ser
                20                  25                  30 cag aag aag agc ata caa ttc cac tgg aaa aac tcc aac cag ata aag      144
Gln Lys Lys Ser Ile Gln Phe His Trp Lys Asn Ser Asn Gln Ile Lys
            35                  40                  45 att ctg gga aat cag ggc tcc ttc tta act aaa ggt cca tcc aag ctg      192
Ile Leu Gly Asn Gln Gly Ser Phe Leu Thr Lys Gly Pro Ser Lys Leu
        50                  55                  60 aat gat cgc gct gac tca aga aga agc ctt tgg gac caa gga aac ttc      240
Asn Asp Arg Ala Asp Ser Arg Arg Ser Leu Trp Asp Gln Gly Asn Phe
65                  70                  75                  80 ccc ctg atc atc aag aat ctt aag ata gaa gac tca gat act tac atc      288
Pro Leu Ile Ile Lys Asn Leu Lys Ile Glu Asp Ser Asp Thr Tyr Ile
                85                  90                  95 tgt gaa gtg gag gac cag aag gag gag gtg caa ttg cta gtg ttc gga      336
Cys Glu Val Glu Asp Gln Lys Glu Glu Val Gln Leu Leu Val Phe Gly
                100                 105                 110 ttg act gcc aac tct gac acc cac ctg ctt cag ggg cag agc ctg acc      384
Leu Thr Ala Asn Ser Asp Thr His Leu Leu Gln Gly Gln Ser Leu Thr
            115                 120                 125 ctg acc ttg gag agc ccc cct ggt agt agc ccc tca gtg caa tgt agg      432
Leu Thr Leu Glu Ser Pro Pro Gly Ser Ser Pro Ser Val Gln Cys Arg
        130                 135                 140 agt cca agg ggt aaa aac ata cag ggg ggg aag acc ctc tcc gtg tct      480
Ser Pro Arg Gly Lys Asn Ile Gln Gly Gly Lys Thr Leu Ser Val Ser
145                 150                 155                 160 cag ctg gag ctc cag gat agt ggc acc tgg aca tgc act gtc ttg cag      528
Gln Leu Glu Leu Gln Asp Ser Gly Thr Trp Thr Cys Thr Val Leu Gln
                165                 170                 175 aac cag aag aag gtg gag ttc aaa ata gac atc gtg gtg cta gct ttc      576
Asn Gln Lys Lys Val Glu Phe Lys Ile Asp Ile Val Val Leu Ala Phe
                180                 185                 190 cag aag gcc tcc acc ggt ggg ggt ggc ggt tca ggc ggt ggg ggt tct      624
Gln Lys Ala Ser Thr Gly Gly Gly Gly Ser Gly Gly Gly Gly Ser
            195                 200                 205 ggt ggg ggt ggt acc gaa gac gcc aaa aac ata aag aaa ggc ccg gcg      672
Gly Gly Gly Gly Thr Glu Asp Ala Lys Asn Ile Lys Lys Gly Pro Ala
        210                 215                 220 cca ttc tat cct cta gag gat gga acc gct gga gag caa ctg cat aag      720
```

-continued

| | | |
|---|---|---|
| Pro Phe Tyr Pro Leu Glu Asp Gly Thr Ala Gly Glu Gln Leu His Lys<br>225                            230                          235                          240 | | |

```
gct atg aag aga tac gcc ctg gtt cct gga aca att gct ttt aca gat       768
Ala Met Lys Arg Tyr Ala Leu Val Pro Gly Thr Ile Ala Phe Thr Asp
            245                 250                 255 gca cat atc gag gtg aac atc acg tac gcg gaa tac ttc gaa atg tcc       816
Ala His Ile Glu Val Asn Ile Thr Tyr Ala Glu Tyr Phe Glu Met Ser
                260                 265                 270 gtt cgg ttg gca gaa gct atg aaa cga tat ggg ctg aat aca aat cac       864
Val Arg Leu Ala Glu Ala Met Lys Arg Tyr Gly Leu Asn Thr Asn His
        275                 280                 285 aga atc gtc gta tgc agt gaa aac tct ctt caa ttc ttt atg ccg gtg       912
Arg Ile Val Val Cys Ser Glu Asn Ser Leu Gln Phe Phe Met Pro Val
    290                 295                 300 ttg ggc gcg tta ttt atc gga gtt gca gtt gcg ccc gcg aac gac att       960
Leu Gly Ala Leu Phe Ile Gly Val Ala Val Ala Pro Ala Asn Asp Ile
305                 310                 315                 320 tat aat gaa cgt gaa ttg ctc aac agt atg aac att tcg cag cct acc      1008
Tyr Asn Glu Arg Glu Leu Leu Asn Ser Met Asn Ile Ser Gln Pro Thr
                325                 330                 335 gta gtg ttt gtt tcc aaa aag ggg ttg caa aaa att ttg aac gtg caa      1056
Val Val Phe Val Ser Lys Lys Gly Leu Gln Lys Ile Leu Asn Val Gln
            340                 345                 350 aaa aaa tta cca ata atc cag aaa att att atc atg gat tct aaa acg      1104
Lys Lys Leu Pro Ile Ile Gln Lys Ile Ile Ile Met Asp Ser Lys Thr
        355                 360                 365 gat tac cag gga ttt cag tcg atg tac acg ttc gtc aca tct cat cta      1152
Asp Tyr Gln Gly Phe Gln Ser Met Tyr Thr Phe Val Thr Ser His Leu
    370                 375                 380 cct ccc ggt ttt aat gaa tac gat ttt gta cca gag tcc ttt gat cgt      1200
Pro Pro Gly Phe Asn Glu Tyr Asp Phe Val Pro Glu Ser Phe Asp Arg
385                 390                 395                 400 gac aaa aca att gca ctg ata atg aat tcc tct gga tct act ggg tta      1248
Asp Lys Thr Ile Ala Leu Ile Met Asn Ser Ser Gly Ser Thr Gly Leu
                405                 410                 415 cct aag ggt gtg gcc ctt ccg cat aga act gcc tgc gtc aga ttc tcg      1296
Pro Lys Gly Val Ala Leu Pro His Arg Thr Ala Cys Val Arg Phe Ser
            420                 425                 430 cat gcc aga gat cct att ttt ggc aat caa atc att ccg gat act gcg      1344
His Ala Arg Asp Pro Ile Phe Gly Asn Gln Ile Ile Pro Asp Thr Ala
        435                 440                 445 att tta agt gtt gtt cca ttc cat cac ggt ttt gga atg ttt act aca      1392
Ile Leu Ser Val Val Pro Phe His His Gly Phe Gly Met Phe Thr Thr
    450                 455                 460 ctc gga tat ttg ata tgt gga ttt cga gtc gtc tta atg tat aga ttt      1440
Leu Gly Tyr Leu Ile Cys Gly Phe Arg Val Val Leu Met Tyr Arg Phe
465                 470                 475                 480 gaa gaa gag ctg ttt tta cga tcc ctt cag gat tac aaa att caa agt      1488
Glu Glu Glu Leu Phe Leu Arg Ser Leu Gln Asp Tyr Lys Ile Gln Ser
                485                 490                 495 gcg ttg cta gta cca acc cta ttt tca ttc ttc gcc aaa agc act ctg      1536
Ala Leu Leu Val Pro Thr Leu Phe Ser Phe Phe Ala Lys Ser Thr Leu
            500                 505                 510 att gac aaa tac gat tta tct aat tta cac gaa att gct tct ggg ggc      1584
Ile Asp Lys Tyr Asp Leu Ser Asn Leu His Glu Ile Ala Ser Gly Gly
        515                 520                 525 gca cct ctt tcg aaa gaa gtc ggg gaa gcg gtt gca aaa cgc ttc cat      1632
Ala Pro Leu Ser Lys Glu Val Gly Glu Ala Val Ala Lys Arg Phe His
    530                 535                 540 ctt cca ggg ata cga caa gga tat ggg ctc act gag act aca tca gct      1680
Leu Pro Gly Ile Arg Gln Gly Tyr Gly Leu Thr Glu Thr Thr Ser Ala
```

-continued

| | | | | | | | | | | | | |
|---|---|---|---|---|---|---|---|---|---|---|---|---|
| Leu | Pro | Gly | Ile | Arg | Gln | Gly | Tyr | Gly | Leu | Thr | Glu | Thr | Thr | Ser | Ala |
| 545 | | | | 550 | | | | | 555 | | | | | | 560 | att ctg att aca ccc gag ggg gat gat aaa ccg ggc gcg gtc ggt aaa    1728
Ile Leu Ile Thr Pro Glu Gly Asp Asp Lys Pro Gly Ala Val Gly Lys
            565                 570                 575 gtt gtt cca ttt ttt gaa gcg aag gtt gtg gat ctg gat acc ggg aaa    1776
Val Val Pro Phe Phe Glu Ala Lys Val Val Asp Leu Asp Thr Gly Lys
            580                 585                 590 acg ctg ggc gtt aat cag aga ggc gaa tta tgt gtc aga gga cct atg    1824
Thr Leu Gly Val Asn Gln Arg Gly Glu Leu Cys Val Arg Gly Pro Met
        595                 600                 605 att atg tcc ggt tat gta aac aat ccg gaa gcg acc aac gcc ttg att    1872
Ile Met Ser Gly Tyr Val Asn Asn Pro Glu Ala Thr Asn Ala Leu Ile
610                 615                 620 gac aag gat gga tga                                                 1887
Asp Lys Asp Gly
625

<210> SEQ ID NO 11
<211> LENGTH: 628
<212> TYPE: PRT
<213> ORGANISM: Artificial Sequence
<220> FEATURE:
<223> OTHER INFORMATION: Synthetic Construct

<400> SEQUENCE: 11

Met Gly Ser Ser His His His His His Ser Gln Asp Pro Lys Val
1               5                   10                  15

Val Leu Gly Lys Lys Gly Asp Thr Val Glu Leu Thr Cys Thr Ala Ser
            20                  25                  30

Gln Lys Lys Ser Ile Gln Phe His Trp Lys Asn Ser Asn Gln Ile Lys
        35                  40                  45

Ile Leu Gly Asn Gln Gly Ser Phe Leu Thr Lys Gly Pro Ser Lys Leu
    50                  55                  60

Asn Asp Arg Ala Asp Ser Arg Arg Ser Leu Trp Asp Gln Gly Asn Phe
65                  70                  75                  80

Pro Leu Ile Ile Lys Asn Leu Lys Ile Glu Asp Ser Asp Thr Tyr Ile
                85                  90                  95

Cys Glu Val Glu Asp Gln Lys Glu Glu Val Gln Leu Leu Val Phe Gly
            100                 105                 110

Leu Thr Ala Asn Ser Asp Thr His Leu Leu Gln Gly Gln Ser Leu Thr
        115                 120                 125

Leu Thr Leu Glu Ser Pro Pro Gly Ser Ser Pro Ser Val Gln Cys Arg
130                 135                 140

Ser Pro Arg Gly Lys Asn Ile Gln Gly Gly Lys Thr Leu Ser Val Ser
145                 150                 155                 160

Gln Leu Glu Leu Gln Asp Ser Gly Thr Trp Thr Cys Thr Val Leu Gln
                165                 170                 175

Asn Gln Lys Lys Val Glu Phe Lys Ile Asp Ile Val Val Leu Ala Phe
            180                 185                 190

Gln Lys Ala Ser Thr Gly Gly Gly Gly Ser Gly Gly Gly Gly Ser
        195                 200                 205

Gly Gly Gly Gly Thr Glu Asp Ala Lys Asn Ile Lys Lys Gly Pro Ala
    210                 215                 220

Pro Phe Tyr Pro Leu Glu Asp Gly Thr Ala Gly Glu Gln Leu His Lys
225                 230                 235                 240

Ala Met Lys Arg Tyr Ala Leu Val Pro Gly Thr Ile Ala Phe Thr Asp
                245                 250                 255

Ala His Ile Glu Val Asn Ile Thr Tyr Ala Glu Tyr Phe Glu Met Ser
            260                 265                 270

Val Arg Leu Ala Glu Ala Met Lys Arg Tyr Gly Leu Asn Thr Asn His
        275                 280                 285

Arg Ile Val Val Cys Ser Glu Asn Ser Leu Gln Phe Phe Met Pro Val
    290                 295                 300

Leu Gly Ala Leu Phe Ile Gly Val Ala Val Ala Pro Ala Asn Asp Ile
305                 310                 315                 320

Tyr Asn Glu Arg Glu Leu Leu Asn Ser Met Asn Ile Ser Gln Pro Thr
                325                 330                 335

Val Val Phe Val Ser Lys Lys Gly Leu Gln Lys Ile Leu Asn Val Gln
            340                 345                 350

Lys Lys Leu Pro Ile Ile Gln Lys Ile Ile Met Asp Ser Lys Thr
        355                 360                 365

Asp Tyr Gln Gly Phe Gln Ser Met Tyr Thr Phe Val Thr Ser His Leu
    370                 375                 380

Pro Pro Gly Phe Asn Glu Tyr Asp Phe Val Pro Glu Ser Phe Asp Arg
385                 390                 395                 400

Asp Lys Thr Ile Ala Leu Ile Met Asn Ser Ser Gly Ser Thr Gly Leu
                405                 410                 415

Pro Lys Gly Val Ala Leu Pro His Arg Thr Ala Cys Val Arg Phe Ser
            420                 425                 430

His Ala Arg Asp Pro Ile Phe Gly Asn Gln Ile Ile Pro Asp Thr Ala
        435                 440                 445

Ile Leu Ser Val Val Pro Phe His His Gly Phe Gly Met Phe Thr Thr
    450                 455                 460

Leu Gly Tyr Leu Ile Cys Gly Phe Arg Val Val Leu Met Tyr Arg Phe
465                 470                 475                 480

Glu Glu Glu Leu Phe Leu Arg Ser Leu Gln Asp Tyr Lys Ile Gln Ser
                485                 490                 495

Ala Leu Leu Val Pro Thr Leu Phe Ser Phe Phe Ala Lys Ser Thr Leu
            500                 505                 510

Ile Asp Lys Tyr Asp Leu Ser Asn Leu His Glu Ile Ala Ser Gly Gly
        515                 520                 525

Ala Pro Leu Ser Lys Glu Val Gly Glu Ala Val Ala Lys Arg Phe His
    530                 535                 540

Leu Pro Gly Ile Arg Gln Gly Tyr Gly Leu Thr Glu Thr Thr Ser Ala
545                 550                 555                 560

Ile Leu Ile Thr Pro Glu Gly Asp Asp Lys Pro Gly Ala Val Gly Lys
                565                 570                 575

Val Val Pro Phe Phe Glu Ala Lys Val Val Asp Leu Asp Thr Gly Lys
            580                 585                 590

Thr Leu Gly Val Asn Gln Arg Gly Glu Leu Cys Val Arg Gly Pro Met
        595                 600                 605

Ile Met Ser Gly Tyr Val Asn Asn Pro Glu Ala Thr Asn Ala Leu Ile
    610                 615                 620

Asp Lys Asp Gly
625

<210> SEQ ID NO 12
<211> LENGTH: 1329
<212> TYPE: DNA
<213> ORGANISM: Artificial Sequence
<220> FEATURE:
<223> OTHER INFORMATION: Synthetic construct: CFluc-4D5 coding -continued

```
      sequence
<220> FEATURE:
<221> NAME/KEY: CDS
<222> LOCATION: (1)..(1326)

<400> SEQUENCE: 12 atg atg tcc ggt tat gta aac aat ccg gaa gcg acc aac gcc ttg att      48
Met Met Ser Gly Tyr Val Asn Asn Pro Glu Ala Thr Asn Ala Leu Ile
1               5                  10                  15 gac aag gat gga tgg cta cat tct gga gac ata gct tac tgg gac gaa      96
Asp Lys Asp Gly Trp Leu His Ser Gly Asp Ile Ala Tyr Trp Asp Glu
            20                  25                  30 gac gaa cac ttc ttc ata gtt gac cgc ttg aag tct tta att aaa tac     144
Asp Glu His Phe Phe Ile Val Asp Arg Leu Lys Ser Leu Ile Lys Tyr
        35                  40                  45 aaa gga tat cag gtg gcc ccc gct gaa ttg gaa tcg ata ttg tta caa     192
Lys Gly Tyr Gln Val Ala Pro Ala Glu Leu Glu Ser Ile Leu Leu Gln
    50                  55                  60 cac ccc aac atc ttc gac gcg ggc gtg gca ggt ctt ccc gac gat gac     240
His Pro Asn Ile Phe Asp Ala Gly Val Ala Gly Leu Pro Asp Asp Asp
65                  70                  75                  80 gcc ggt gaa ctt ccc gcc gcc gtt gtt gtt ttg gag cac gga aag acg     288
Ala Gly Glu Leu Pro Ala Ala Val Val Val Leu Glu His Gly Lys Thr
                85                  90                  95 atg acg gaa aaa gag atc gtg gat tac gtc gcc agt caa gta aca acc     336
Met Thr Glu Lys Glu Ile Val Asp Tyr Val Ala Ser Gln Val Thr Thr
            100                 105                 110 gcg aaa aag ttg cgc gga gga gtt gtg ttt gtg gac gaa gta ccg aaa     384
Ala Lys Lys Leu Arg Gly Gly Val Val Phe Val Asp Glu Val Pro Lys
        115                 120                 125 ggt ctt acc gga aaa ctc gac gca aga aaa atc aga gag atc ctc ata     432
Gly Leu Thr Gly Lys Leu Asp Ala Arg Lys Ile Arg Glu Ile Leu Ile
    130                 135                 140 aag gcc aag aag ggc gga aag tcc aaa ttg ggc ctg cag ggc ggt tca     480
Lys Ala Lys Lys Gly Gly Lys Ser Lys Leu Gly Leu Gln Gly Gly Ser
145                 150                 155                 160 ggc ggt ggg ggt tct ggc ggg ggt ggg agc ccc ggg gag gtg cag ctg     528
Gly Gly Gly Gly Ser Gly Gly Gly Gly Ser Pro Gly Glu Val Gln Leu
                165                 170                 175 gtg gag agc ggc ggc ggc ctg gtg cag ccc ggc ggc agc ctg agg ctg     576
Val Glu Ser Gly Gly Gly Leu Val Gln Pro Gly Gly Ser Leu Arg Leu
            180                 185                 190 agc tgc gcc gcc agc ggc ttc aac atc aag gac acc tac atc cac tgg     624
Ser Cys Ala Ala Ser Gly Phe Asn Ile Lys Asp Thr Tyr Ile His Trp
        195                 200                 205 gtg agg cag gcc ccc ggc aag ggc ctg gag tgg gtg gcc agg atc tac     672
Val Arg Gln Ala Pro Gly Lys Gly Leu Glu Trp Val Ala Arg Ile Tyr
    210                 215                 220 ccc acc aac ggc tac acc agg tac gcc gac agc gtg aag ggc agg ttc     720
Pro Thr Asn Gly Tyr Thr Arg Tyr Ala Asp Ser Val Lys Gly Arg Phe
225                 230                 235                 240 acc atc agc gcc gac acc agc aag aac acc gcc tac ctc cag atg aac     768
Thr Ile Ser Ala Asp Thr Ser Lys Asn Thr Ala Tyr Leu Gln Met Asn
                245                 250                 255 agc ctg agg gcc gag gac acc gcc gtg tac tac tgt agc agg tgg ggc     816
Ser Leu Arg Ala Glu Asp Thr Ala Val Tyr Tyr Cys Ser Arg Trp Gly
            260                 265                 270 ggc gac ggc ttc tac gcc atg gac tac tgg ggc cag ggc acc ctg gtg     864
Gly Asp Gly Phe Tyr Ala Met Asp Tyr Trp Gly Gln Gly Thr Leu Val
        275                 280                 285 acc gtg agc agc acg cgt ggt gga ggc ggt tca ggc gga ggt ggc tct     912
```

```
Thr Val Ser Ser Thr Arg Gly Gly Gly Ser Gly Gly Gly Ser
    290                 295                 300 ggc ggt ggc gga tcg gct agc gac atc cag atg acc cag agc ccc agc     960
Gly Gly Gly Gly Ser Ala Ser Asp Ile Gln Met Thr Gln Ser Pro Ser
305                 310                 315                 320 agc ctg agc gcc agc gtg ggc gac agg gtg acc atc acc tgt agg gcc    1008
Ser Leu Ser Ala Ser Val Gly Asp Arg Val Thr Ile Thr Cys Arg Ala
                325                 330                 335 agc cag gac gtg aac acc gcc gtg gcc tgg tat cag cag aag ccc ggc    1056
Ser Gln Asp Val Asn Thr Ala Val Ala Trp Tyr Gln Gln Lys Pro Gly
            340                 345                 350 aag gcc ccc aag ctg ctg atc tac agc gcc agc ttc ctg tac agc ggc    1104
Lys Ala Pro Lys Leu Leu Ile Tyr Ser Ala Ser Phe Leu Tyr Ser Gly
        355                 360                 365 gtg ccc agc agg ttc agc ggc agc agg agc ggc acc gac ttc acc ctg    1152
Val Pro Ser Arg Phe Ser Gly Ser Arg Ser Gly Thr Asp Phe Thr Leu
    370                 375                 380 acc atc agc agc ctc cag ccc gag gac ttc gcc acc tac tac tgc cag    1200
Thr Ile Ser Ser Leu Gln Pro Glu Asp Phe Ala Thr Tyr Tyr Cys Gln
385                 390                 395                 400 cag cac tac acc acc cct ccc acc ttc ggc cag ggc acc aag gtg gag    1248
Gln His Tyr Thr Thr Pro Pro Thr Phe Gly Gln Gly Thr Lys Val Glu
                405                 410                 415 atc aag gtc gag tct ggt aaa gaa acc gct gct gcg aaa ttt gaa cgc    1296
Ile Lys Val Glu Ser Gly Lys Glu Thr Ala Ala Ala Lys Phe Glu Arg
            420                 425                 430 cag cac atg gac tcg tct act agc gca gct taa                        1329
Gln His Met Asp Ser Ser Thr Ser Ala Ala
        435                 440

<210> SEQ ID NO 13
<211> LENGTH: 442
<212> TYPE: PRT
<213> ORGANISM: Artificial Sequence
<220> FEATURE:
<223> OTHER INFORMATION: Synthetic Construct

<400> SEQUENCE: 13

Met Met Ser Gly Tyr Val Asn Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
        35                  40                  45

Lys Gly Tyr Gln Val Ala Pro Ala Glu Leu Glu Ser Ile Leu Leu Gln
    50                  55                  60

His Pro Asn Ile Phe Asp Ala Gly Val Ala Gly Leu Pro Asp Asp Asp
65                  70                  75                  80

Ala Gly Glu Leu Pro Ala Ala Val Val Val Leu Glu His Gly Lys Thr
                85                  90                  95

Met Thr Glu Lys Glu Ile Val Asp Tyr Val Ala Ser Gln Val Thr Thr
            100                 105                 110

Ala Lys Lys Leu Arg Gly Gly Val Val Phe Val Asp Glu Val Pro Lys
        115                 120                 125

Gly Leu Thr Gly Lys Leu Asp Ala Arg Lys Ile Arg Glu Ile Leu Ile
    130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Gly Ser Pro Gly Glu Val Gln Leu
```

165                 170                 175
Val Glu Ser Gly Gly Gly Leu Val Gln Pro Gly Gly Ser Leu Arg Leu
            180                 185                 190

Ser Cys Ala Ala Ser Gly Phe Asn Ile Lys Asp Thr Tyr Ile His Trp
        195                 200                 205

Val Arg Gln Ala Pro Gly Lys Gly Leu Glu Trp Val Ala Arg Ile Tyr
    210                 215                 220

Pro Thr Asn Gly Tyr Thr Arg Tyr Ala Asp Ser Val Lys Gly Arg Phe
225                 230                 235                 240

Thr Ile Ser Ala Asp Thr Ser Lys Asn Thr Ala Tyr Leu Gln Met Asn
                245                 250                 255

Ser Leu Arg Ala Glu Asp Thr Ala Val Tyr Tyr Cys Ser Arg Trp Gly
            260                 265                 270

Gly Asp Gly Phe Tyr Ala Met Asp Tyr Trp Gly Gln Gly Thr Leu Val
        275                 280                 285

Thr Val Ser Ser Thr Arg Gly Gly Gly Ser Gly Gly Gly Gly Ser
    290                 295                 300

Gly Gly Gly Gly Ser Ala Ser Asp Ile Gln Met Thr Gln Ser Pro Ser
305                 310                 315                 320

Ser Leu Ser Ala Ser Val Gly Asp Arg Val Thr Ile Thr Cys Arg Ala
                325                 330                 335

Ser Gln Asp Val Asn Thr Ala Val Ala Trp Tyr Gln Gln Lys Pro Gly
            340                 345                 350

Lys Ala Pro Lys Leu Leu Ile Tyr Ser Ala Ser Phe Leu Tyr Ser Gly
        355                 360                 365

Val Pro Ser Arg Phe Ser Gly Ser Arg Ser Gly Thr Asp Phe Thr Leu
    370                 375                 380

Thr Ile Ser Ser Leu Gln Pro Glu Asp Phe Ala Thr Tyr Tyr Cys Gln
385                 390                 395                 400

Gln His Tyr Thr Thr Pro Pro Thr Phe Gly Gly Gly Thr Lys Val Glu
                405                 410                 415

Ile Lys Val Glu Ser Gly Lys Glu Thr Ala Ala Ala Lys Phe Glu Arg
            420                 425                 430

Gln His Met Asp Ser Ser Thr Ser Ala Ala
        435                 440

<210> SEQ ID NO 14
<211> LENGTH: 2076
<212> TYPE: DNA
<213> ORGANISM: Artificial Sequence
<220> FEATURE:
<223> OTHER INFORMATION: Synthetic construct: 2C4-NFluc coding sequence
<220> FEATURE:
<221> NAME/KEY: CDS
<222> LOCATION: (1)..(2073)

<400> SEQUENCE: 14 atg ggc agc agc cat cac cat cat cac cac agc cag gat ccg gag gtg     48
Met Gly Ser Ser His His His His His His Ser Gln Asp Pro Glu Val
1               5                  10                  15 cag ctg gtg gag agc ggc gga ggc ctg gtg cag ccc gga ggc agc ctg     96
Gln Leu Val Glu Ser Gly Gly Gly Leu Val Gln Pro Gly Gly Ser Leu
            20                  25                  30 agg ctg agc tgc gcc gcc agc ggc ttc acc ttc acc gac tac acc atg    144
Arg Leu Ser Cys Ala Ala Ser Gly Phe Thr Phe Thr Asp Tyr Thr Met
        35                  40                  45 gac tgg gtg agg cag gcc ccc ggc aag ggc ctg gag tgg gtg gcc gac    192
Asp Trp Val Arg Gln Ala Pro Gly Lys Gly Leu Glu Trp Val Ala Asp

```
                50                  55                  60
gtg aac ccc aac agc ggc ggc agc atc tac aac cag agg ttc aag ggc      240
Val Asn Pro Asn Ser Gly Gly Ser Ile Tyr Asn Gln Arg Phe Lys Gly
 65                  70                  75                  80 agg ttc acc ctg agc gtg gac agg agc aag aac acc ctg tac ctc cag      288
Arg Phe Thr Leu Ser Val Asp Arg Ser Lys Asn Thr Leu Tyr Leu Gln
                 85                  90                  95 atg aac agc ctg agg gcc gag gac acc gcc gtg tac tac tgc gcc agg      336
Met Asn Ser Leu Arg Ala Glu Asp Thr Ala Val Tyr Tyr Cys Ala Arg
            100                 105                 110 aac ctg ggc ccc agc ttc tac ttc gac tac tgg ggc cag ggc acc ctg      384
Asn Leu Gly Pro Ser Phe Tyr Phe Asp Tyr Trp Gly Gln Gly Thr Leu
                115                 120                 125 gtg acc gtg agc tcc acg cgt ggt gga ggc ggt tca ggc gga ggt ggc      432
Val Thr Val Ser Ser Thr Arg Gly Gly Gly Gly Ser Gly Gly Gly Gly
        130                 135                 140 tct ggc ggt ggc gga tcg gct agc gac atc cag atg acc cag agc ccc      480
Ser Gly Gly Gly Gly Ser Ala Ser Asp Ile Gln Met Thr Gln Ser Pro
145                 150                 155                 160 agc tcc ctg agc gcc agc gtg ggc gac agg gtg acc atc acc tgc aag      528
Ser Ser Leu Ser Ala Ser Val Gly Asp Arg Val Thr Ile Thr Cys Lys
                165                 170                 175 gcc agc cag gac gtg agc atc ggc gtg gcc tgg tat cag cag aag ccc      576
Ala Ser Gln Asp Val Ser Ile Gly Val Ala Trp Tyr Gln Gln Lys Pro
            180                 185                 190 ggc aag gcc ccc aag ctg ctg atc tac agc gcc agc tac agg tac acc      624
Gly Lys Ala Pro Lys Leu Leu Ile Tyr Ser Ala Ser Tyr Arg Tyr Thr
                195                 200                 205 ggc gtg ccc agc agg ttc agc ggc agc ggc agc ggc acc gac ttc acc      672
Gly Val Pro Ser Arg Phe Ser Gly Ser Gly Ser Gly Thr Asp Phe Thr
        210                 215                 220 ctg acc atc agc tcc ctc cag ccc gag gac ttc gcc acc tac tac tgc      720
Leu Thr Ile Ser Ser Leu Gln Pro Glu Asp Phe Ala Thr Tyr Tyr Cys
225                 230                 235                 240 cag cag tac tat atc tac ccc tac acc ttc ggc cag ggc acc aag gtg      768
Gln Gln Tyr Tyr Ile Tyr Pro Tyr Thr Phe Gly Gln Gly Thr Lys Val
                245                 250                 255 gag atc aag acc ggt ggg ggt ggc ggt tca ggc ggt ggg ggt tct ggt      816
Glu Ile Lys Thr Gly Gly Gly Gly Gly Ser Gly Gly Gly Gly Ser Gly
            260                 265                 270 ggg ggt ggt acc gaa gac gcc aaa aac ata aag aaa ggc ccg gcg cca      864
Gly Gly Gly Thr Glu Asp Ala Lys Asn Ile Lys Lys Gly Pro Ala Pro
        275                 280                 285 ttc tat cct cta gag gat gga acc gct gga gag caa ctg cat aag gct      912
Phe Tyr Pro Leu Glu Asp Gly Thr Ala Gly Glu Gln Leu His Lys Ala
                290                 295                 300 atg aag aga tac gcc ctg gtt cct gga aca att gct ttt aca gat gca      960
Met Lys Arg Tyr Ala Leu Val Pro Gly Thr Ile Ala Phe Thr Asp Ala
305                 310                 315                 320 cat atc gag gtg aac atc acg tac gcg gaa tac ttc gaa atg tcc gtt     1008
His Ile Glu Val Asn Ile Thr Tyr Ala Glu Tyr Phe Glu Met Ser Val
                325                 330                 335 cgg ttg gca gaa gct atg aaa cga tat ggg ctg aat aca aat cac aga     1056
Arg Leu Ala Glu Ala Met Lys Arg Tyr Gly Leu Asn Thr Asn His Arg
            340                 345                 350 atc gtc gta tgc agt gaa aac tct ctt caa ttc ttt atg ccg gtg ttg     1104
Ile Val Val Cys Ser Glu Asn Ser Leu Gln Phe Phe Met Pro Val Leu
        355                 360                 365 ggc gcg tta ttt atc gga gtt gca gtt gcg ccc gcg aac gac att tat     1152
Gly Ala Leu Phe Ile Gly Val Ala Val Ala Pro Ala Asn Asp Ile Tyr
```

-continued

```
               370                 375                 380
aat gaa cgt gaa ttg ctc aac agt atg aac att tcg cag cct acc gta       1200
Asn Glu Arg Glu Leu Leu Asn Ser Met Asn Ile Ser Gln Pro Thr Val
385                 390                 395                 400 gtg ttt gtt tcc aaa aag ggg ttg caa aaa att ttg aac gtg caa aaa       1248
Val Phe Val Ser Lys Lys Gly Leu Gln Lys Ile Leu Asn Val Gln Lys
                405                 410                 415 aaa tta cca ata atc cag aaa att att atc atg gat tct aaa acg gat       1296
Lys Leu Pro Ile Ile Gln Lys Ile Ile Ile Met Asp Ser Lys Thr Asp
        420                 425                 430 tac cag gga ttt cag tcg atg tac acg ttc gtc aca tct cat cta cct       1344
Tyr Gln Gly Phe Gln Ser Met Tyr Thr Phe Val Thr Ser His Leu Pro
            435                 440                 445 ccc ggt ttt aat gaa tac gat ttt gta cca gag tcc ttt gat cgt gac       1392
Pro Gly Phe Asn Glu Tyr Asp Phe Val Pro Glu Ser Phe Asp Arg Asp
450                 455                 460 aaa aca att gca ctg ata atg aat tcc tct gga tct act ggg tta cct       1440
Lys Thr Ile Ala Leu Ile Met Asn Ser Ser Gly Ser Thr Gly Leu Pro
465                 470                 475                 480 aag ggt gtg gcc ctt ccg cat aga act gcc tgc gtc aga ttc tcg cat       1488
Lys Gly Val Ala Leu Pro His Arg Thr Ala Cys Val Arg Phe Ser His
                485                 490                 495 gcc aga gat cct att ttt ggc aat caa atc att ccg gat act gcg att       1536
Ala Arg Asp Pro Ile Phe Gly Asn Gln Ile Ile Pro Asp Thr Ala Ile
        500                 505                 510 tta agt gtt gtt cca ttc cat cac ggt ttt gga atg ttt act aca ctc       1584
Leu Ser Val Val Pro Phe His His Gly Phe Gly Met Phe Thr Thr Leu
            515                 520                 525 gga tat ttg ata tgt gga ttt cga gtc gtc tta atg tat aga ttt gaa       1632
Gly Tyr Leu Ile Cys Gly Phe Arg Val Val Leu Met Tyr Arg Phe Glu
530                 535                 540 gaa gag ctg ttt tta cga tcc ctt cag gat tac aaa att caa agt gcg       1680
Glu Glu Leu Phe Leu Arg Ser Leu Gln Asp Tyr Lys Ile Gln Ser Ala
545                 550                 555                 560 ttg cta gta cca acc cta ttt tca ttc ttc gcc aaa agc act ctg att       1728
Leu Leu Val Pro Thr Leu Phe Ser Phe Phe Ala Lys Ser Thr Leu Ile
                565                 570                 575 gac aaa tac gat tta tct aat tta cac gaa att gct tct ggg ggc gca       1776
Asp Lys Tyr Asp Leu Ser Asn Leu His Glu Ile Ala Ser Gly Gly Ala
        580                 585                 590 cct ctt tcg aaa gaa gtc ggg gaa gcg gtt gca aaa cgc ttc cat ctt       1824
Pro Leu Ser Lys Glu Val Gly Glu Ala Val Ala Lys Arg Phe His Leu
            595                 600                 605 cca ggg ata cga caa gga tat ggg ctc act gag act aca tca gct att       1872
Pro Gly Ile Arg Gln Gly Tyr Gly Leu Thr Glu Thr Thr Ser Ala Ile
610                 615                 620 ctg att aca ccc gag ggg gat gat aaa ccg ggc gcg gtc ggt aaa gtt       1920
Leu Ile Thr Pro Glu Gly Asp Asp Lys Pro Gly Ala Val Gly Lys Val
625                 630                 635                 640 gtt cca ttt ttt gaa gcg aag gtt gtg gat ctg gat acc ggg aaa acg       1968
Val Pro Phe Phe Glu Ala Lys Val Val Asp Leu Asp Thr Gly Lys Thr
                645                 650                 655 ctg ggc gtt aat cag aga ggc gaa tta tgt gtc aga gga cct atg att       2016
Leu Gly Val Asn Gln Arg Gly Glu Leu Cys Val Arg Gly Pro Met Ile
        660                 665                 670 atg tcc ggt tat gta aac aat ccg gaa gcg acc aac gcc ttg att gac       2064
Met Ser Gly Tyr Val Asn Asn Pro Glu Ala Thr Asn Ala Leu Ile Asp
            675                 680                 685 aag gat gga tga                                                       2076
Lys Asp Gly
```

<210> SEQ ID NO 15
<211> LENGTH: 691
<212> TYPE: PRT
<213> ORGANISM: Artificial Sequence
<220> FEATURE:
<223> OTHER INFORMATION: Synthetic Construct

<400> SEQUENCE: 15

```
Met Gly Ser Ser His His His His His His Ser Gln Asp Pro Glu Val
1               5                   10                  15

Gln Leu Val Glu Ser Gly Gly Gly Leu Val Gln Pro Gly Gly Ser Leu
            20                  25                  30

Arg Leu Ser Cys Ala Ala Ser Gly Phe Thr Phe Thr Asp Tyr Thr Met
        35                  40                  45

Asp Trp Val Arg Gln Ala Pro Gly Lys Gly Leu Glu Trp Val Ala Asp
    50                  55                  60

Val Asn Pro Asn Ser Gly Gly Ser Ile Tyr Asn Gln Arg Phe Lys Gly
65                  70                  75                  80

Arg Phe Thr Leu Ser Val Asp Arg Ser Lys Asn Thr Leu Tyr Leu Gln
                85                  90                  95

Met Asn Ser Leu Arg Ala Glu Asp Thr Ala Val Tyr Tyr Cys Ala Arg
            100                 105                 110

Asn Leu Gly Pro Ser Phe Tyr Phe Asp Tyr Trp Gly Gln Gly Thr Leu
        115                 120                 125

Val Thr Val Ser Ser Thr Arg Gly Gly Gly Ser Gly Gly Gly Gly
    130                 135                 140

Ser Gly Gly Gly Gly Ser Ala Ser Asp Ile Gln Met Thr Gln Ser Pro
145                 150                 155                 160

Ser Ser Leu Ser Ala Ser Val Gly Asp Arg Val Thr Ile Thr Cys Lys
                165                 170                 175

Ala Ser Gln Asp Val Ser Ile Gly Val Ala Trp Tyr Gln Gln Lys Pro
            180                 185                 190

Gly Lys Ala Pro Lys Leu Leu Ile Tyr Ser Ala Ser Tyr Arg Tyr Thr
        195                 200                 205

Gly Val Pro Ser Arg Phe Ser Gly Ser Gly Ser Gly Thr Asp Phe Thr
    210                 215                 220

Leu Thr Ile Ser Ser Leu Gln Pro Glu Asp Phe Ala Thr Tyr Tyr Cys
225                 230                 235                 240

Gln Gln Tyr Tyr Ile Tyr Pro Tyr Thr Phe Gly Gln Gly Thr Lys Val
                245                 250                 255

Glu Ile Lys Thr Gly Gly Gly Gly Ser Gly Gly Gly Gly Ser Gly
            260                 265                 270

Gly Gly Gly Thr Glu Asp Ala Lys Asn Ile Lys Lys Gly Pro Ala Pro
        275                 280                 285

Phe Tyr Pro Leu Glu Asp Gly Thr Ala Gly Glu Gln Leu His Lys Ala
    290                 295                 300

Met Lys Arg Tyr Ala Leu Val Pro Gly Thr Ile Ala Phe Thr Asp Ala
305                 310                 315                 320

His Ile Glu Val Asn Ile Thr Tyr Ala Glu Tyr Phe Glu Met Ser Val
                325                 330                 335

Arg Leu Ala Glu Ala Met Lys Arg Tyr Gly Leu Asn Thr Asn His Arg
            340                 345                 350

Ile Val Val Cys Ser Glu Asn Ser Leu Gln Phe Phe Met Pro Val Leu
        355                 360                 365
```

Gly Ala Leu Phe Ile Gly Val Ala Val Ala Pro Ala Asn Asp Ile Tyr
    370                 375                 380

Asn Glu Arg Glu Leu Leu Asn Ser Met Asn Ile Ser Gln Pro Thr Val
385                 390                 395                 400

Val Phe Val Ser Lys Lys Gly Leu Gln Lys Ile Leu Asn Val Gln Lys
                405                 410                 415

Lys Leu Pro Ile Ile Gln Lys Ile Ile Met Asp Ser Lys Thr Asp
            420                 425                 430

Tyr Gln Gly Phe Gln Ser Met Tyr Thr Phe Val Thr Ser His Leu Pro
            435                 440                 445

Pro Gly Phe Asn Glu Tyr Asp Phe Val Pro Glu Ser Phe Asp Arg Asp
        450                 455                 460

Lys Thr Ile Ala Leu Ile Met Asn Ser Ser Gly Ser Thr Gly Leu Pro
465                 470                 475                 480

Lys Gly Val Ala Leu Pro His Arg Thr Ala Cys Val Arg Phe Ser His
                485                 490                 495

Ala Arg Asp Pro Ile Phe Gly Asn Gln Ile Ile Pro Asp Thr Ala Ile
            500                 505                 510

Leu Ser Val Val Pro Phe His His Gly Phe Gly Met Phe Thr Thr Leu
        515                 520                 525

Gly Tyr Leu Ile Cys Gly Phe Arg Val Val Leu Met Tyr Arg Phe Glu
    530                 535                 540

Glu Glu Leu Phe Leu Arg Ser Leu Gln Asp Tyr Lys Ile Gln Ser Ala
545                 550                 555                 560

Leu Leu Val Pro Thr Leu Phe Ser Phe Phe Ala Lys Ser Thr Leu Ile
                565                 570                 575

Asp Lys Tyr Asp Leu Ser Asn Leu His Glu Ile Ala Ser Gly Gly Ala
            580                 585                 590

Pro Leu Ser Lys Glu Val Gly Glu Ala Val Ala Lys Arg Phe His Leu
        595                 600                 605

Pro Gly Ile Arg Gln Gly Tyr Gly Leu Thr Glu Thr Thr Ser Ala Ile
    610                 615                 620

Leu Ile Thr Pro Glu Gly Asp Asp Lys Pro Gly Ala Val Gly Lys Val
625                 630                 635                 640

Val Pro Phe Phe Glu Ala Lys Val Val Asp Leu Asp Thr Gly Lys Thr
                645                 650                 655

Leu Gly Val Asn Gln Arg Gly Glu Leu Cys Val Arg Gly Pro Met Ile
            660                 665                 670

Met Ser Gly Tyr Val Asn Asn Pro Glu Ala Thr Asn Ala Leu Ile Asp
        675                 680                 685

Lys Asp Gly
    690

<210> SEQ ID NO 16
<211> LENGTH: 1371
<212> TYPE: DNA
<213> ORGANISM: Artificial Sequence
<220> FEATURE:
<223> OTHER INFORMATION: Synthetic construct: PKI-NFluc(2-416) coding
      sequence
<220> FEATURE:
<221> NAME/KEY: CDS
<222> LOCATION: (1)..(1362)

<400> SEQUENCE: 16 atg gga ggt act acg tat gct gac ttt ata gcg agt ggt cga aca gga         48
Met Gly Gly Thr Thr Tyr Ala Asp Phe Ile Ala Ser Gly Arg Thr Gly -continued

```
1               5                   10                  15
aga agg aat gca att cat gat ggt gga gca ggc ggt gct gca ggt ggg        96
Arg Arg Asn Ala Ile His Asp Gly Gly Ala Gly Gly Ala Ala Gly Gly
                20                  25                  30 ggt tct ggt ggg ggt ggt acc gaa gac gcc aaa aac ata aag aaa ggc       144
Gly Ser Gly Gly Gly Gly Thr Glu Asp Ala Lys Asn Ile Lys Lys Gly
    35                  40                  45 ccg gcg cca ttc tat cct cta gag gat gga acc gct gga gag caa ctg       192
Pro Ala Pro Phe Tyr Pro Leu Glu Asp Gly Thr Ala Gly Glu Gln Leu
50                  55                  60 cat aag gct atg aag aga tac gcc ctg gtt cct gga aca att gct ttt       240
His Lys Ala Met Lys Arg Tyr Ala Leu Val Pro Gly Thr Ile Ala Phe
65                  70                  75                  80 aca gat gca cat atc gag gtg aac atc acg tac gcg gaa tac ttc gaa       288
Thr Asp Ala His Ile Glu Val Asn Ile Thr Tyr Ala Glu Tyr Phe Glu
                85                  90                  95 atg tcc gtt cgg ttg gca gaa gct atg aaa cga tat ggg ctg aat aca       336
Met Ser Val Arg Leu Ala Glu Ala Met Lys Arg Tyr Gly Leu Asn Thr
                100                 105                 110 aat cac aga atc gtc gta tgc agt gaa aac tct ctt caa ttc ttt atg       384
Asn His Arg Ile Val Val Cys Ser Glu Asn Ser Leu Gln Phe Phe Met
            115                 120                 125 ccg gtg ttg ggc gcg tta ttt atc gga gtt gca gtt gcg ccc gcg aac       432
Pro Val Leu Gly Ala Leu Phe Ile Gly Val Ala Val Ala Pro Ala Asn
        130                 135                 140 gac att tat aat gaa cgt gaa ttg ctc aac agt atg aac att tcg cag       480
Asp Ile Tyr Asn Glu Arg Glu Leu Leu Asn Ser Met Asn Ile Ser Gln
145                 150                 155                 160 cct acc gta gtg ttt gtt tcc aaa aag ggg ttg caa aaa att ttg aac       528
Pro Thr Val Val Phe Val Ser Lys Lys Gly Leu Gln Lys Ile Leu Asn
                165                 170                 175 gtg caa aaa aaa tta cca ata atc cag aaa att att atc atg gat tct       576
Val Gln Lys Lys Leu Pro Ile Ile Gln Lys Ile Ile Ile Met Asp Ser
                180                 185                 190 aaa acg gat tac cag gga ttt cag tcg atg tac acg ttc gtc aca tct       624
Lys Thr Asp Tyr Gln Gly Phe Gln Ser Met Tyr Thr Phe Val Thr Ser
            195                 200                 205 cat cta cct ccc ggt ttt aat gaa tac gat ttt gta cca gag tcc ttt       672
His Leu Pro Pro Gly Phe Asn Glu Tyr Asp Phe Val Pro Glu Ser Phe
        210                 215                 220 gat cgt gac aaa aca att gca ctg ata atg aat tcc tct gga tct act       720
Asp Arg Asp Lys Thr Ile Ala Leu Ile Met Asn Ser Ser Gly Ser Thr
225                 230                 235                 240 ggg tta cct aag ggt gtg gcc ctt ccg cat aga act gcc tgc gtc aga       768
Gly Leu Pro Lys Gly Val Ala Leu Pro His Arg Thr Ala Cys Val Arg
                245                 250                 255 ttc tcg cat gcc aga gat cct att ttt ggc aat caa atc att ccg gat       816
Phe Ser His Ala Arg Asp Pro Ile Phe Gly Asn Gln Ile Ile Pro Asp
                260                 265                 270 act gcg att tta agt gtt gtt cca ttc cat cac ggt ttt gga atg ttt       864
Thr Ala Ile Leu Ser Val Val Pro Phe His His Gly Phe Gly Met Phe
            275                 280                 285 act aca ctc gga tat ttg ata tgt gga ttt cga gtc gtc tta atg tat       912
Thr Thr Leu Gly Tyr Leu Ile Cys Gly Phe Arg Val Val Leu Met Tyr
        290                 295                 300 aga ttt gaa gaa gag ctg ttt tta cga tcc ctt cag gat tac aaa att       960
Arg Phe Glu Glu Glu Leu Phe Leu Arg Ser Leu Gln Asp Tyr Lys Ile
305                 310                 315                 320 caa agt gcg ttg cta gta cca acc cta ttt tca ttc ttc gcc aaa agc      1008
Gln Ser Ala Leu Leu Val Pro Thr Leu Phe Ser Phe Phe Ala Lys Ser
```

```
                    325                 330                 335
act ctg att gac aaa tac gat tta tct aat tta cac gaa att gct tct      1056
Thr Leu Ile Asp Lys Tyr Asp Leu Ser Asn Leu His Glu Ile Ala Ser
            340                 345                 350 ggg ggc gca cct ctt tcg aaa gaa gtc ggg gaa gcg gtt gca aaa cgc      1104
Gly Gly Ala Pro Leu Ser Lys Glu Val Gly Glu Ala Val Ala Lys Arg
        355                 360                 365 ttc cat ctt cca ggg ata cga caa gga tat ggg ctc act gag act aca      1152
Phe His Leu Pro Gly Ile Arg Gln Gly Tyr Gly Leu Thr Glu Thr Thr
    370                 375                 380 tca gct att ctg att aca ccc gag ggg gat gat aaa ccg ggc gcg gtc      1200
Ser Ala Ile Leu Ile Thr Pro Glu Gly Asp Asp Lys Pro Gly Ala Val
385                 390                 395                 400 ggt aaa gtt gtt cca ttt ttt gaa gcg aag gtt gtg gat ctg gat acc      1248
Gly Lys Val Val Pro Phe Phe Glu Ala Lys Val Val Asp Leu Asp Thr
                405                 410                 415 ggg aaa acg ctg ggc gtt aat cag aga ggc gaa tta tgt gtc aga gga      1296
Gly Lys Thr Leu Gly Val Asn Gln Arg Gly Glu Leu Cys Val Arg Gly
            420                 425                 430 cct atg att atg tcc ggt tat gta aac aat ccg gaa gcg acc aac gcc      1344
Pro Met Ile Met Ser Gly Tyr Val Asn Asn Pro Glu Ala Thr Asn Ala
        435                 440                 445 ttg att gac aag gat gga tgataagcg                                    1371
Leu Ile Asp Lys Asp Gly
    450

<210> SEQ ID NO 17
<211> LENGTH: 454
<212> TYPE: PRT
<213> ORGANISM: Artificial Sequence
<220> FEATURE:
<223> OTHER INFORMATION: Synthetic Construct

<400> SEQUENCE: 17

Met Gly Gly Thr Thr Tyr Ala Asp Phe Ile Ala Ser Gly Arg Thr Gly
1               5                   10                  15

Arg Arg Asn Ala Ile His Asp Gly Gly Ala Gly Gly Ala Ala Gly Gly
            20                  25                  30

Gly Ser Gly Gly Gly Gly Thr Glu Asp Ala Lys Asn Ile Lys Lys Gly
        35                  40                  45

Pro Ala Pro Phe Tyr Pro Leu Glu Asp Gly Thr Ala Gly Glu Gln Leu
    50                  55                  60

His Lys Ala Met Lys Arg Tyr Ala Leu Val Pro Gly Thr Ile Ala Phe
65                  70                  75                  80

Thr Asp Ala His Ile Glu Val Asn Ile Thr Tyr Ala Glu Tyr Phe Glu
                85                  90                  95

Met Ser Val Arg Leu Ala Glu Ala Met Lys Arg Tyr Gly Leu Asn Thr
            100                 105                 110

Asn His Arg Ile Val Val Cys Ser Glu Asn Ser Leu Gln Phe Phe Met
        115                 120                 125

Pro Val Leu Gly Ala Leu Phe Ile Gly Val Ala Val Ala Pro Ala Asn
    130                 135                 140

Asp Ile Tyr Asn Glu Arg Glu Leu Leu Asn Ser Met Asn Ile Ser Gln
145                 150                 155                 160

Pro Thr Val Val Phe Val Ser Lys Lys Gly Leu Gln Lys Ile Leu Asn
                165                 170                 175

Val Gln Lys Lys Leu Pro Ile Ile Gln Lys Ile Ile Ile Met Asp Ser
            180                 185                 190
```

```
Lys Thr Asp Tyr Gln Gly Phe Gln Ser Met Tyr Thr Phe Val Thr Ser
        195                 200                 205
His Leu Pro Pro Gly Phe Asn Glu Tyr Asp Phe Val Pro Glu Ser Phe
        210                 215                 220
Asp Arg Asp Lys Thr Ile Ala Leu Ile Met Asn Ser Ser Gly Ser Thr
225                 230                 235                 240
Gly Leu Pro Lys Gly Val Ala Leu Pro His Arg Thr Ala Cys Val Arg
                245                 250                 255
Phe Ser His Ala Arg Asp Pro Ile Phe Gly Asn Gln Ile Ile Pro Asp
            260                 265                 270
Thr Ala Ile Leu Ser Val Val Pro Phe His His Gly Phe Gly Met Phe
        275                 280                 285
Thr Thr Leu Gly Tyr Leu Ile Cys Gly Phe Arg Val Val Leu Met Tyr
    290                 295                 300
Arg Phe Glu Glu Glu Leu Phe Leu Arg Ser Leu Gln Asp Tyr Lys Ile
305                 310                 315                 320
Gln Ser Ala Leu Leu Val Pro Thr Leu Phe Ser Phe Phe Ala Lys Ser
                325                 330                 335
Thr Leu Ile Asp Lys Tyr Asp Leu Ser Asn Leu His Glu Ile Ala Ser
            340                 345                 350
Gly Gly Ala Pro Leu Ser Lys Glu Val Gly Glu Ala Val Ala Lys Arg
        355                 360                 365
Phe His Leu Pro Gly Ile Arg Gln Gly Tyr Gly Leu Thr Glu Thr Thr
    370                 375                 380
Ser Ala Ile Leu Ile Thr Pro Glu Gly Asp Asp Lys Pro Gly Ala Val
385                 390                 395                 400
Gly Lys Val Val Pro Phe Phe Glu Ala Lys Val Val Asp Leu Asp Thr
                405                 410                 415
Gly Lys Thr Leu Gly Val Asn Gln Arg Gly Glu Leu Cys Val Arg Gly
            420                 425                 430
Pro Met Ile Met Ser Gly Tyr Val Asn Asn Pro Glu Ala Thr Asn Ala
        435                 440                 445
Leu Ile Asp Lys Asp Gly
        450

<210> SEQ ID NO 18
<211> LENGTH: 1584
<212> TYPE: DNA
<213> ORGANISM: Artificial Sequence
<220> FEATURE:
<223> OTHER INFORMATION: Synthetic construct: CFluc(398-550)-PKA
      coding sequence
<220> FEATURE:
<221> NAME/KEY: CDS
<222> LOCATION: (1)..(1563)

<400> SEQUENCE: 18 atg atg tcc ggt tat gta aac aat ccg gaa gcg acc aac gcc ttg att    48
Met Met Ser Gly Tyr Val Asn Asn Pro Glu Ala Thr Asn Ala Leu Ile
1               5                   10                  15 gac aag gat gga tgg cta cat tct gga gac ata gct tac tgg gac gaa    96
Asp Lys Asp Gly Trp Leu His Ser Gly Asp Ile Ala Tyr Trp Asp Glu
            20                  25                  30 gac gaa cac ttc ttc ata gtt gac cgc ttg aag tct tta att aaa tac   144
Asp Glu His Phe Phe Ile Val Asp Arg Leu Lys Ser Leu Ile Lys Tyr
        35                  40                  45 aaa gga tat cag gtg gcc ccc gct gaa ttg gaa tcg ata ttg tta caa   192
Lys Gly Tyr Gln Val Ala Pro Ala Glu Leu Glu Ser Ile Leu Leu Gln
    50                  55                  60
```

|  |  |  |  |  |  |  |  |  |  |  |  |  |  |  |  |
|---|---|---|---|---|---|---|---|---|---|---|---|---|---|---|---|
| cac | ccc | aac | atc | ttc | gac | gcg | ggc | gtg | gca | ggt | ctt | ccc | gac | gat | gac | 240 |
| His | Pro | Asn | Ile | Phe | Asp | Ala | Gly | Val | Ala | Gly | Leu | Pro | Asp | Asp | Asp |
| 65 |  |  |  | 70 |  |  |  |  | 75 |  |  |  |  | 80 |  |

| gcc | ggt | gaa | ctt | ccc | gcc | gcc | gtt | gtt | gtt | ttg | gag | cac | gga | aag | acg | 288 |
| Ala | Gly | Glu | Leu | Pro | Ala | Ala | Val | Val | Val | Leu | Glu | His | Gly | Lys | Thr |
|  |  |  |  | 85 |  |  |  |  | 90 |  |  |  |  | 95 |  |

| atg | acg | gaa | aaa | gag | atc | gtg | gat | tac | gtc | gcc | agt | caa | gta | aca | acc | 336 |
| Met | Thr | Glu | Lys | Glu | Ile | Val | Asp | Tyr | Val | Ala | Ser | Gln | Val | Thr | Thr |
|  |  |  | 100 |  |  |  |  | 105 |  |  |  |  | 110 |  |  |

| gcg | aaa | aag | ttg | cgc | gga | gga | gtt | gtg | ttt | gtg | gac | gaa | gta | ccg | aaa | 384 |
| Ala | Lys | Lys | Leu | Arg | Gly | Gly | Val | Val | Phe | Val | Asp | Glu | Val | Pro | Lys |
| 115 |  |  |  |  | 120 |  |  |  |  | 125 |  |  |  |  |  |

| ggt | ctt | acc | gga | aaa | ctc | gac | gca | aga | aaa | atc | aga | gag | atc | ctc | ata | 432 |
| Gly | Leu | Thr | Gly | Lys | Leu | Asp | Ala | Arg | Lys | Ile | Arg | Glu | Ile | Leu | Ile |
| 130 |  |  |  |  | 135 |  |  |  |  | 140 |  |  |  |  |  |

| aag | gcc | aag | aag | ggc | gga | aag | tcc | aaa | ttg | ggc | ctg | cag | ggc | ggt | tca | 480 |
| Lys | Ala | Lys | Lys | Gly | Gly | Lys | Ser | Lys | Leu | Gly | Leu | Gln | Gly | Gly | Ser |
| 145 |  |  |  | 150 |  |  |  |  | 155 |  |  |  |  | 160 |  |

| ggc | ggt | ggg | ggt | tct | ggc | ggg | ggt | ggg | agc | ccc | ggg | aac | gcc | gcc | gcc | 528 |
| Gly | Gly | Gly | Gly | Ser | Gly | Gly | Gly | Gly | Ser | Pro | Gly | Asn | Ala | Ala | Ala |
|  |  |  | 165 |  |  |  |  | 170 |  |  |  |  | 175 |  |  |

| gcc | aag | aag | ggc | agc | gag | cag | gag | agc | gtg | aaa | gag | ttc | cta | gcc | aaa | 576 |
| Ala | Lys | Lys | Gly | Ser | Glu | Gln | Glu | Ser | Val | Lys | Glu | Phe | Leu | Ala | Lys |
|  | 180 |  |  |  |  | 185 |  |  |  |  | 190 |  |  |  |  |

| gcc | aag | gaa | gat | ttc | ctg | aaa | aaa | tgg | gag | acc | cct | tct | cag | aat | aca | 624 |
| Ala | Lys | Glu | Asp | Phe | Leu | Lys | Lys | Trp | Glu | Thr | Pro | Ser | Gln | Asn | Thr |
|  |  | 195 |  |  |  |  | 200 |  |  |  |  | 205 |  |  |  |

| gcc | cag | ttg | gat | cag | ttt | gat | aga | atc | aag | acc | ctt | ggc | acc | ggc | tcc | 672 |
| Ala | Gln | Leu | Asp | Gln | Phe | Asp | Arg | Ile | Lys | Thr | Leu | Gly | Thr | Gly | Ser |
|  | 210 |  |  |  |  | 215 |  |  |  |  | 220 |  |  |  |  |

| ttt | ggg | cga | gtg | atg | ctg | gtg | aag | cac | aag | gag | agt | ggg | aac | cac | tac | 720 |
| Phe | Gly | Arg | Val | Met | Leu | Val | Lys | His | Lys | Glu | Ser | Gly | Asn | His | Tyr |
| 225 |  |  |  |  | 230 |  |  |  |  | 235 |  |  |  |  | 240 |

| gcc | atg | aag | atc | tta | gac | aag | cag | aag | gtg | gtg | aag | cta | aag | cag | atc | 768 |
| Ala | Met | Lys | Ile | Leu | Asp | Lys | Gln | Lys | Val | Val | Lys | Leu | Lys | Gln | Ile |
|  |  |  |  | 245 |  |  |  |  | 250 |  |  |  |  | 255 |  |

| gag | cac | act | ctg | aat | gag | aag | cgc | atc | ctg | cag | gcc | gtc | aac | ttc | ccg | 816 |
| Glu | His | Thr | Leu | Asn | Glu | Lys | Arg | Ile | Leu | Gln | Ala | Val | Asn | Phe | Pro |
|  |  |  | 260 |  |  |  |  | 265 |  |  |  |  | 270 |  |  |

| ttc | ctg | gtc | aaa | ctt | gaa | ttc | tcc | ttc | aag | gac | aac | tca | aac | ctg | tac | 864 |
| Phe | Leu | Val | Lys | Leu | Glu | Phe | Ser | Phe | Lys | Asp | Asn | Ser | Asn | Leu | Tyr |
|  |  | 275 |  |  |  |  | 280 |  |  |  |  | 285 |  |  |  |

| atg | gtc | atg | gag | tat | gta | gct | ggt | ggc | gag | atg | ttc | tcc | cac | cta | cgg | 912 |
| Met | Val | Met | Glu | Tyr | Val | Ala | Gly | Gly | Glu | Met | Phe | Ser | His | Leu | Arg |
|  | 290 |  |  |  |  | 295 |  |  |  |  | 300 |  |  |  |  |

| cgg | att | gga | agg | ttc | agc | gag | ccc | cat | gcc | cgt | ttc | tac | gcg | gcg | cag | 960 |
| Arg | Ile | Gly | Arg | Phe | Ser | Glu | Pro | His | Ala | Arg | Phe | Tyr | Ala | Ala | Gln |
| 305 |  |  |  |  | 310 |  |  |  |  | 315 |  |  |  |  | 320 |

| atc | gtc | ctg | acc | ttt | gag | tat | ctg | cac | tcc | ctg | gac | ctc | atc | tac | cgg | 1008 |
| Ile | Val | Leu | Thr | Phe | Glu | Tyr | Leu | His | Ser | Leu | Asp | Leu | Ile | Tyr | Arg |
|  |  |  |  | 325 |  |  |  |  | 330 |  |  |  |  | 335 |  |

| gac | ctg | aag | ccc | gag | aat | ctt | ctc | atc | gac | cag | cag | ggc | tat | att | cag | 1056 |
| Asp | Leu | Lys | Pro | Glu | Asn | Leu | Leu | Ile | Asp | Gln | Gln | Gly | Tyr | Ile | Gln |
|  |  |  | 340 |  |  |  |  | 345 |  |  |  |  | 350 |  |  |

| gtg | aca | gac | ttc | ggt | ttt | gcc | aag | cgt | gtg | aaa | ggc | cgt | act | tgg | acc | 1104 |
| Val | Thr | Asp | Phe | Gly | Phe | Ala | Lys | Arg | Val | Lys | Gly | Arg | Thr | Trp | Thr |
|  |  | 355 |  |  |  |  | 360 |  |  |  |  | 365 |  |  |  |

| ttg | tgt | ggg | acc | cct | gag | tac | ttg | gcc | ccc | gag | att | atc | ctg | agc | aaa | 1152 |
| Leu | Cys | Gly | Thr | Pro | Glu | Tyr | Leu | Ala | Pro | Glu | Ile | Ile | Leu | Ser | Lys |
| 370 |  |  |  |  | 375 |  |  |  |  | 380 |  |  |  |  |  |

| | | | | | | | | | | | | | | | | |
|---|---|---|---|---|---|---|---|---|---|---|---|---|---|---|---|---|
| ggc | tac | aac | aag | gct | gtg | gac | tgg | tgg | gct | ctc | gga | gtc | ctc | atc | tac | 1200 |
| Gly | Tyr | Asn | Lys | Ala | Val | Asp | Trp | Trp | Ala | Leu | Gly | Val | Leu | Ile | Tyr | |
| 385 | | | | 390 | | | | | 395 | | | | | 400 | | |
| gag | atg | gct | gct | ggt | tac | cca | ccc | ttc | ttc | gct | gac | cag | cct | atc | cag | 1248 |
| Glu | Met | Ala | Ala | Gly | Tyr | Pro | Pro | Phe | Phe | Ala | Asp | Gln | Pro | Ile | Gln | |
| | | | | 405 | | | | | 410 | | | | | 415 | | |
| atc | tat | gag | aaa | atc | gtc | tct | ggg | aag | gtg | cgg | ttc | cca | tcc | cac | ttc | 1296 |
| Ile | Tyr | Glu | Lys | Ile | Val | Ser | Gly | Lys | Val | Arg | Phe | Pro | Ser | His | Phe | |
| | | | 420 | | | | | 425 | | | | | 430 | | | |
| agc | tct | gac | ttg | aag | gac | ctg | ctg | cgg | aac | ctt | ctg | caa | gtg | gat | ctc | 1344 |
| Ser | Ser | Asp | Leu | Lys | Asp | Leu | Leu | Arg | Asn | Leu | Leu | Gln | Val | Asp | Leu | |
| | | 435 | | | | | 440 | | | | | 445 | | | | |
| acc | aag | cgc | ttt | ggg | aac | ctc | aag | aac | ggg | gtc | aat | gac | atc | aag | aac | 1392 |
| Thr | Lys | Arg | Phe | Gly | Asn | Leu | Lys | Asn | Gly | Val | Asn | Asp | Ile | Lys | Asn | |
| | 450 | | | | | 455 | | | | | 460 | | | | | |
| cac | aag | tgg | ttt | gcc | acg | act | gac | tgg | att | gcc | atc | tat | cag | aga | aag | 1440 |
| His | Lys | Trp | Phe | Ala | Thr | Thr | Asp | Trp | Ile | Ala | Ile | Tyr | Gln | Arg | Lys | |
| 465 | | | | 470 | | | | | 475 | | | | | 480 | | |
| gtg | gaa | gct | ccc | ttc | ata | cca | aag | ttt | aaa | ggc | cct | ggg | gac | acg | agt | 1488 |
| Val | Glu | Ala | Pro | Phe | Ile | Pro | Lys | Phe | Lys | Gly | Pro | Gly | Asp | Thr | Ser | |
| | | | | 485 | | | | | 490 | | | | | 495 | | |
| aac | ttt | gac | gac | tat | gag | gag | gaa | gag | atc | cgg | gtc | tcc | atc | aat | gag | 1536 |
| Asn | Phe | Asp | Asp | Tyr | Glu | Glu | Glu | Glu | Ile | Arg | Val | Ser | Ile | Asn | Glu | |
| | | | | 500 | | | | | 505 | | | | | 510 | | |
| aag | tgt | ggc | aag | gag | ttt | act | gag | ttt | tagggctcg | | agtctggtaa | | a | | | 1584 |
| Lys | Cys | Gly | Lys | Glu | Phe | Thr | Glu | Phe | | | | | | | | |
| | | | 515 | | | | | 520 | | | | | | | | |

<210> SEQ ID NO 19
<211> LENGTH: 521
<212> TYPE: PRT
<213> ORGANISM: Artificial Sequence
<220> FEATURE:
<223> OTHER INFORMATION: Synthetic Construct

<400> SEQUENCE: 19

Met Met Ser Gly Tyr Val Asn Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
        35                  40                  45

Lys Gly Tyr Gln Val Ala Pro Ala Glu Leu Glu Ser Ile Leu Leu Gln
    50                  55                  60

His Pro Asn Ile Phe Asp Ala Gly Val Ala Gly Leu Pro Asp Asp Asp
65                  70                  75                  80

Ala Gly Glu Leu Pro Ala Ala Val Val Leu Glu His Gly Lys Thr
            85                  90                  95

Met Thr Glu Lys Glu Ile Val Asp Tyr Val Ala Ser Gln Val Thr Thr
            100                 105                 110

Ala Lys Lys Leu Arg Gly Gly Val Val Phe Val Asp Glu Val Pro Lys
        115                 120                 125

Gly Leu Thr Gly Lys Leu Asp Ala Arg Lys Ile Arg Glu Ile Leu Ile
    130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Ser Pro Gly Asn Ala Ala Ala
            165                 170                 175

```
Ala Lys Lys Gly Ser Glu Gln Glu Ser Val Lys Glu Phe Leu Ala Lys
            180                 185                 190

Ala Lys Glu Asp Phe Leu Lys Lys Trp Glu Thr Pro Ser Gln Asn Thr
        195                 200                 205

Ala Gln Leu Asp Gln Phe Asp Arg Ile Lys Thr Leu Gly Thr Gly Ser
    210                 215                 220

Phe Gly Arg Val Met Leu Val Lys His Lys Glu Ser Gly Asn His Tyr
225                 230                 235                 240

Ala Met Lys Ile Leu Asp Lys Gln Lys Val Val Lys Leu Lys Gln Ile
                245                 250                 255

Glu His Thr Leu Asn Glu Lys Arg Ile Leu Gln Ala Val Asn Phe Pro
            260                 265                 270

Phe Leu Val Lys Leu Glu Phe Ser Phe Lys Asp Asn Ser Asn Leu Tyr
        275                 280                 285

Met Val Met Glu Tyr Val Ala Gly Gly Glu Met Phe Ser His Leu Arg
    290                 295                 300

Arg Ile Gly Arg Phe Ser Glu Pro His Ala Arg Phe Tyr Ala Ala Gln
305                 310                 315                 320

Ile Val Leu Thr Phe Glu Tyr Leu His Ser Leu Asp Leu Ile Tyr Arg
                325                 330                 335

Asp Leu Lys Pro Glu Asn Leu Leu Ile Asp Gln Gln Gly Tyr Ile Gln
            340                 345                 350

Val Thr Asp Phe Gly Phe Ala Lys Arg Val Lys Gly Arg Thr Trp Thr
        355                 360                 365

Leu Cys Gly Thr Pro Glu Tyr Leu Ala Pro Glu Ile Ile Leu Ser Lys
    370                 375                 380

Gly Tyr Asn Lys Ala Val Asp Trp Trp Ala Leu Gly Val Leu Ile Tyr
385                 390                 395                 400

Glu Met Ala Ala Gly Tyr Pro Pro Phe Phe Ala Asp Gln Pro Ile Gln
                405                 410                 415

Ile Tyr Glu Lys Ile Val Ser Gly Lys Val Arg Phe Pro Ser His Phe
            420                 425                 430

Ser Ser Asp Leu Lys Asp Leu Leu Arg Asn Leu Leu Gln Val Asp Leu
        435                 440                 445

Thr Lys Arg Phe Gly Asn Leu Lys Asn Gly Val Asn Asp Ile Lys Asn
    450                 455                 460

His Lys Trp Phe Ala Thr Thr Asp Trp Ile Ala Ile Tyr Gln Arg Lys
465                 470                 475                 480

Val Glu Ala Pro Phe Ile Pro Lys Phe Lys Gly Pro Gly Asp Thr Ser
                485                 490                 495

Asn Phe Asp Asp Tyr Glu Glu Glu Glu Ile Arg Val Ser Ile Asn Glu
            500                 505                 510

Lys Cys Gly Lys Glu Phe Thr Glu Phe
            515                 520

<210> SEQ ID NO 20
<211> LENGTH: 1611
<212> TYPE: DNA
<213> ORGANISM: Artificial Sequence
<220> FEATURE:
<223> OTHER INFORMATION: Synthetic construct: p300-NFluc(2-416) coding
      sequence
<220> FEATURE:
<221> NAME/KEY: CDS
<222> LOCATION: (1)..(1599)

<400> SEQUENCE: 20
```

```
atg ggc agc ggc gcg cat acc gcc gat ccg gaa aaa cgt aaa ctg att        48
Met Gly Ser Gly Ala His Thr Ala Asp Pro Glu Lys Arg Lys Leu Ile
1               5                   10                  15 cag cag cag ctg gtg ctg ctg cat gcg cat aaa tgc cag cgc cgt        96
Gln Gln Gln Leu Val Leu Leu His Ala His Lys Cys Gln Arg Arg
            20                  25                  30 gaa cag gcg aat ggc gaa gtt cgt cag tgc aat ctg ccg cat tgc cgc      144
Glu Gln Ala Asn Gly Glu Val Arg Gln Cys Asn Leu Pro His Cys Arg
        35                  40                  45 acc atg aaa aac gtg ctg aac cat atg acc cat tgt cag agc ggt aaa      192
Thr Met Lys Asn Val Leu Asn His Met Thr His Cys Gln Ser Gly Lys
    50                  55                  60 agc tgc cag gtt gcc cat tgc gcg agc agc cgc cag att att agc cac      240
Ser Cys Gln Val Ala His Cys Ala Ser Ser Arg Gln Ile Ile Ser His
65                  70                  75                  80 tgg aaa aac tgc acc cgc cat gat tgc ccg gtg tgc ctg ccg ctg aaa      288
Trp Lys Asn Cys Thr Arg His Asp Cys Pro Val Cys Leu Pro Leu Lys
                85                  90                  95 aac gcg ggc gat aaa acc ggt ggg ggt ggc ggt tca ggc ggt ggg ggt      336
Asn Ala Gly Asp Lys Thr Gly Gly Gly Gly Gly Ser Gly Gly Gly Gly
            100                 105                 110 tct ggt ggg ggt ggt acc gaa gac gcc aaa aac ata aag aaa ggc ccg      384
Ser Gly Gly Gly Gly Thr Glu Asp Ala Lys Asn Ile Lys Lys Gly Pro
        115                 120                 125 gcg cca ttc tat cct cta gag gat gga acc gct gga gag caa ctg cat      432
Ala Pro Phe Tyr Pro Leu Glu Asp Gly Thr Ala Gly Glu Gln Leu His
    130                 135                 140 aag gct atg aag aga tac gcc ctg gtt cct gga aca att gct ttt aca      480
Lys Ala Met Lys Arg Tyr Ala Leu Val Pro Gly Thr Ile Ala Phe Thr
145                 150                 155                 160 gat gca cat atc gag gtg aac atc acg tac gcg gaa tac ttc gaa atg      528
Asp Ala His Ile Glu Val Asn Ile Thr Tyr Ala Glu Tyr Phe Glu Met
                165                 170                 175 tcc gtt cgg ttg gca gaa gct atg aaa cga tat ggg ctg aat aca aat      576
Ser Val Arg Leu Ala Glu Ala Met Lys Arg Tyr Gly Leu Asn Thr Asn
            180                 185                 190 cac aga atc gtc gta tgc agt gaa aac tct ctt caa ttc ttt atg ccg      624
His Arg Ile Val Val Cys Ser Glu Asn Ser Leu Gln Phe Phe Met Pro
        195                 200                 205 gtg ttg ggc gcg tta ttt atc gga gtt gca gtt gcg ccc gcg aac gac      672
Val Leu Gly Ala Leu Phe Ile Gly Val Ala Val Ala Pro Ala Asn Asp
    210                 215                 220 att tat aat gaa cgt gaa ttg ctc aac agt atg aac att tcg cag cct      720
Ile Tyr Asn Glu Arg Glu Leu Leu Asn Ser Met Asn Ile Ser Gln Pro
225                 230                 235                 240 acc gta gtg ttt gtt tcc aaa aag ggg ttg caa aaa att ttg aac gtg      768
Thr Val Val Phe Val Ser Lys Lys Gly Leu Gln Lys Ile Leu Asn Val
                245                 250                 255 caa aaa aaa tta cca ata atc cag aaa att att atc atg gat tct aaa      816
Gln Lys Lys Leu Pro Ile Ile Gln Lys Ile Ile Ile Met Asp Ser Lys
            260                 265                 270 acg gat tac cag gga ttt cag tcg atg tac acg ttc gtc aca tct cat      864
Thr Asp Tyr Gln Gly Phe Gln Ser Met Tyr Thr Phe Val Thr Ser His
        275                 280                 285 cta cct ccc ggt ttt aat gaa tac gat ttt gta cca gag tcc ttt gat      912
Leu Pro Pro Gly Phe Asn Glu Tyr Asp Phe Val Pro Glu Ser Phe Asp
    290                 295                 300 cgt gac aaa aca att gca ctg ata atg aat tcc tct gga tct act ggg      960
Arg Asp Lys Thr Ile Ala Leu Ile Met Asn Ser Ser Gly Ser Thr Gly
305                 310                 315                 320
```

-continued

```
tta cct aag ggt gtg gcc ctt ccg cat aga act gcg tgc gtc aga ttc    1008
Leu Pro Lys Gly Val Ala Leu Pro His Arg Thr Ala Cys Val Arg Phe
                325                 330                 335 tcg cat gcc aga gat cct att ttt ggc aat caa atc att ccg gat act    1056
Ser His Ala Arg Asp Pro Ile Phe Gly Asn Gln Ile Ile Pro Asp Thr
            340                 345                 350 gcg att tta agt gtt gtt cca ttc cat cac ggt ttt gga atg ttt act    1104
Ala Ile Leu Ser Val Val Pro Phe His His Gly Phe Gly Met Phe Thr
        355                 360                 365 aca ctc gga tat ttg ata tgt gga ttt cga gtc gtc tta atg tat aga    1152
Thr Leu Gly Tyr Leu Ile Cys Gly Phe Arg Val Val Leu Met Tyr Arg
    370                 375                 380 ttt gaa gaa gag ctg ttt tta cga tcc ctt cag gat tac aaa att caa    1200
Phe Glu Glu Glu Leu Phe Leu Arg Ser Leu Gln Asp Tyr Lys Ile Gln
385                 390                 395                 400 agt gcg ttg cta gta cca acc cta ttt tca ttc ttc gcc aaa agc act    1248
Ser Ala Leu Leu Val Pro Thr Leu Phe Ser Phe Phe Ala Lys Ser Thr
                405                 410                 415 ctg att gac aaa tac gat tta tct aat tta cac gaa att gct tct ggg    1296
Leu Ile Asp Lys Tyr Asp Leu Ser Asn Leu His Glu Ile Ala Ser Gly
            420                 425                 430 ggc gca cct ctt tcg aaa gaa gtc ggg gaa gcg gtt gca aaa cgc ttc    1344
Gly Ala Pro Leu Ser Lys Glu Val Gly Glu Ala Val Ala Lys Arg Phe
        435                 440                 445 cat ctt cca ggg ata cga caa gga tat ggg ctc act gag act aca tca    1392
His Leu Pro Gly Ile Arg Gln Gly Tyr Gly Leu Thr Glu Thr Thr Ser
    450                 455                 460 gct att ctg att aca ccc gag ggg gat gat aaa ccg ggc gcg gtc ggt    1440
Ala Ile Leu Ile Thr Pro Glu Gly Asp Asp Lys Pro Gly Ala Val Gly
465                 470                 475                 480 aaa gtt gtt cca ttt ttt gaa gcg aag gtt gtg gat ctg gat acc ggg    1488
Lys Val Val Pro Phe Phe Glu Ala Lys Val Val Asp Leu Asp Thr Gly
                485                 490                 495 aaa acg ctg ggc gtt aat cag aga ggc gaa tta tgt gtc aga gga cct    1536
Lys Thr Leu Gly Val Asn Gln Arg Gly Glu Leu Cys Val Arg Gly Pro
            500                 505                 510 atg att atg tcc ggt tat gta aac aat ccg gaa gcg acc aac gcc ttg    1584
Met Ile Met Ser Gly Tyr Val Asn Asn Pro Glu Ala Thr Asn Ala Leu
        515                 520                 525 att gac aag gat gga tgataagcgg cc                                  1611
Ile Asp Lys Asp Gly
    530
```

<210> SEQ ID NO 21
<211> LENGTH: 533
<212> TYPE: PRT
<213> ORGANISM: Artificial Sequence
<220> FEATURE:
<223> OTHER INFORMATION: Synthetic Construct

<400> SEQUENCE: 21

```
Met Gly Ser Gly Ala His Thr Ala Asp Pro Glu Lys Arg Lys Leu Ile
1               5                   10                  15

Gln Gln Gln Leu Val Leu Leu His Ala His Lys Cys Gln Arg Arg
                20                  25                  30

Glu Gln Ala Asn Gly Glu Val Arg Gln Cys Asn Leu Pro His Cys Arg
            35                  40                  45

Thr Met Lys Asn Val Leu Asn His Met Thr His Cys Gln Ser Gly Lys
        50                  55                  60

Ser Cys Gln Val Ala His Cys Ala Ser Ser Arg Gln Ile Ile Ser His
65                  70                  75                  80
```

-continued

```
Trp Lys Asn Cys Thr Arg His Asp Cys Pro Val Cys Leu Pro Leu Lys
                85                  90                  95

Asn Ala Gly Asp Lys Thr Gly Gly Gly Ser Gly Gly Gly Gly
            100                 105                 110

Ser Gly Gly Gly Gly Thr Glu Asp Ala Lys Asn Ile Lys Lys Gly Pro
            115                 120                 125

Ala Pro Phe Tyr Pro Leu Glu Asp Gly Thr Ala Gly Glu Gln Leu His
        130                 135                 140

Lys Ala Met Lys Arg Tyr Ala Leu Val Pro Gly Thr Ile Ala Phe Thr
145                 150                 155                 160

Asp Ala His Ile Glu Val Asn Ile Thr Tyr Ala Glu Tyr Phe Glu Met
                165                 170                 175

Ser Val Arg Leu Ala Glu Ala Met Lys Arg Tyr Gly Leu Asn Thr Asn
            180                 185                 190

His Arg Ile Val Val Cys Ser Glu Asn Ser Leu Gln Phe Phe Met Pro
        195                 200                 205

Val Leu Gly Ala Leu Phe Ile Gly Val Ala Val Ala Pro Ala Asn Asp
    210                 215                 220

Ile Tyr Asn Glu Arg Glu Leu Leu Asn Ser Met Asn Ile Ser Gln Pro
225                 230                 235                 240

Thr Val Val Phe Val Ser Lys Lys Gly Leu Gln Lys Ile Leu Asn Val
                245                 250                 255

Gln Lys Lys Leu Pro Ile Ile Gln Lys Ile Ile Met Asp Ser Lys
            260                 265                 270

Thr Asp Tyr Gln Gly Phe Gln Ser Met Tyr Thr Phe Val Thr Ser His
        275                 280                 285

Leu Pro Pro Gly Phe Asn Glu Tyr Asp Phe Val Pro Glu Ser Phe Asp
    290                 295                 300

Arg Asp Lys Thr Ile Ala Leu Ile Met Asn Ser Ser Gly Ser Thr Gly
305                 310                 315                 320

Leu Pro Lys Gly Val Ala Leu Pro His Arg Thr Ala Cys Val Arg Phe
                325                 330                 335

Ser His Ala Arg Asp Pro Ile Phe Gly Asn Gln Ile Ile Pro Asp Thr
            340                 345                 350

Ala Ile Leu Ser Val Val Pro Phe His His Gly Phe Gly Met Phe Thr
        355                 360                 365

Thr Leu Gly Tyr Leu Ile Cys Gly Phe Arg Val Val Leu Met Tyr Arg
    370                 375                 380

Phe Glu Glu Glu Leu Phe Leu Arg Ser Leu Gln Asp Tyr Lys Ile Gln
385                 390                 395                 400

Ser Ala Leu Leu Val Pro Thr Leu Phe Ser Phe Ala Lys Ser Thr
                405                 410                 415

Leu Ile Asp Lys Tyr Asp Leu Ser Asn Leu His Glu Ile Ala Ser Gly
            420                 425                 430

Gly Ala Pro Leu Ser Lys Glu Val Gly Glu Ala Val Ala Lys Arg Phe
        435                 440                 445

His Leu Pro Gly Ile Arg Gln Gly Tyr Gly Leu Thr Glu Thr Thr Ser
    450                 455                 460

Ala Ile Leu Ile Thr Pro Glu Gly Asp Asp Lys Pro Gly Ala Val Gly
465                 470                 475                 480

Lys Val Val Pro Phe Phe Glu Ala Lys Val Val Asp Leu Asp Thr Gly
                485                 490                 495

Lys Thr Leu Gly Val Asn Gln Arg Gly Glu Leu Cys Val Arg Gly Pro
```

```
                      500                 505                 510
Met Ile Met Ser Gly Tyr Val Asn Asn Pro Glu Ala Thr Asn Ala Leu
            515                 520                 525

Ile Asp Lys Asp Gly
        530

<210> SEQ ID NO 22
<211> LENGTH: 714
<212> TYPE: DNA
<213> ORGANISM: Artificial Sequence
<220> FEATURE:
<223> OTHER INFORMATION: Synthetic construct:  CFluc(398-550)-Hif-1alpha
      coding sequence
<220> FEATURE:
<221> NAME/KEY: CDS
<222> LOCATION: (1)..(669)

<400> SEQUENCE: 22 atg atg tcc ggt tat gta aac aat ccg gaa gcg acc aac gcc ttg att        48
Met Met Ser Gly Tyr Val Asn Asn Pro Glu Ala Thr Asn Ala Leu Ile
1               5                   10                  15 gac aag gat gga tgg cta cat tct gga gac ata gct tac tgg gac gaa        96
Asp Lys Asp Gly Trp Leu His Ser Gly Asp Ile Ala Tyr Trp Asp Glu
            20                  25                  30 gac gaa cac ttc ttc ata gtt gac cgc ttg aag tct tta att aaa tac       144
Asp Glu His Phe Phe Ile Val Asp Arg Leu Lys Ser Leu Ile Lys Tyr
        35                  40                  45 aaa gga tat cag gtg gcc ccc gct gaa ttg gaa tcg ata ttg tta caa       192
Lys Gly Tyr Gln Val Ala Pro Ala Glu Leu Glu Ser Ile Leu Leu Gln
    50                  55                  60 cac ccc aac atc ttc gac gcg ggc gtg gca ggt ctt ccc gac gat gac       240
His Pro Asn Ile Phe Asp Ala Gly Val Ala Gly Leu Pro Asp Asp Asp
65                  70                  75                  80 gcc ggt gaa ctt ccc gcc gcc gtt gtt gtt ttg gag cac gga aag acg       288
Ala Gly Glu Leu Pro Ala Ala Val Val Val Leu Glu His Gly Lys Thr
                85                  90                  95 atg acg gaa aaa gag atc gtg gat tac gtc gcc agt caa gta aca acc       336
Met Thr Glu Lys Glu Ile Val Asp Tyr Val Ala Ser Gln Val Thr Thr
            100                 105                 110 gcg aaa aag ttg cgc gga gga gtt gtg ttt gtg gac gaa gta ccg aaa       384
Ala Lys Lys Leu Arg Gly Gly Val Val Phe Val Asp Glu Val Pro Lys
        115                 120                 125 ggt ctt acc gga aaa ctc gac gca aga aaa atc aga gag atc ctc ata       432
Gly Leu Thr Gly Lys Leu Asp Ala Arg Lys Ile Arg Glu Ile Leu Ile
    130                 135                 140 aag gcc aag aag ggc gga aag tcc aaa ttg ggc ctg cag ggc ggt tca       480
Lys Ala Lys Lys Gly Gly Lys Ser Lys Leu Gly Leu Gln Gly Gly Ser
145                 150                 155                 160 ggc ggt ggg ggt tct ggc ggg ggt ggg agc ccc ggg agc gat ctg gcg       528
Gly Gly Gly Gly Ser Gly Gly Gly Gly Ser Pro Gly Ser Asp Leu Ala
                165                 170                 175 tgc cgc ctg ctg ggc cag agc atg gat gaa agc ggc ctg ccg cag ctg       576
Cys Arg Leu Leu Gly Gln Ser Met Asp Glu Ser Gly Leu Pro Gln Leu
            180                 185                 190 acc agc tat gat tgc gaa gtg aac gcg ccg att cag ggc agc cgc aac       624
Thr Ser Tyr Asp Cys Glu Val Asn Ala Pro Ile Gln Gly Ser Arg Asn
        195                 200                 205 ctg ctg cag ggc gaa gaa ctg ctg cgc gcg ctg gat cag gtg aac           669
Leu Leu Gln Gly Glu Glu Leu Leu Arg Ala Leu Asp Gln Val Asn
    210                 215                 220 tgactcgagt ctggtaaaga aaccgctgct gcgaaatttg aacgc                     714
```

-continued

<210> SEQ ID NO 23
<211> LENGTH: 223
<212> TYPE: PRT
<213> ORGANISM: Artificial Sequence
<220> FEATURE:
<223> OTHER INFORMATION: Synthetic Construct

<400> SEQUENCE: 23

```
Met Met Ser Gly Tyr Val Asn Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
        35                  40                  45

Lys Gly Tyr Gln Val Ala Pro Ala Glu Leu Gly Ser Ile Leu Leu Gln
    50                  55                  60

His Pro Asn Ile Phe Asp Ala Gly Val Ala Gly Leu Pro Asp Asp Asp
65                  70                  75                  80

Ala Gly Glu Leu Pro Ala Ala Val Val Val Leu Glu His Gly Lys Thr
                85                  90                  95

Met Thr Glu Lys Glu Ile Val Asp Tyr Val Ala Ser Gln Val Thr Thr
            100                 105                 110

Ala Lys Lys Leu Arg Gly Gly Val Val Phe Val Asp Glu Val Pro Lys
        115                 120                 125

Gly Leu Thr Gly Lys Leu Asp Ala Arg Lys Ile Arg Glu Ile Leu Ile
    130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Ser Pro Gly Ser Asp Leu Ala
                165                 170                 175

Cys Arg Leu Leu Gly Gln Ser Met Asp Glu Ser Gly Leu Pro Gln Leu
            180                 185                 190

Thr Ser Tyr Asp Cys Glu Val Asn Ala Pro Ile Gln Gly Ser Arg Asn
        195                 200                 205

Leu Leu Gln Gly Glu Glu Leu Leu Arg Ala Leu Asp Gln Val Asn
    210                 215                 220
```

<210> SEQ ID NO 24
<211> LENGTH: 1611
<212> TYPE: DNA
<213> ORGANISM: Artificial Sequence
<220> FEATURE:
<223> OTHER INFORMATION: Synthetic construct: PBSII-NFluc(2-416) coding sequence
<220> FEATURE:
<221> NAME/KEY: CDS
<222> LOCATION: (1)..(1590)

<400> SEQUENCE: 24

```
atg ggc agc agc cat cac cat cat cac cac agc cag gat ccg aat tcg     48
Met Gly Ser Ser His His His His His His Ser Gln Asp Pro Asn Ser
1               5                   10                  15 gag aag ccc tat gct tgt ccg gaa tgt ggt aag tcc ttc agc cag cgc     96
Glu Lys Pro Tyr Ala Cys Pro Glu Cys Gly Lys Ser Phe Ser Gln Arg
            20                  25                  30 gca aac ctg cgc gcc cac cag cgt acc cac acg ggt gaa aaa ccg tat    144
Ala Asn Leu Arg Ala His Gln Arg Thr His Thr Gly Glu Lys Pro Tyr
        35                  40                  45 aag tgc cca gag tgc ggc aaa tct ttt agc cgc agc gat cac ctg act    192
Lys Cys Pro Glu Cys Gly Lys Ser Phe Ser Arg Ser Asp His Leu Thr
```

-continued

```
              50                   55                  60
acc cat caa cgc act cat act ggc gag aag cca tac aaa tgt cca gaa    240
Thr His Gln Arg Thr His Thr Gly Glu Lys Pro Tyr Lys Cys Pro Glu
 65                  70                  75                  80 tgt ggc aag tct ttc agt cgc agc gat gtg ctg gtg cgc cac caa cgt    288
Cys Gly Lys Ser Phe Ser Arg Ser Asp Val Leu Val Arg His Gln Arg
                 85                  90                  95 act cac acc ggt ggg ggt ggc ggt tca ggc ggt ggg ggt tct ggt ggg    336
Thr His Thr Gly Gly Gly Gly Gly Ser Gly Gly Gly Gly Ser Gly Gly
                100                 105                 110 ggt ggt acc gaa gac gcc aaa aac ata aag aaa ggc ccg gcg cca ttc    384
Gly Gly Thr Glu Asp Ala Lys Asn Ile Lys Lys Gly Pro Ala Pro Phe
            115                 120                 125 tat cct cta gag gat gga acc gct gga gag caa ctg cat aag gct atg    432
Tyr Pro Leu Glu Asp Gly Thr Ala Gly Glu Gln Leu His Lys Ala Met
130                 135                 140 aag aga tac gcc ctg gtt cct gga aca att gct ttt aca gat gca cat    480
Lys Arg Tyr Ala Leu Val Pro Gly Thr Ile Ala Phe Thr Asp Ala His
145                 150                 155                 160 atc gag gtg aac atc acg tac gcg gaa tac ttc gaa atg tcc gtt cgg    528
Ile Glu Val Asn Ile Thr Tyr Ala Glu Tyr Phe Glu Met Ser Val Arg
                165                 170                 175 ttg gca gaa gct atg aaa cga tat ggg ctg aat aca aat cac aga atc    576
Leu Ala Glu Ala Met Lys Arg Tyr Gly Leu Asn Thr Asn His Arg Ile
            180                 185                 190 gtc gta tgc agt gaa aac tct ctt caa ttc ttt atg ccg gtg ttg ggc    624
Val Val Cys Ser Glu Asn Ser Leu Gln Phe Phe Met Pro Val Leu Gly
            195                 200                 205 gcg tta ttt atc gga gtt gca gtt gcg ccc gcg aac gac att tat aat    672
Ala Leu Phe Ile Gly Val Ala Val Ala Pro Ala Asn Asp Ile Tyr Asn
210                 215                 220 gaa cgt gaa ttg ctc aac agt atg aac att tcg cag cct acc gta gtg    720
Glu Arg Glu Leu Leu Asn Ser Met Asn Ile Ser Gln Pro Thr Val Val
225                 230                 235                 240 ttt gtt tcc aaa aag ggg ttg caa aaa att ttg aac gtg caa aaa aaa    768
Phe Val Ser Lys Lys Gly Leu Gln Lys Ile Leu Asn Val Gln Lys Lys
                245                 250                 255 tta cca ata atc cag aaa att att atc atg gat tct aaa acg gat tac    816
Leu Pro Ile Ile Gln Lys Ile Ile Ile Met Asp Ser Lys Thr Asp Tyr
            260                 265                 270 cag gga ttt cag tcg atg tac acg ttc gtc aca tct cat cta cct ccc    864
Gln Gly Phe Gln Ser Met Tyr Thr Phe Val Thr Ser His Leu Pro Pro
            275                 280                 285 ggt ttt aat gaa tac gat ttt gta cca gag tcc ttt gat cgt gac aaa    912
Gly Phe Asn Glu Tyr Asp Phe Val Pro Glu Ser Phe Asp Arg Asp Lys
290                 295                 300 aca att gca ctg ata atg aat tcc tct gga tct act ggg tta cct aag    960
Thr Ile Ala Leu Ile Met Asn Ser Ser Gly Ser Thr Gly Leu Pro Lys
305                 310                 315                 320 ggt gtg gcc ctt ccg cat aga act gcc tgc gtc aga ttc tcg cat gcc   1008
Gly Val Ala Leu Pro His Arg Thr Ala Cys Val Arg Phe Ser His Ala
                325                 330                 335 aga gat cct att ttt ggc aat caa atc att ccg gat act gcg att tta   1056
Arg Asp Pro Ile Phe Gly Asn Gln Ile Ile Pro Asp Thr Ala Ile Leu
            340                 345                 350 agt gtt gtt cca ttc cat cac ggt ttt gga atg ttt act aca ctc gga   1104
Ser Val Val Pro Phe His His Gly Phe Gly Met Phe Thr Thr Leu Gly
            355                 360                 365 tat ttg ata tgt gga ttt cga gtc gtc tta atg tat aga ttt gaa gaa   1152
Tyr Leu Ile Cys Gly Phe Arg Val Val Leu Met Tyr Arg Phe Glu Glu
```

```
                    370                 375                 380
gag ctg ttt tta cga tcc ctt cag gat tac aaa att caa agt gcg ttg   1200
Glu Leu Phe Leu Arg Ser Leu Gln Asp Tyr Lys Ile Gln Ser Ala Leu
385                 390                 395                 400 cta gta cca acc cta ttt tca ttc ttc gcc aaa agc act ctg att gac   1248
Leu Val Pro Thr Leu Phe Ser Phe Phe Ala Lys Ser Thr Leu Ile Asp
            405                 410                 415 aaa tac gat tta tct aat tta cac gaa att gct tct ggg ggc gca cct   1296
Lys Tyr Asp Leu Ser Asn Leu His Glu Ile Ala Ser Gly Gly Ala Pro
        420                 425                 430 ctt tcg aaa gaa gtc ggg gaa gcg gtt gca aaa cgc ttc cat ctt cca   1344
Leu Ser Lys Glu Val Gly Glu Ala Val Ala Lys Arg Phe His Leu Pro
    435                 440                 445 ggg ata cga caa gga tat ggg ctc act gag act aca tca gct att ctg   1392
Gly Ile Arg Gln Gly Tyr Gly Leu Thr Glu Thr Thr Ser Ala Ile Leu
450                 455                 460 att aca ccc gag ggg gat gat aaa ccg ggc gcg gtc ggt aaa gtt gtt   1440
Ile Thr Pro Glu Gly Asp Asp Lys Pro Gly Ala Val Gly Lys Val Val
465                 470                 475                 480 cca ttt ttt gaa gcg aag gtt gtg gat ctg gat acc ggg aaa acg ctg   1488
Pro Phe Phe Glu Ala Lys Val Val Asp Leu Asp Thr Gly Lys Thr Leu
            485                 490                 495 ggc gtt aat cag aga ggc gaa tta tgt gtc aga gga cct atg att atg   1536
Gly Val Asn Gln Arg Gly Glu Leu Cys Val Arg Gly Pro Met Ile Met
        500                 505                 510 tcc ggt tat gta aac aat ccg gaa gcg acc aac gcc ttg att gac aag   1584
Ser Gly Tyr Val Asn Asn Pro Glu Ala Thr Asn Ala Leu Ile Asp Lys
    515                 520                 525 gat gga tgataagcgg ccgcataatg c                                    1611
Asp Gly
    530

<210> SEQ ID NO 25
<211> LENGTH: 530
<212> TYPE: PRT
<213> ORGANISM: Artificial Sequence
<220> FEATURE:
<223> OTHER INFORMATION: Synthetic Construct

<400> SEQUENCE: 25

Met Gly Ser Ser His His His His His His Ser Gln Asp Pro Asn Ser
1               5                   10                  15

Glu Lys Pro Tyr Ala Cys Pro Glu Cys Gly Lys Ser Phe Ser Gln Arg
            20                  25                  30

Ala Asn Leu Arg Ala His Gln Arg Thr His Thr Gly Glu Lys Pro Tyr
        35                  40                  45

Lys Cys Pro Glu Cys Gly Lys Ser Phe Ser Arg Ser Asp His Leu Thr
    50                  55                  60

Thr His Gln Arg Thr His Thr Gly Glu Lys Pro Tyr Lys Cys Pro Glu
65                  70                  75                  80

Cys Gly Lys Ser Phe Ser Arg Ser Asp Val Leu Val Arg His Gln Arg
                85                  90                  95

Thr His Thr Gly Gly Gly Gly Ser Gly Gly Gly Ser Gly Gly
            100                 105                 110

Gly Gly Thr Glu Asp Ala Lys Asn Ile Lys Lys Gly Pro Ala Pro Phe
        115                 120                 125

Tyr Pro Leu Glu Asp Gly Thr Ala Gly Glu Gln Leu His Lys Ala Met
    130                 135                 140

Lys Arg Tyr Ala Leu Val Pro Gly Thr Ile Ala Phe Thr Asp Ala His
```

```
                145                 150                 155                 160
Ile Glu Val Asn Ile Thr Tyr Ala Glu Tyr Phe Glu Met Ser Val Arg
            165                 170                 175

Leu Ala Glu Ala Met Lys Arg Tyr Gly Leu Asn Thr Asn His Arg Ile
            180                 185                 190

Val Val Cys Ser Glu Asn Ser Leu Gln Phe Phe Met Pro Val Leu Gly
            195                 200                 205

Ala Leu Phe Ile Gly Val Ala Val Ala Pro Ala Asn Asp Ile Tyr Asn
        210                 215                 220

Glu Arg Glu Leu Leu Asn Ser Met Asn Ile Ser Gln Pro Thr Val Val
225                 230                 235                 240

Phe Val Ser Lys Lys Gly Leu Gln Lys Ile Leu Asn Val Gln Lys Lys
                245                 250                 255

Leu Pro Ile Ile Gln Lys Ile Ile Met Asp Ser Lys Thr Asp Tyr
                260                 265                 270

Gln Gly Phe Gln Ser Met Tyr Thr Phe Val Thr Ser His Leu Pro Pro
            275                 280                 285

Gly Phe Asn Glu Tyr Asp Phe Val Pro Glu Ser Phe Asp Arg Asp Lys
        290                 295                 300

Thr Ile Ala Leu Ile Met Asn Ser Ser Gly Ser Thr Gly Leu Pro Lys
305                 310                 315                 320

Gly Val Ala Leu Pro His Arg Thr Ala Cys Val Arg Phe Ser His Ala
                325                 330                 335

Arg Asp Pro Ile Phe Gly Asn Gln Ile Ile Pro Asp Thr Ala Ile Leu
                340                 345                 350

Ser Val Val Pro Phe His His Gly Phe Gly Met Phe Thr Thr Leu Gly
                355                 360                 365

Tyr Leu Ile Cys Gly Phe Arg Val Val Leu Met Tyr Arg Phe Glu Glu
        370                 375                 380

Glu Leu Phe Leu Arg Ser Leu Gln Asp Tyr Lys Ile Gln Ser Ala Leu
385                 390                 395                 400

Leu Val Pro Thr Leu Phe Ser Phe Phe Ala Lys Ser Thr Leu Ile Asp
                405                 410                 415

Lys Tyr Asp Leu Ser Asn Leu His Glu Ile Ala Ser Gly Gly Ala Pro
            420                 425                 430

Leu Ser Lys Glu Val Gly Glu Ala Val Ala Lys Arg Phe His Leu Pro
            435                 440                 445

Gly Ile Arg Gln Gly Tyr Gly Leu Thr Glu Thr Thr Ser Ala Ile Leu
        450                 455                 460

Ile Thr Pro Glu Gly Asp Asp Lys Pro Gly Ala Val Gly Lys Val Val
465                 470                 475                 480

Pro Phe Phe Glu Ala Lys Val Val Asp Leu Asp Thr Gly Lys Thr Leu
                485                 490                 495

Gly Val Asn Gln Arg Gly Glu Leu Cys Val Arg Gly Pro Met Ile Met
            500                 505                 510

Ser Gly Tyr Val Asn Asn Pro Glu Ala Thr Asn Ala Leu Ile Asp Lys
        515                 520                 525

Asp Gly
    530

<210> SEQ ID NO 26
<211> LENGTH: 894
<212> TYPE: DNA
<213> ORGANISM: Artificial Sequence
<220> FEATURE:
```

<223> OTHER INFORMATION: Synthetic construct: CFluc-(398-550)-Zif268
      coding sequence
<220> FEATURE:
<221> NAME/KEY: CDS
<222> LOCATION: (1)..(855)

<400> SEQUENCE: 26

```
atg atg tcc ggt tat gta aac aat ccg gaa gcg acc aac gcc ttg att        48
Met Met Ser Gly Tyr Val Asn Asn Pro Glu Ala Thr Asn Ala Leu Ile
1               5                   10                  15 gac aag gat gga tgg cta cat tct gga gac ata gct tac tgg gac gaa        96
Asp Lys Asp Gly Trp Leu His Ser Gly Asp Ile Ala Tyr Trp Asp Glu
            20                  25                  30 gac gaa cac ttc ttc ata gtt gac cgc ttg aag tct tta att aaa tac       144
Asp Glu His Phe Phe Ile Val Asp Arg Leu Lys Ser Leu Ile Lys Tyr
        35                  40                  45 aaa gga tat cag gtg gcc ccc gct gaa ttg gaa tcg ata ttg tta caa       192
Lys Gly Tyr Gln Val Ala Pro Ala Glu Leu Glu Ser Ile Leu Leu Gln
50                  55                  60 cac ccc aac atc ttc gac gcg ggc gtg gca ggt ctt ccc gac gat gac       240
His Pro Asn Ile Phe Asp Ala Gly Val Ala Gly Leu Pro Asp Asp Asp
65                  70                  75                  80 gcc ggt gaa ctt ccc gcc gcc gtt gtt gtt ttg gag cac gga aag acg       288
Ala Gly Glu Leu Pro Ala Ala Val Val Val Leu Glu His Gly Lys Thr
                85                  90                  95 atg acg gaa aaa gag atc gtg gat tac gtc gcc agt caa gta aca acc       336
Met Thr Glu Lys Glu Ile Val Asp Tyr Val Ala Ser Gln Val Thr Thr
            100                 105                 110 gcg aaa aag ttg cgc gga gga gtt gtg ttt gtg gac gaa gta ccg aaa       384
Ala Lys Lys Leu Arg Gly Gly Val Val Phe Val Asp Glu Val Pro Lys
        115                 120                 125 ggt ctt acc gga aaa ctc gac gca aga aaa atc aga gag atc ctc ata       432
Gly Leu Thr Gly Lys Leu Asp Ala Arg Lys Ile Arg Glu Ile Leu Ile
130                 135                 140 aag gcc aag aag ggc gga aag tcc aaa ttg ggc ctg cag ggc ggt tca       480
Lys Ala Lys Lys Gly Gly Lys Ser Lys Leu Gly Leu Gln Gly Gly Ser
145                 150                 155                 160 ggc ggt ggg ggt tct ggc ggg ggt ggg agc ccc ggg gaa cgc cct tac       528
Gly Gly Gly Gly Ser Gly Gly Gly Gly Ser Pro Gly Glu Arg Pro Tyr
                165                 170                 175 gct tgc cca gtg gag tcc tgt gat cgc cgc ttc tcc cgc tcc gac gag       576
Ala Cys Pro Val Glu Ser Cys Asp Arg Arg Phe Ser Arg Ser Asp Glu
            180                 185                 190 ctc acc cgc cac atc cgc atc cac aca ggc cag aag ccc ttc cag tgc       624
Leu Thr Arg His Ile Arg Ile His Thr Gly Gln Lys Pro Phe Gln Cys
        195                 200                 205 cgc atc tgc atg cgc aac ttc agc cgc agc gac cac ctc acc acc cac       672
Arg Ile Cys Met Arg Asn Phe Ser Arg Ser Asp His Leu Thr Thr His
    210                 215                 220 atc cgc acc cac aca ggc gaa aag ccc ttt gcc tgc gac atc tgt gga       720
Ile Arg Thr His Thr Gly Glu Lys Pro Phe Ala Cys Asp Ile Cys Gly
225                 230                 235                 240 aga aag ttt gcc agg agc gat gaa cgc aag agg cat acc aag atc cac       768
Arg Lys Phe Ala Arg Ser Asp Glu Arg Lys Arg His Thr Lys Ile His
                245                 250                 255 ttg cgg cag aag gac ctc gag tct ggt aaa gaa acc gct gct gcg aaa       816
Leu Arg Gln Lys Asp Leu Glu Ser Gly Lys Glu Thr Ala Ala Ala Lys
            260                 265                 270 ttt gaa cgc cag cac atg gac tcg tct act agc gca gct taattaacct       865
Phe Glu Arg Gln His Met Asp Ser Ser Thr Ser Ala Ala
        275                 280                 285
```
aggctgctgc caccgctgag caataacta                                894

<210> SEQ ID NO 27
<211> LENGTH: 285
<212> TYPE: PRT
<213> ORGANISM: Artificial Sequence
<220> FEATURE:
<223> OTHER INFORMATION: Synthetic Construct

<400> SEQUENCE: 27

```
Met Met Ser Gly Tyr Val Asn Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
        35                  40                  45

Lys Gly Tyr Gln Val Ala Pro Ala Glu Leu Glu Ser Ile Leu Leu Gln
    50                  55                  60

His Pro Asn Ile Phe Asp Ala Gly Val Ala Gly Leu Pro Asp Asp Asp
65                  70                  75                  80

Ala Gly Glu Leu Pro Ala Ala Val Val Val Leu Glu His Gly Lys Thr
                85                  90                  95

Met Thr Glu Lys Glu Ile Val Asp Tyr Val Ala Ser Gln Val Thr Thr
            100                 105                 110

Ala Lys Lys Leu Arg Gly Gly Val Val Phe Val Asp Glu Val Pro Lys
        115                 120                 125

Gly Leu Thr Gly Lys Leu Asp Ala Arg Lys Ile Arg Glu Ile Leu Ile
    130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Ser Pro Gly Glu Arg Pro Tyr
                165                 170                 175

Ala Cys Pro Val Glu Ser Cys Asp Arg Arg Phe Ser Arg Ser Asp Glu
            180                 185                 190

Leu Thr Arg His Ile Arg Ile His Thr Gly Gln Lys Pro Phe Gln Cys
        195                 200                 205

Arg Ile Cys Met Arg Asn Phe Ser Arg Ser Asp His Leu Thr Thr His
    210                 215                 220

Ile Arg Thr His Thr Gly Glu Lys Pro Phe Ala Cys Asp Ile Cys Gly
225                 230                 235                 240

Arg Lys Phe Ala Arg Ser Asp Glu Arg Lys Arg His Thr Lys Ile His
                245                 250                 255

Leu Arg Gln Lys Asp Leu Glu Ser Gly Lys Glu Thr Ala Ala Ala Lys
            260                 265                 270

Phe Glu Arg Gln His Met Asp Ser Ser Thr Ser Ala Ala
        275                 280                 285
```

<210> SEQ ID NO 28
<211> LENGTH: 1035
<212> TYPE: DNA
<213> ORGANISM: Artificial Sequence
<220> FEATURE:
<223> OTHER INFORMATION: Synthetic construct: CFluc-2EC coding sequence
<220> FEATURE:
<221> NAME/KEY: CDS
<222> LOCATION: (1)..(1032)

<400> SEQUENCE: 28 atg atg tcc ggt tat gta aac aat ccg gaa gcg acc aac gcc ttg att        48

```
                Met Met Ser Gly Tyr Val Asn Asn Pro Glu Ala Thr Asn Ala Leu Ile
                 1               5                  10                  15 gac aag gat gga tgg cta cat tct gga gac ata gct tac tgg gac gaa                96
Asp Lys Asp Gly Trp Leu His Ser Gly Asp Ile Ala Tyr Trp Asp Glu
             20                  25                  30 gac gaa cac ttc ttc ata gtt gac cgc ttg aag tct tta att aaa tac               144
Asp Glu His Phe Phe Ile Val Asp Arg Leu Lys Ser Leu Ile Lys Tyr
         35                  40                  45 aaa gga tat cag gtg gcc ccc gct gaa ttg gaa tcg ata ttg tta caa               192
Lys Gly Tyr Gln Val Ala Pro Ala Glu Leu Glu Ser Ile Leu Leu Gln
     50                  55                  60 cac ccc aac atc ttc gac gcg ggc gtg gca ggt ctt ccc gac gat gac               240
His Pro Asn Ile Phe Asp Ala Gly Val Ala Gly Leu Pro Asp Asp Asp
 65                  70                  75                  80 gcc ggt gaa ctt ccc gcc gcc gtt gtt gtt ttg gag cac gga aag acg               288
Ala Gly Glu Leu Pro Ala Ala Val Val Val Leu Glu His Gly Lys Thr
                 85                  90                  95 atg acg gaa aaa gag atc gtg gat tac gtc gcc agt caa gta aca acc               336
Met Thr Glu Lys Glu Ile Val Asp Tyr Val Ala Ser Gln Val Thr Thr
             100                 105                 110 gcg aaa aag ttg cgc gga gga gtt gtg ttt gtg gac gaa gta ccg aaa               384
Ala Lys Lys Leu Arg Gly Gly Val Val Phe Val Asp Glu Val Pro Lys
         115                 120                 125 ggt ctt acc gga aaa ctc gac gca aga aaa atc aga gag atc ctc ata               432
Gly Leu Thr Gly Lys Leu Asp Ala Arg Lys Ile Arg Glu Ile Leu Ile
     130                 135                 140 aag gcc aag aag ggc gga aag tcc aaa ttg ggc ctg cag ggt ggt tca               480
Lys Ala Lys Lys Gly Gly Lys Ser Lys Leu Gly Leu Gln Gly Gly Ser
145                 150                 155                 160 ggc ggt ggg ggt tct ggc ggg ggt ggg agc ccc ggg gag aag ccc tat               528
Gly Gly Gly Gly Ser Gly Gly Gly Gly Ser Pro Gly Glu Lys Pro Tyr
                 165                 170                 175 gct tgt ccg gaa tgt ggt aag tcc ttc agt agg aag gat tcg ctt gtg               576
Ala Cys Pro Glu Cys Gly Lys Ser Phe Ser Arg Lys Asp Ser Leu Val
             180                 185                 190 agg cac cag cgt acc cac acg ggt gaa aaa ccg tat aaa tgc cca gag               624
Arg His Gln Arg Thr His Thr Gly Glu Lys Pro Tyr Lys Cys Pro Glu
         195                 200                 205 tgc ggc aaa tct ttt agt cag tcg ggg gat ctt agg cgt cat caa cgc               672
Cys Gly Lys Ser Phe Ser Gln Ser Gly Asp Leu Arg Arg His Gln Arg
     210                 215                 220 act cat act ggc gag aag cca tac aaa tgt cca gaa tgt ggc aag tct               720
Thr His Thr Gly Glu Lys Pro Tyr Lys Cys Pro Glu Cys Gly Lys Ser
225                 230                 235                 240 ttc agt gat tgt cgt gat ctt gcg agg cac caa cgt act cac acc ggg               768
Phe Ser Asp Cys Arg Asp Leu Ala Arg His Gln Arg Thr His Thr Gly
                 245                 250                 255 gag aag ccc tat gct tgt ccg gaa tgt ggt aag tcc ttc tct cag agc               816
Glu Lys Pro Tyr Ala Cys Pro Glu Cys Gly Lys Ser Phe Ser Gln Ser
             260                 265                 270 tct cac ctg gtg cgc cac cag cgt acc cac acg ggt gaa aaa ccg tat               864
Ser His Leu Val Arg His Gln Arg Thr His Thr Gly Glu Lys Pro Tyr
         275                 280                 285 aaa tgc cca gag tgc ggc aaa tct ttt agt gac tgc cgc gac ctt gct               912
Lys Cys Pro Glu Cys Gly Lys Ser Phe Ser Asp Cys Arg Asp Leu Ala
     290                 295                 300 cgc cat caa cgc act cat act ggc gag aag cca tac aaa tgt cca gaa               960
Arg His Gln Arg Thr His Thr Gly Glu Lys Pro Tyr Lys Cys Pro Glu
305                 310                 315                 320 tgt ggc aag tct ttc agc cgc tct gac aag ctg gtg cgt cac caa cgt              1008
```

```
Cys Gly Lys Ser Phe Ser Arg Ser Asp Lys Leu Val Arg His Gln Arg
                325                 330                 335 act cac acc ggt aaa aaa act agt taa                              1035
Thr His Thr Gly Lys Lys Thr Ser
                340
```

<210> SEQ ID NO 29
<211> LENGTH: 344
<212> TYPE: PRT
<213> ORGANISM: Artificial Sequence
<220> FEATURE:
<223> OTHER INFORMATION: Synthetic Construct

<400> SEQUENCE: 29

```
Met Met Ser Gly Tyr Val Asn Asn Pro Glu Ala Thr Asn Ala Leu Ile
1               5                   10                  15

Asp Lys Asp Gly Trp Leu His Ser Asp Ile Ala Tyr Trp Asp Glu
            20                  25                  30

Asp Glu His Phe Phe Ile Val Asp Arg Leu Lys Ser Leu Ile Lys Tyr
                35                  40                  45

Lys Gly Tyr Gln Val Ala Pro Ala Glu Leu Glu Ser Ile Leu Leu Gln
    50                  55                  60

His Pro Asn Ile Phe Asp Ala Gly Val Ala Gly Leu Pro Asp Asp
65                  70                  75                  80

Ala Gly Glu Leu Pro Ala Ala Val Val Leu Glu His Gly Lys Thr
                85                  90                  95

Met Thr Glu Lys Glu Ile Val Asp Tyr Val Ala Ser Gln Val Thr Thr
            100                 105                 110

Ala Lys Lys Leu Arg Gly Gly Val Val Phe Val Asp Glu Val Pro Lys
        115                 120                 125

Gly Leu Thr Gly Lys Leu Asp Ala Arg Lys Ile Arg Glu Ile Leu Ile
    130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Ser Pro Gly Glu Lys Pro Tyr
                165                 170                 175

Ala Cys Pro Glu Cys Gly Lys Ser Phe Ser Arg Lys Asp Ser Leu Val
            180                 185                 190

Arg His Gln Arg Thr His Thr Gly Glu Lys Pro Tyr Lys Cys Pro Glu
        195                 200                 205

Cys Gly Lys Ser Phe Ser Gln Ser Gly Asp Leu Arg Arg His Gln Arg
    210                 215                 220

Thr His Thr Gly Glu Lys Pro Tyr Lys Cys Pro Glu Cys Gly Lys Ser
225                 230                 235                 240

Phe Ser Asp Cys Arg Asp Leu Ala Arg His Gln Arg Thr His Thr Gly
                245                 250                 255

Glu Lys Pro Tyr Ala Cys Pro Glu Cys Gly Lys Ser Phe Ser Gln Ser
            260                 265                 270

Ser His Leu Val Arg His Gln Arg Thr His Thr Gly Glu Lys Pro Tyr
        275                 280                 285

Lys Cys Pro Glu Cys Gly Lys Ser Phe Ser Cys Arg Asp Leu Ala
    290                 295                 300

Arg His Gln Arg Thr His Thr Gly Glu Lys Pro Tyr Lys Cys Pro Glu
305                 310                 315                 320

Cys Gly Lys Ser Phe Ser Arg Ser Asp Lys Leu Val Arg His Gln Arg
                325                 330                 335
```

-continued

```
Thr His Thr Gly Lys Lys Thr Ser
            340

<210> SEQ ID NO 30
<211> LENGTH: 1863
<212> TYPE: DNA
<213> ORGANISM: Artificial Sequence
<220> FEATURE:
<223> OTHER INFORMATION: Synthetic construct: Aart-NFluc coding
      sequence
<220> FEATURE:
<221> NAME/KEY: CDS
<222> LOCATION: (1)..(1860)

<400> SEQUENCE: 30 atg ggc agc agc cat cac cat cat cac cac agc cag gat ccc ccg ggg      48
Met Gly Ser Ser His His His His His His Ser Gln Asp Pro Pro Gly
1               5                   10                  15 gag aag ccc tat gct tgt ccg gaa tgt ggt aag tcc ttc agc cgc agc      96
Glu Lys Pro Tyr Ala Cys Pro Glu Cys Gly Lys Ser Phe Ser Arg Ser
            20                  25                  30 gat cac ctg gcc gaa cac cag cgt acc cac acg ggt gaa aaa ccg tat     144
Asp His Leu Ala Glu His Gln Arg Thr His Thr Gly Glu Lys Pro Tyr
        35                  40                  45 aaa tgc cca gag tgc ggc aaa tct ttt agc gat aag aaa gat ctg acc     192
Lys Cys Pro Glu Cys Gly Lys Ser Phe Ser Asp Lys Lys Asp Leu Thr
    50                  55                  60 cgg cat caa cgc act cat act ggc gag aag cca tac aaa tgt cca gaa     240
Arg His Gln Arg Thr His Thr Gly Glu Lys Pro Tyr Lys Cys Pro Glu
65                  70                  75                  80 tgt ggc aag tct ttc agc cag cgc gca aac ctg cgc gcc cac caa cgt     288
Cys Gly Lys Ser Phe Ser Gln Arg Ala Asn Leu Arg Ala His Gln Arg
                85                  90                  95 act cac acc ggg gag aag cct tat gct tgt ccg gaa tgt ggt aag tcc     336
Thr His Thr Gly Glu Lys Pro Tyr Ala Cys Pro Glu Cys Gly Lys Ser
            100                 105                 110 ttc tct cag ctg gcc cac ctg cgc gcc cac cag cgt acc cac acg ggt     384
Phe Ser Gln Leu Ala His Leu Arg Ala His Gln Arg Thr His Thr Gly
        115                 120                 125 gaa aaa ccg tat aaa tgc cca gag tgc ggc aaa tct ttt agc cgc gag     432
Glu Lys Pro Tyr Lys Cys Pro Glu Cys Gly Lys Ser Phe Ser Arg Glu
    130                 135                 140 gat aac ctg cac acc cat caa cgt act cat act ggc gag aag cca tac     480
Asp Asn Leu His Thr His Gln Arg Thr His Thr Gly Glu Lys Pro Tyr
145                 150                 155                 160 aaa tgt cca gaa tgt ggc aag tct ttc tcc cgc cgc gat gct ctg aac     528
Lys Cys Pro Glu Cys Gly Lys Ser Phe Ser Arg Arg Asp Ala Leu Asn
                165                 170                 175 gtg cac caa cgt act cac acc ggc aaa aaa act agc acc ggt ggg ggt     576
Val His Gln Arg Thr His Thr Gly Lys Lys Thr Ser Thr Gly Gly Gly
            180                 185                 190 ggc ggt tca ggt ggt ggg ggt tct ggt ggg ggt ggt acc gaa gac gcc     624
Gly Gly Ser Gly Gly Gly Gly Ser Gly Gly Gly Gly Thr Glu Asp Ala
        195                 200                 205 aaa aac ata aag aaa ggc ccg gcg cca ttc tat cct cta gag gat gga     672
Lys Asn Ile Lys Lys Gly Pro Ala Pro Phe Tyr Pro Leu Glu Asp Gly
    210                 215                 220 acc gct gga gag caa ctg cat aag gct atg aag aga tac gcc ctg gtt     720
Thr Ala Gly Glu Gln Leu His Lys Ala Met Lys Arg Tyr Ala Leu Val
225                 230                 235                 240 cct gga aca att gct ttt aca gat gca cat atc gag gtg aac atc acg     768
Pro Gly Thr Ile Ala Phe Thr Asp Ala His Ile Glu Val Asn Ile Thr
                245                 250                 255
```

| | | |
|---|---|---|
| tac gcg gaa tac ttc gaa atg tcc gtt cgg ttg gca gaa gct atg aaa<br>Tyr Ala Glu Tyr Phe Glu Met Ser Val Arg Leu Ala Glu Ala Met Lys<br>260 265 270 | | 816 |
| cga tat ggg ctg aat aca aat cac aga atc gtc gta tgc agt gaa aac<br>Arg Tyr Gly Leu Asn Thr Asn His Arg Ile Val Val Cys Ser Glu Asn<br>275 280 285 | | 864 |
| tct ctt caa ttc ttt atg ccg gtt ttg ggc gcg tta ttt atc gga gtt<br>Ser Leu Gln Phe Phe Met Pro Val Leu Gly Ala Leu Phe Ile Gly Val<br>290 295 300 | | 912 |
| gca gtt gcg ccc gcg aac gac att tat aat gaa cgt gaa ttg ctc aac<br>Ala Val Ala Pro Ala Asn Asp Ile Tyr Asn Glu Arg Glu Leu Leu Asn<br>305 310 315 320 | | 960 |
| agt atg aac att tcg cag cct acc gta gtg ttt gtt tcc aaa aag ggg<br>Ser Met Asn Ile Ser Gln Pro Thr Val Val Phe Val Ser Lys Lys Gly<br>325 330 335 | | 1008 |
| ttg caa aaa att ttg aac gtg caa aaa aaa tta cca ata atc cag aaa<br>Leu Gln Lys Ile Leu Asn Val Gln Lys Lys Leu Pro Ile Ile Gln Lys<br>340 345 350 | | 1056 |
| att atc atc atg gat tct aaa acg gat tac cag gga ttt cag tcg atg<br>Ile Ile Ile Met Asp Ser Lys Thr Asp Tyr Gln Gly Phe Gln Ser Met<br>355 360 365 | | 1104 |
| tac acg ttc gtc aca tct cat cta cct ccc ggt ttt aat gaa tac gat<br>Tyr Thr Phe Val Thr Ser His Leu Pro Pro Gly Phe Asn Glu Tyr Asp<br>370 375 380 | | 1152 |
| ttt gta cca gag tcc ttt gat cgt gac aaa aca att gca ctg ata atg<br>Phe Val Pro Glu Ser Phe Asp Arg Asp Lys Thr Ile Ala Leu Ile Met<br>385 390 395 400 | | 1200 |
| aat tcc tct gga tct act ggg tta cct aag ggt gtg gcc ctt ccg cat<br>Asn Ser Ser Gly Ser Thr Gly Leu Pro Lys Gly Val Ala Leu Pro His<br>405 410 415 | | 1248 |
| aga act gcc tgc gtc aga ttc tcg cat gcc aga gat cct att ttt ggc<br>Arg Thr Ala Cys Val Arg Phe Ser His Ala Arg Asp Pro Ile Phe Gly<br>420 425 430 | | 1296 |
| aat caa atc att ccg gat act gcg att tta agt gtt gtt cca ttc cat<br>Asn Gln Ile Ile Pro Asp Thr Ala Ile Leu Ser Val Val Pro Phe His<br>435 440 445 | | 1344 |
| cac ggt ttt gga atg ttt act aca ctc gga tat ttg ata tgt gga ttt<br>His Gly Phe Gly Met Phe Thr Thr Leu Gly Tyr Leu Ile Cys Gly Phe<br>450 455 460 | | 1392 |
| cga gtc gtc tta atg tat aga ttt gaa gaa gag ctg ttt tta cga tcc<br>Arg Val Val Leu Met Tyr Arg Phe Glu Glu Glu Leu Phe Leu Arg Ser<br>465 470 475 480 | | 1440 |
| ctt cag gat tac aaa att caa agt gcg ttg cta gta cca acc cta ttt<br>Leu Gln Asp Tyr Lys Ile Gln Ser Ala Leu Leu Val Pro Thr Leu Phe<br>485 490 495 | | 1488 |
| tca ttc ttc gcc aaa agc act ctg att gac aaa tac gat tta tct aat<br>Ser Phe Phe Ala Lys Ser Thr Leu Ile Asp Lys Tyr Asp Leu Ser Asn<br>500 505 510 | | 1536 |
| tta cac gaa att gct tct ggg ggc gca cct ctt tcg aaa gaa gtc ggg<br>Leu His Glu Ile Ala Ser Gly Gly Ala Pro Leu Ser Lys Glu Val Gly<br>515 520 525 | | 1584 |
| gaa gcg gtt gca aaa cgc ttc cat ctt cca ggg ata cga caa gga tat<br>Glu Ala Val Ala Lys Arg Phe His Leu Pro Gly Ile Arg Gln Gly Tyr<br>530 535 540 | | 1632 |
| ggg ctc act gag act aca tca gct att ctg att aca ccc gag ggg gat<br>Gly Leu Thr Glu Thr Thr Ser Ala Ile Leu Ile Thr Pro Glu Gly Asp<br>545 550 555 560 | | 1680 |
| gat aaa ccg ggc gcg gtc ggt aaa gtt gtt cca ttt ttt gaa gcg aag<br>Asp Lys Pro Gly Ala Val Gly Lys Val Val Pro Phe Phe Glu Ala Lys<br>565 570 575 | | 1728 |

```
gtt gtg gat ctg gat acc ggg aaa acg ctg ggc gtt aat cag aga ggc    1776
Val Val Asp Leu Asp Thr Gly Lys Thr Leu Gly Val Asn Gln Arg Gly
            580                 585                 590 gaa tta tgt gtc aga gga cct atg att atg tcc ggt tat gta aac aat    1824
Glu Leu Cys Val Arg Gly Pro Met Ile Met Ser Gly Tyr Val Asn Asn
        595                 600                 605 ccg gaa gcg acc aac gcc ttg att gac aag gat gga tga                1863
Pro Glu Ala Thr Asn Ala Leu Ile Asp Lys Asp Gly
    610                 615                 620

<210> SEQ ID NO 31
<211> LENGTH: 620
<212> TYPE: PRT
<213> ORGANISM: Artificial Sequence
<220> FEATURE:
<223> OTHER INFORMATION: Synthetic Construct

<400> SEQUENCE: 31

Met Gly Ser Ser His His His His His His Ser Gln Asp Pro Gly
1               5                   10                  15

Glu Lys Pro Tyr Ala Cys Pro Glu Cys Gly Lys Ser Phe Ser Arg Ser
            20                  25                  30

Asp His Leu Ala Glu His Gln Arg Thr His Thr Gly Glu Lys Pro Tyr
        35                  40                  45

Lys Cys Pro Glu Cys Gly Lys Ser Phe Ser Asp Lys Lys Asp Leu Thr
    50                  55                  60

Arg His Gln Arg Thr His Thr Gly Glu Lys Pro Tyr Lys Cys Pro Glu
65                  70                  75                  80

Cys Gly Lys Ser Phe Ser Gln Arg Ala Asn Leu Arg Ala His Gln Arg
                85                  90                  95

Thr His Thr Gly Glu Lys Pro Tyr Ala Cys Pro Glu Cys Gly Lys Ser
            100                 105                 110

Phe Ser Gln Leu Ala His Leu Arg Ala His Gln Arg Thr His Thr Gly
        115                 120                 125

Glu Lys Pro Tyr Lys Cys Pro Glu Cys Gly Lys Ser Phe Ser Arg Glu
    130                 135                 140

Asp Asn Leu His Thr His Gln Arg Thr His Thr Gly Glu Lys Pro Tyr
145                 150                 155                 160

Lys Cys Pro Glu Cys Gly Lys Ser Phe Ser Arg Arg Asp Ala Leu Asn
                165                 170                 175

Val His Gln Arg Thr His Thr Gly Lys Lys Thr Ser Thr Gly Gly Gly
            180                 185                 190

Gly Gly Ser Gly Gly Gly Gly Ser Gly Gly Gly Gly Thr Glu Asp Ala
        195                 200                 205

Lys Asn Ile Lys Lys Gly Pro Ala Pro Phe Tyr Pro Leu Glu Asp Gly
    210                 215                 220

Thr Ala Gly Glu Gln Leu His Lys Ala Met Lys Arg Tyr Ala Leu Val
225                 230                 235                 240

Pro Gly Thr Ile Ala Phe Thr Asp Ala His Ile Glu Val Asn Ile Thr
                245                 250                 255

Tyr Ala Glu Tyr Phe Glu Met Ser Val Arg Leu Ala Glu Ala Met Lys
            260                 265                 270

Arg Tyr Gly Leu Asn Thr Asn His Arg Ile Val Val Cys Ser Glu Asn
        275                 280                 285

Ser Leu Gln Phe Phe Met Pro Val Leu Gly Ala Leu Phe Ile Gly Val
    290                 295                 300
```

```
Ala Val Ala Pro Ala Asn Asp Ile Tyr Asn Glu Arg Glu Leu Leu Asn
305                 310                 315                 320

Ser Met Asn Ile Ser Gln Pro Thr Val Val Phe Val Ser Lys Lys Gly
            325                 330                 335

Leu Gln Lys Ile Leu Asn Val Gln Lys Lys Leu Pro Ile Ile Gln Lys
        340                 345                 350

Ile Ile Ile Met Asp Ser Lys Thr Asp Tyr Gln Gly Phe Gln Ser Met
    355                 360                 365

Tyr Thr Phe Val Thr Ser His Leu Pro Pro Gly Phe Asn Glu Tyr Asp
370                 375                 380

Phe Val Pro Glu Ser Phe Asp Arg Asp Lys Thr Ile Ala Leu Ile Met
385                 390                 395                 400

Asn Ser Ser Gly Ser Thr Gly Leu Pro Lys Gly Val Ala Leu Pro His
                405                 410                 415

Arg Thr Ala Cys Val Arg Phe Ser His Ala Arg Asp Pro Ile Phe Gly
            420                 425                 430

Asn Gln Ile Ile Pro Asp Thr Ala Ile Leu Ser Val Val Pro Phe His
        435                 440                 445

His Gly Phe Gly Met Phe Thr Thr Leu Gly Tyr Leu Ile Cys Gly Phe
    450                 455                 460

Arg Val Val Leu Met Tyr Arg Phe Glu Glu Glu Leu Phe Leu Arg Ser
465                 470                 475                 480

Leu Gln Asp Tyr Lys Ile Gln Ser Ala Leu Leu Val Pro Thr Leu Phe
                485                 490                 495

Ser Phe Phe Ala Lys Ser Thr Leu Ile Asp Lys Tyr Asp Leu Ser Asn
            500                 505                 510

Leu His Glu Ile Ala Ser Gly Gly Ala Pro Leu Ser Lys Glu Val Gly
        515                 520                 525

Glu Ala Val Ala Lys Arg Phe His Leu Pro Gly Ile Arg Gln Gly Tyr
    530                 535                 540

Gly Leu Thr Glu Thr Thr Ser Ala Ile Leu Ile Thr Pro Glu Gly Asp
545                 550                 555                 560

Asp Lys Pro Gly Ala Val Gly Lys Val Val Pro Phe Phe Glu Ala Lys
                565                 570                 575

Val Val Asp Leu Asp Thr Gly Lys Thr Leu Gly Val Asn Gln Arg Gly
            580                 585                 590

Glu Leu Cys Val Arg Gly Pro Met Ile Met Ser Gly Tyr Val Asn Asn
        595                 600                 605

Pro Glu Ala Thr Asn Ala Leu Ile Asp Lys Asp Gly
    610                 615                 620

<210> SEQ ID NO 32
<211> LENGTH: 1560
<212> TYPE: DNA
<213> ORGANISM: Artificial Sequence
<220> FEATURE:
<223> OTHER INFORMATION: Synthetic construct: MFD2-NFluc(2-416) coding
      sequence
<220> FEATURE:
<221> NAME/KEY: CDS
<222> LOCATION: (1)..(1551)

<400> SEQUENCE: 32 atg ggc agc agc cat cac cat cat cac cac agc cag gat ccg aat tcg      48
Met Gly Ser Ser His His His His His His Ser Gln Asp Pro Asn Ser
1               5                   10                  15 gaa agc ggc aaa cgc atg gat tgc ccg gcg ctg ccg ccg ggt tgg aaa      96
Glu Ser Gly Lys Arg Met Asp Cys Pro Ala Leu Pro Pro Gly Trp Lys
```

```
                  20                  25                  30
aaa gaa gaa gtg att cgt aaa agc ggc ctg agc gcg ggc aaa agc gat        144
Lys Glu Glu Val Ile Arg Lys Ser Gly Leu Ser Ala Gly Lys Ser Asp
             35                  40                  45 gtg tat tat ttt agc ccg agc ggc aaa aaa ttt cgt agc aaa ccg cag        192
Val Tyr Tyr Phe Ser Pro Ser Gly Lys Lys Phe Arg Ser Lys Pro Gln
 50                  55                  60 ctg gcg cgt tat ctg ggc aac acc gtg gat ctg agc agc ttt gat ttt        240
Leu Ala Arg Tyr Leu Gly Asn Thr Val Asp Leu Ser Ser Phe Asp Phe
 65                  70                  75                  80 cgt acc ggc aaa atg acc ggt ggg ggc ggt tca ggc ggt ggg ggt            288
Arg Thr Gly Lys Met Thr Gly Gly Gly Gly Ser Gly Gly Gly Gly
                 85                  90                  95 tct ggt ggg ggt ggt acc gaa gac gcc aaa aac ata aag aaa ggc ccg        336
Ser Gly Gly Gly Gly Thr Glu Asp Ala Lys Asn Ile Lys Lys Gly Pro
             100                 105                 110 gcg cca ttc tat cct cta gag gat gga acc gct gga gag caa ctg cat        384
Ala Pro Phe Tyr Pro Leu Glu Asp Gly Thr Ala Gly Glu Gln Leu His
             115                 120                 125 aag gct atg aag aga tac gcc ctg gtt cct gga aca att gct ttt aca        432
Lys Ala Met Lys Arg Tyr Ala Leu Val Pro Gly Thr Ile Ala Phe Thr
130                 135                 140 gat gca cat atc gag gtg aac atc acg tac gcg gaa tac ttc gaa atg        480
Asp Ala His Ile Glu Val Asn Ile Thr Tyr Ala Glu Tyr Phe Glu Met
145                 150                 155                 160 tcc gtt cgg ttg gca gaa gct atg aaa cga tat ggg ctg gat aca aat        528
Ser Val Arg Leu Ala Glu Ala Met Lys Arg Tyr Gly Leu Asp Thr Asn
                165                 170                 175 cac aga atc gtc gta tgc agt gaa aac tct ctt caa ttc ttt atg ccg        576
His Arg Ile Val Val Cys Ser Glu Asn Ser Leu Gln Phe Phe Met Pro
             180                 185                 190 gtg ttg ggc gcg tta ttt atc gga gtt gca gtt gcg ccc gcg aac gac        624
Val Leu Gly Ala Leu Phe Ile Gly Val Ala Val Ala Pro Ala Asn Asp
             195                 200                 205 att tat aat gaa cgt gaa ttg ctc aac agt atg aac att tcg cag cct        672
Ile Tyr Asn Glu Arg Glu Leu Leu Asn Ser Met Asn Ile Ser Gln Pro
210                 215                 220 acc gta gtg ttt gtt tcc aaa aag ggg ttg caa aaa att ttg aac gtg        720
Thr Val Val Phe Val Ser Lys Lys Gly Leu Gln Lys Ile Leu Asn Val
225                 230                 235                 240 caa aaa aaa tta cca ata atc cag aaa att att atc atg gat tct aaa        768
Gln Lys Lys Leu Pro Ile Ile Gln Lys Ile Ile Ile Met Asp Ser Lys
                245                 250                 255 acg gat tac cag gga ttt cag tcg atg tac acg ttc gtc aca tct cat        816
Thr Asp Tyr Gln Gly Phe Gln Ser Met Tyr Thr Phe Val Thr Ser His
             260                 265                 270 cta cct ccc ggt ttt aat gaa tac gat ttt gta cca gag tcc ttt gat        864
Leu Pro Pro Gly Phe Asn Glu Tyr Asp Phe Val Pro Glu Ser Phe Asp
             275                 280                 285 cgt gac aaa aca att gca ctg aca atg aat tcc tct gga tct act ggg        912
Arg Asp Lys Thr Ile Ala Leu Thr Met Asn Ser Ser Gly Ser Thr Gly
             290                 295                 300 tta cct aag ggt gtg gcc ctt ccg cat aga act gcc tgc gtc aga ttc        960
Leu Pro Lys Gly Val Ala Leu Pro His Arg Thr Ala Cys Val Arg Phe
305                 310                 315                 320 tcg cat gcc aga gat cct att ttt ggc aat caa atc att ccg gat act       1008
Ser His Ala Arg Asp Pro Ile Phe Gly Asn Gln Ile Ile Pro Asp Thr
                325                 330                 335 gcg att tta agt gtt gtt cca ttc cat cac ggt ttt gga atg ttt act       1056
Ala Ile Leu Ser Val Val Pro Phe His His Gly Phe Gly Met Phe Thr
```

```
                    340                 345                 350
aca ctc gga tat ttg ata tgt gga ttt cga gtc gtc tta atg tat aga      1104
Thr Leu Gly Tyr Leu Ile Cys Gly Phe Arg Val Val Leu Met Tyr Arg
            355                 360                 365 ttt gaa gaa gag ctg ttt tta cga tcc ctt cag gat tac aaa att caa      1152
Phe Glu Glu Glu Leu Phe Leu Arg Ser Leu Gln Asp Tyr Lys Ile Gln
        370                 375                 380 agt gcg ttg cta gta cca acc cta ttt tca ttc ttc gcc aaa agc act      1200
Ser Ala Leu Leu Val Pro Thr Leu Phe Ser Phe Phe Ala Lys Ser Thr
385                 390                 395                 400 ctg att gac aaa tac gat tta tct aat tta cac gaa att gct tct ggg      1248
Leu Ile Asp Lys Tyr Asp Leu Ser Asn Leu His Glu Ile Ala Ser Gly
            405                 410                 415 ggc gca cct ctt tcg aaa gaa gtc ggg gaa gcg gtt gca aaa cgc ttc      1296
Gly Ala Pro Leu Ser Lys Glu Val Gly Glu Ala Val Ala Lys Arg Phe
        420                 425                 430 cat ctt cca ggg ata cga caa gga tat ggg ctc act gag act aca tca      1344
His Leu Pro Gly Ile Arg Gln Gly Tyr Gly Leu Thr Glu Thr Thr Ser
    435                 440                 445 gct att ctg att aca ccc gag ggg gat gat aaa ccg ggc gcg gtc ggt      1392
Ala Ile Leu Ile Thr Pro Glu Gly Asp Asp Lys Pro Gly Ala Val Gly
450                 455                 460 aaa gtt gtt cca ttt ttt gaa gcg aag gtt gtg gat ctg gat acc ggg      1440
Lys Val Val Pro Phe Phe Glu Ala Lys Val Val Asp Leu Asp Thr Gly
465                 470                 475                 480 aaa acg ctg ggc gtt aat cag aga ggc gaa tta tgt gtc aga gga cct      1488
Lys Thr Leu Gly Val Asn Gln Arg Gly Glu Leu Cys Val Arg Gly Pro
            485                 490                 495 atg att atg tcc ggt tat gta aac aat ccg gaa gcg acc aac gcc ttg      1536
Met Ile Met Ser Gly Tyr Val Asn Asn Pro Glu Ala Thr Asn Ala Leu
        500                 505                 510 att gac aag gat gga tgataagcg                                        1560
Ile Asp Lys Asp Gly
            515

<210> SEQ ID NO 33
<211> LENGTH: 517
<212> TYPE: PRT
<213> ORGANISM: Artificial Sequence
<220> FEATURE:
<223> OTHER INFORMATION: Synthetic Construct

<400> SEQUENCE: 33

Met Gly Ser Ser His His His His His His Ser Gln Asp Pro Asn Ser
1               5                   10                  15

Glu Ser Gly Lys Arg Met Asp Cys Pro Ala Leu Pro Pro Gly Trp Lys
            20                  25                  30

Lys Glu Glu Val Ile Arg Lys Ser Gly Leu Ser Ala Gly Lys Ser Asp
        35                  40                  45

Val Tyr Tyr Phe Ser Pro Ser Gly Lys Lys Phe Arg Ser Lys Pro Gln
    50                  55                  60

Leu Ala Arg Tyr Leu Gly Asn Thr Val Asp Leu Ser Ser Phe Asp Phe
65                  70                  75                  80

Arg Thr Gly Lys Met Thr Gly Gly Gly Ser Gly Gly Gly Gly
            85                  90                  95

Ser Gly Gly Gly Gly Thr Glu Asp Ala Lys Asn Ile Lys Lys Gly Pro
        100                 105                 110

Ala Pro Phe Tyr Pro Leu Glu Asp Gly Thr Ala Gly Glu Gln Leu His
    115                 120                 125
```

-continued

```
Lys Ala Met Lys Arg Tyr Ala Leu Val Pro Gly Thr Ile Ala Phe Thr
            130                 135                 140

Asp Ala His Ile Glu Val Asn Ile Thr Tyr Ala Glu Tyr Phe Glu Met
145                 150                 155                 160

Ser Val Arg Leu Ala Glu Ala Met Lys Arg Tyr Gly Leu Asp Thr Asn
                165                 170                 175

His Arg Ile Val Val Cys Ser Glu Asn Ser Leu Gln Phe Phe Met Pro
            180                 185                 190

Val Leu Gly Ala Leu Phe Ile Gly Val Ala Val Ala Pro Ala Asn Asp
            195                 200                 205

Ile Tyr Asn Glu Arg Glu Leu Leu Asn Ser Met Asn Ile Ser Gln Pro
210                 215                 220

Thr Val Val Phe Val Ser Lys Lys Gly Leu Gln Lys Ile Leu Asn Val
225                 230                 235                 240

Gln Lys Lys Leu Pro Ile Ile Gln Lys Ile Ile Met Asp Ser Lys
                245                 250                 255

Thr Asp Tyr Gln Gly Phe Gln Ser Met Tyr Thr Phe Val Thr Ser His
            260                 265                 270

Leu Pro Pro Gly Phe Asn Glu Tyr Asp Phe Val Pro Glu Ser Phe Asp
            275                 280                 285

Arg Asp Lys Thr Ile Ala Leu Thr Met Asn Ser Ser Gly Ser Thr Gly
290                 295                 300

Leu Pro Lys Gly Val Ala Leu Pro His Arg Thr Ala Cys Val Arg Phe
305                 310                 315                 320

Ser His Ala Arg Asp Pro Ile Phe Gly Asn Gln Ile Ile Pro Asp Thr
                325                 330                 335

Ala Ile Leu Ser Val Val Pro Phe His His Gly Phe Gly Met Phe Thr
            340                 345                 350

Thr Leu Gly Tyr Leu Ile Cys Gly Phe Arg Val Val Leu Met Tyr Arg
            355                 360                 365

Phe Glu Glu Glu Leu Phe Leu Arg Ser Leu Gln Asp Tyr Lys Ile Gln
            370                 375                 380

Ser Ala Leu Leu Val Pro Thr Leu Phe Ser Phe Phe Ala Lys Ser Thr
385                 390                 395                 400

Leu Ile Asp Lys Tyr Asp Leu Ser Asn Leu His Glu Ile Ala Ser Gly
                405                 410                 415

Gly Ala Pro Leu Ser Lys Glu Val Gly Glu Ala Val Ala Lys Arg Phe
            420                 425                 430

His Leu Pro Gly Ile Arg Gln Gly Tyr Gly Leu Thr Glu Thr Thr Ser
            435                 440                 445

Ala Ile Leu Ile Thr Pro Glu Gly Asp Asp Lys Pro Gly Ala Val Gly
450                 455                 460

Lys Val Val Pro Phe Phe Glu Ala Lys Val Val Asp Leu Asp Thr Gly
465                 470                 475                 480

Lys Thr Leu Gly Val Asn Gln Arg Gly Glu Leu Cys Val Arg Gly Pro
                485                 490                 495

Met Ile Met Ser Gly Tyr Val Asn Asn Pro Glu Ala Thr Asn Ala Leu
            500                 505                 510

Ile Asp Lys Asp Gly
            515

<210> SEQ ID NO 34
<211> LENGTH: 1566
<212> TYPE: DNA
<213> ORGANISM: Artificial Sequence
```

-continued

<220> FEATURE:
<223> OTHER INFORMATION: Synthetic construct: Cfluc-PKA coding
      sequence
<220> FEATURE:
<221> NAME/KEY: CDS
<222> LOCATION: (1)..(1563)

<400> SEQUENCE: 34

```
atg atg tcc ggt tat gta aac aat ccg gaa gcg acc aac gcc ttg att        48
Met Met Ser Gly Tyr Val Asn Asn Pro Glu Ala Thr Asn Ala Leu Ile
1               5                   10                  15 gac aag gat gga tgg cta cat tct gga gac ata gct tac tgg gac gaa        96
Asp Lys Asp Gly Trp Leu His Ser Gly Asp Ile Ala Tyr Trp Asp Glu
            20                  25                  30 gac gaa cac ttc ttc ata gtt gac cgc ttg aag tct tta att aaa tac       144
Asp Glu His Phe Phe Ile Val Asp Arg Leu Lys Ser Leu Ile Lys Tyr
        35                  40                  45 aaa gga tat cag gtg gcc ccc gct gaa ttg gaa tcg ata ttg tta caa       192
Lys Gly Tyr Gln Val Ala Pro Ala Glu Leu Glu Ser Ile Leu Leu Gln
    50                  55                  60 cac ccc aac atc ttc gac gcg ggc gtg gca ggt ctt ccc gac gat gac       240
His Pro Asn Ile Phe Asp Ala Gly Val Ala Gly Leu Pro Asp Asp Asp
65                  70                  75                  80 gcc ggt gaa ctt ccc gcc gcc gtt gtt gtt ttg gag cac gga aag acg       288
Ala Gly Glu Leu Pro Ala Ala Val Val Val Leu Glu His Gly Lys Thr
                85                  90                  95 atg acg gaa aaa gag atc gtg gat tac gtc gcc agt caa gta aca acc       336
Met Thr Glu Lys Glu Ile Val Asp Tyr Val Ala Ser Gln Val Thr Thr
            100                 105                 110 gcg aaa aag ttg cgc gga gga gtt gtg ttt gtg gac gaa gta ccg aaa       384
Ala Lys Lys Leu Arg Gly Gly Val Val Phe Val Asp Glu Val Pro Lys
        115                 120                 125 ggt ctt acc gga aaa ctc gac gca aga aaa atc aga gag atc ctc ata       432
Gly Leu Thr Gly Lys Leu Asp Ala Arg Lys Ile Arg Glu Ile Leu Ile
    130                 135                 140 aag gcc aag aag ggc gga aag tcc aaa ttg ggc ctg cag ggc ggt tca       480
Lys Ala Lys Lys Gly Gly Lys Ser Lys Leu Gly Leu Gln Gly Gly Ser
145                 150                 155                 160 ggc ggt ggg ggt tct ggc ggg ggt ggg agc ccc ggg aac gcc gcc gcc       528
Gly Gly Gly Gly Ser Gly Gly Gly Gly Ser Pro Gly Asn Ala Ala Ala
                165                 170                 175 gcc aag aag ggc agc gag cag gag agc gtg aaa gag ttc cta gcc aaa       576
Ala Lys Lys Gly Ser Glu Gln Glu Ser Val Lys Glu Phe Leu Ala Lys
            180                 185                 190 gcc aag gaa gat ttc ctg aaa aaa tgg gag acc cct tct cag aat aca       624
Ala Lys Glu Asp Phe Leu Lys Lys Trp Glu Thr Pro Ser Gln Asn Thr
        195                 200                 205 gcc cag ttg gat cag ttt gat aga atc aag acc ctt ggc acc ggc tcc       672
Ala Gln Leu Asp Gln Phe Asp Arg Ile Lys Thr Leu Gly Thr Gly Ser
    210                 215                 220 ttt ggg cga gtg atg ctg gtg aag cac aag gag agt ggg aac cac tac       720
Phe Gly Arg Val Met Leu Val Lys His Lys Glu Ser Gly Asn His Tyr
225                 230                 235                 240 gcc atg aag atc tta gac aag cag aag gtg gtg aag cta aag cag atc       768
Ala Met Lys Ile Leu Asp Lys Gln Lys Val Val Lys Leu Lys Gln Ile
                245                 250                 255 gag cac act ctg aat gag aag cgc atc ctg cag gcc gtc aac ttc ccg       816
Glu His Thr Leu Asn Glu Lys Arg Ile Leu Gln Ala Val Asn Phe Pro
            260                 265                 270 ttc ctg gtc aaa ctt gaa ttc tcc ttc aag gac aac tca aac ctg tac       864
Phe Leu Val Lys Leu Glu Phe Ser Phe Lys Asp Asn Ser Asn Leu Tyr
        275                 280                 285
```

| | | | | | | | | | | | | | | | |
|---|---|---|---|---|---|---|---|---|---|---|---|---|---|---|---|
| atg | gtc | atg | gag | tat | gta | gct | ggt | ggc | gag | atg | ttc | tcc | cac | cta | cgg | 912 |
| Met | Val | Met | Glu | Tyr | Val | Ala | Gly | Gly | Glu | Met | Phe | Ser | His | Leu | Arg |
| | 290 | | | | 295 | | | | | 300 | | | | | |

| cgg | att | gga | agg | ttc | agc | gag | ccc | cat | gcc | cgt | ttc | tac | gcg | gcg | cag | 960 |
|---|---|---|---|---|---|---|---|---|---|---|---|---|---|---|---|---|
| Arg | Ile | Gly | Arg | Phe | Ser | Glu | Pro | His | Ala | Arg | Phe | Tyr | Ala | Ala | Gln |
| 305 | | | | | 310 | | | | | 315 | | | | | 320 |

| atc | gtc | ctg | acc | ttt | gag | tat | ctg | cac | tcc | ctg | gac | ctc | atc | tac | cgg | 1008 |
|---|---|---|---|---|---|---|---|---|---|---|---|---|---|---|---|---|
| Ile | Val | Leu | Thr | Phe | Glu | Tyr | Leu | His | Ser | Leu | Asp | Leu | Ile | Tyr | Arg |
| | | | | 325 | | | | | 330 | | | | | 335 | |

| gac | ctg | aag | ccc | gag | aat | ctt | ctc | atc | gac | cag | cag | ggc | tat | att | cag | 1056 |
|---|---|---|---|---|---|---|---|---|---|---|---|---|---|---|---|---|
| Asp | Leu | Lys | Pro | Glu | Asn | Leu | Leu | Ile | Asp | Gln | Gln | Gly | Tyr | Ile | Gln |
| | | | 340 | | | | | 345 | | | | | 350 | | |

| gtg | aca | gac | ttc | ggt | ttt | gcc | aag | cgt | gtg | aaa | ggc | cgt | act | tgg | acc | 1104 |
|---|---|---|---|---|---|---|---|---|---|---|---|---|---|---|---|---|
| Val | Thr | Asp | Phe | Gly | Phe | Ala | Lys | Arg | Val | Lys | Gly | Arg | Thr | Trp | Thr |
| | | 355 | | | | | 360 | | | | | 365 | | | |

| ttg | tgt | ggg | acc | cct | gag | tac | ttg | gcc | ccc | gag | att | atc | ctg | agc | aaa | 1152 |
|---|---|---|---|---|---|---|---|---|---|---|---|---|---|---|---|---|
| Leu | Cys | Gly | Thr | Pro | Glu | Tyr | Leu | Ala | Pro | Glu | Ile | Ile | Leu | Ser | Lys |
| 370 | | | | | 375 | | | | | 380 | | | | | |

| ggc | tac | aac | aag | gct | gtg | gac | tgg | tgg | gct | ctc | gga | gtc | ctc | atc | tac | 1200 |
|---|---|---|---|---|---|---|---|---|---|---|---|---|---|---|---|---|
| Gly | Tyr | Asn | Lys | Ala | Val | Asp | Trp | Trp | Ala | Leu | Gly | Val | Leu | Ile | Tyr |
| 385 | | | | 390 | | | | | 395 | | | | | 400 | |

| gag | atg | gct | gct | ggt | tac | cca | ccc | ttc | ttc | gct | gac | cag | cct | atc | cag | 1248 |
|---|---|---|---|---|---|---|---|---|---|---|---|---|---|---|---|---|
| Glu | Met | Ala | Ala | Gly | Tyr | Pro | Pro | Phe | Phe | Ala | Asp | Gln | Pro | Ile | Gln |
| | | | 405 | | | | | 410 | | | | | 415 | | |

| atc | tat | gag | aaa | atc | gtc | tct | ggg | aag | gtg | cgg | ttc | cca | tcc | cac | ttc | 1296 |
|---|---|---|---|---|---|---|---|---|---|---|---|---|---|---|---|---|
| Ile | Tyr | Glu | Lys | Ile | Val | Ser | Gly | Lys | Val | Arg | Phe | Pro | Ser | His | Phe |
| | | | 420 | | | | | 425 | | | | | 430 | | |

| agc | tct | gac | ttg | aag | gac | ctg | ctg | cgg | aac | ctt | ctg | caa | gtg | gat | ctc | 1344 |
|---|---|---|---|---|---|---|---|---|---|---|---|---|---|---|---|---|
| Ser | Ser | Asp | Leu | Lys | Asp | Leu | Leu | Arg | Asn | Leu | Leu | Gln | Val | Asp | Leu |
| | | 435 | | | | | 440 | | | | | 445 | | | |

| acc | aag | cgc | ttt | ggg | aac | ctc | aag | aac | ggg | gtc | aat | gac | atc | aag | aac | 1392 |
|---|---|---|---|---|---|---|---|---|---|---|---|---|---|---|---|---|
| Thr | Lys | Arg | Phe | Gly | Asn | Leu | Lys | Asn | Gly | Val | Asn | Asp | Ile | Lys | Asn |
| | 450 | | | | | 455 | | | | | 460 | | | | |

| cac | aag | tgg | ttt | gcc | acg | act | gac | tgg | att | gcc | atc | tat | cag | aga | aag | 1440 |
|---|---|---|---|---|---|---|---|---|---|---|---|---|---|---|---|---|
| His | Lys | Trp | Phe | Ala | Thr | Thr | Asp | Trp | Ile | Ala | Ile | Tyr | Gln | Arg | Lys |
| 465 | | | | 470 | | | | | 475 | | | | | 480 | |

| gtg | gaa | gct | ccc | ttc | ata | cca | aag | ttt | aaa | ggc | cct | ggg | gac | acg | agt | 1488 |
|---|---|---|---|---|---|---|---|---|---|---|---|---|---|---|---|---|
| Val | Glu | Ala | Pro | Phe | Ile | Pro | Lys | Phe | Lys | Gly | Pro | Gly | Asp | Thr | Ser |
| | | | 485 | | | | | 490 | | | | | 495 | | |

| aac | ttt | gac | gac | tat | gag | gag | gaa | gag | atc | cgg | gtc | tcc | atc | aat | gag | 1536 |
|---|---|---|---|---|---|---|---|---|---|---|---|---|---|---|---|---|
| Asn | Phe | Asp | Asp | Tyr | Glu | Glu | Glu | Glu | Ile | Arg | Val | Ser | Ile | Asn | Glu |
| | | | 500 | | | | | 505 | | | | | 510 | | |

| aag | tgt | ggc | aag | gag | ttt | act | gag | ttt | tag | | | | | | | 1566 |
|---|---|---|---|---|---|---|---|---|---|---|---|---|---|---|---|---|
| Lys | Cys | Gly | Lys | Glu | Phe | Thr | Glu | Phe | | | | | | | |
| | | | 515 | | | | | 520 | | | | | | | |

<210> SEQ ID NO 35
<211> LENGTH: 521
<212> TYPE: PRT
<213> ORGANISM: Artificial Sequence
<220> FEATURE:
<223> OTHER INFORMATION: Synthetic Construct

<400> SEQUENCE: 35

Met Met Ser Gly Tyr Val Asn Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
        35                  40                  45

```
          Lys Gly Tyr Gln Val Ala Pro Ala Glu Leu Glu Ser Ile Leu Leu Gln
           50                  55                  60

His Pro Asn Ile Phe Asp Ala Gly Val Ala Gly Leu Pro Asp Asp Asp
           65                  70                  75                  80

Ala Gly Glu Leu Pro Ala Ala Val Val Leu Glu His Gly Lys Thr
                           85                  90                  95

Met Thr Glu Lys Glu Ile Val Asp Tyr Val Ala Ser Gln Val Thr Thr
                          100                 105                 110

Ala Lys Lys Leu Arg Gly Gly Val Phe Val Asp Glu Val Pro Lys
                      115                 120                 125

Gly Leu Thr Gly Lys Leu Asp Ala Arg Lys Ile Arg Glu Ile Leu Ile
          130                 135                 140

Lys Ala Lys Lys Gly Gly Lys Ser Lys Leu Gly Leu Gln Gly Gly Ser
          145                 150                 155                 160

Gly Gly Gly Gly Ser Gly Gly Gly Ser Pro Gly Asn Ala Ala Ala
                          165                 170                 175

Ala Lys Lys Gly Ser Glu Gln Glu Ser Val Lys Glu Phe Leu Ala Lys
                      180                 185                 190

Ala Lys Glu Asp Phe Leu Lys Lys Trp Glu Thr Pro Ser Gln Asn Thr
                      195                 200                 205

Ala Gln Leu Asp Gln Phe Asp Arg Ile Lys Thr Leu Gly Thr Gly Ser
                      210                 215                 220

Phe Gly Arg Val Met Leu Val Lys His Lys Glu Ser Gly Asn His Tyr
          225                 230                 235                 240

Ala Met Lys Ile Leu Asp Lys Gln Lys Val Val Lys Leu Lys Gln Ile
                          245                 250                 255

Glu His Thr Leu Asn Glu Lys Arg Ile Leu Gln Ala Val Asn Phe Pro
                          260                 265                 270

Phe Leu Val Lys Leu Glu Phe Ser Phe Lys Asp Asn Ser Asn Leu Tyr
                      275                 280                 285

Met Val Met Glu Tyr Val Ala Gly Gly Glu Met Phe Ser His Leu Arg
                      290                 295                 300

Arg Ile Gly Arg Phe Ser Glu Pro His Ala Arg Phe Tyr Ala Ala Gln
          305                 310                 315                 320

Ile Val Leu Thr Phe Glu Tyr Leu His Ser Leu Asp Leu Ile Tyr Arg
                          325                 330                 335

Asp Leu Lys Pro Glu Asn Leu Leu Ile Asp Gln Gln Gly Tyr Ile Gln
                      340                 345                 350

Val Thr Asp Phe Gly Phe Ala Lys Arg Val Lys Gly Arg Thr Trp Thr
                      355                 360                 365

Leu Cys Gly Thr Pro Glu Tyr Leu Ala Pro Glu Ile Ile Leu Ser Lys
                      370                 375                 380

Gly Tyr Asn Lys Ala Val Asp Trp Trp Ala Leu Gly Val Leu Ile Tyr
          385                 390                 395                 400

Glu Met Ala Ala Gly Tyr Pro Pro Phe Phe Ala Asp Gln Pro Ile Gln
                          405                 410                 415

Ile Tyr Glu Lys Ile Val Ser Gly Lys Val Arg Phe Pro Ser His Phe
                      420                 425                 430

Ser Ser Asp Leu Lys Asp Leu Leu Arg Asn Leu Leu Gln Val Asp Leu
                      435                 440                 445

Thr Lys Arg Phe Gly Asn Leu Lys Asn Gly Val Asn Asp Ile Lys Asn
                      450                 455                 460

His Lys Trp Phe Ala Thr Thr Asp Trp Ile Ala Ile Tyr Gln Arg Lys
          465                 470                 475                 480
```

```
Val Glu Ala Pro Phe Ile Pro Lys Phe Lys Gly Pro Gly Asp Thr Ser
            485                 490                 495

Asn Phe Asp Asp Tyr Glu Glu Glu Ile Arg Val Ser Ile Asn Glu
        500                 505                 510

Lys Cys Gly Lys Glu Phe Thr Glu Phe
        515                 520

<210> SEQ ID NO 36
<211> LENGTH: 1638
<212> TYPE: DNA
<213> ORGANISM: Artificial Sequence
<220> FEATURE:
<223> OTHER INFORMATION: Synthetic construct: Cfluc-PDGFRB coding
      sequence
<220> FEATURE:
<221> NAME/KEY: CDS
<222> LOCATION: (1)..(1635)

<400> SEQUENCE: 36 atg ggt atg tcc ggt tat gta aac aat ccg gaa gcg acc aac gcc ttg      48
Met Gly Met Ser Gly Tyr Val Asn Asn Pro Glu Ala Thr Asn Ala Leu
1               5                   10                  15 att gac aag gat gga tgg cta cat tct gga gac ata gct tac tgg gac      96
Ile Asp Lys Asp Gly Trp Leu His Ser Gly Asp Ile Ala Tyr Trp Asp
            20                  25                  30 gaa gac gaa cac ttc ttc ata gtt gac cgc ttg aag tct tta att aaa     144
Glu Asp Glu His Phe Phe Ile Val Asp Arg Leu Lys Ser Leu Ile Lys
        35                  40                  45 tac aaa gga tat cag gtg gcc ccc gct gaa ttg gaa tcg ata ttg tta     192
Tyr Lys Gly Tyr Gln Val Ala Pro Ala Glu Leu Glu Ser Ile Leu Leu
    50                  55                  60 caa cac ccc aac atc ttc gac gcg ggc gtg gca ggt ctt ccc gac gat     240
Gln His Pro Asn Ile Phe Asp Ala Gly Val Ala Gly Leu Pro Asp Asp
65                  70                  75                  80 gac gcc ggt gaa ctt ccc gcc gcc gtt gtt gtt ttg gag cac gga aag     288
Asp Ala Gly Glu Leu Pro Ala Ala Val Val Val Leu Glu His Gly Lys
                85                  90                  95 acg atg acg gaa aaa gag atc gtg gat tac gtc gcc agt caa gta aca     336
Thr Met Thr Glu Lys Glu Ile Val Asp Tyr Val Ala Ser Gln Val Thr
            100                 105                 110 acc gcg aaa aag ttg cgc gga gga gtt gtg ttt gtg gac gaa gta ccg     384
Thr Ala Lys Lys Leu Arg Gly Gly Val Val Phe Val Asp Glu Val Pro
        115                 120                 125 aaa ggt ctt acc gga aaa ctc gac gca aga aaa atc aga gag atc ctc     432
Lys Gly Leu Thr Gly Lys Leu Asp Ala Arg Lys Ile Arg Glu Ile Leu
    130                 135                 140 ata aag gcc aag aag ggc gga aag tcc aaa ttg ggc ctg cag ggc ggt     480
Ile Lys Ala Lys Lys Gly Gly Lys Ser Lys Leu Gly Leu Gln Gly Gly
145                 150                 155                 160 tca ggc ggt ggg ggt tct ggc ggg ggt ggg agc gtc gac tcc acg tgg     528
Ser Gly Gly Gly Gly Ser Gly Gly Gly Gly Ser Val Asp Ser Thr Trp
                165                 170                 175 gag ctg ccg cgg gac cag ctt gtg ctg gga cgc acc ctc ggc tct ggg     576
Glu Leu Pro Arg Asp Gln Leu Val Leu Gly Arg Thr Leu Gly Ser Gly
            180                 185                 190 gcc ttt ggg cag gtg gtg gag gcc acg gct cat ggc ctg agc cat tct     624
Ala Phe Gly Gln Val Val Glu Ala Thr Ala His Gly Leu Ser His Ser
        195                 200                 205 cag gcc acg atg aaa gtg gcc gtc aag atg ctt aaa tcc aca gcc cgc     672
Gln Ala Thr Met Lys Val Ala Val Lys Met Leu Lys Ser Thr Ala Arg
    210                 215                 220
```

```
                                        -continued agc agt gag aag caa gcc ctt atg tcg gag ctg aag atc atg agt cac    720
Ser Ser Glu Lys Gln Ala Leu Met Ser Glu Leu Lys Ile Met Ser His
225                 230                 235                 240 ctt ggg ccc cac ctg aac gtg gtc aac ctg ttg ggg gcc tgc acc aaa    768
Leu Gly Pro His Leu Asn Val Val Asn Leu Leu Gly Ala Cys Thr Lys
            245                 250                 255 gga gga ccc atc tat atc atc act gag tac tgc cgc tac gga gac ctg    816
Gly Gly Pro Ile Tyr Ile Ile Thr Glu Tyr Cys Arg Tyr Gly Asp Leu
        260                 265                 270 gtg gac tac ctg cac cgc aac aaa cac acc ttc ctg cag cac cac tcc    864
Val Asp Tyr Leu His Arg Asn Lys His Thr Phe Leu Gln His His Ser
    275                 280                 285 gac aag cgc cgc ccg ccc agc gcg gag ctc tac agc aat gct ctg ccc    912
Asp Lys Arg Arg Pro Pro Ser Ala Glu Leu Tyr Ser Asn Ala Leu Pro
290                 295                 300 gtt ggg ctc ccc ctg ccc agc cat gtg tcc ttg acc ggg gag agc gac    960
Val Gly Leu Pro Leu Pro Ser His Val Ser Leu Thr Gly Glu Ser Asp
305                 310                 315                 320 ggt ggc tac atg gac atg agc aag gac gag tcg gtg gac tat gtg ccc   1008
Gly Gly Tyr Met Asp Met Ser Lys Asp Glu Ser Val Asp Tyr Val Pro
            325                 330                 335 atg ctg gac atg aaa gga gac gtc aaa tat gca gac atc gag tcc tcc   1056
Met Leu Asp Met Lys Gly Asp Val Lys Tyr Ala Asp Ile Glu Ser Ser
        340                 345                 350 aac tac atg gcc cct tac gat aac tac gtt ccc tct gcc cct gag agg   1104
Asn Tyr Met Ala Pro Tyr Asp Asn Tyr Val Pro Ser Ala Pro Glu Arg
    355                 360                 365 acc tgc cga gca act ttg atc aac gag tct cca gtg cta agc tac atg   1152
Thr Cys Arg Ala Thr Leu Ile Asn Glu Ser Pro Val Leu Ser Tyr Met
370                 375                 380 gac ctc gtg ggc ttc agc tac cag gtg gcc aat ggc atg gag ttt ctg   1200
Asp Leu Val Gly Phe Ser Tyr Gln Val Ala Asn Gly Met Glu Phe Leu
385                 390                 395                 400 gcc tcc aag aac tgc gtc cac aga gac ctg gcg gct agg aac gtg ctc   1248
Ala Ser Lys Asn Cys Val His Arg Asp Leu Ala Ala Arg Asn Val Leu
            405                 410                 415 atc tgt gaa ggc aag ctg gtc aag atc tgt gac ttt ggc ctg gct cga   1296
Ile Cys Glu Gly Lys Leu Val Lys Ile Cys Asp Phe Gly Leu Ala Arg
        420                 425                 430 gac atc atg cgg gac tcg aat tac atc tcc aaa ggc agc acc ttt ttg   1344
Asp Ile Met Arg Asp Ser Asn Tyr Ile Ser Lys Gly Ser Thr Phe Leu
    435                 440                 445 cct tta aag tgg atg gct ccg gag agc atc ttc aac agc ctc tac acc   1392
Pro Leu Lys Trp Met Ala Pro Glu Ser Ile Phe Asn Ser Leu Tyr Thr
450                 455                 460 acc ctg agc gac gtg tgg tcc ttc ggg atc ctg ctc tgg gag atc ttc   1440
Thr Leu Ser Asp Val Trp Ser Phe Gly Ile Leu Leu Trp Glu Ile Phe
465                 470                 475                 480 acc ttg ggt ggc acc cct tac cca gag ctg ccc atg aac gag cag ttc   1488
Thr Leu Gly Gly Thr Pro Tyr Pro Glu Leu Pro Met Asn Glu Gln Phe
            485                 490                 495 tac aat gcc atc aaa cgg ggt tac cgc atg gcc cag cct gcc cat gcc   1536
Tyr Asn Ala Ile Lys Arg Gly Tyr Arg Met Ala Gln Pro Ala His Ala
        500                 505                 510 tcc gac gag atc tat gag atc atg cag aag tgc tgg gaa gag aag ttt   1584
Ser Asp Glu Ile Tyr Glu Ile Met Gln Lys Cys Trp Glu Glu Lys Phe
    515                 520                 525 gag att cgg ccc ccc ttc tcc cag ctg gtg ctg ctt ctc gag aga ctg   1632
Glu Ile Arg Pro Pro Phe Ser Gln Leu Val Leu Leu Leu Glu Arg Leu
530                 535                 540
```

```
ttg tga                                                              1638
Leu
545
```

<210> SEQ ID NO 37
<211> LENGTH: 545
<212> TYPE: PRT
<213> ORGANISM: Artificial Sequence
<220> FEATURE:
<223> OTHER INFORMATION: Synthetic Construct

<400> SEQUENCE: 37

```
Met Gly Met Ser Gly Tyr Val Asn Asn Pro Glu Ala Thr Asn Ala Leu
1               5                   10                  15

Ile Asp Lys Asp Gly Trp Leu His Ser Gly Asp Ile Ala Tyr Trp Asp
            20                  25                  30

Glu Asp Glu His Phe Phe Ile Val Asp Arg Leu Lys Ser Leu Ile Lys
        35                  40                  45

Tyr Lys Gly Tyr Gln Val Ala Pro Ala Glu Leu Glu Ser Ile Leu Leu
    50                  55                  60

Gln His Pro Asn Ile Phe Asp Ala Gly Val Ala Gly Leu Pro Asp Asp
65                  70                  75                  80

Asp Ala Gly Glu Leu Pro Ala Ala Val Val Val Leu Glu His Gly Lys
                85                  90                  95

Thr Met Thr Glu Lys Glu Ile Val Asp Tyr Val Ala Ser Gln Val Thr
            100                 105                 110

Thr Ala Lys Lys Leu Arg Gly Gly Val Phe Val Asp Glu Val Pro
        115                 120                 125

Lys Gly Leu Thr Gly Lys Leu Asp Ala Arg Lys Ile Arg Glu Ile Leu
    130                 135                 140

Ile Lys Ala Lys Lys Gly Gly Lys Ser Lys Leu Gly Leu Gln Gly Gly
145                 150                 155                 160

Ser Gly Gly Gly Gly Ser Gly Gly Gly Ser Val Asp Ser Thr Trp
                165                 170                 175

Glu Leu Pro Arg Asp Gln Leu Val Leu Gly Arg Thr Leu Gly Ser Gly
            180                 185                 190

Ala Phe Gly Gln Val Val Glu Ala Thr Ala His Gly Leu Ser His Ser
        195                 200                 205

Gln Ala Thr Met Lys Val Ala Val Lys Met Leu Lys Ser Thr Ala Arg
    210                 215                 220

Ser Ser Glu Lys Gln Ala Leu Met Ser Glu Leu Lys Ile Met Ser His
225                 230                 235                 240

Leu Gly Pro His Leu Asn Val Val Asn Leu Leu Gly Ala Cys Thr Lys
                245                 250                 255

Gly Gly Pro Ile Tyr Ile Ile Thr Glu Tyr Cys Arg Tyr Gly Asp Leu
            260                 265                 270

Val Asp Tyr Leu His Arg Asn Lys His Thr Phe Leu Gln His His Ser
        275                 280                 285

Asp Lys Arg Arg Pro Pro Ser Ala Glu Leu Tyr Ser Asn Ala Leu Pro
    290                 295                 300

Val Gly Leu Pro Leu Pro Ser His Val Ser Leu Thr Gly Glu Ser Asp
305                 310                 315                 320

Gly Gly Tyr Met Asp Met Ser Lys Asp Glu Ser Val Asp Tyr Val Pro
                325                 330                 335

Met Leu Asp Met Lys Gly Asp Val Lys Tyr Ala Asp Ile Glu Ser Ser
            340                 345                 350
```

```
Asn Tyr Met Ala Pro Tyr Asp Asn Tyr Val Pro Ser Ala Pro Glu Arg
        355                 360                 365

Thr Cys Arg Ala Thr Leu Ile Asn Glu Ser Pro Val Leu Ser Tyr Met
    370                 375                 380

Asp Leu Val Gly Phe Ser Tyr Gln Val Ala Asn Gly Met Glu Phe Leu
385                 390                 395                 400

Ala Ser Lys Asn Cys Val His Arg Asp Leu Ala Ala Arg Asn Val Leu
                405                 410                 415

Ile Cys Glu Gly Lys Leu Val Lys Ile Cys Asp Phe Gly Leu Ala Arg
            420                 425                 430

Asp Ile Met Arg Asp Ser Asn Tyr Ile Ser Lys Gly Ser Thr Phe Leu
                435                 440                 445

Pro Leu Lys Trp Met Ala Pro Glu Ser Ile Phe Asn Ser Leu Tyr Thr
        450                 455                 460

Thr Leu Ser Asp Val Trp Ser Phe Gly Ile Leu Leu Trp Glu Ile Phe
465                 470                 475                 480

Thr Leu Gly Gly Thr Pro Tyr Pro Glu Leu Pro Met Asn Glu Gln Phe
                485                 490                 495

Tyr Asn Ala Ile Lys Arg Gly Tyr Arg Met Ala Gln Pro Ala His Ala
            500                 505                 510

Ser Asp Glu Ile Tyr Glu Ile Met Gln Lys Cys Trp Glu Glu Lys Phe
        515                 520                 525

Glu Ile Arg Pro Pro Phe Ser Gln Leu Val Leu Leu Leu Glu Arg Leu
530                 535                 540

Leu
545

<210> SEQ ID NO 38
<211> LENGTH: 1416
<212> TYPE: DNA
<213> ORGANISM: Artificial Sequence
<220> FEATURE:
<223> OTHER INFORMATION: Synthetic construct:  Cfluc-CDK2 coding
      sequence
<220> FEATURE:
<221> NAME/KEY: CDS
<222> LOCATION: (1)..(1413)

<400> SEQUENCE: 38 atg ggt atg tcc ggt tat gta aac aat ccg gaa gcg acc aac gcc ttg      48
Met Gly Met Ser Gly Tyr Val Asn Asn Pro Glu Ala Thr Asn Ala Leu
1               5                   10                  15 att gac aag gat gga tgg cta cat tct gga gac ata gct tac tgg gac      96
Ile Asp Lys Asp Gly Trp Leu His Ser Gly Asp Ile Ala Tyr Trp Asp
            20                  25                  30 gaa gac gaa cac ttc ttc ata gtt gac cgc ttg aag tct tta att aaa     144
Glu Asp Glu His Phe Phe Ile Val Asp Arg Leu Lys Ser Leu Ile Lys
        35                  40                  45 tac aaa gga tat cag gtg gcc ccc gct gaa ttg gaa tcg ata ttg tta     192
Tyr Lys Gly Tyr Gln Val Ala Pro Ala Glu Leu Glu Ser Ile Leu Leu
    50                  55                  60 caa cac ccc aac atc ttc gac gcg ggc gtg gca ggt ctt ccc gac gat     240
Gln His Pro Asn Ile Phe Asp Ala Gly Val Ala Gly Leu Pro Asp Asp
65                  70                  75                  80 gac gcc ggt gaa ctt ccc gcc gcc gtt gtt gtt ttg gag cac gga aag     288
Asp Ala Gly Glu Leu Pro Ala Ala Val Val Val Leu Glu His Gly Lys
                85                  90                  95 acg atg acg gaa aaa gag atc gtg gat tac gtc gcc agt caa gta aca     336
Thr Met Thr Glu Lys Glu Ile Val Asp Tyr Val Ala Ser Gln Val Thr
            100                 105                 110
```

| | | |
|---|---|---|
| acc gcg aaa aag ttg cgc gga gga gtt gtg ttt gtg gac gaa gta ccg<br>Thr Ala Lys Lys Leu Arg Gly Gly Val Val Phe Val Asp Glu Val Pro<br>              115                    120                    125 | 384 |
| aaa ggt ctt acc gga aaa ctc gac gca aga aaa atc aga gag atc ctc<br>Lys Gly Leu Thr Gly Lys Leu Asp Ala Arg Lys Ile Arg Glu Ile Leu<br>130                    135                    140 | 432 |
| ata aag gcc aag aag ggc gga aag tcc aaa ttg ggc ctg cag ggc ggt<br>Ile Lys Ala Lys Lys Gly Gly Lys Ser Lys Leu Gly Leu Gln Gly Gly<br>145                    150                    155                    160 | 480 |
| tca ggc ggt ggg ggt tct ggc ggg ggt ggg agc gtc gac atg gag aac<br>Ser Gly Gly Gly Gly Ser Gly Gly Gly Gly Ser Val Asp Met Glu Asn<br>              165                    170                    175 | 528 |
| ttc caa aag gtg gaa aag atc gga gag ggc acg tac gga gtt gtg tac<br>Phe Gln Lys Val Glu Lys Ile Gly Glu Gly Thr Tyr Gly Val Val Tyr<br>            180                    185                    190 | 576 |
| aaa gcc aga aac aag ttg acg gga gag gtg gtg gcg ctt aag aaa atc<br>Lys Ala Arg Asn Lys Leu Thr Gly Glu Val Val Ala Leu Lys Lys Ile<br>        195                    200                    205 | 624 |
| cgc ctg gac act gag act gag ggt gtg ccc agt act gcc atc cga gag<br>Arg Leu Asp Thr Glu Thr Glu Gly Val Pro Ser Thr Ala Ile Arg Glu<br>210                    215                    220 | 672 |
| atc tct ctg ctt aag gag ctt aac cat cct aat att gtc aag ctg ctg<br>Ile Ser Leu Leu Lys Glu Leu Asn His Pro Asn Ile Val Lys Leu Leu<br>225                    230                    235                    240 | 720 |
| gat gtc att cac aca gaa aat aaa ctc tac ctg gtt ttt gaa ttt ctg<br>Asp Val Ile His Thr Glu Asn Lys Leu Tyr Leu Val Phe Glu Phe Leu<br>              245                    250                    255 | 768 |
| cac caa gat ctc aag aaa ttc atg gat gcc tct gct ctc act ggc att<br>His Gln Asp Leu Lys Lys Phe Met Asp Ala Ser Ala Leu Thr Gly Ile<br>            260                    265                    270 | 816 |
| cct ctt ccc ctc atc aag agc tat ctg ttc cag ctg ctc cag ggc cta<br>Pro Leu Pro Leu Ile Lys Ser Tyr Leu Phe Gln Leu Leu Gln Gly Leu<br>        275                    280                    285 | 864 |
| gct ttc tgc cat tct cat cgg gtc ctc cac cga gac ctt aaa cct cag<br>Ala Phe Cys His Ser His Arg Val Leu His Arg Asp Leu Lys Pro Gln<br>290                    295                    300 | 912 |
| aat ctg ctt att aac aca gag ggg gcc atc aag cta gca gac ttt gga<br>Asn Leu Leu Ile Asn Thr Glu Gly Ala Ile Lys Leu Ala Asp Phe Gly<br>305                    310                    315                    320 | 960 |
| cta gcc aga gct ttt gga gtc cct gtt cgt act tac acc cat gag gtg<br>Leu Ala Arg Ala Phe Gly Val Pro Val Arg Thr Tyr Thr His Glu Val<br>                  325                    330                    335 | 1008 |
| gtg acc ctg tgg tac cga gct cct gaa atc ctc ctg ggc tgc aaa tat<br>Val Thr Leu Trp Tyr Arg Ala Pro Glu Ile Leu Leu Gly Cys Lys Tyr<br>            340                    345                    350 | 1056 |
| tat tcc aca gct gtg gac atc tgg agc ctg ggc tgc atc ttt gct gag<br>Tyr Ser Thr Ala Val Asp Ile Trp Ser Leu Gly Cys Ile Phe Ala Glu<br>        355                    360                    365 | 1104 |
| atg gtg act cgc cgg gcc cta ttc cct gga gat tct gag att gac cag<br>Met Val Thr Arg Arg Ala Leu Phe Pro Gly Asp Ser Glu Ile Asp Gln<br>370                    375                    380 | 1152 |
| ctc ttc cgg atc ttt cgg act ctg ggg acc cca gat gag gtg gtg tgg<br>Leu Phe Arg Ile Phe Arg Thr Leu Gly Thr Pro Asp Glu Val Val Trp<br>385                    390                    395                    400 | 1200 |
| cca gga gtt act tct atg cct gat tac aag cca agt ttc ccc aag tgg<br>Pro Gly Val Thr Ser Met Pro Asp Tyr Lys Pro Ser Phe Pro Lys Trp<br>                  405                    410                    415 | 1248 |
| gcc cgg caa gat ttt agt aaa gtt gta cct ccc ctg gat gaa gat gga<br>Ala Arg Gln Asp Phe Ser Lys Val Val Pro Pro Leu Asp Glu Asp Gly<br>        420                    425                    430 | 1296 |

```
cgg agc ttg tta tcg caa atg ctg cac tac gac cct aac aag cgg att      1344
Arg Ser Leu Leu Ser Gln Met Leu His Tyr Asp Pro Asn Lys Arg Ile
        435                 440                 445 tcg gcc aag gca gcc ctg gct cac cct ttc ttc cag gat gtg acc aag      1392
Ser Ala Lys Ala Ala Leu Ala His Pro Phe Phe Gln Asp Val Thr Lys
450                 455                 460 cca gta ccc cat ctt cga ctc tga                                      1416
Pro Val Pro His Leu Arg Leu
465                 470

<210> SEQ ID NO 39
<211> LENGTH: 471
<212> TYPE: PRT
<213> ORGANISM: Artificial Sequence
<220> FEATURE:
<223> OTHER INFORMATION: Synthetic Construct

<400> SEQUENCE: 39

Met Gly Met Ser Gly Tyr Val Asn Asn Pro Glu Ala Thr Asn Ala Leu
1               5                  10                  15

Ile Asp Lys Asp Gly Trp Leu His Ser Gly Asp Ile Ala Tyr Trp Asp
            20                  25                  30

Glu Asp Glu His Phe Phe Ile Val Asp Arg Leu Lys Ser Leu Ile Lys
        35                  40                  45

Tyr Lys Gly Tyr Gln Val Ala Pro Ala Glu Leu Ser Ile Leu Leu
    50                  55                  60

Gln His Pro Asn Ile Phe Asp Ala Gly Val Ala Gly Leu Pro Asp Asp
65                  70                  75                  80

Asp Ala Gly Glu Leu Pro Ala Ala Val Val Leu Glu His Gly Lys
                85                  90                  95

Thr Met Thr Glu Lys Glu Ile Val Asp Tyr Val Ala Ser Gln Val Thr
            100                 105                 110

Thr Ala Lys Lys Leu Arg Gly Gly Val Val Phe Val Asp Glu Val Pro
        115                 120                 125

Lys Gly Leu Thr Gly Lys Leu Asp Ala Arg Lys Ile Arg Glu Ile Leu
    130                 135                 140

Ile Lys Ala Lys Lys Gly Gly Lys Ser Lys Leu Gly Leu Gln Gly Gly
145                 150                 155                 160

Ser Gly Gly Gly Gly Ser Gly Gly Gly Ser Val Asp Met Glu Asn
                165                 170                 175

Phe Gln Lys Val Glu Lys Ile Gly Glu Gly Thr Tyr Gly Val Val Tyr
            180                 185                 190

Lys Ala Arg Asn Lys Leu Thr Gly Glu Val Val Ala Leu Lys Lys Ile
        195                 200                 205

Arg Leu Asp Thr Glu Thr Glu Gly Val Pro Ser Thr Ala Ile Arg Glu
    210                 215                 220

Ile Ser Leu Leu Lys Glu Leu Asn His Pro Asn Ile Val Lys Leu Leu
225                 230                 235                 240

Asp Val Ile His Thr Glu Asn Lys Leu Tyr Leu Val Phe Glu Phe Leu
                245                 250                 255

His Gln Asp Leu Lys Lys Phe Met Asp Ala Ser Ala Leu Thr Gly Ile
            260                 265                 270

Pro Leu Pro Leu Ile Lys Ser Tyr Leu Phe Gln Leu Leu Gln Gly Leu
        275                 280                 285

Ala Phe Cys His Ser His Arg Val Leu His Arg Asp Leu Lys Pro Gln
    290                 295                 300
```

```
Asn Leu Leu Ile Asn Thr Glu Gly Ala Ile Lys Leu Ala Asp Phe Gly
305                 310                 315                 320

Leu Ala Arg Ala Phe Gly Val Pro Val Arg Thr Tyr Thr His Glu Val
                325                 330                 335

Val Thr Leu Trp Tyr Arg Ala Pro Glu Ile Leu Leu Gly Cys Lys Tyr
            340                 345                 350

Tyr Ser Thr Ala Val Asp Ile Trp Ser Leu Gly Cys Ile Phe Ala Glu
        355                 360                 365

Met Val Thr Arg Arg Ala Leu Phe Pro Gly Asp Ser Glu Ile Asp Gln
    370                 375                 380

Leu Phe Arg Ile Phe Arg Thr Leu Gly Thr Pro Asp Glu Val Val Trp
385                 390                 395                 400

Pro Gly Val Thr Ser Met Pro Asp Tyr Lys Pro Ser Phe Pro Lys Trp
                405                 410                 415

Ala Arg Gln Asp Phe Ser Lys Val Val Pro Pro Leu Asp Glu Asp Gly
                420                 425                 430

Arg Ser Leu Leu Ser Gln Met Leu His Tyr Asp Pro Asn Lys Arg Ile
                435                 440                 445

Ser Ala Lys Ala Ala Leu Ala His Pro Phe Phe Gln Asp Val Thr Lys
    450                 455                 460

Pro Val Pro His Leu Arg Leu
465                 470

<210> SEQ ID NO 40
<211> LENGTH: 1431
<212> TYPE: DNA
<213> ORGANISM: Artificial Sequence
<220> FEATURE:
<223> OTHER INFORMATION: Synthetic construct:  CFluc-FYN coding
      sequence
<220> FEATURE:
<221> NAME/KEY: CDS
<222> LOCATION: (1)..(1428)

<400> SEQUENCE: 40 atg ggt atg tcc ggt tat gta aac aat ccg gaa gcg acc aac gcc ttg      48
Met Gly Met Ser Gly Tyr Val Asn Asn Pro Glu Ala Thr Asn Ala Leu
1               5                   10                  15 att gac aag gat gga tgg cta cat tct gga gac ata gct tac tgg gac      96
Ile Asp Lys Asp Gly Trp Leu His Ser Gly Asp Ile Ala Tyr Trp Asp
            20                  25                  30 gaa gac gaa cac ttc ttc ata gtt gac cgc ttg aag tct tta att aaa     144
Glu Asp Glu His Phe Phe Ile Val Asp Arg Leu Lys Ser Leu Ile Lys
        35                  40                  45 tac aaa gga tat cag gtg gcc ccc gct gaa ttg gaa tcg ata ttg tta     192
Tyr Lys Gly Tyr Gln Val Ala Pro Ala Glu Leu Glu Ser Ile Leu Leu
    50                  55                  60 caa cac ccc aac atc ttc gac gcg ggc gtg gca ggt ctt ccc gac gat     240
Gln His Pro Asn Ile Phe Asp Ala Gly Val Ala Gly Leu Pro Asp Asp
65                  70                  75                  80 gac gcc ggt gaa ctt ccc gcc gcc gtt gtt gtt ttg gag cac gga aag     288
Asp Ala Gly Glu Leu Pro Ala Ala Val Val Val Leu Glu His Gly Lys
                85                  90                  95 acg atg acg gaa aaa gag atc gtg gat tac gtc gcc agt caa gta aca     336
Thr Met Thr Glu Lys Glu Ile Val Asp Tyr Val Ala Ser Gln Val Thr
            100                 105                 110 acc gcg aaa aag ttg cgc gga gga gtt gtg ttt gtg gac gaa gta ccg     384
Thr Ala Lys Lys Leu Arg Gly Gly Val Val Phe Val Asp Glu Val Pro
        115                 120                 125 aaa ggt ctt acc gga aaa ctc gac gca aga aaa atc aga gag atc ctc     432
```

```
                Lys Gly Leu Thr Gly Lys Leu Asp Ala Arg Lys Ile Arg Glu Ile Leu
                    130                 135                 140 ata aag gcc aag aag ggc gga aag tcc aaa ttg ggc ctg cag ggc ggt            480
Ile Lys Ala Lys Lys Gly Gly Lys Ser Lys Leu Gly Leu Gln Gly Gly
145                 150                 155                 160 tca ggc ggt ggg ggt tct ggg ggt ggg agc gtc gac gct gca ggt               528
Ser Gly Gly Gly Gly Ser Gly Gly Gly Ser Val Asp Ala Ala Gly
                165                 170                 175 ctc tgc tgc cgc cta gta gtt ccc tgt cac aaa ggg atg cca agg ctt           576
Leu Cys Cys Arg Leu Val Val Pro Cys His Lys Gly Met Pro Arg Leu
            180                 185                 190 acc gat ctg tct gtc aaa acc aaa gat gtc tgg gaa atc cct cga gaa           624
Thr Asp Leu Ser Val Lys Thr Lys Asp Val Trp Glu Ile Pro Arg Glu
        195                 200                 205 tcc ctg cag ttg atc aag aga ctg gga aat ggg cag ttt ggg gaa gta           672
Ser Leu Gln Leu Ile Lys Arg Leu Gly Asn Gly Gln Phe Gly Glu Val
    210                 215                 220 tgg atg ggt acc tgg aat gga aac aca aaa gta gcc ata aag act ctt           720
Trp Met Gly Thr Trp Asn Gly Asn Thr Lys Val Ala Ile Lys Thr Leu
225                 230                 235                 240 aaa cca ggc aca atg tcc ccc gaa tca ttc ctt gag gaa gcg cag atc           768
Lys Pro Gly Thr Met Ser Pro Glu Ser Phe Leu Glu Glu Ala Gln Ile
                245                 250                 255 atg aag aag ctg aag cac gac aag ctg gtc cag ctc tat gca gtg gtg           816
Met Lys Lys Leu Lys His Asp Lys Leu Val Gln Leu Tyr Ala Val Val
            260                 265                 270 tct gag gag ccc atc tac atc gtc acc gag tat atg aac aaa gga agt           864
Ser Glu Glu Pro Ile Tyr Ile Val Thr Glu Tyr Met Asn Lys Gly Ser
        275                 280                 285 tta ctg gat ttc tta aaa gat gga gaa gga aga gct ctg aaa tta cca           912
Leu Leu Asp Phe Leu Lys Asp Gly Glu Gly Arg Ala Leu Lys Leu Pro
    290                 295                 300 aat ctt gtg gac atg gca gca cag gtg gct gca gga atg gct tac atc           960
Asn Leu Val Asp Met Ala Ala Gln Val Ala Ala Gly Met Ala Tyr Ile
305                 310                 315                 320 gag cgc atg aat tat atc cat aga gat ctg cga tca gca aac att cta          1008
Glu Arg Met Asn Tyr Ile His Arg Asp Leu Arg Ser Ala Asn Ile Leu
                325                 330                 335 gtg ggg aat gga ctc ata tgc aag att gct gac ttc gga ttg gcc cga          1056
Val Gly Asn Gly Leu Ile Cys Lys Ile Ala Asp Phe Gly Leu Ala Arg
            340                 345                 350 ttg ata gaa gac aat gag tac aca gca aga caa ggt gca aag ttc ccc          1104
Leu Ile Glu Asp Asn Glu Tyr Thr Ala Arg Gln Gly Ala Lys Phe Pro
        355                 360                 365 atc aag tgg acg gcc ccc gag gca gcc ctg tac ggg agg ttc aca atc          1152
Ile Lys Trp Thr Ala Pro Glu Ala Ala Leu Tyr Gly Arg Phe Thr Ile
    370                 375                 380 aag tct gac gtg tgg tct ttt gga atc tta ctc aca gag ctg gtc acc          1200
Lys Ser Asp Val Trp Ser Phe Gly Ile Leu Leu Thr Glu Leu Val Thr
385                 390                 395                 400 aaa gga aga gtg cca tac cca ggc atg aac aac cgg gag gtg ctg gag          1248
Lys Gly Arg Val Pro Tyr Pro Gly Met Asn Asn Arg Glu Val Leu Glu
                405                 410                 415 cag gtg gag cga ggc tac agg atg ccc tgc ccg cag gac tgc ccc atc          1296
Gln Val Glu Arg Gly Tyr Arg Met Pro Cys Pro Gln Asp Cys Pro Ile
            420                 425                 430 tct ctg cat gag ctc atg atc cac tgc tgg aaa aag gac cct gaa gaa          1344
Ser Leu His Glu Leu Met Ile His Cys Trp Lys Lys Asp Pro Glu Glu
        435                 440                 445 cgc ccc act ttt gag tac ttg cag agc ttc ctg gaa gac tac ttt acc          1392
```

```
Arg Pro Thr Phe Glu Tyr Leu Gln Ser Phe Leu Glu Asp Tyr Phe Thr
        450                 455                 460 gcg aca gag ccc cag tac caa cct ggt gaa aac ctg taa              1431
Ala Thr Glu Pro Gln Tyr Gln Pro Gly Glu Asn Leu
465                 470                 475
```

<210> SEQ ID NO 41
<211> LENGTH: 476
<212> TYPE: PRT
<213> ORGANISM: Artificial Sequence
<220> FEATURE:
<223> OTHER INFORMATION: Synthetic Construct

<400> SEQUENCE: 41

```
Met Gly Met Ser Gly Tyr Val Asn Asn Pro Glu Ala Thr Asn Ala Leu
1               5                   10                  15

Ile Asp Lys Asp Gly Trp Leu His Ser Gly Asp Ile Ala Tyr Trp Asp
                20                  25                  30

Glu Asp His Phe Phe Ile Val Asp Arg Leu Lys Ser Leu Ile Lys
            35                  40                  45

Tyr Lys Gly Tyr Gln Val Ala Pro Ala Glu Leu Glu Ser Ile Leu Leu
50                  55                  60

Gln His Pro Asn Ile Phe Asp Ala Gly Val Ala Gly Leu Pro Asp Asp
65                  70                  75                  80

Asp Ala Gly Glu Leu Pro Ala Ala Val Val Val Leu Glu His Gly Lys
                85                  90                  95

Thr Met Thr Glu Lys Glu Ile Val Asp Tyr Val Ala Ser Gln Val Thr
            100                 105                 110

Thr Ala Lys Lys Leu Arg Gly Gly Val Val Phe Val Asp Glu Val Pro
        115                 120                 125

Lys Gly Leu Thr Gly Lys Leu Asp Ala Arg Lys Ile Arg Glu Ile Leu
130                 135                 140

Ile Lys Ala Lys Lys Gly Gly Lys Ser Lys Leu Gly Leu Gln Gly Gly
145                 150                 155                 160

Ser Gly Gly Gly Gly Ser Gly Gly Gly Ser Val Asp Ala Ala Gly
                165                 170                 175

Leu Cys Cys Arg Leu Val Val Pro Cys His Lys Gly Met Pro Arg Leu
            180                 185                 190

Thr Asp Leu Ser Val Lys Thr Lys Asp Val Trp Glu Ile Pro Arg Glu
        195                 200                 205

Ser Leu Gln Leu Ile Lys Arg Leu Gly Asn Gly Gln Phe Gly Glu Val
210                 215                 220

Trp Met Gly Thr Trp Asn Gly Asn Thr Lys Val Ala Ile Lys Thr Leu
225                 230                 235                 240

Lys Pro Gly Thr Met Ser Pro Glu Ser Phe Leu Glu Glu Ala Gln Ile
                245                 250                 255

Met Lys Lys Leu Lys His Asp Lys Leu Val Gln Leu Tyr Ala Val Val
            260                 265                 270

Ser Glu Glu Pro Ile Tyr Ile Val Thr Glu Tyr Met Asn Lys Gly Ser
        275                 280                 285

Leu Leu Asp Phe Leu Lys Asp Gly Glu Gly Arg Ala Leu Lys Leu Pro
290                 295                 300

Asn Leu Val Asp Met Ala Ala Gln Val Ala Ala Gly Met Ala Tyr Ile
305                 310                 315                 320

Glu Arg Met Asn Tyr Ile His Arg Asp Leu Arg Ser Ala Asn Ile Leu
                325                 330                 335
```

-continued

```
Val Gly Asn Gly Leu Ile Cys Lys Ile Ala Asp Phe Gly Leu Ala Arg
            340                 345                 350

Leu Ile Glu Asp Asn Glu Tyr Thr Ala Arg Gln Gly Ala Lys Phe Pro
        355                 360                 365

Ile Lys Trp Thr Ala Pro Glu Ala Ala Leu Tyr Gly Arg Phe Thr Ile
370                 375                 380

Lys Ser Asp Val Trp Ser Phe Gly Ile Leu Leu Thr Glu Leu Val Thr
385                 390                 395                 400

Lys Gly Arg Val Pro Tyr Pro Gly Met Asn Asn Arg Glu Val Leu Glu
                405                 410                 415

Gln Val Glu Arg Gly Tyr Arg Met Pro Cys Pro Gln Cys Pro Ile
            420                 425                 430

Ser Leu His Glu Leu Met Ile His Cys Trp Lys Lys Asp Pro Glu Glu
        435                 440                 445

Arg Pro Thr Phe Glu Tyr Leu Gln Ser Phe Leu Glu Asp Tyr Phe Thr
    450                 455                 460

Ala Thr Glu Pro Gln Tyr Gln Pro Gly Glu Asn Leu
465                 470                 475
```

<210> SEQ ID NO 42
<211> LENGTH: 1821
<212> TYPE: DNA
<213> ORGANISM: Artificial Sequence
<220> FEATURE:
<223> OTHER INFORMATION: Synthetic construct: DHFR-NFluc(2-416)
<220> FEATURE:
<221> NAME/KEY: CDS
<222> LOCATION: (1)..(1812)

<400> SEQUENCE: 42

```
atg ggc agc agc cat cac cat cat cac cac agc cag gat ccg atc agt       48
Met Gly Ser Ser His His His His His His Ser Gln Asp Pro Ile Ser
1               5                   10                  15 ctg att gcg gcg tta gcg gta gat cgc gtt atc ggc atg gaa aac gcc       96
Leu Ile Ala Ala Leu Ala Val Asp Arg Val Ile Gly Met Glu Asn Ala
            20                  25                  30 atg ccg tgg aac ctg cct gcc gat ctc gcc tgg ttt aaa cgc aac acc      144
Met Pro Trp Asn Leu Pro Ala Asp Leu Ala Trp Phe Lys Arg Asn Thr
        35                  40                  45 tta aat aaa ccc gtg att atg ggc cgc cat acc tgg gaa tca atc ggt      192
Leu Asn Lys Pro Val Ile Met Gly Arg His Thr Trp Glu Ser Ile Gly
    50                  55                  60 cgt ccg ttg cca gga cgc aaa aat att atc ctc agc agt caa ccg ggt      240
Arg Pro Leu Pro Gly Arg Lys Asn Ile Ile Leu Ser Ser Gln Pro Gly
65                  70                  75                  80 acg gac gat cgc gta acg tgg gtg aag tcg gtg gat gaa gcc atc gcg      288
Thr Asp Asp Arg Val Thr Trp Val Lys Ser Val Asp Glu Ala Ile Ala
                85                  90                  95 gcg tgt ggt gac gta cca gaa atc atg gtg att ggc ggc ggt cgc gtt      336
Ala Cys Gly Asp Val Pro Glu Ile Met Val Ile Gly Gly Gly Arg Val
            100                 105                 110 tat gaa cag ttc ttg cca aaa gcg caa aaa ctg tat ctg acg cat atc      384
Tyr Glu Gln Phe Leu Pro Lys Ala Gln Lys Leu Tyr Leu Thr His Ile
        115                 120                 125 gac gca gaa gtg gaa ggc gac acc cat ttc ccg gat tac gag ccg gat      432
Asp Ala Glu Val Glu Gly Asp Thr His Phe Pro Asp Tyr Glu Pro Asp
    130                 135                 140 gac tgg gaa tcg gta ttc agc gaa ttc cac gat gct gat gcg cag aac      480
Asp Trp Glu Ser Val Phe Ser Glu Phe His Asp Ala Asp Ala Gln Asn
145                 150                 155                 160
```

|  |  |
|---|---|
| tct cac agc tat tgc ttt gag att ctg gag cgg cgg acc ggt ggg ggt<br>Ser His Ser Tyr Cys Phe Glu Ile Leu Glu Arg Arg Thr Gly Gly Gly<br>165 170 175 | 528 |
| ggc ggt tca ggc ggt ggg ggt tct ggt ggg ggt ggt acc gaa gac gcc<br>Gly Gly Ser Gly Gly Gly Gly Ser Gly Gly Gly Gly Thr Glu Asp Ala<br>180 185 190 | 576 |
| aaa aac ata aag aaa ggc ccg gcg cca ttc tat cct cta gag gat gga<br>Lys Asn Ile Lys Lys Gly Pro Ala Pro Phe Tyr Pro Leu Glu Asp Gly<br>195 200 205 | 624 |
| acc gct gga gag caa ctg cat aag gct atg aag aga tac gcc ctg gtt<br>Thr Ala Gly Glu Gln Leu His Lys Ala Met Lys Arg Tyr Ala Leu Val<br>210 215 220 | 672 |
| cct gga aca att gct ttt aca gat gca cat atc gag gtg aac atc acg<br>Pro Gly Thr Ile Ala Phe Thr Asp Ala His Ile Glu Val Asn Ile Thr<br>225 230 235 240 | 720 |
| tac gcg gaa tac ttc gaa atg tcc gtt cgg ttg gca gaa gct atg aaa<br>Tyr Ala Glu Tyr Phe Glu Met Ser Val Arg Leu Ala Glu Ala Met Lys<br>245 250 255 | 768 |
| cga tat ggg ctg gat aca aat cac aga atc gtc gta tgc agt gaa aac<br>Arg Tyr Gly Leu Asp Thr Asn His Arg Ile Val Val Cys Ser Glu Asn<br>260 265 270 | 816 |
| tct ctt caa ttc ttt atg ccg gtg ttg ggc gcg tta ttt atc gga gtt<br>Ser Leu Gln Phe Phe Met Pro Val Leu Gly Ala Leu Phe Ile Gly Val<br>275 280 285 | 864 |
| gca gtt gcg ccc gcg aac gac att tat aat gaa cgt gaa ttg ctc aac<br>Ala Val Ala Pro Ala Asn Asp Ile Tyr Asn Glu Arg Glu Leu Leu Asn<br>290 295 300 | 912 |
| agt atg aac att tcg cag cct acc gta gtg ttt gtt tcc aaa aag ggg<br>Ser Met Asn Ile Ser Gln Pro Thr Val Val Phe Val Ser Lys Lys Gly<br>305 310 315 320 | 960 |
| ttg caa aaa att ttg aac gtg caa aaa aaa tta cca ata atc cag aaa<br>Leu Gln Lys Ile Leu Asn Val Gln Lys Lys Leu Pro Ile Ile Gln Lys<br>325 330 335 | 1008 |
| att att atc atg gat tct aaa acg gat tac cag gga ttt cag tcg atg<br>Ile Ile Ile Met Asp Ser Lys Thr Asp Tyr Gln Gly Phe Gln Ser Met<br>340 345 350 | 1056 |
| tac acg ttc gtc aca tct cat cta cct ccc ggt ttt aat gaa tac gat<br>Tyr Thr Phe Val Thr Ser His Leu Pro Pro Gly Phe Asn Glu Tyr Asp<br>355 360 365 | 1104 |
| ttt gta cca gag tcc ttt gat cgt gac aaa aca att gca ctg aca atg<br>Phe Val Pro Glu Ser Phe Asp Arg Asp Lys Thr Ile Ala Leu Thr Met<br>370 375 380 | 1152 |
| aat tcc tct gga tct act ggg tta cct aag ggt gtg gcc ctt ccg cat<br>Asn Ser Ser Gly Ser Thr Gly Leu Pro Lys Gly Val Ala Leu Pro His<br>385 390 395 400 | 1200 |
| aga act gcc tgc gtc aga ttc tcg cat gcc aga gat cct att ttt ggc<br>Arg Thr Ala Cys Val Arg Phe Ser His Ala Arg Asp Pro Ile Phe Gly<br>405 410 415 | 1248 |
| aat caa atc att ccg gat act gcg att tta agt gtt gtt cca ttc cat<br>Asn Gln Ile Ile Pro Asp Thr Ala Ile Leu Ser Val Val Pro Phe His<br>420 425 430 | 1296 |
| cac ggt ttt gga atg ttt act aca ctc gga tat ttg ata tgt gga ttt<br>His Gly Phe Gly Met Phe Thr Thr Leu Gly Tyr Leu Ile Cys Gly Phe<br>435 440 445 | 1344 |
| cga gtc gtc tta atg tat aga ttt gaa gaa gag ctg ttt tta cga tcc<br>Arg Val Val Leu Met Tyr Arg Phe Glu Glu Glu Leu Phe Leu Arg Ser<br>450 455 460 | 1392 |
| ctt cag gat tac aaa att caa agt gcg ttg cta gta cca acc cta ttt<br>Leu Gln Asp Tyr Lys Ile Gln Ser Ala Leu Leu Val Pro Thr Leu Phe<br>465 470 475 480 | 1440 |

```
tca ttc ttc gcc aaa agc act ctg att gac aaa tac gat tta tct aat    1488
Ser Phe Phe Ala Lys Ser Thr Leu Ile Asp Lys Tyr Asp Leu Ser Asn
                485                 490                 495 tta cac gaa att gct tct ggg ggc gca cct ctt tcg aaa gaa gtc ggg    1536
Leu His Glu Ile Ala Ser Gly Gly Ala Pro Leu Ser Lys Glu Val Gly
            500                 505                 510 gaa gcg gtt gca aaa cgc ttc cat ctt cca ggg ata cga caa gga tat    1584
Glu Ala Val Ala Lys Arg Phe His Leu Pro Gly Ile Arg Gln Gly Tyr
        515                 520                 525 ggg ctc act gag act aca tca gct att ctg att aca ccc gag ggg gat    1632
Gly Leu Thr Glu Thr Thr Ser Ala Ile Leu Ile Thr Pro Glu Gly Asp
    530                 535                 540 gat aaa ccg ggc gcg gtc ggt aaa gtt gtt cca ttt ttt gaa gcg aag    1680
Asp Lys Pro Gly Ala Val Gly Lys Val Val Pro Phe Phe Glu Ala Lys
545                 550                 555                 560 gtt gtg gat ctg gat acc ggg aaa acg ctg ggc gtt aat cag aga ggc    1728
Val Val Asp Leu Asp Thr Gly Lys Thr Leu Gly Val Asn Gln Arg Gly
                565                 570                 575 gaa tta tgt gtc aga gga cct atg att atg tcc ggt tat gta aac aat    1776
Glu Leu Cys Val Arg Gly Pro Met Ile Met Ser Gly Tyr Val Asn Asn
            580                 585                 590 ccg gaa gcg acc aac gcc ttg att gac aag gat gga tgataagcg          1821
Pro Glu Ala Thr Asn Ala Leu Ile Asp Lys Asp Gly
        595                 600

<210> SEQ ID NO 43
<211> LENGTH: 604
<212> TYPE: PRT
<213> ORGANISM: Artificial Sequence
<220> FEATURE:
<223> OTHER INFORMATION: Synthetic Construct

<400> SEQUENCE: 43

Met Gly Ser Ser His His His His His His Ser Gln Asp Pro Ile Ser
1               5                   10                  15

Leu Ile Ala Ala Leu Ala Val Asp Arg Val Ile Gly Met Glu Asn Ala
            20                  25                  30

Met Pro Trp Asn Leu Pro Ala Asp Leu Ala Trp Phe Lys Arg Asn Thr
        35                  40                  45

Leu Asn Lys Pro Val Ile Met Gly Arg His Thr Trp Glu Ser Ile Gly
    50                  55                  60

Arg Pro Leu Pro Gly Arg Lys Asn Ile Ile Leu Ser Ser Gln Pro Gly
65                  70                  75                  80

Thr Asp Asp Arg Val Thr Trp Val Lys Ser Val Asp Glu Ala Ile Ala
                85                  90                  95

Ala Cys Gly Asp Val Pro Glu Ile Met Val Ile Gly Gly Gly Arg Val
            100                 105                 110

Tyr Glu Gln Phe Leu Pro Lys Ala Gln Lys Leu Tyr Leu Thr His Ile
        115                 120                 125

Asp Ala Glu Val Glu Gly Asp Thr His Phe Pro Asp Tyr Glu Pro Asp
    130                 135                 140

Asp Trp Glu Ser Val Phe Ser Glu Phe His Asp Ala Asp Ala Gln Asn
145                 150                 155                 160

Ser His Ser Tyr Cys Phe Glu Ile Leu Glu Arg Arg Thr Gly Gly Gly
                165                 170                 175

Gly Gly Ser Gly Gly Gly Gly Ser Gly Gly Gly Gly Thr Glu Asp Ala
            180                 185                 190

Lys Asn Ile Lys Lys Gly Pro Ala Pro Phe Tyr Pro Leu Glu Asp Gly
        195                 200                 205
```

Thr Ala Gly Glu Gln Leu His Lys Ala Met Lys Arg Tyr Ala Leu Val
    210                 215                 220
Pro Gly Thr Ile Ala Phe Thr Asp Ala His Ile Glu Val Asn Ile Thr
225                 230                 235                 240
Tyr Ala Glu Tyr Phe Glu Met Ser Val Arg Leu Ala Glu Ala Met Lys
                245                 250                 255
Arg Tyr Gly Leu Asp Thr Asn His Arg Ile Val Val Cys Ser Glu Asn
            260                 265                 270
Ser Leu Gln Phe Phe Met Pro Val Leu Gly Ala Leu Phe Ile Gly Val
        275                 280                 285
Ala Val Ala Pro Ala Asn Asp Ile Tyr Asn Glu Arg Glu Leu Leu Asn
    290                 295                 300
Ser Met Asn Ile Ser Gln Pro Thr Val Val Phe Val Ser Lys Lys Gly
305                 310                 315                 320
Leu Gln Lys Ile Leu Asn Val Gln Lys Lys Leu Pro Ile Ile Gln Lys
                325                 330                 335
Ile Ile Ile Met Asp Ser Lys Thr Asp Tyr Gln Gly Phe Gln Ser Met
            340                 345                 350
Tyr Thr Phe Val Thr Ser His Leu Pro Pro Gly Phe Asn Glu Tyr Asp
        355                 360                 365
Phe Val Pro Glu Ser Phe Asp Arg Asp Lys Thr Ile Ala Leu Thr Met
    370                 375                 380
Asn Ser Ser Gly Ser Thr Gly Leu Pro Lys Gly Val Ala Leu Pro His
385                 390                 395                 400
Arg Thr Ala Cys Val Arg Phe Ser His Ala Arg Asp Pro Ile Phe Gly
                405                 410                 415
Asn Gln Ile Ile Pro Asp Thr Ala Ile Leu Ser Val Val Pro Phe His
            420                 425                 430
His Gly Phe Gly Met Phe Thr Thr Leu Gly Tyr Leu Ile Cys Gly Phe
        435                 440                 445
Arg Val Val Leu Met Tyr Arg Phe Glu Glu Glu Leu Phe Leu Arg Ser
    450                 455                 460
Leu Gln Asp Tyr Lys Ile Gln Ser Ala Leu Leu Val Pro Thr Leu Phe
465                 470                 475                 480
Ser Phe Phe Ala Lys Ser Thr Leu Ile Asp Lys Tyr Asp Leu Ser Asn
                485                 490                 495
Leu His Glu Ile Ala Ser Gly Gly Ala Pro Leu Ser Lys Glu Val Gly
            500                 505                 510
Glu Ala Val Ala Lys Arg Phe His Leu Pro Gly Ile Arg Gln Gly Tyr
        515                 520                 525
Gly Leu Thr Glu Thr Thr Ser Ala Ile Leu Ile Thr Pro Glu Gly Asp
    530                 535                 540
Asp Lys Pro Gly Ala Val Gly Lys Val Val Pro Phe Phe Glu Ala Lys
545                 550                 555                 560
Val Val Asp Leu Asp Thr Gly Lys Thr Leu Gly Val Asn Gln Arg Gly
                565                 570                 575
Glu Leu Cys Val Arg Gly Pro Met Ile Met Ser Gly Tyr Val Asn Asn
            580                 585                 590
Pro Glu Ala Thr Asn Ala Leu Ile Asp Lys Asp Gly
        595                 600

<210> SEQ ID NO 44
<211> LENGTH: 1461
<212> TYPE: DNA

<213> ORGANISM: Artificial Sequence
<220> FEATURE:
<223> OTHER INFORMATION: Synthetic construct: Fos-NFluc coding
      sequence
<220> FEATURE:
<221> NAME/KEY: CDS
<222> LOCATION: (1)..(1458)

<400> SEQUENCE: 44

```
atg ggc agc agc cat cac cat cat cac cac agc cag gat ccg aat tcg         48
Met Gly Ser Ser His His His His His His Ser Gln Asp Pro Asn Ser
 1               5                  10                  15 agc tcg ctt act gat act ctt caa gct gaa act gat caa ctt gaa gat         96
Ser Ser Leu Thr Asp Thr Leu Gln Ala Glu Thr Asp Gln Leu Glu Asp
            20                  25                  30 gaa aaa agt gct ctt caa act gaa att gct aat ctt ctt aaa gaa aaa        144
Glu Lys Ser Ala Leu Gln Thr Glu Ile Ala Asn Leu Leu Lys Glu Lys
        35                  40                  45 gaa aaa ctt gaa ttt att ctt gct ggt ggt ggt tct ggt ggt ggt ggt        192
Glu Lys Leu Glu Phe Ile Leu Ala Gly Gly Gly Ser Gly Gly Gly Gly
    50                  55                  60 tct ggt ggt ggt ggt aag ctt gaa gac gcc aaa aac ata aag aaa ggc        240
Ser Gly Gly Gly Gly Lys Leu Glu Asp Ala Lys Asn Ile Lys Lys Gly
65                  70                  75                  80 ccg gcg cca ttc tat cct cta gag gat gga acc gct gga gag caa ctg        288
Pro Ala Pro Phe Tyr Pro Leu Glu Asp Gly Thr Ala Gly Glu Gln Leu
                85                  90                  95 cat aag gct atg aag aga tac gcc ctg gtt cct gga aca att gct ttt        336
His Lys Ala Met Lys Arg Tyr Ala Leu Val Pro Gly Thr Ile Ala Phe
            100                 105                 110 aca gat gca cat atc gag gtg aac atc acg tac gcg gaa tac ttc gaa        384
Thr Asp Ala His Ile Glu Val Asn Ile Thr Tyr Ala Glu Tyr Phe Glu
        115                 120                 125 atg tcc gtt cgg ttg gca gaa gct atg aaa cga tat ggg ctg aat aca        432
Met Ser Val Arg Leu Ala Glu Ala Met Lys Arg Tyr Gly Leu Asn Thr
    130                 135                 140 aat cac aga atc gtc gta tgc agt gaa aac tct ctt caa ttc ttt atg        480
Asn His Arg Ile Val Val Cys Ser Glu Asn Ser Leu Gln Phe Phe Met
145                 150                 155                 160 ccg gtg ttg ggc gcg tta ttt atc gga gtt gca gtt gcg ccc gcg aac        528
Pro Val Leu Gly Ala Leu Phe Ile Gly Val Ala Val Ala Pro Ala Asn
                165                 170                 175 gac att tat aat gaa cgt gaa ttg ctc aac agt atg aac att tcg cag        576
Asp Ile Tyr Asn Glu Arg Glu Leu Leu Asn Ser Met Asn Ile Ser Gln
            180                 185                 190 cct acc gta gtg ttt gtt tcc aaa aag ggg ttg caa aaa att ttg aac        624
Pro Thr Val Val Phe Val Ser Lys Lys Gly Leu Gln Lys Ile Leu Asn
        195                 200                 205 gtg caa aaa aaa tta cca ata atc cag aaa att att atc atg gat tct        672
Val Gln Lys Lys Leu Pro Ile Ile Gln Lys Ile Ile Ile Met Asp Ser
    210                 215                 220 aaa acg gat tac cag gga ttt cag tcg atg tac acg ttc gtc aca tct        720
Lys Thr Asp Tyr Gln Gly Phe Gln Ser Met Tyr Thr Phe Val Thr Ser
225                 230                 235                 240 cat cta cct ccc ggt ttt aat gaa tac gat ttt gta cca gag tcc ttt        768
His Leu Pro Pro Gly Phe Asn Glu Tyr Asp Phe Val Pro Glu Ser Phe
                245                 250                 255 gat cgt gac aaa aca att gca ctg ata atg aat tcc tct gga tct act        816
Asp Arg Asp Lys Thr Ile Ala Leu Ile Met Asn Ser Ser Gly Ser Thr
            260                 265                 270 ggg tta cct aag ggt gtg gcc ctt ccg cat aga act gcc tgc gtc aga        864
Gly Leu Pro Lys Gly Val Ala Leu Pro His Arg Thr Ala Cys Val Arg
```

```
                275                 280                 285
ttc tcg cat gcc aga gat cct att ttt ggc aat caa atc att ccg gat     912
Phe Ser His Ala Arg Asp Pro Ile Phe Gly Asn Gln Ile Ile Pro Asp
290                 295                 300 act gcg att tta agt gtt gtt cca ttc cat cac ggt ttt gga atg ttt     960
Thr Ala Ile Leu Ser Val Val Pro Phe His His Gly Phe Gly Met Phe
305                 310                 315                 320 act aca ctc gga tat ttg ata tgt gga ttt cga gtc gtc tta atg tat    1008
Thr Thr Leu Gly Tyr Leu Ile Cys Gly Phe Arg Val Val Leu Met Tyr
                    325                 330                 335 aga ttt gaa gaa gag ctg ttt tta cga tcc ctt cag gat tac aaa att    1056
Arg Phe Glu Glu Glu Leu Phe Leu Arg Ser Leu Gln Asp Tyr Lys Ile
                340                 345                 350 caa agt gcg ttg cta gta cca acc cta ttt tca ttc ttc gcc aaa agc    1104
Gln Ser Ala Leu Leu Val Pro Thr Leu Phe Ser Phe Phe Ala Lys Ser
            355                 360                 365 act ctg att gac aaa tac gat tta tct aat tta cac gaa att gct tct    1152
Thr Leu Ile Asp Lys Tyr Asp Leu Ser Asn Leu His Glu Ile Ala Ser
    370                 375                 380 ggg ggc gca cct ctt tcg aaa gaa gtc ggg gaa gcg gtt gca aaa cgc    1200
Gly Gly Ala Pro Leu Ser Lys Glu Val Gly Glu Ala Val Ala Lys Arg
385                 390                 395                 400 ttc cat ctt cca ggg ata cga caa gga tat ggg ctc act gag act aca    1248
Phe His Leu Pro Gly Ile Arg Gln Gly Tyr Gly Leu Thr Glu Thr Thr
                    405                 410                 415 tca gct att ctg att aca ccc gag ggg gat gat aaa ccg ggc gcg gtc    1296
Ser Ala Ile Leu Ile Thr Pro Glu Gly Asp Asp Lys Pro Gly Ala Val
                420                 425                 430 ggt aaa gtt gtt cca ttt ttt gaa gcg aag gtt gtg gat ctg gat acc    1344
Gly Lys Val Val Pro Phe Phe Glu Ala Lys Val Val Asp Leu Asp Thr
            435                 440                 445 ggg aaa acg ctg ggc gtt aat cag aga ggc gaa tta tgt gtc aga gga    1392
Gly Lys Thr Leu Gly Val Asn Gln Arg Gly Glu Leu Cys Val Arg Gly
    450                 455                 460 cct atg att atg tcc ggt tat gta aac aat ccg gaa gcg acc aac gcc    1440
Pro Met Ile Met Ser Gly Tyr Val Asn Asn Pro Glu Ala Thr Asn Ala
465                 470                 475                 480 ttg att gac aag gat gga tga                                        1461
Leu Ile Asp Lys Asp Gly
                485

<210> SEQ ID NO 45
<211> LENGTH: 486
<212> TYPE: PRT
<213> ORGANISM: Artificial Sequence
<220> FEATURE:
<223> OTHER INFORMATION: Synthetic Construct

<400> SEQUENCE: 45

Met Gly Ser Ser His His His His His His Ser Gln Asp Pro Asn Ser
1               5                   10                  15

Ser Ser Leu Thr Asp Thr Leu Gln Ala Glu Thr Asp Gln Leu Glu Asp
            20                  25                  30

Glu Lys Ser Ala Leu Gln Thr Glu Ile Ala Asn Leu Leu Lys Glu Lys
        35                  40                  45

Glu Lys Leu Glu Phe Ile Leu Ala Gly Gly Ser Gly Gly Gly Gly
    50                  55                  60

Ser Gly Gly Gly Gly Lys Leu Glu Asp Ala Lys Asn Ile Lys Lys Gly
65                  70                  75                  80

Pro Ala Pro Phe Tyr Pro Leu Glu Asp Gly Thr Ala Gly Glu Gln Leu
```

85                  90                  95
His Lys Ala Met Lys Arg Tyr Ala Leu Val Pro Gly Thr Ile Ala Phe
                100                 105                 110

Thr Asp Ala His Ile Glu Val Asn Ile Thr Tyr Ala Glu Tyr Phe Glu
                115                 120                 125

Met Ser Val Arg Leu Ala Glu Ala Met Lys Arg Tyr Gly Leu Asn Thr
                130                 135                 140

Asn His Arg Ile Val Val Cys Ser Glu Asn Ser Leu Gln Phe Phe Met
145                 150                 155                 160

Pro Val Leu Gly Ala Leu Phe Ile Gly Val Ala Val Ala Pro Ala Asn
                165                 170                 175

Asp Ile Tyr Asn Glu Arg Glu Leu Leu Asn Ser Met Asn Ile Ser Gln
                180                 185                 190

Pro Thr Val Val Phe Val Ser Lys Lys Gly Leu Gln Lys Ile Leu Asn
                195                 200                 205

Val Gln Lys Lys Leu Pro Ile Ile Gln Lys Ile Ile Met Asp Ser
210                 215                 220

Lys Thr Asp Tyr Gln Gly Phe Gln Ser Met Tyr Thr Phe Val Thr Ser
225                 230                 235                 240

His Leu Pro Pro Gly Phe Asn Glu Tyr Asp Phe Val Pro Glu Ser Phe
                245                 250                 255

Asp Arg Asp Lys Thr Ile Ala Leu Ile Met Asn Ser Ser Gly Ser Thr
                260                 265                 270

Gly Leu Pro Lys Gly Val Ala Leu Pro His Arg Thr Ala Cys Val Arg
                275                 280                 285

Phe Ser His Ala Arg Asp Pro Ile Phe Gly Asn Gln Ile Ile Pro Asp
                290                 295                 300

Thr Ala Ile Leu Ser Val Val Pro Phe His His Gly Phe Gly Met Phe
305                 310                 315                 320

Thr Thr Leu Gly Tyr Leu Ile Cys Gly Phe Arg Val Val Leu Met Tyr
                325                 330                 335

Arg Phe Glu Glu Glu Leu Phe Leu Arg Ser Leu Gln Asp Tyr Lys Ile
                340                 345                 350

Gln Ser Ala Leu Leu Val Pro Thr Leu Phe Ser Phe Phe Ala Lys Ser
                355                 360                 365

Thr Leu Ile Asp Lys Tyr Asp Leu Ser Asn Leu His Glu Ile Ala Ser
                370                 375                 380

Gly Gly Ala Pro Leu Ser Lys Glu Val Gly Glu Ala Val Ala Lys Arg
385                 390                 395                 400

Phe His Leu Pro Gly Ile Arg Gln Gly Tyr Gly Leu Thr Glu Thr Thr
                405                 410                 415

Ser Ala Ile Leu Ile Thr Pro Glu Gly Asp Asp Lys Pro Gly Ala Val
                420                 425                 430

Gly Lys Val Val Pro Phe Phe Glu Ala Lys Val Val Asp Leu Asp Thr
                435                 440                 445

Gly Lys Thr Leu Gly Val Asn Gln Arg Gly Glu Leu Cys Val Arg Gly
                450                 455                 460

Pro Met Ile Met Ser Gly Tyr Val Asn Asn Pro Glu Ala Thr Asn Ala
465                 470                 475                 480

Leu Ile Asp Lys Asp Gly
                485

<210> SEQ ID NO 46
<211> LENGTH: 30

```
<212> TYPE: DNA
<213> ORGANISM: Artificial Sequence
<220> FEATURE:
<223> OTHER INFORMATION: Synthetic construct: oligonucleotide useful
      as primer.

<400> SEQUENCE: 46
gggatacccg gggcacagcc agtaatcgag                                30

<210> SEQ ID NO 47
<211> LENGTH: 30
<212> TYPE: DNA
<213> ORGANISM: Artificial Sequence
<220> FEATURE:
<223> OTHER INFORMATION: Synthetic construct: oligonucleotide useful
      as primer

<400> SEQUENCE: 47
ccctatctcg agcgacctag cagtcgctct                                30

<210> SEQ ID NO 48
<211> LENGTH: 31
<212> TYPE: DNA
<213> ORGANISM: Artificial Sequence
<220> FEATURE:
<223> OTHER INFORMATION: Synthetic construct: oligonucleotide useful
      as primer

<400> SEQUENCE: 48
gggataggat ccggcacagc cagtaatcga g                              31

<210> SEQ ID NO 49
<211> LENGTH: 30
<212> TYPE: DNA
<213> ORGANISM: Artificial Sequence
<220> FEATURE:
<223> OTHER INFORMATION: Synthetic construct: oligonucleotide useful
      as primer

<400> SEQUENCE: 49
ccctataccg gtcgacctag cagtcgctct                                30

<210> SEQ ID NO 50
<211> LENGTH: 31
<212> TYPE: DNA
<213> ORGANISM: Artificial Sequence
<220> FEATURE:
<223> OTHER INFORMATION: Synthetic construct: oligonucleotide

<400> SEQUENCE: 50
caugguguau auagucuuuu gauauagcgg c                              31

<210> SEQ ID NO 51
<211> LENGTH: 16
<212> TYPE: DNA
<213> ORGANISM: Artificial Sequence
<220> FEATURE:
<223> OTHER INFORMATION: Synthetic construct: oligonucleotide

<400> SEQUENCE: 51
cuauauacac cauguu                                               16

<210> SEQ ID NO 52
<211> LENGTH: 15
<212> TYPE: DNA
<213> ORGANISM: Artificial Sequence
<220> FEATURE:
<223> OTHER INFORMATION: Synthetic construct: oligonucleotide
```

```
<400> SEQUENCE: 52
gccgcuauau caauu                                                    15

<210> SEQ ID NO 53
<211> LENGTH: 80
<212> TYPE: DNA
<213> ORGANISM: Artificial Sequence
<220> FEATURE:
<223> OTHER INFORMATION: Synthetic construct:  oligonucleotide useful
      as primer

<400> SEQUENCE: 53
gcagctaata cgactcacta taggaacaga ccaccatgcg gccttctctc tggaaaatga   60
tgctgaatat tgatgtgtca                                               80

<210> SEQ ID NO 54
<211> LENGTH: 53
<212> TYPE: DNA
<213> ORGANISM: Artificial Sequence
<220> FEATURE:
<223> OTHER INFORMATION: Synthetic construct:  oliognucleotide useful
      as primer

<400> SEQUENCE: 54
ccgcacacca gtaaggtgtg cggttatcat ccatccttgt caatcaaggc gtt          53

<210> SEQ ID NO 55
<211> LENGTH: 68
<212> TYPE: DNA
<213> ORGANISM: Artificial Sequence
<220> FEATURE:
<223> OTHER INFORMATION: Synthetic construct:  oligonucleotide useful
      as primer

<400> SEQUENCE: 55
gcagctaata cgactcacta taggaacaga ccaccatgtc cggttatgta aacaatccgg   60
aagcgacc                                                            68

<210> SEQ ID NO 56
<211> LENGTH: 60
<212> TYPE: DNA
<213> ORGANISM: Artificial Sequence
<220> FEATURE:
<223> OTHER INFORMATION: Synthetic construct:  oligonucleotide useful
      as primer

<400> SEQUENCE: 56
ccgcacacca gtaaggtgtg cggttcatta agctgcgcta gtagacgagt ccatgtgctg   60

<210> SEQ ID NO 57
<211> LENGTH: 16
<212> TYPE: DNA
<213> ORGANISM: Artificial Sequence
<220> FEATURE:
<223> OTHER INFORMATION: Synthetic construct:  oligonucleotide useful
      as guide RNA

<400> SEQUENCE: 57
uuguaccaca uauauc                                                   16

<210> SEQ ID NO 58
<211> LENGTH: 31
<212> TYPE: DNA
<213> ORGANISM: Artificial Sequence
<220> FEATURE:
```

```
<223> OTHER INFORMATION: Synthetic construct: oigonucleotide useful
      as target RNA

<400> SEQUENCE: 58
caugguguau auagucuuuu gauauagcgg c                               31

<210> SEQ ID NO 59
<211> LENGTH: 20
<212> TYPE: DNA
<213> ORGANISM: Artificial Sequence
<220> FEATURE:
<223> OTHER INFORMATION: Synthetic construct: oligonucleotide useful
      as half-site target RNA

<400> SEQUENCE: 59
ccgagaauug uauauauucg                                            20

<210> SEQ ID NO 60
<211> LENGTH: 61
<212> TYPE: DNA
<213> ORGANISM: Artificial Sequence
<220> FEATURE:
<223> OTHER INFORMATION: Synthetic construct: oligonucleotide useful
      as primer

<400> SEQUENCE: 60
gcagctaata cgactcacta taggcatcac gaagtggtga agttcatgga tgtctatcag  60
c                                                                61

<210> SEQ ID NO 61
<211> LENGTH: 42
<212> TYPE: DNA
<213> ORGANISM: Artificial Sequence
<220> FEATURE:
<223> OTHER INFORMATION: Synthetic construct: oligonucleotide useful
      as primer

<400> SEQUENCE: 61
ctttctttgg tctgcattca catttgttgt gctgtaggaa gc                   42

<210> SEQ ID NO 62
<211> LENGTH: 50
<212> TYPE: DNA
<213> ORGANISM: Artificial Sequence
<220> FEATURE:
<223> OTHER INFORMATION: Synthetic construct: oligonucleotide useful
      as primer

<400> SEQUENCE: 62
gcagctaata cgactcacta taggctgata gacaccaacc gctctcgggc           50

<210> SEQ ID NO 63
<211> LENGTH: 20
<212> TYPE: DNA
<213> ORGANISM: Artificial Sequence
<220> FEATURE:
<223> OTHER INFORMATION: Synthetic construct: oligonucleotide useful
      as primer

<400> SEQUENCE: 63
gtgcttgggg cccgtgcagc                                            20

<210> SEQ ID NO 64
<211> LENGTH: 66
<212> TYPE: DNA
<213> ORGANISM: Artificial Sequence
<220> FEATURE:
```

```
<223> OTHER INFORMATION: Synthetic construct:  oligonucleotide useful
      as guide

<400> SEQUENCE: 64
gaggggccgg agccgcagtg cgtcctcgca ctgcggctcc ggcccctcaa aactatatac    60
accatg                                                                66

<210> SEQ ID NO 65
<211> LENGTH: 65
<212> TYPE: DNA
<213> ORGANISM: Artificial Sequence
<220> FEATURE:
<223> OTHER INFORMATION: Synthetic construct:  oligonucleotide useful
      as guide

<400> SEQUENCE: 65
gccgctatat caaaaaactc cgggcttttc cctacatgct cctgcatgta gggaaaagcc    60
cggag                                                                 65

<210> SEQ ID NO 66
<211> LENGTH: 71
<212> TYPE: DNA
<213> ORGANISM: Artificial Sequence
<220> FEATURE:
<223> OTHER INFORMATION: Synthetic construct:  oligonucleotide useful
      as guide

<400> SEQUENCE: 66
gaggggccgg agccgcagtg cgtcctcgca ctgcggctcc ggcccctcaa agaagatgt     60 ccaccagggt c                                                          71

<210> SEQ ID NO 67
<211> LENGTH: 71
<212> TYPE: DNA
<213> ORGANISM: Artificial Sequence
<220> FEATURE:
<223> OTHER INFORMATION: Synthetic construct:  oligonucleotide useful
      as guide

<400> SEQUENCE: 67
gatctcatca gggtactcca aaactccggg cttttcccta catgctcctg catgtaggga    60
aaagcccgga g                                                          71

<210> SEQ ID NO 68
<211> LENGTH: 71
<212> TYPE: DNA
<213> ORGANISM: Artificial Sequence
<220> FEATURE:
<223> OTHER INFORMATION: Synthetic construct:  oligonucleotide useful
      as guide

<400> SEQUENCE: 68
gaggggccgg agccgcagtg cgtcctcgca ctgcggctcc ggcccctcaa aacggcacag    60
acagtgcgcg t                                                          71

<210> SEQ ID NO 69
<211> LENGTH: 71
<212> TYPE: DNA
<213> ORGANISM: Artificial Sequence
<220> FEATURE:
<223> OTHER INFORMATION: Synthetic construct:  oligonucleotide useful
      as guide

<400> SEQUENCE: 69
```

```
cccttgcagc gggcacagca aaactccggg cttttcccta catgctcctg catgtaggga      60
aaagcccgga g                                                          71

<210> SEQ ID NO 70
<211> LENGTH: 31
<212> TYPE: DNA
<213> ORGANISM: Artificial Sequence
<220> FEATURE:
<223> OTHER INFORMATION: Synthetic construct: oligonucleotide useful
      as target

<400> SEQUENCE: 70
catggtgtat atagtctttt gatatagcgg c                                    31

<210> SEQ ID NO 71
<211> LENGTH: 31
<212> TYPE: DNA
<213> ORGANISM: Artificial Sequence
<220> FEATURE:
<223> OTHER INFORMATION: Synthetic construct: oligonucleotide useful
      as target

<400> SEQUENCE: 71
catggtttat atagtctttt gatatagcgg c                                    31

<210> SEQ ID NO 72
<211> LENGTH: 39
<212> TYPE: DNA
<213> ORGANISM: Artificial Sequence
<220> FEATURE:
<223> OTHER INFORMATION: Synthetic construct:  oligonucleotide useful
      as target

<400> SEQUENCE: 72
gcgtagcgtg ggcgagatgt agggaaaagc ccggtaccg                            39

<210> SEQ ID NO 73
<211> LENGTH: 47
<212> TYPE: DNA
<213> ORGANISM: Artificial Sequence
<220> FEATURE:
<223> OTHER INFORMATION: Synthetic construct:  oligonucleotide useful
      as target

<400> SEQUENCE: 73
gcgtaggggc cggagccgca gtggatgtag ggaaaagccc ggtaccg                   47

<210> SEQ ID NO 74
<211> LENGTH: 22
<212> TYPE: DNA
<213> ORGANISM: Artificial Sequence
<220> FEATURE:
<223> OTHER INFORMATION: Synthetic construct:  oligonucleotide useful
      as target
<220> FEATURE:
<221> NAME/KEY: misc_feature
<222> LOCATION: (5)..(5)
<223> OTHER INFORMATION: A at position 5 can be repeated an unspecified
      number of times
<220> FEATURE:
<221> NAME/KEY: misc_feature
<222> LOCATION: (8)..(8)
<223> OTHER INFORMATION: N at position 8 in given sequence can be A, T,
      C or G

<400> SEQUENCE: 74
gcgtacgncg cccacgccac cg                                              22
```

```
<210> SEQ ID NO 75
<211> LENGTH: 32
<212> TYPE: DNA
<213> ORGANISM: Artificial Sequence
<220> FEATURE:
<223> OTHER INFORMATION: Synthetic construct: oligonucleotide useful
      as target
<220> FEATURE:
<221> NAME/KEY: misc_feature
<222> LOCATION: (5)..(5)
<223> OTHER INFORMATION: A at position 5 in given sequence can be
      repeated an unspecified number of times

<400> SEQUENCE: 75
gcgtacgtac actgcggctc cggcccctac cg                                     32

<210> SEQ ID NO 76
<211> LENGTH: 31
<212> TYPE: DNA
<213> ORGANISM: Artificial Sequence
<220> FEATURE:
<223> OTHER INFORMATION: Synthetic construct: oligonucleotide useful
      as target
<220> FEATURE:
<221> NAME/KEY: misc_feature
<222> LOCATION: (55)..()
<223> OTHER INFORMATION: A at positive 5 of given sequence can be
      repeated an unspecified number of times

<400> SEQUENCE: 76
gcctacgact atcaccgcgg gtgatacagc c                                      31

<210> SEQ ID NO 77
<211> LENGTH: 31
<212> TYPE: DNA
<213> ORGANISM: Artificial Sequence
<220> FEATURE:
<223> OTHER INFORMATION: Synthetic construct: oligonucleotide useful
      as target

<400> SEQUENCE: 77
gcctacgact atcaccgcgg gtgatacagc c                                      31

<210> SEQ ID NO 78
<211> LENGTH: 20
<212> TYPE: DNA
<213> ORGANISM: Artificial Sequence
<220> FEATURE:
<223> OTHER INFORMATION: Synthetic construct: oligonucleotide useful
      as target
<220> FEATURE:
<221> NAME/KEY: misc_feature
<222> LOCATION: (5)..(13)
<223> OTHER INFORMATION: A residues at positions 5 and 13 in given
      sequence can be repeated an unspecified number of times

<400> SEQUENCE: 78
gatcacgatg gtacgactag                                                   20

<210> SEQ ID NO 79
<211> LENGTH: 36
<212> TYPE: DNA
<213> ORGANISM: Artificial Sequence
<220> FEATURE:
<223> OTHER INFORMATION: Synthetic construct: oligonucleotide useful
      as target
<220> FEATURE:
<221> NAME/KEY: misc_feature
<222> LOCATION: (5)..(28)
<223> OTHER INFORMATION: Residues at positions 5 and 28 in the given
      sequence can be repeated an unspecified number of times
```

-continued

```
<400> SEQUENCE: 79
gcctacgact atcaccgcgg gtgatagtcg gtaggc                                36

<210> SEQ ID NO 80
<211> LENGTH: 28
<212> TYPE: DNA
<213> ORGANISM: Artificial Sequence
<220> FEATURE:
<223> OTHER INFORMATION: Synthetic construct: oligonucleotide useful
      as target

<400> SEQUENCE: 80
gcgtagcgtg ggcggtgtgg aaacaccg                                        28

<210> SEQ ID NO 81
<211> LENGTH: 21
<212> TYPE: DNA
<213> ORGANISM: Artificial Sequence
<220> FEATURE:
<223> OTHER INFORMATION: Synthetic construct: oligonucleotide useful
      as target
<220> FEATURE:
<221> NAME/KEY: misc_feature
<222> LOCATION: (5)..(5)
<223> OTHER INFORMATION: A at position 5 in given sequence can be
      repeated an unspecified number of times

<400> SEQUENCE: 81
gcgtacgcgc ccacgccacc g                                               21

<210> SEQ ID NO 82
<211> LENGTH: 22
<212> TYPE: DNA
<213> ORGANISM: Artificial Sequence
<220> FEATURE:
<223> OTHER INFORMATION: Synthetic construct: oligonucleotide useful
      as target
<220> FEATURE:
<221> NAME/KEY: misc_feature
<222> LOCATION: (5)..(5)
<223> OTHER INFORMATION: A at position 5 of given sequence can be
      repeated an unspecified number of times

<400> SEQUENCE: 82
gcgtacgtcg cccacgccac cg                                              22

<210> SEQ ID NO 83
<211> LENGTH: 23
<212> TYPE: DNA
<213> ORGANISM: Artificial Sequence
<220> FEATURE:
<223> OTHER INFORMATION: Synthetic construct: oligonucleotide useful
      as target
<220> FEATURE:
<221> NAME/KEY: misc_feature
<222> LOCATION: (5)..(5)
<223> OTHER INFORMATION: A at position 5 of given sequence can be
      repeated an unspecified number of times

<400> SEQUENCE: 83
gcgtacgtac gcccacgcca ccg                                             23

<210> SEQ ID NO 84
<211> LENGTH: 24
<212> TYPE: DNA
<213> ORGANISM: Artificial Sequence
<220> FEATURE:
<223> OTHER INFORMATION: Synthetic construct: oligonucleotide useful
      as target
<220> FEATURE:
```

```
<221> NAME/KEY: misc_feature
<222> LOCATION: (5)..(5)
<223> OTHER INFORMATION: A at position 5 can be repeated an unspecified
      number of times

<400> SEQUENCE: 84
gcgtacgtag cgcccacgcc accg                                              24

<210> SEQ ID NO 85
<211> LENGTH: 27
<212> TYPE: DNA
<213> ORGANISM: Artificial Sequence
<220> FEATURE:
<223> OTHER INFORMATION: Synthetic construct:  oligonucleotide useful
      as target
<220> FEATURE:
<221> NAME/KEY: misc_feature
<222> LOCATION: (5)..(5)
<223> OTHER INFORMATION: A at position 5 can be repeated an unspecified
      number of times

<400> SEQUENCE: 85
gcgtacgtag gaccgcccac gccaccg                                           27

<210> SEQ ID NO 86
<211> LENGTH: 31
<212> TYPE: DNA
<213> ORGANISM: Artificial Sequence
<220> FEATURE:
<223> OTHER INFORMATION: Synthetic construct:  oligonucleotide useful
      as target
<220> FEATURE:
<221> NAME/KEY: misc_feature
<222> LOCATION: (5)..(5)
<223> OTHER INFORMATION: A at position 5 can be repeated an unspecified
      number of times

<400> SEQUENCE: 86
gcgtacgtag gacgatacgc ccacgccacc g                                      31

<210> SEQ ID NO 87
<211> LENGTH: 48
<212> TYPE: DNA
<213> ORGANISM: Artificial Sequence
<220> FEATURE:
<223> OTHER INFORMATION: Synthetic construct:  consensus oligonucleotide

<400> SEQUENCE: 87
gcatgtaggg aaaagcccgg cgtcctcgcc gggcttttcc ctacatgc                    48

<210> SEQ ID NO 88
<211> LENGTH: 48
<212> TYPE: DNA
<213> ORGANISM: Artificial Sequence
<220> FEATURE:
<223> OTHER INFORMATION: Synthetic construct:  consensus ATA sequence

<400> SEQUENCE: 88
gcatgtaggg aatagcccgg cgtcctcgcc gggctattcc ctacatgc                    48

<210> SEQ ID NO 89
<211> LENGTH: 48
<212> TYPE: DNA
<213> ORGANISM: Artificial Sequence
<220> FEATURE:
<223> OTHER INFORMATION: Synthetic construct:  designed sequence

<400> SEQUENCE: 89
gcatgtagag aaaaaccagg cgtcctcgcc tggttttttct ctacatgc                   48
```

<210> SEQ ID NO 90
<211> LENGTH: 48
<212> TYPE: DNA
<213> ORGANISM: Artificial Sequence
<220> FEATURE:
<223> OTHER INFORMATION: Synthetic construct: designed ATA sequence

<400> SEQUENCE: 90
gcatgtagag aataaccagg cgtcctcgcc tggttattct ctacatgc                48

<210> SEQ ID NO 91
<211> LENGTH: 12
<212> TYPE: PRT
<213> ORGANISM: Artificial Sequence
<220> FEATURE:
<223> OTHER INFORMATION: Synthetic construct

<400> SEQUENCE: 91

Gly Gly Gly Ser Gly Gly Gly Ser Gly Gly Gly Ser
1               5                   10

<210> SEQ ID NO 92
<211> LENGTH: 690
<212> TYPE: DNA
<213> ORGANISM: Artificial Sequence
<220> FEATURE:
<223> OTHER INFORMATION: Synthetic construct: CFluc-TJ10 coding
      sequence
<220> FEATURE:
<221> NAME/KEY: CDS
<222> LOCATION: (1)..(690)

<400> SEQUENCE: 92 atg atg tcc ggt tat gta aac aat ccg gaa gcg acc aac gcc ttg att    48
Met Met Ser Gly Tyr Val Asn Asn Pro Glu Ala Thr Asn Ala Leu Ile
1               5                   10                  15 gac aag gat gga tgg cta cat tct gga gac ata gct tac tgg gac gaa    96
Asp Lys Asp Gly Trp Leu His Ser Gly Asp Ile Ala Tyr Trp Asp Glu
                20                  25                  30 gac gaa cac ttc ttc ata gtt gac cgc ttg aag tct tta att aaa tac   144
Asp Glu His Phe Phe Ile Val Asp Arg Leu Lys Ser Leu Ile Lys Tyr
            35                  40                  45 aaa gga tat cag gtg gcc ccc gct gaa ttg gaa tcg ata ttg tta caa   192
Lys Gly Tyr Gln Val Ala Pro Ala Glu Leu Glu Ser Ile Leu Leu Gln
        50                  55                  60 cac ccc aac atc ttc gac gcg ggc gtg gca ggt ctt ccc gac gat gac   240
His Pro Asn Ile Phe Asp Ala Gly Val Ala Gly Leu Pro Asp Asp Asp
65                  70                  75                  80 gcc ggt gaa ctt ccc gcc gcc gtt gtt gtt ttg gag cac gga aag acg   288
Ala Gly Glu Leu Pro Ala Ala Val Val Val Leu Glu His Gly Lys Thr
                85                  90                  95 atg acg gaa aaa gag atc gtg gat tac gtc gcc agt caa gta aca acc   336
Met Thr Glu Lys Glu Ile Val Asp Tyr Val Ala Ser Gln Val Thr Thr
            100                 105                 110 gcg aaa aag ttg cgc gga gga gtt gtg ttt gtg gac gaa gta ccg aaa   384
Ala Lys Lys Leu Arg Gly Gly Val Val Phe Val Asp Glu Val Pro Lys
        115                 120                 125 ggt ctt acc gga aaa ctc gac gca aga aaa atc aga gag atc ctc ata   432
Gly Leu Thr Gly Lys Leu Asp Ala Arg Lys Ile Arg Glu Ile Leu Ile
    130                 135                 140 aag gcc aag aag ggc gga aag tcc aaa ttg ggc ctg cag ggt ggt tca   480
Lys Ala Lys Lys Gly Gly Lys Ser Lys Leu Gly Leu Gln Gly Gly Ser
145                 150                 155                 160

```
ggc ggt ggg ggt tct ggc ggg ggt ggg agc ccc ggg atg gcc cag acc      528
Gly Gly Gly Gly Ser Gly Gly Gly Gly Ser Pro Gly Met Ala Gln Thr
            165                 170                 175 ttc tgg ctt agt ata cag ggt aaa acc ctg tat tgg cag atc agg atc      576
Phe Trp Leu Ser Ile Gln Gly Lys Thr Leu Tyr Trp Gln Ile Arg Ile
            180                 185                 190 tat gct att gac gct gca gaa gct gaa aaa atc ttc aaa cag tac gct      624
Tyr Ala Ile Asp Ala Ala Glu Ala Glu Lys Ile Phe Lys Gln Tyr Ala
            195                 200                 205 aac gac aac ggt atc gac ggt gaa tgg acc tac gac gac gct acc aaa      672
Asn Asp Asn Gly Ile Asp Gly Glu Trp Thr Tyr Asp Asp Ala Thr Lys
        210                 215                 220 acc ttc acc gtt acc gaa                                              690
Thr Phe Thr Val Thr Glu
225                 230
```

<210> SEQ ID NO 93
<211> LENGTH: 230
<212> TYPE: PRT
<213> ORGANISM: Artificial Sequence
<220> FEATURE:
<223> OTHER INFORMATION: Synthetic Construct

<400> SEQUENCE: 93

```
Met Met Ser Gly Tyr Val Asn Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
        35                  40                  45

Lys Gly Tyr Gln Val Ala Pro Ala Glu Leu Glu Ser Ile Leu Leu Gln
50                  55                  60

His Pro Asn Ile Phe Asp Ala Gly Val Ala Gly Leu Pro Asp Asp Asp
65                  70                  75                  80

Ala Gly Glu Leu Pro Ala Ala Val Val Leu Glu His Gly Lys Thr
            85                  90                  95

Met Thr Glu Lys Glu Ile Val Asp Tyr Val Ala Ser Gln Val Thr Thr
        100                 105                 110

Ala Lys Lys Leu Arg Gly Gly Val Val Phe Val Asp Glu Val Pro Lys
    115                 120                 125

Gly Leu Thr Gly Lys Leu Asp Ala Arg Lys Ile Arg Glu Ile Leu Ile
130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Gly Ser Pro Gly Met Ala Gln Thr
            165                 170                 175

Phe Trp Leu Ser Ile Gln Gly Lys Thr Leu Tyr Trp Gln Ile Arg Ile
        180                 185                 190

Tyr Ala Ile Asp Ala Ala Glu Ala Glu Lys Ile Phe Lys Gln Tyr Ala
    195                 200                 205

Asn Asp Asn Gly Ile Asp Gly Glu Trp Thr Tyr Asp Asp Ala Thr Lys
    210                 215                 220

Thr Phe Thr Val Thr Glu
225                 230
```

<210> SEQ ID NO 94
<211> LENGTH: 1497
<212> TYPE: DNA
<213> ORGANISM: Artificial Sequence
<220> FEATURE:
<223> OTHER INFORMATION: Synthetic construct: TJ10-Nfluc coding sequence
<220> FEATURE:
<221> NAME/KEY: CDS
<222> LOCATION: (1)..(1494)

<400> SEQUENCE: 94

| | | | | | | | | | | | | | | | | |
|---|---|---|---|---|---|---|---|---|---|---|---|---|---|---|---|---|
| cat | cac | gga | tcc | gca | gct | cat | tat | atg | gcc | cag | acc | ttc | tgg | ctt | agt | 48 |
| His | His | Gly | Ser | Ala | Ala | His | Tyr | Met | Ala | Gln | Thr | Phe | Trp | Leu | Ser | |
| 1 | | | | 5 | | | | | 10 | | | | | 15 | | |
| ata | cag | ggt | aaa | acc | ctg | tat | tgg | cag | atc | agg | atc | tat | gct | att | gac | 96 |
| Ile | Gln | Gly | Lys | Thr | Leu | Tyr | Trp | Gln | Ile | Arg | Ile | Tyr | Ala | Ile | Asp | |
| | | | 20 | | | | | 25 | | | | | 30 | | | |
| gct | gca | gaa | gct | gaa | aaa | atc | ttc | aaa | cag | tac | gct | aac | gac | aac | ggt | 144 |
| Ala | Ala | Glu | Ala | Glu | Lys | Ile | Phe | Lys | Gln | Tyr | Ala | Asn | Asp | Asn | Gly | |
| | | 35 | | | | | 40 | | | | | 45 | | | | |
| atc | gac | ggt | gaa | tgg | acc | tac | gac | gac | gct | acc | aaa | acc | ttc | acc | gtt | 192 |
| Ile | Asp | Gly | Glu | Trp | Thr | Tyr | Asp | Asp | Ala | Thr | Lys | Thr | Phe | Thr | Val | |
| 50 | | | | | 55 | | | | | 60 | | | | | | |
| acc | gaa | acc | ggt | ggg | ggt | ggc | ggt | tca | ggc | ggt | ggg | ggt | tct | ggt | ggg | 240 |
| Thr | Glu | Thr | Gly | Gly | Gly | Gly | Gly | Ser | Gly | Gly | Gly | Gly | Ser | Gly | Gly | |
| 65 | | | | 70 | | | | | 75 | | | | | 80 | | |
| ggt | ggt | acc | gaa | gac | gcc | aaa | aac | ata | aag | aaa | ggc | ccg | gcg | cca | ttc | 288 |
| Gly | Gly | Thr | Glu | Asp | Ala | Lys | Asn | Ile | Lys | Lys | Gly | Pro | Ala | Pro | Phe | |
| | | | 85 | | | | | 90 | | | | | 95 | | | |
| tat | cct | cta | gag | gat | gga | acc | gct | gga | gag | caa | ctg | cat | aag | gct | atg | 336 |
| Tyr | Pro | Leu | Glu | Asp | Gly | Thr | Ala | Gly | Glu | Gln | Leu | His | Lys | Ala | Met | |
| | | | 100 | | | | | 105 | | | | | 110 | | | |
| aag | aga | tac | gcc | ctg | gtt | cct | gga | aca | att | gct | ttt | aca | gat | gca | cat | 384 |
| Lys | Arg | Tyr | Ala | Leu | Val | Pro | Gly | Thr | Ile | Ala | Phe | Thr | Asp | Ala | His | |
| | | 115 | | | | | 120 | | | | | 125 | | | | |
| atc | gag | gtg | aac | atc | acg | tac | gcg | gaa | tac | ttc | gaa | atg | tcc | gtt | cgg | 432 |
| Ile | Glu | Val | Asn | Ile | Thr | Tyr | Ala | Glu | Tyr | Phe | Glu | Met | Ser | Val | Arg | |
| 130 | | | | | 135 | | | | | 140 | | | | | | |
| ttg | gca | gaa | gct | atg | aaa | cga | tat | ggg | ctg | aat | aca | aat | cac | aga | atc | 480 |
| Leu | Ala | Glu | Ala | Met | Lys | Arg | Tyr | Gly | Leu | Asn | Thr | Asn | His | Arg | Ile | |
| 145 | | | | | 150 | | | | | 155 | | | | | 160 | |
| gtc | gta | tgc | agt | gaa | aac | tct | ctt | caa | ttc | ttt | atg | ccg | gtg | ttg | ggc | 528 |
| Val | Val | Cys | Ser | Glu | Asn | Ser | Leu | Gln | Phe | Phe | Met | Pro | Val | Leu | Gly | |
| | | | | 165 | | | | | 170 | | | | | 175 | | |
| gcg | tta | ttt | atc | gga | gtt | gca | gtt | gcg | ccc | gcg | aac | gac | att | tat | aat | 576 |
| Ala | Leu | Phe | Ile | Gly | Val | Ala | Val | Ala | Pro | Ala | Asn | Asp | Ile | Tyr | Asn | |
| | | | 180 | | | | | 185 | | | | | 190 | | | |
| gaa | cgt | gaa | ttg | ctc | aac | agt | atg | aac | att | tcg | cag | cct | acc | gta | gtg | 624 |
| Glu | Arg | Glu | Leu | Leu | Asn | Ser | Met | Asn | Ile | Ser | Gln | Pro | Thr | Val | Val | |
| | | 195 | | | | | 200 | | | | | 205 | | | | |
| ttt | gtt | tcc | aaa | aag | ggg | ttg | caa | aaa | att | ttg | aac | gtg | caa | aaa | aaa | 672 |
| Phe | Val | Ser | Lys | Lys | Gly | Leu | Gln | Lys | Ile | Leu | Asn | Val | Gln | Lys | Lys | |
| 210 | | | | | 215 | | | | | 220 | | | | | | |
| tta | cca | ata | atc | cag | aaa | att | att | atc | atg | gat | tct | aaa | acg | gat | tac | 720 |
| Leu | Pro | Ile | Ile | Gln | Lys | Ile | Ile | Ile | Met | Asp | Ser | Lys | Thr | Asp | Tyr | |
| 225 | | | | | 230 | | | | | 235 | | | | | 240 | |
| cag | gga | ttt | cag | tcg | atg | tac | acg | ttc | gtc | aca | tct | cat | cta | cct | ccc | 768 |
| Gln | Gly | Phe | Gln | Ser | Met | Tyr | Thr | Phe | Val | Thr | Ser | His | Leu | Pro | Pro | |
| | | | | 245 | | | | | 250 | | | | | 255 | | |
| ggt | ttt | aat | gaa | tac | gat | ttt | gta | cca | gag | tcc | ttt | gat | cgt | gac | aaa | 816 |
| Gly | Phe | Asn | Glu | Tyr | Asp | Phe | Val | Pro | Glu | Ser | Phe | Asp | Arg | Asp | Lys | |
| | | | 260 | | | | | 265 | | | | | 270 | | | |
| aca | att | gca | ctg | ata | atg | aat | tcc | tct | gga | tct | act | ggg | tta | cct | aag | 864 |
| Thr | Ile | Ala | Leu | Ile | Met | Asn | Ser | Ser | Gly | Ser | Thr | Gly | Leu | Pro | Lys | |
| | | 275 | | | | | 280 | | | | | 285 | | | | |

```
ggt gtg gcc ctt ccg cat aga act gcc tgc gtc aga ttc tcg cat gcc      912
Gly Val Ala Leu Pro His Arg Thr Ala Cys Val Arg Phe Ser His Ala
        290                 295                 300 aga gat cct att ttt ggc aat caa atc att ccg gat act gcg att tta      960
Arg Asp Pro Ile Phe Gly Asn Gln Ile Ile Pro Asp Thr Ala Ile Leu
305                 310                 315                 320 agt gtt gtt cca ttc cat cac ggt ttt gga atg ttt act aca ctc gga     1008
Ser Val Val Pro Phe His His Gly Phe Gly Met Phe Thr Thr Leu Gly
                325                 330                 335 tat ttg ata tgt gga ttt cga gtc gtc tta atg tat aga ttt gaa gaa     1056
Tyr Leu Ile Cys Gly Phe Arg Val Val Leu Met Tyr Arg Phe Glu Glu
            340                 345                 350 gag ctg ttt tta cga tcc ctt cag gat tac aaa att caa agt gcg ttg     1104
Glu Leu Phe Leu Arg Ser Leu Gln Asp Tyr Lys Ile Gln Ser Ala Leu
        355                 360                 365 cta gta cca acc cta ttt tca ttc ttc gcc aaa agc act ctg att gac     1152
Leu Val Pro Thr Leu Phe Ser Phe Phe Ala Lys Ser Thr Leu Ile Asp
370                 375                 380 aaa tac gat tta tct aat tta cac gaa att gct tct ggg ggc gca cct     1200
Lys Tyr Asp Leu Ser Asn Leu His Glu Ile Ala Ser Gly Gly Ala Pro
                390                 395                 400
385 ctt tcg aaa gaa gtc ggg gaa gcg gtt gca aaa cgc ttc cat ctt cca     1248
Leu Ser Lys Glu Val Gly Glu Ala Val Ala Lys Arg Phe His Leu Pro
            405                 410                 415 ggg ata cga caa gga tat ggg ctc act gag act aca tca gct att ctg     1296
Gly Ile Arg Gln Gly Tyr Gly Leu Thr Glu Thr Thr Ser Ala Ile Leu
        420                 425                 430 att aca ccc gag ggg gat gat aaa ccg ggc gcg gtc ggt aaa gtt gtt     1344
Ile Thr Pro Glu Gly Asp Asp Lys Pro Gly Ala Val Gly Lys Val Val
    435                 440                 445 cca ttt ttt gaa gcg aag gtt gtg gat ctg gat acc ggg aaa acg ctg     1392
Pro Phe Phe Glu Ala Lys Val Val Asp Leu Asp Thr Gly Lys Thr Leu
450                 455                 460 ggc gtt aat cag aga ggc gaa tta tgt gtc aga gga cct atg att atg     1440
Gly Val Asn Gln Arg Gly Glu Leu Cys Val Arg Gly Pro Met Ile Met
465                 470                 475                 480 tcc ggt tat gta aac aat ccg gaa gcg acc aac gcc ttg att gac aag     1488
Ser Gly Tyr Val Asn Asn Pro Glu Ala Thr Asn Ala Leu Ile Asp Lys
                485                 490                 495 gat gga tga                                                         1497
Asp Gly <210> SEQ ID NO 95
<211> LENGTH: 498
<212> TYPE: PRT
<213> ORGANISM: Artificial Sequence
<220> FEATURE:
<223> OTHER INFORMATION: Synthetic Construct

<400> SEQUENCE: 95

His His Gly Ser Ala Ala His Tyr Met Ala Gln Thr Phe Trp Leu Ser
1               5                   10                  15

Ile Gln Gly Lys Thr Leu Tyr Trp Gln Ile Arg Ile Tyr Ala Ile Asp
            20                  25                  30

Ala Ala Glu Ala Glu Lys Ile Phe Lys Gln Tyr Ala Asn Asp Asn Gly
        35                  40                  45

Ile Asp Gly Glu Trp Thr Tyr Asp Asp Ala Lys Thr Phe Thr Val
    50                  55                  60

Thr Glu Thr Gly Gly Gly Gly Ser Gly Gly Gly Ser Gly Gly
65                  70                  75                  80
```

```
Gly Gly Thr Glu Asp Ala Lys Asn Ile Lys Lys Gly Pro Ala Pro Phe
                 85                  90                  95

Tyr Pro Leu Glu Asp Gly Thr Ala Gly Glu Gln Leu His Lys Ala Met
            100                 105                 110

Lys Arg Tyr Ala Leu Val Pro Gly Thr Ile Ala Phe Thr Asp Ala His
            115                 120                 125

Ile Glu Val Asn Ile Thr Tyr Ala Glu Tyr Phe Glu Met Ser Val Arg
130                 135                 140

Leu Ala Glu Ala Met Lys Arg Tyr Gly Leu Asn Thr Asn His Arg Ile
145                 150                 155                 160

Val Val Cys Ser Glu Asn Ser Leu Gln Phe Phe Met Pro Val Leu Gly
                165                 170                 175

Ala Leu Phe Ile Gly Val Ala Val Ala Pro Ala Asn Asp Ile Tyr Asn
            180                 185                 190

Glu Arg Glu Leu Leu Asn Ser Met Asn Ile Ser Gln Pro Thr Val Val
            195                 200                 205

Phe Val Ser Lys Lys Gly Leu Gln Lys Ile Leu Asn Val Gln Lys Lys
210                 215                 220

Leu Pro Ile Ile Gln Lys Ile Ile Ile Met Asp Ser Lys Thr Asp Tyr
225                 230                 235                 240

Gln Gly Phe Gln Ser Met Tyr Thr Phe Val Thr Ser His Leu Pro Pro
                245                 250                 255

Gly Phe Asn Glu Tyr Asp Phe Val Pro Glu Ser Phe Asp Arg Asp Lys
            260                 265                 270

Thr Ile Ala Leu Ile Met Asn Ser Ser Gly Ser Thr Gly Leu Pro Lys
            275                 280                 285

Gly Val Ala Leu Pro His Arg Thr Ala Cys Val Arg Phe Ser His Ala
290                 295                 300

Arg Asp Pro Ile Phe Gly Asn Gln Ile Ile Pro Asp Thr Ala Ile Leu
305                 310                 315                 320

Ser Val Val Pro Phe His His Gly Phe Gly Met Phe Thr Thr Leu Gly
                325                 330                 335

Tyr Leu Ile Cys Gly Phe Arg Val Val Leu Met Tyr Arg Phe Glu Glu
            340                 345                 350

Glu Leu Phe Leu Arg Ser Leu Gln Asp Tyr Lys Ile Gln Ser Ala Leu
            355                 360                 365

Leu Val Pro Thr Leu Phe Ser Phe Phe Ala Lys Ser Thr Leu Ile Asp
370                 375                 380

Lys Tyr Asp Leu Ser Asn Leu His Glu Ile Ala Ser Gly Gly Ala Pro
385                 390                 395                 400

Leu Ser Lys Glu Val Gly Glu Ala Val Ala Lys Arg Phe His Leu Pro
                405                 410                 415

Gly Ile Arg Gln Gly Tyr Gly Leu Thr Glu Thr Thr Ser Ala Ile Leu
            420                 425                 430

Ile Thr Pro Glu Gly Asp Asp Lys Pro Gly Ala Val Gly Lys Val Val
            435                 440                 445

Pro Phe Phe Glu Ala Lys Val Val Asp Leu Asp Thr Gly Lys Thr Leu
450                 455                 460

Gly Val Asn Gln Arg Gly Glu Leu Cys Val Arg Gly Pro Met Ile Met
465                 470                 475                 480

Ser Gly Tyr Val Asn Asn Pro Glu Ala Thr Asn Ala Leu Ile Asp Lys
                485                 490                 495

Asp Gly
```

<210> SEQ ID NO 96
<211> LENGTH: 744
<212> TYPE: DNA
<213> ORGANISM: Artificial Sequence
<220> FEATURE:
<223> OTHER INFORMATION: Synthetic construct: Cfluc-HTB1 coding sequence
<220> FEATURE:
<221> NAME/KEY: CDS
<222> LOCATION: (4)..(744)

<400> SEQUENCE: 96

```
cat atg atg tcc ggt tat gta aac aat ccg gaa gcg acc aac gcc ttg      48
    Met Met Ser Gly Tyr Val Asn Asn Pro Glu Ala Thr Asn Ala Leu
    1               5                  10                  15 att gac aag gat gga tgg cta cat tct gga gac ata gct tac tgg gac      96
Ile Asp Lys Asp Gly Trp Leu His Ser Gly Asp Ile Ala Tyr Trp Asp
            20                  25                  30 gaa gac gaa cac ttc ttc ata gtt gac cgc ttg aag tct tta att aaa     144
Glu Asp Glu His Phe Phe Ile Val Asp Arg Leu Lys Ser Leu Ile Lys
        35                  40                  45 tac aaa gga tat cag gtg gcc ccc gct gaa ttg gaa tcg ata ttg tta     192
Tyr Lys Gly Tyr Gln Val Ala Pro Ala Glu Leu Glu Ser Ile Leu Leu
    50                  55                  60 caa cac ccc aac atc ttc gac gcg ggc gtg gca ggt ctt ccc gac gat     240
Gln His Pro Asn Ile Phe Asp Ala Gly Val Ala Gly Leu Pro Asp Asp
65                  70                  75 gac gcc ggt gaa ctt ccc gcc gcc gtt gtt gtt ttg gag cac gga aag     288
Asp Ala Gly Glu Leu Pro Ala Ala Val Val Val Leu Glu His Gly Lys
            80                  85                  90              95 acg atg acg gaa aaa gag atc gtg gat tac gtc gcc agt caa gta aca     336
Thr Met Thr Glu Lys Glu Ile Val Asp Tyr Val Ala Ser Gln Val Thr
        100                 105                 110 acc gcg aaa aag ttg cgc gga gga gtt gtg ttt gtg gac gaa gta ccg     384
Thr Ala Lys Lys Leu Arg Gly Gly Val Val Phe Val Asp Glu Val Pro
    115                 120                 125 aaa ggt ctt acc gga aaa ctc gac gca aga aaa atc aga gag atc ctc     432
Lys Gly Leu Thr Gly Lys Leu Asp Ala Arg Lys Ile Arg Glu Ile Leu
130                 135                 140 ata aag gcc aag aag ggc gga aag tcc aaa ttg ggc ctg cag ggc ggt     480
Ile Lys Ala Lys Lys Gly Gly Lys Ser Lys Leu Gly Leu Gln Gly Gly
145                 150                 155 tca ggc ggt ggg ggt tct ggc ggg ggt ggg agc ccc ggg atg gcc cag     528
Ser Gly Gly Gly Gly Ser Gly Gly Gly Gly Ser Pro Gly Met Ala Gln
            160                 165                 170             175 acc ttc aaa ctt atc atc aac ggt aaa acc ctg aaa ggt gaa atc acc     576
Thr Phe Lys Leu Ile Ile Asn Gly Lys Thr Leu Lys Gly Glu Ile Thr
        180                 185                 190 atc gaa gct gtt gac gct gca gaa gct gaa aaa atc ttc aaa cag tac     624
Ile Glu Ala Val Asp Ala Ala Glu Ala Glu Lys Ile Phe Lys Gln Tyr
    195                 200                 205 gct aac gac aac ggt atc gac ggt gaa tgg acc tac gac gac gct acc     672
Ala Asn Asp Asn Gly Ile Asp Gly Glu Trp Thr Tyr Asp Asp Ala Thr
210                 215                 220 aaa acc ttc acc gtt acc gaa ctc gag tct ggt aaa gaa acc gct gct     720
Lys Thr Phe Thr Val Thr Glu Leu Glu Ser Gly Lys Glu Thr Ala Ala
225                 230                 235 gcg aaa ttt gaa cgc cag cac atg                                     744
Ala Lys Phe Glu Arg Gln His Met
        240                 245
```

```
<210> SEQ ID NO 97
<211> LENGTH: 247
<212> TYPE: PRT
<213> ORGANISM: Artificial Sequence
<220> FEATURE:
<223> OTHER INFORMATION: Synthetic Construct

<400> SEQUENCE: 97

Met Met Ser Gly Tyr Val Asn Asn Pro Glu Ala Thr Asn Ala Leu Ile
1               5                   10                  15

Asp Lys Asp Gly Trp Leu His Ser Gly Asp Ile Ala Tyr Trp Asp Glu
            20                  25                  30

Asp Glu His Phe Phe Ile Val Asp Arg Leu Lys Ser Leu Ile Lys Tyr
        35                  40                  45

Lys Gly Tyr Gln Val Ala Pro Ala Glu Leu Glu Ser Ile Leu Leu Gln
    50                  55                  60

His Pro Asn Ile Phe Asp Ala Gly Val Ala Gly Leu Pro Asp Asp Asp
65                  70                  75                  80

Ala Gly Glu Leu Pro Ala Ala Val Val Val Leu Glu His Gly Lys Thr
                85                  90                  95

Met Thr Glu Lys Glu Ile Val Asp Tyr Val Ala Ser Gln Val Thr Thr
            100                 105                 110

Ala Lys Lys Leu Arg Gly Gly Val Val Phe Val Asp Glu Val Pro Lys
        115                 120                 125

Gly Leu Thr Gly Lys Leu Asp Ala Arg Lys Ile Arg Glu Ile Leu Ile
    130                 135                 140

Lys Ala Lys Lys Gly Gly Lys Ser Lys Leu Gly Leu Gln Gly Gly Ser
145                 150                 155                 160

Gly Gly Gly Gly Ser Gly Gly Gly Ser Pro Gly Met Ala Gln Thr
                165                 170                 175

Phe Lys Leu Ile Ile Asn Gly Lys Thr Leu Lys Gly Glu Ile Thr Ile
            180                 185                 190

Glu Ala Val Asp Ala Ala Glu Ala Glu Lys Ile Phe Lys Gln Tyr Ala
        195                 200                 205

Asn Asp Asn Gly Ile Asp Gly Glu Trp Thr Tyr Asp Asp Ala Thr Lys
    210                 215                 220

Thr Phe Thr Val Thr Glu Leu Glu Ser Gly Lys Glu Thr Ala Ala Ala
225                 230                 235                 240

Lys Phe Glu Arg Gln His Met
                245

<210> SEQ ID NO 98
<211> LENGTH: 1521
<212> TYPE: DNA
<213> ORGANISM: Artificial Sequence
<220> FEATURE:
<223> OTHER INFORMATION: Synthetic construct: HTB1-Nfluc coding
      sequence
<220> FEATURE:
<221> NAME/KEY: CDS
<222> LOCATION: (1)..(1518)

<400> SEQUENCE: 98 atg ggc gga tcg cat cac cat cac cat cac gga tcc gca gct cat tat     48
Met Gly Gly Ser His His His His His His Gly Ser Ala Ala His Tyr
1               5                   10                  15 atg gcc cag acc ttc aag ctt atc atc aac ggt aaa acc ctg aaa ggt     96
Met Ala Gln Thr Phe Lys Leu Ile Ile Asn Gly Lys Thr Leu Lys Gly
            20                  25                  30 gaa atc acc atc gaa gct gtt gac gct gca gaa gct gaa aaa atc ttc    144
```

-continued

```
Glu Ile Thr Ile Glu Ala Val Asp Ala Ala Glu Ala Glu Lys Ile Phe
        35                  40                  45 aaa cag tac gct aac gac aac ggt atc gac ggt gaa tgg acc tac gac    192
Lys Gln Tyr Ala Asn Asp Asn Gly Ile Asp Gly Glu Trp Thr Tyr Asp
 50                  55                  60 gac gct acc aaa acc ttc acc gtt acc gaa acc ggt ggg ggt ggc ggt    240
Asp Ala Thr Lys Thr Phe Thr Val Thr Glu Thr Gly Gly Gly Gly Gly
 65                  70                  75                  80 tca ggc ggt ggg ggt tct ggt ggg ggt acc gaa gac gcc aaa aac        288
Ser Gly Gly Gly Gly Ser Gly Gly Gly Thr Glu Asp Ala Lys Asn
                 85                  90                  95 ata aag aaa ggc ccg gcg cca ttc tat cct cta gag gat gga acc gct    336
Ile Lys Lys Gly Pro Ala Pro Phe Tyr Pro Leu Glu Asp Gly Thr Ala
            100                 105                 110 gga gag caa ctg cat aag gct atg aag aga tac gcc ctg gtt cct gga    384
Gly Glu Gln Leu His Lys Ala Met Lys Arg Tyr Ala Leu Val Pro Gly
        115                 120                 125 aca att gct ttt aca gat gca cat atc gag gtg aac atc acg tac gcg    432
Thr Ile Ala Phe Thr Asp Ala His Ile Glu Val Asn Ile Thr Tyr Ala
130                 135                 140 gaa tac ttc gaa atg tcc gtt cgg ttg gca gaa gct atg aaa cga tat    480
Glu Tyr Phe Glu Met Ser Val Arg Leu Ala Glu Ala Met Lys Arg Tyr
145                 150                 155                 160 ggg ctg aat aca aat cac aga atc gtc gta tgc agt gaa aac tct ctt    528
Gly Leu Asn Thr Asn His Arg Ile Val Val Cys Ser Glu Asn Ser Leu
                165                 170                 175 caa ttc ttt atg ccg gtg ttg ggc gcg tta ttt atc gga gtt gca gtt    576
Gln Phe Phe Met Pro Val Leu Gly Ala Leu Phe Ile Gly Val Ala Val
            180                 185                 190 gcg ccc gcg aac gac att tat aat gaa cgt gaa ttg ctc aac agt atg    624
Ala Pro Ala Asn Asp Ile Tyr Asn Glu Arg Glu Leu Leu Asn Ser Met
        195                 200                 205 aac att tcg cag cct acc gta gtg ttt gtt tcc aaa aag ggg ttg caa    672
Asn Ile Ser Gln Pro Thr Val Val Phe Val Ser Lys Lys Gly Leu Gln
    210                 215                 220 aaa att ttg aac gtg caa aaa aaa tta cca ata atc cag aaa att att    720
Lys Ile Leu Asn Val Gln Lys Lys Leu Pro Ile Ile Gln Lys Ile Ile
225                 230                 235                 240 atc atg gat tct aaa acg gat tac cag gga ttt cag tcg atg tac acg    768
Ile Met Asp Ser Lys Thr Asp Tyr Gln Gly Phe Gln Ser Met Tyr Thr
                245                 250                 255 ttc gtc aca tct cat cta cct ccc ggt ttt aat gaa tac gat ttt gta    816
Phe Val Thr Ser His Leu Pro Pro Gly Phe Asn Glu Tyr Asp Phe Val
            260                 265                 270 cca gag tcc ttt gat cgt gac aaa aca att gca ctg ata atg aat tcc    864
Pro Glu Ser Phe Asp Arg Asp Lys Thr Ile Ala Leu Ile Met Asn Ser
        275                 280                 285 tct gga tct act ggg tta cct aag ggt gtg gcc ctt ccg cat aga act    912
Ser Gly Ser Thr Gly Leu Pro Lys Gly Val Ala Leu Pro His Arg Thr
    290                 295                 300 gcc tgc gtc aga ttc tcg cat gcc aga gat cct att ttt ggc aat caa    960
Ala Cys Val Arg Phe Ser His Ala Arg Asp Pro Ile Phe Gly Asn Gln
305                 310                 315                 320 atc att ccg gat act gcg att tta agt gtt gtt cca ttc cat cac ggt   1008
Ile Ile Pro Asp Thr Ala Ile Leu Ser Val Val Pro Phe His His Gly
                325                 330                 335 ttt gga atg ttt act aca ctc gga tat ttg ata tgt gga ttt cga gtc   1056
Phe Gly Met Phe Thr Thr Leu Gly Tyr Leu Ile Cys Gly Phe Arg Val
            340                 345                 350 gtc tta atg tat aga ttt gaa gaa gag ctg ttt tta cga tcc ctt cag   1104
```

```
                Val Leu Met Tyr Arg Phe Glu Glu Leu Phe Leu Arg Ser Leu Gln
                            355                 360                 365 gat tac aaa att caa agt gcg ttg cta gta cca acc cta ttt tca ttc         1152
Asp Tyr Lys Ile Gln Ser Ala Leu Val Pro Thr Leu Phe Ser Phe
        370                 375                 380 ttc gcc aaa agc act ctg att gac aaa tac gat tta tct aat tta cac         1200
Phe Ala Lys Ser Thr Leu Ile Asp Lys Tyr Asp Leu Ser Asn Leu His
385                 390                 395                 400 gaa att gct tct ggg ggc gca cct ctt tcg aaa gaa gtc ggg gaa gcg         1248
Glu Ile Ala Ser Gly Gly Ala Pro Leu Ser Lys Glu Val Gly Glu Ala
                405                 410                 415 gtt gca aaa cgc ttc cat ctt cca ggg ata cga caa gga tat ggg ctc         1296
Val Ala Lys Arg Phe His Leu Pro Gly Ile Arg Gln Gly Tyr Gly Leu
            420                 425                 430 act gag act aca tca gct att ctg att aca ccc gag ggg gat gat aaa         1344
Thr Glu Thr Thr Ser Ala Ile Leu Ile Thr Pro Glu Gly Asp Asp Lys
        435                 440                 445 ccg ggc gcg gtc ggt aaa gtt gtt cca ttt ttt gaa gcg aag gtt gtg         1392
Pro Gly Ala Val Gly Lys Val Val Pro Phe Phe Glu Ala Lys Val Val
450                 455                 460 gat ctg gat acc ggg aaa acg ctg ggc gtt aat cag aga ggc gaa tta         1440
Asp Leu Asp Thr Gly Lys Thr Leu Gly Val Asn Gln Arg Gly Glu Leu
465                 470                 475                 480 tgt gtc aga gga cct atg att atg tcc ggt tat gta aac aat ccg gaa         1488
Cys Val Arg Gly Pro Met Ile Met Ser Gly Tyr Val Asn Asn Pro Glu
                485                 490                 495 gcg acc aac gcc ttg att gac aag gat gga tga                             1521
Ala Thr Asn Ala Leu Ile Asp Lys Asp Gly
                500                 505

<210> SEQ ID NO 99
<211> LENGTH: 506
<212> TYPE: PRT
<213> ORGANISM: Artificial Sequence
<220> FEATURE:
<223> OTHER INFORMATION: Synthetic Construct

<400> SEQUENCE: 99

Met Gly Gly Ser His His His His His His Gly Ser Ala Ala His Tyr
1               5                   10                  15

Met Ala Gln Thr Phe Lys Leu Ile Ile Asn Gly Lys Thr Leu Lys Gly
            20                  25                  30

Glu Ile Thr Ile Glu Ala Val Asp Ala Ala Glu Ala Glu Lys Ile Phe
        35                  40                  45

Lys Gln Tyr Ala Asn Asp Asn Gly Ile Asp Gly Glu Trp Thr Tyr Asp
    50                  55                  60

Asp Ala Thr Lys Thr Phe Thr Val Thr Glu Thr Gly Gly Gly Gly Gly
65                  70                  75                  80

Ser Gly Gly Gly Gly Ser Gly Gly Gly Gly Thr Glu Asp Ala Lys Asn
                85                  90                  95

Ile Lys Lys Gly Pro Ala Pro Phe Tyr Pro Leu Glu Asp Gly Thr Ala
            100                 105                 110

Gly Glu Gln Leu His Lys Ala Met Lys Arg Tyr Ala Leu Val Pro Gly
        115                 120                 125

Thr Ile Ala Phe Thr Asp Ala His Ile Glu Val Asn Ile Thr Tyr Ala
    130                 135                 140

Glu Tyr Phe Glu Met Ser Val Arg Leu Ala Glu Ala Met Lys Arg Tyr
145                 150                 155                 160

Gly Leu Asn Thr Asn His Arg Ile Val Val Cys Ser Glu Asn Ser Leu
```

-continued

```
                165                 170                 175
Gln Phe Phe Met Pro Val Leu Gly Ala Leu Phe Ile Gly Val Ala Val
            180                 185                 190
Ala Pro Ala Asn Asp Ile Tyr Asn Glu Arg Glu Leu Leu Asn Ser Met
        195                 200                 205
Asn Ile Ser Gln Pro Thr Val Val Phe Val Ser Lys Lys Gly Leu Gln
    210                 215                 220
Lys Ile Leu Asn Val Gln Lys Lys Leu Pro Ile Ile Gln Lys Ile Ile
225                 230                 235                 240
Ile Met Asp Ser Lys Thr Asp Tyr Gln Gly Phe Gln Ser Met Tyr Thr
            245                 250                 255
Phe Val Thr Ser His Leu Pro Pro Gly Phe Asn Glu Tyr Asp Phe Val
        260                 265                 270
Pro Glu Ser Phe Asp Arg Asp Lys Thr Ile Ala Leu Ile Met Asn Ser
    275                 280                 285
Ser Gly Ser Thr Gly Leu Pro Lys Gly Val Ala Leu Pro His Arg Thr
290                 295                 300
Ala Cys Val Arg Phe Ser His Ala Arg Asp Pro Ile Phe Gly Asn Gln
305                 310                 315                 320
Ile Ile Pro Asp Thr Ala Ile Leu Ser Val Val Pro Phe His His Gly
            325                 330                 335
Phe Gly Met Phe Thr Thr Leu Gly Tyr Leu Ile Cys Gly Phe Arg Val
        340                 345                 350
Val Leu Met Tyr Arg Phe Glu Glu Leu Phe Leu Arg Ser Leu Gln
    355                 360                 365
Asp Tyr Lys Ile Gln Ser Ala Leu Leu Val Pro Thr Leu Phe Ser Phe
    370                 375                 380
Phe Ala Lys Ser Thr Leu Ile Asp Lys Tyr Asp Leu Ser Asn Leu His
385                 390                 395                 400
Glu Ile Ala Ser Gly Gly Ala Pro Leu Ser Lys Glu Val Gly Glu Ala
            405                 410                 415
Val Ala Lys Arg Phe His Leu Pro Gly Ile Arg Gln Gly Tyr Gly Leu
        420                 425                 430
Thr Glu Thr Thr Ser Ala Ile Leu Ile Thr Pro Glu Gly Asp Asp Lys
    435                 440                 445
Pro Gly Ala Val Gly Lys Val Val Pro Phe Phe Glu Ala Lys Val Val
    450                 455                 460
Asp Leu Asp Thr Gly Lys Thr Leu Gly Val Asn Gln Arg Gly Glu Leu
465                 470                 475                 480
Cys Val Arg Gly Pro Met Ile Met Ser Gly Tyr Val Asn Asn Pro Glu
            485                 490                 495
Ala Thr Asn Ala Leu Ile Asp Lys Asp Gly
        500                 505
```

CELL FREE METHODS FOR DETECTING PROTEIN-LIGAND BINDING

CROSS-REFERENCE TO RELATED APPLICATIONS

This application claims the benefit of U.S. Provisional Application No. 61/001,370, filed Nov. 1, 2007; U.S. Provisional Application No. 61/072,581, filed Apr. 1, 2008; and U.S. Provisional Application No. 61/072,616, filed Apr. 1, 2008, all of which are incorporated by reference herein to the extent there is no inconsistency with the present disclosure.

STATEMENT REGARDING FEDERALLY SPONSORED RESEARCH OR DEVELOPMENT

This invention was made with government support under R21 CA122630, R01 Al068414 and R21AGO25954 awarded by the National Institutes of Health. The government has certain rights in the invention.

BACKGROUND OF THE INVENTION

The present invention relates to the field of molecular biology, especially as related to methods for sensitive assays for assessing protein-protein, protein-ligand or protein-nucleic acid interactions, and antagonists and/or agonists of such interactions. Specifically this invention relates to split monomeric reporter protein systems including, but not limited to, split luciferase, β-lactamase or fluorescent protein reporter systems, and excluding beta-galactosidase, where a functional protein results when the portions interact, with the result that there is a detectable signal produced in the assay. In particular, the split reporter is expressed in a cell-free system.

Protein-protein (1) and protein-nucleic acid (2) interactions are central to cellular function and are also emerging targets for pharmacological intervention when implicated in a particular disease pathway. Thus numerous in vitro and in vivo methods have been developed to target (3-7) and study these biomolecular interactions. Widely utilized in vitro methods for interrogating protein-protein and protein-DNA interactions and their antagonists include variations of enzyme linked immunosorbent assays (ELISAs), surface plasmon resonance (SPR), fluorescence resonance energy transfer (FRET) and fluorescence polarization (FP), which either require the use of antibodies or purified proteins and in some cases require chemical derivatization. On the other hand, powerful in vivo methods such as the yeast two-hybrid (8) assays have the advantage of speed by eliminating the need for protein purification but can be subject to false positives and negatives due to the multifactorial nature of signal generation (9). In between these two extremes lies the protein fragment based methods, where a specific biomolecular interaction drives the reassembly of a previously split reporter protein (10) (FIG. 1).

Whereas there are various methods employing split reporter proteins, the present inventors are not aware of any methods in which there is cell-free expression of one or both of the split monomeric reporter proteins and subsequent assay of the expressed, assembled reporter in such an assay. Examples of methods employing living cells or transgenic organisms are provided in US Patent Publications 2005/0144661, 2004/0235064; 2007/0161067; 2006/0224331; and U.S. Pat. Nos. 6,897,017; 6,872,871; 7,166,424; 7,160,691; 6,828,099; 6,428,951; 6,929,916; 7,062,219; and 7,176,287. See also Kim et al. (130); Porter et al. (23); Porter et al. (58); Paulmurugan et al. (131).

There is a need in the art for assays of molecular interactions which are fast, require relatively little culture and handling of samples, and are sensitive, accurate and precise.

SUMMARY OF THE INVENTION

The present invention provides methods for rapid and sensitive assays for detecting protein-protein, protein-nucleic acid, protein-small molecule or other protein-ligand interactions, and antagonists and/or agonists of such an interaction using split monomeric protein reporter systems including, but not limited to those generating enzymatic activity, bioluminescence, chemiluminescence, fluorescence or absorbance, for example using luciferase, β-lactamase or a fluorescent protein reporter system, but excluding beta-galactosidase in a cell-free assay system. The two portions of the reporter protein come together in a cell-free assay and their association is mediated by an interaction of an attached protein and its specific binding ligand, which can be an antibody or other protein, a specific nucleic acid sequence or a methylated or nonmethylated nucleic acid molecule, a single- or double-stranded RNA molecule, a small molecule, hormone or growth factor, among others. Protein-ligand and protein-small molecule interactions can be assessed when at least one portion of the reporter protein is covalently or noncovalently linked to either a ligand or to an antagonist or agonist of a bimolecular interaction and the second, complementing portion of the reporter protein is expressed in a cell-free translation system. Interaction of the two binding partners, with either their ligands or each other, brings the two portions of the split reporter protein into sufficiently close proximity that the two portions reassemble into a functional protein with, for example, detectable enzymatic or other activity. Antagonists or agonists of such interactions can be assessed by detecting the displacement of one binding partner, and the resulting decrease in reporter signal or by detecting enhanced interaction via increased reporter signal, respectively. Within the present methods, at least one portion of the reporter protein is synthesized in an in vitro translation assay, and it may be synthesized after in vitro transcription of the mRNA encoding that protein.

The fusion protein supplying the ligand binding portion associated with a split reporter can be one which interacts specifically with another protein. In the context of the assay, the ligand binding portion can be a protein, modified protein (e.g. phosphorylated, glycosylated), enzyme, hormone, antibody (Ab), single chain Ab, antigen-binding fragment of an Ab (e.g., Fab) or other protein. The Ab, single chain Ab, antigen-binding fragment of an Ab can be recombinant or derived from a natural source including, without limitation, e.g. camel, chicken, rabbit, mouse, rat, monkey, sheep, and goat. The ligand can be a small molecule, peptide, protein, single-stranded or double-stranded DNA or RNA molecule, or methylated or nonmethylated DNA molecule. Where the ligand binding domain and ligand are both proteins, the protein can be, without limitation, p53 and HDM2; Bcl and Bak; FKBP and FRAP; BAD and $BCL_{XL}$; p38α MAPK and MAPK-activated protein kinase 2; cMyc and Max; HIF1α and p300; Fos and Jun; PIN1 and Jun; and PKA and PKI, or an antigen and its cognate Fab fragment or antigen-binding fragment of a single chain Ab. Where the ligand is a small molecule or peptide, the ligand can be an agonist or antagonist of the ligand binding protein.

Where the ligand is a DNA, the protein segment binding the DNA can be a zinc finger, a helix-turn-helix protein, a leucine zipper protein, a helix-loop-helix protein, a transcriptional activation factor or a negative regulatory protein or other protein involved in transcription or DNA recognition. The protein segment binding the DNA is advantageously fused to a split reporter protein. Advantageously the DNA-binding segment and the split reporter are encoded as a fusion protein coding sequence.

Where the ligand is an RNA molecule, the RNA-binding segment can be a pumilio domain, a KH domain, RRM domain, Argonaute, MS2 coat protein, eukaryotic initiation factor 4a, or other proteins or protein-RNA complexes involved in translation or RNA recognition. The protein segment binding the RNA is advantageously bound or fused to a split reporter protein component. Advantageously the RNA-binding segment and the split reporter are encoded as a fusion protein coding sequence.

It is understood that there can be a linker region between the ligand binding portion and the reporter fragment portion of one or both components of the split reporter system, especially if necessary to avoid steric hindrance of the bound ligand with respect to the reassembly of the split reporter proteins.

A fluorescent protein can be a naturally occurring or engineered or enhanced green, blue, yellow, red or other fluorescent protein. A green fluorescent protein or variant can be one derived in sequence from or modified from *Aequoria*, or *Discosoma*. Luciferase can be one derived in sequence from or modified from firefly (i.e. *Photinus pyralis*), *Renilla* or *Gaussia*. Beta-lactamases are known to the art, as are its chromogenic or fluorogenic or luminescent substrates, for example, nitrocefin or CCF2FA.

The cell-free translation machinery can be a mammalian, plant, fungal or bacterial translation system. A cell-free translation system, often a crude cell extract, contains all the macromolecular components (70S or 80S ribosomes, tRNAs, aminoacyl tRNA synthetases, initiation, translocation and termination factors, etc) necessary for translation of exogenous RNA (mRNA). For efficient translation, the cell-free translation system is supplemented with amino acids, energy sources (e.g., ATP, GTP) energy regenerating systems (such as creatine phosphate and creatine phosphokinase for eukaryotic systems or phosphoenol pyruvate and pyruvate kinase for *Escherichia coli* lysate) and other cofactors including magnesium and potassium cations. The mammalian system can be rabbit reticulocyte lysate, HeLa cell extract, among others, and the plant cell extract can be from wheat, wheat germ, corn, pea, tobacco or other plant. The fungal cell-free extract can be from a fungus such as *Aspergillus nidulans* or *Neurospora crassa*, among others, and it can be from a yeast such as *Saccharomyces cerevisiae, Pichia pastoris* or *Candida albicans*. A bacterial cell-free extract can be prepared from *Escherichia coli*, among others. Besides cell-free extracts, the translation machinery can be in the form of purified components, as known to the art. Many of the foregoing systems are commercially available. An advantageous use of purified translation machinery is with the addition of unnatural amino acids used in translation, for example, amino acid analogues. In such systems tRNAs charged with natural and/or unnatural amino acids, as desired. A coupled transcription-translation system is one in which DNA serves as the template for the synthesis of RNA, which is not isolated or purified but is directly translated into protein in the assay system. Such systems generally employ a bacteriophage RNA polymerase and promoter (especially T7, T3 or SP6) used to drive expression of the split reporter protein in vitro. There are commercially available products of various types, and the art knows the appropriate vector and sequence modifications for the system in which the split reporter(s) are produced.

With respect to nucleic acids, there can be sensitive and quantitative measurement of particular sequences of DNA or RNA, thus enabling the assessment of disease markers, for example, identification of up-regulated genes associated with diseased cells (including but not limited to cancer cells or cells with metabolic abnormalities), and deletions and recombination events in the genome or nucleic acids associated with genome or expression products of a pathogen, thereby permitting prediction of particular diseases. In addition, particular polymorphisms can be detected, as relevant to personalized medicine or predicting or diagnosing a disease. Finally, specific nucleic acid molecules characteristic of a particular pathogen can be detected, thereby permitting confirmation of the presence of the pathogen in a biological, environmental, commercial, pharmaceutical, food (e.g. vegetables, fruit, dairy product, meat, poultry, fish for human or animal consumption) or water sample.

With respect to proteins, there can be sensitive and quantitative measurement of particular proteins, thus enabling the assessment of disease markers, for example, identification of up-regulated, down-regulated, mutated, or post-translationally modified proteins associated with particular diseases and therapies as relevant to personalized medicine or predicting or diagnosing a disease or following the progress of therapies. Finally, specific proteins characteristic of a particular pathogen can be detected, thereby permitting confirmation of the presence of the pathogen in a biological, environmental, commercial, pharmaceutical, food (e.g. vegetables, fruit, dairy product, meat, poultry, fish for human or animal consumption) or water sample. In addition, the ligand can be an amyloidogenic protein comprising beta-amyloid (1-40, 1-41, 1-42, 1-43), prion protein, alpha-synuclein, tau, immunoglobulin, islet amyloid polypeptide or huntington protein, and there can be achieved a diagnosis or prognosis of Alzheimers disease or a prion disease or contamination of a sample with a prior, especially one associated with human or animal disease.

The ligand can be contained within a sample, biological or otherwise as set forth above or it can be a recombinant or synthetic molecule.

In the case where a nucleic acid molecule, binding or interacting region of a protein, small molecule or other ligand is tethered to a segment of a split reporter protein, the tether can be from 0-50 amino acids in length. In other words, the binding or interacting portion is fused to the split reporter portion via a sequence of 0-50 amino acids.

The present invention further embodies a method for identifying an antagonist or an agonist of protein-protein interaction using a cell-free system comprising coupled or uncoupled transcription and translation machinery; containing RNA or DNA encoding a first fragment of a reporter operably linked and in frame to RNA or DNA encoding a first interacting protein, wherein the cell-free system expresses at least one of the split reporter-binding segment proteins and a mixture containing both (complementing) fragments is in contact with the cognate ligand in the presence and absence of a test composition. The signal of the detectable reporter is measured in the presence and absence of the test composition, and an antagonist is identified when the signal in the presence of the test compositions is lower than in its absence and an agonist of binding is identified when the signal in the presence of the test composition is greater than in its absence. This methodology is fully adaptable to other ligand-ligand binding protein interactions (protein-small molecule, protein-nucleic acid, and the like).

In any of the methods provided herein it is advantageous that the transcription product encoding one or both of the binding region-split reporter portions comprises a stabilizing element such as a 5' stem-loop, including but not limited to a 5' stem-loop derived in sequence from bacteriophage T7 and advantageously a 3' stem-loop such as that derived in sequence from bacteriophage T3 (see, e.g., 134, 135); and also advantageously a Kozak sequence 5' to the translation start site (see, e.g., 133) and a polyadenylated 3' end (see, e.g., 136) when the cell-free translation system is a eukaryotic system or a Shine-Delgarno sequence when the cell-free translation system is a bacterial translation system.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14. ALU values for four kinases assayed with three known small-molecule kinase inhibitors. All inhibitor samples contain 125 nM Jun-staurosporine (jun-st.) in addition to 50 µM inhibitor.

FIG. 15. Ternary complex formation facilitated by Tri-Staur. Addition of a kinase active site binding small molecule induces complex dissociation and loss of luciferase activity.

DETAILED DESCRIPTION OF THE INVENTION

Figure 1:
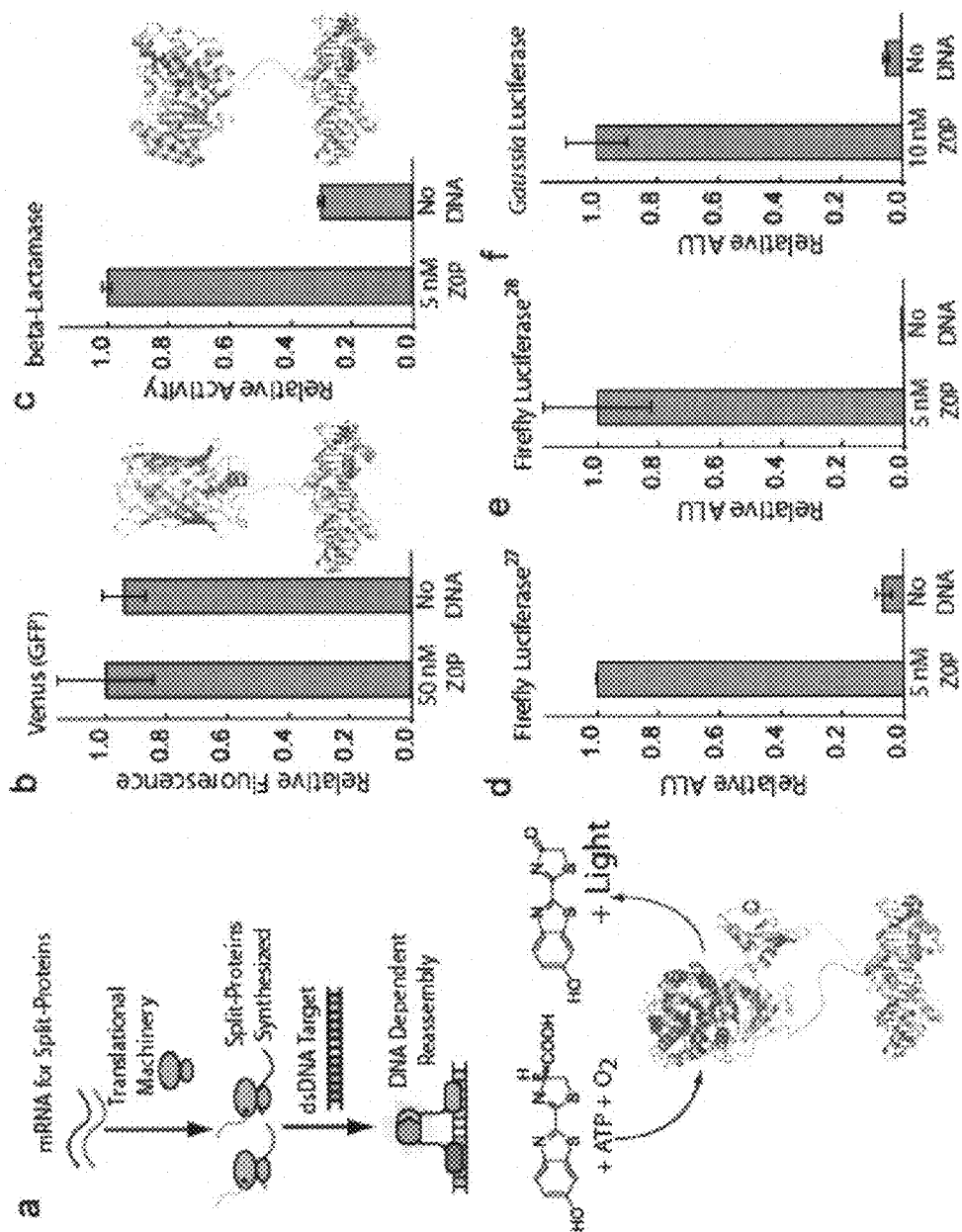
FIG. 1. Cell-free detection utilizing split-proteins. (a) Cartoon representation of a split protein-system with zinc-fingers tethered to the split-proteins in the presence of target dsDNA oligonucleotide. Different split-protein reporters tethered to sequence specific zinc-fingers in the presence and absence of target dsDNA; (b) split-Venus (a GFP variant); (c) split-β-lactamase; (d) split-firefly luciferase as described by Luker (27) et. al.; (e) split-firefly luciferase as described by Paulmurugan (28) et. al.; (f) split-Gaussia luciferase as described by Remy et al. (20).

Whereas there are various methods employing split reporter proteins, the present inventors are not aware of any methods in which there is cell-free expression of one or both of the split reporter proteins and subsequent assay of the expressed, assembled reporter in such an assay wherein there is detection of protein-protein, protein-nucleic acid or protein-ligand interactions or of agonists or antagonists of such interactions. Important advantages are that there is no requirement for introducing nucleic acid molecules encoding the segments of the reporter protein into living cells and subsequently obtaining gene expression therein and there is no need to purify the split reporter proteins prior to the assay. The methods of the present invention are readily adapted for high throughput (HTP) assays. As specifically shown herein, the measurement of bioluminescence in a split luciferase system is especially useful in an interaction monitoring assay.

Split-protein reporters have emerged as a powerful methodology for imaging biomolecular interactions which are of much interest as targets for chemical intervention. Here we describe a systematic evaluation of split-proteins, specifically the green fluorescent protein, beta-lactamase, and several luciferases, for their ability to function as reporters in completely cell-free systems to allow for the extremely rapid and sensitive determination of a wide range of biomolecular interactions without the requirement for laborious transfection, cell-culture, or protein purification (12-48 hours). We demonstrate that the cell-free split-luciferase system in particular is amenable for directly interrogating protein-protein, protein-DNA, and protein-RNA interactions in homogenous assays with very high sensitivity (22-1800 fold) starting from the corresponding mRNA or DNA. Importantly, we show that the cell-free system allows for the rapid (2 hours) identification of target site specificity for protein-nucleic acid interactions and in evaluating antagonists of protein-protein and protein-peptide and protein-small molecule complexes circumventing protein purification bottle necks. Moreover, we show that the cell-free split-protein system is adaptable for analysis of both protein-protein and protein-nucleic acid interactions in artificial cell systems comprising water-in-oil emulsions. Thus this study provides a general and enabling methodology for the rapid interrogation of a wide variety of biomolecular interactions and their antagonists without the limitations imposed by current in vivo and in vitro approaches.

The present methods can readily be adapted for use in the sensitive, qualitative or quantitative determination of RNA and DNA, for example, specific disease markers such as those which are up-regulated in cancer or for specific sequences which are not expressed due to a genetic defect or a disease, for identifying deletions and recombination events in the genome which are associated with genetic defect or a genotype of interest, detecting single nucleotide polymorphisms associated with disease and detection of a pathogenic organism based on known DNA or RNA sequences or proteins The reconstitution of a functional protein from split-peptide fragments was first demonstrated for ribonuclease in 1959. Since then "split-protein reassembly" or "protein complementation" has been applied to the in vivo detection of a wide variety of protein-protein interactions utilizing numerous split-protein hosts including ubiquitin (12), beta-galactosidase (13), dihydrofolate reductase (14), beta-lactamase (15), GFP (16), GFP-variants (17,18), firefly luciferase (19) and Gaussia luciferase (20). Recently, we and others have also described methods for detecting nucleic acids and their chemical modification by the reassembly of ternary complexes of split-GFP and split-β-lactamase tethered to nucleic acid binding proteins (21-24). Thus split-protein systems or "protein complementation assays" (PCAs) can directly image most biomolecular interactions. Though the current methods are useful, all of these split-protein methods have certain limitations for interrogating protein-protein and protein-nucleic acid interactions and their inhibitors in a rapid and high-throughput fashion. For example, current in vitro methods require extensive protein purification and also rely on proper folding of recombinant proteins, while in vivo methods require lengthy transfection and propagation of cellular cultures prior to analysis, both approaches being time intensive (16, 24-26). Such methods are also prone to problems arising from proteolysis of intracellularly expressed proteins and peptides as well as a lack of control over interfering co-expressed cellular factors, as is also the case with yeast n-hybrid methods.

To provide a rapid and general method that circumvents many of the limitations discussed above, we determined that fragmented reporter proteins fused to functional (ligand-binding) proteins can be rapidly generated directly from mRNA utilizing cell-free translation systems and immediately interrogated for biomolecular interaction-dependent signal generation. The use of split reporter proteins in cell-free translation expression systems takes advantage of fast protein synthesis rates, from 60 to 90 minutes, and easy adaptation to homogeneous assays and high throughput analyses; these systems also avoid immobilization, washing and/or purification protocols. This cell-free approach provides a general platform for rapidly detecting protein-protein, protein-small molecule, protein-DNA, protein-methylated DNA, and protein-RNA interactions starting from mRNA or directly from DNA corresponding to the desired interaction pair in less than two hours. Moreover, we demonstrate how this approach aids in determining specificity of protein-nucleic acid interactions as well as in determining small molecule antagonists and/or agonists of protein-protein interactions. The identification of antagonists and agonists is important in selecting potential new therapeutic agents to be used in methods of treatment and for methods for decreasing, delaying or reducing severity of disease conditions associated with ligand-protein interactions, as understood in the art.

Evaluation of Split Protein Reporters for the Cell-Free Interrogation of Biomolecular Interactions.

Initially we evaluated the ability of our previously reported split-GFP (22) and split-β-lactamase (23,25) systems appended to specific zinc-fingers to reassemble in the presence of target DNA utilizing in vitro transcribed mRNA in a purified wheat germ extract translation system (FIGS. 1b and 1c). Signal from the DNA-dependent reassembled GFP (22) in the early experiments was too low to observe over background using standard fluorescence measurements, while DNA dependent β-lactamase activity (25) yielded measurable but low signal-to-background ratios. Thus, we turned to in vivo split-luciferase systems which have the significant advantage of negligible background from the translation system due to the generation of a bioluminescent signal (FIG. 1a). We first examined the fragmented firefly luciferase (Fluc) reported by Luker et al (27) which when appended to our zinc fingers showed significant signal over background luminescence upon addition of target DNA (FIG. 1d). This constitutes the first demonstration of the bioluminescent read-out of a specific nucleic acid sequence, and this split-luciferase system was chosen for further studies in cell-free systems. The split-Gaussia luciferase (20) and alternatively split-firefly luciferase complementation systems (27,28) were also tethered to our zinc-finger proteins and displayed surprisingly strong signal over background bioluminescence (FIGS. 1e and 1f) in a DNA-dependent fashion in cell-free assays.

To test the general applicability of the cell-free split-luciferase approach to monitoring protein-protein and protein-nucleic acid interactions, we utilized seven well characterized and widely studied biomolecular interactions (FIG. 2) including (a) the catalytic subunit of cAMP-dependent protein kinase (PKA) with its inhibitor PKI (PKA/PKI) (29-31); (b) the rapamycin-dependent interaction between human FK506-binding protein 12 (FKBP) and the FKBP12-rapamycin binding (FRB) domain of human mTOR (FKBP/FRB) (32-34). Akin to the yeast three hybrid systems (35), we also investigated the ternary association of (c) two sequence specific zinc-fingers (36) with a target DNA (Zif268/PBSII); (d) a zinc-finger and methyl CpG-binding domain with a target CpG-methylated DNA (Zif268/MBD2) (37-40); and finally (e) two RNA-specific pumilio domains[41] with a target RNA (Pum1/Pum2). Additionally, the widely utilized coiled-coil domains of the transcription factors Fos and Jun (Fos/Jun) (42-44) and the interaction between hypoxia inducible factor-1α (HIF-1α) and the CH1 domain of the transcriptional coactivator p300 (HIF-1α/p300) (45,46) were also tested The overall sensitivity (signal/background) of these systems (FIG. 2, panels a-e) was excellent and varied from 22 to 1800-fold, and the total assay time from translation to analysis was less than two hours.

Figure 3:
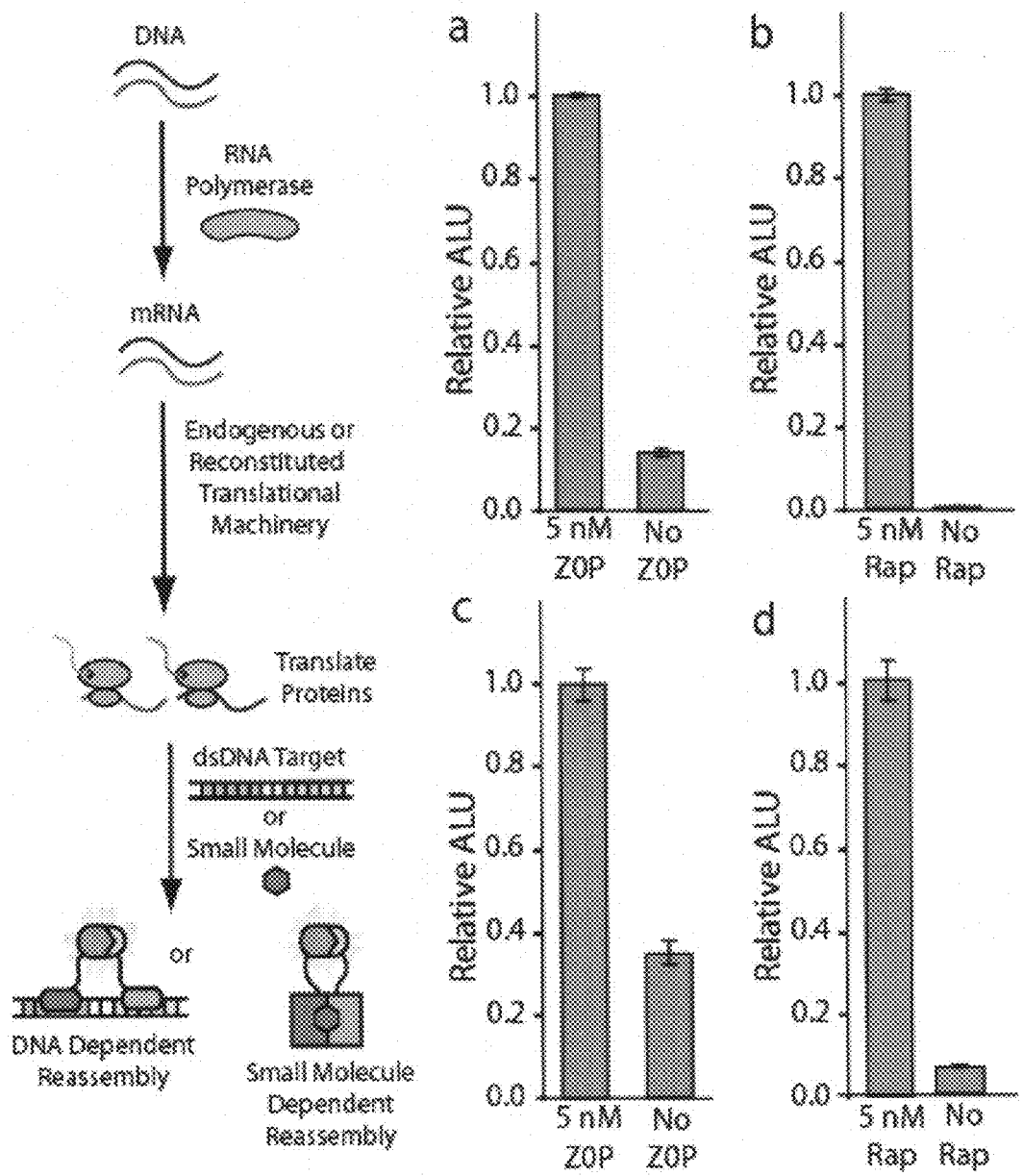
FIG. 3. Cell-free detection of biomolecular interactions with split-luciferase starting from DNA, cartooned in (a). Utilizing transcription and translation coupled unpurified cell-free lysate system: (b) protein-DNA interaction between PBSII-NFluc, CFluc-Zif268, and 5 nM target dsDNA oligonucleotides and (c) rapamycin (5 nM) induced interaction between FRB-NFluc and CFluc-FKBP. Detection of biomolecular interactions utilizing purified DNA in the PURESYSTEM classic II system consisting of completely purified transcriptional and translational components (d) protein-DNA interaction between PBSII-NFluc, CFluc-Zif268, and 5 nM target dsDNA oligonucleotide and (e) rapamycin (5 nM) induced interaction between FRB-NFluc and CFluc-FKBP.

We also investigated whether it was possible to directly couple transcription and translation in a cell-free lysate system, which could eliminate the need for the separate in vitro transcription step as was used in these experiments (FIG. 3). These experiments were successful for both DNA-protein and protein-small molecule dependent interactions (FIG. 3, panels a and b). In addition to using purified lysates, we further interrogated whether we could detect the above interactions using a system composed entirely of purified translational components (47) (FIG. 3, panels c and e, the so-called "PURE System"), to demonstrate that reconstituted transcription and translation machinery is sufficient for detecting biomolecular interactions after split reporter protein expression. This set of experiments clearly demonstrated that a cell-free split-luciferase assay format allows the rapid, sensitive, and direct detection of protein-protein, protein-small molecule, protein-DNA, protein-methylated DNA, and protein-RNA interactions starting from either mRNA or directly from DNA corresponding to the desired interaction pair. Having established that our methods provide robust signals for a wide variety of biomolecular interactions, we also investigated whether this system is amenable to reporting upon inhibitors of protein-nucleic acid and protein-protein interactions.

Figure 4:
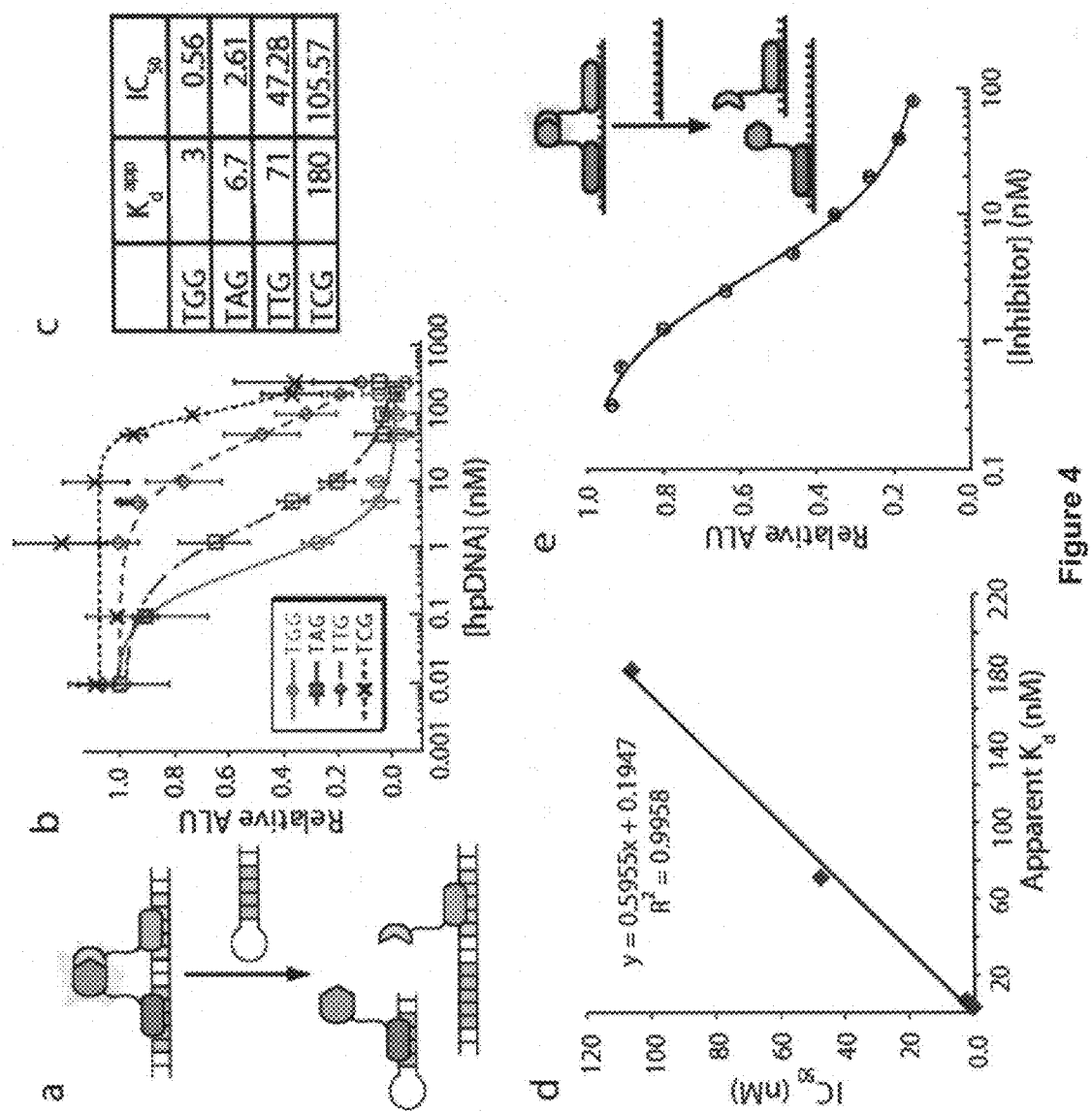
FIG. 4. Interrogation of protein-nucleic acid interactions utilizing split-luciferase cell-free assay. (a) Cartoon showing dissociation of dsDNA dependent firefly luciferase ternary complex by the addition of a competitor hairpin DNA containing one of the two zinc-finger binding sites. (b) Dissociation of the reassembled PBSII-NFluc, CFluc-Zif268, dsDNA ternary complex by the addition of Zif268 hairpin DNA targets containing TGG (wild type), TAG, TTG, and TCG triplet basepairs. (c) and (d) Previously reported relative affinities (49) of target oligonucleotides with Zif268 with $IC_{50}$ values derived from the cell-free firefly luciferase reassembly assay and their correlation. (e) Dissociation of the Pum2-NFluc, CFluc-Pum1, RNA ternary complex by the addition of an RNA target containing a Pum1 binding site.

In order to detect antagonists of protein-protein or protein nucleic acid interaction, we first established the thermodynamic reversibility of the ternary complex consisting of reassembled firefly luciferase fragments tethered to two zinc fingers (PBSII and Zif268) and the cognate target DNA (FIG. 4a). Towards this goal, translations using mRNA encoding PBSII-NFluc and CFluc-Zif268 were initiated in the presence of the target oligonucleotide (Zif268-0-PBSII). Post DNA-dependent firefly luciferase reassembly, a hairpin DNA (hpDNA-Zif268) which is a competitor for only Zif268 binding was added at increasing concentrations and the system was allowed to equilibrate for 30 min. A concentration-dependent decrease in luminescence was observed, clearly demonstrating that the formation of the ternary complex of the firefly luciferase was reversible and it could be inhibited by addition of the dominant-negative (hpDNA-Zif268) oligonucleotide (FIG. 4b, TGG containing hpDNA). The general applicability of the cell-free system for probing protein-nucleic acid inhibition was further demonstrated with translations containing mRNA encoding Pum2-NFluc and CFluc-Pum1 in the presence of target RNA. As earlier, a concentration-dependent decrease in luminescence was observed only upon the addition of increasing amounts of a competitor half-site RNA target that is known to selectively bind one of the pumilio domains (41) (FIG. 4e). We recognized that our split-luciferase based cell-free system can be readily utilized to analyze the relative target site specificity of nucleic acid binding proteins through competition binding experiments.

We studied protein-DNA target site specificity using the present methods. A number of methods have been developed to interrogate the relative affinity of DNA-binding proteins for their target site, including traditional EMSAs and DNA microarrays (48,49). Though powerful, these techniques require the use of purified components, specialized equipment, and/or radioactive materials. Having established that ternary zinc finger-DNA complexes can be disrupted by a competitor oligonucleotide added in trans, we next correlated the known binding affinities of Zif268 for single nucleotide changes in its binding site to $IC_{50}$ values obtained from our cell-free firefly luciferase approach in a 96-well format. Separate translation reactions of PBSII-NFluc and CFluc-Zif268 mRNA in the presence of the dsDNA target oligonucleotide Zif268-0-PBSII were initiated. Duplicate experiments containing ternary complexes were allowed to assemble for 90 minutes followed by the addition of increasing concentrations of competitor hpDNA, containing one of four different Zif268 binding sites having either A, T, C, or G at the central position. In each case a competitor hpDNA-concentration dependent decrease in luminescence was observed (FIG. 4b) within 30 min. $IC_{50}$ values for each competitor hpDNA (FIG. 4c) were shown to correlate extremely well ($R^2=0.996$) (FIG. 4d) with previously reported relative affinities of these target sites (49). These results validate the use of the split-luciferase cell-free system for the determination of relative binding affinities of nucleic acid-binding proteins for their cognate target sites, and more generally, in studying inhibitors of protein-nucleic acid interactions. Thus, this cell-free system provides an advantageous alternative to current methods for interrogating protein-nucleic acid binding as they can be performed in a simple, rapid, high-throughput and homogeneous format without having to purify or refold the protein of interest and without having to transform and manipulate living cells.

Having demonstrated the ability to measure antagonists of protein-nucleic acid interactions, we next sought to interrogate the ability of cell-free firefly luciferase reassembly to assess antagonists and agonists (for example, small molecules) of protein-protein interactions. As a first test of small molecule modulation of split-luciferase activity, we chose the well characterized rapamycin-dependent interaction between the human FK506-binding protein 12 (FKBP) and the FKBP12-rapamycin binding (FRB) domain of human mTOR (residues 2024-2113) (27,28,32). This system has been a standard test for several split-protein reporter systems. A rapamycin concentration dependent increase in luminescence was observed from the cell-free translations of the split reporters (FIG. 5, panel a) (27).

Figure 2:
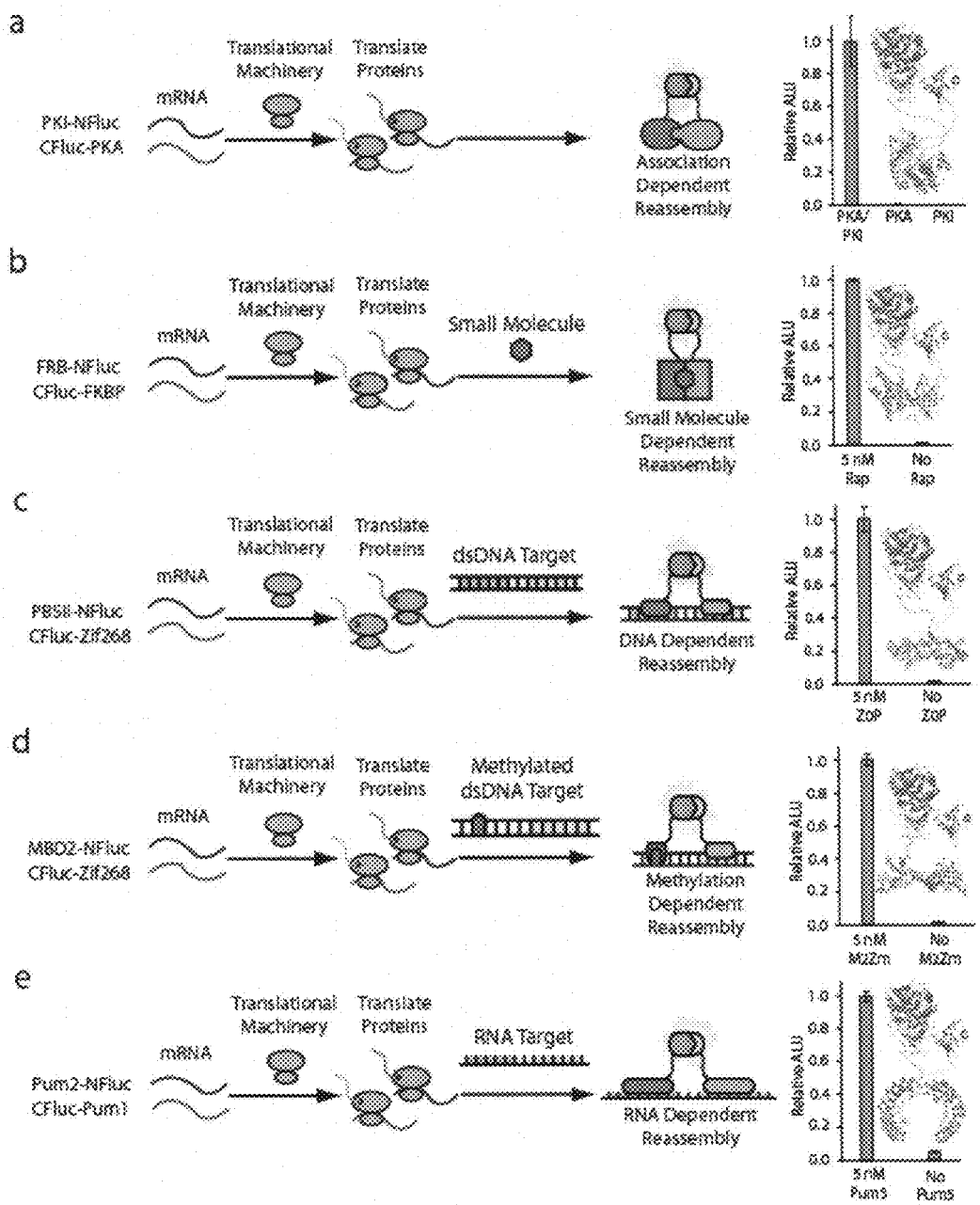
FIG. 2. Cell-free detection of a wide variety of biomolecular interactions utilizing split-luciferase starting from mRNA. Detection of (a) protein-protein interaction between PKI-NFluc and CFluc-PKA; (b) rapamycin induced interaction between FRB-NFluc and CFluc-FKBP; (c) protein-DNA interaction between PBSII-NFluc, CFluc-Zif268, and a target dsDNA oligonucleotide; (d) methylation dependent protein-DNA interaction between MBD2-NFluc, CFluc-Zif268, and a target methylated CpG dsDNA oligonucleotide; and (e) protein-RNA interaction between Pum2-NFluc, CFluc-Pum1, and a target RNA oligonucleotide.
Figure 5:
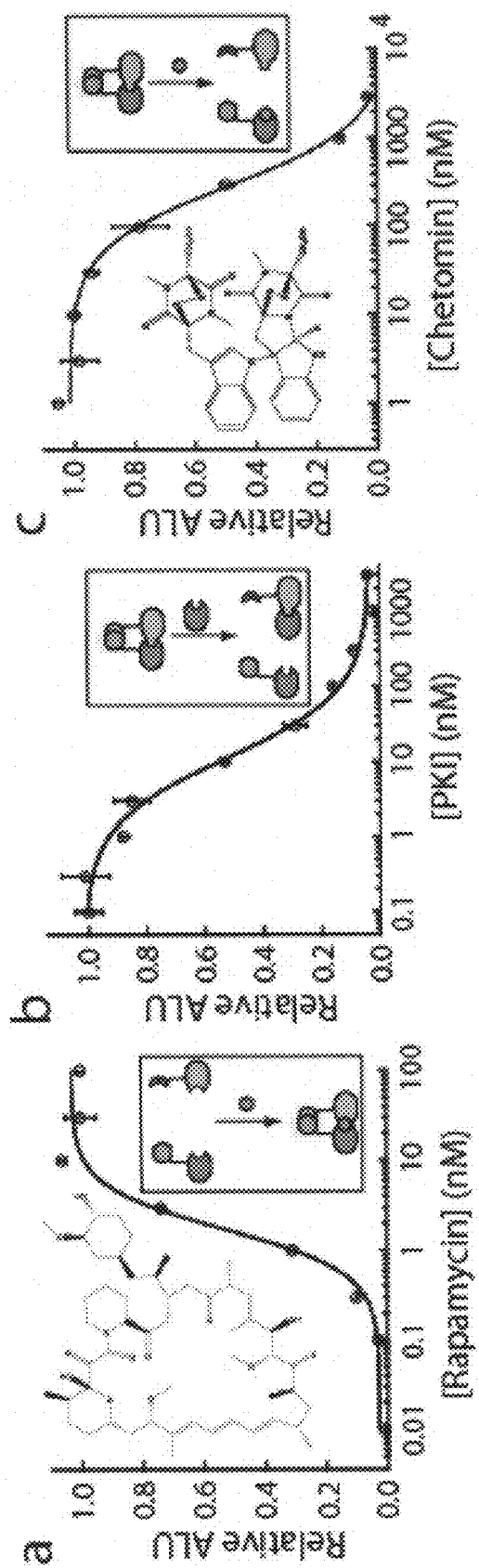
FIG. 5. Interrogation of small molecule and peptide modulators of protein-protein interactions utilizing the split-firefly cell-free assay. (a) Concentration dependent association of FRB-NFluc and CFluc-FKBP mediated by rapamycin (inset). (b) Concentration dependent dissociation of PKI-NFluc/CFluc-PKA complex by PKI peptide. (c) Concentration dependent dissociation of the reassembled p300-NFluc/CFluc-Hif1α complex by chetomin (inset).

As our first test for determining antagonism of protein-protein interactions, we chose the well characterized interaction between the catalytic subunit of cAMP-dependent protein kinase (PKA) with its inhibitor PKI (residues 5-24) (29). Initial experiments had demonstrated that the fusion proteins PKI-NFluc and CFluc-PKA could be translated in vitro from mRNA and that their association could be monitored via luminescence (FIG. 2, panel a). Given that reassembly of fragmented firefly luciferase is dependent on PKA/PKI complex formation, the inhibition of this interaction was interrogated by the addition of increasing concentrations of a PKI peptide (44), with the result of an observed $IC_{50}$ value of 11 nM (FIG. 5, panel b). To provide further evidence of the general applicability of this cell-free format, we interrogated the inhibition of the interaction of hypoxia inducible factor-1α (HIF-1α) and the CH1 domain of the transcriptional coactivator p300 (50). HIF-α is an emerging anti-cancer target. Initial experiments demonstrated that the fusion proteins p300-NFluc and CFluc-HIF-1α could be translated in vitro from mRNA and their association could be monitored via luminescence. The small molecule chetomin has been identified as a first-in class inhibitor of the interaction between HIF-1α and p300 (46). To evaluate if our method can aid in the identification of small-molecule inhibitors, mRNA encoding p300-NFluc and CFluc-HIF-1α fusion proteins were translated followed by the addition of increasing concentrations of the chetomin post reassembly. Luminescence measurements following chetomin incubation revealed a concentration-dependent decrease in signal, with an $IC_{50}$ value of 290 nM (FIG. 5, panel c). Importantly, control experiments with excess chetomin or PKI-peptide showed no effect on signal generation in the irrelevant zinc finger/DNA cell-free assay, which verified that the loss in signal was dependent on the disruption of specific protein-protein interactions rather than on off-target effects such as inhibition of luciferase activity. Thus, these three systems demonstrate that both peptide and small molecule modulators of protein-protein interactions can be rapidly evaluated in the cell-free split-luciferase system without the need for transfection and cell-culture (current yeast n-hybrids and PCA methods); protein purification, selective fluorophore labeling (FP); or immobilization on solid surfaces (SPR and ELISA).

Figure 6:
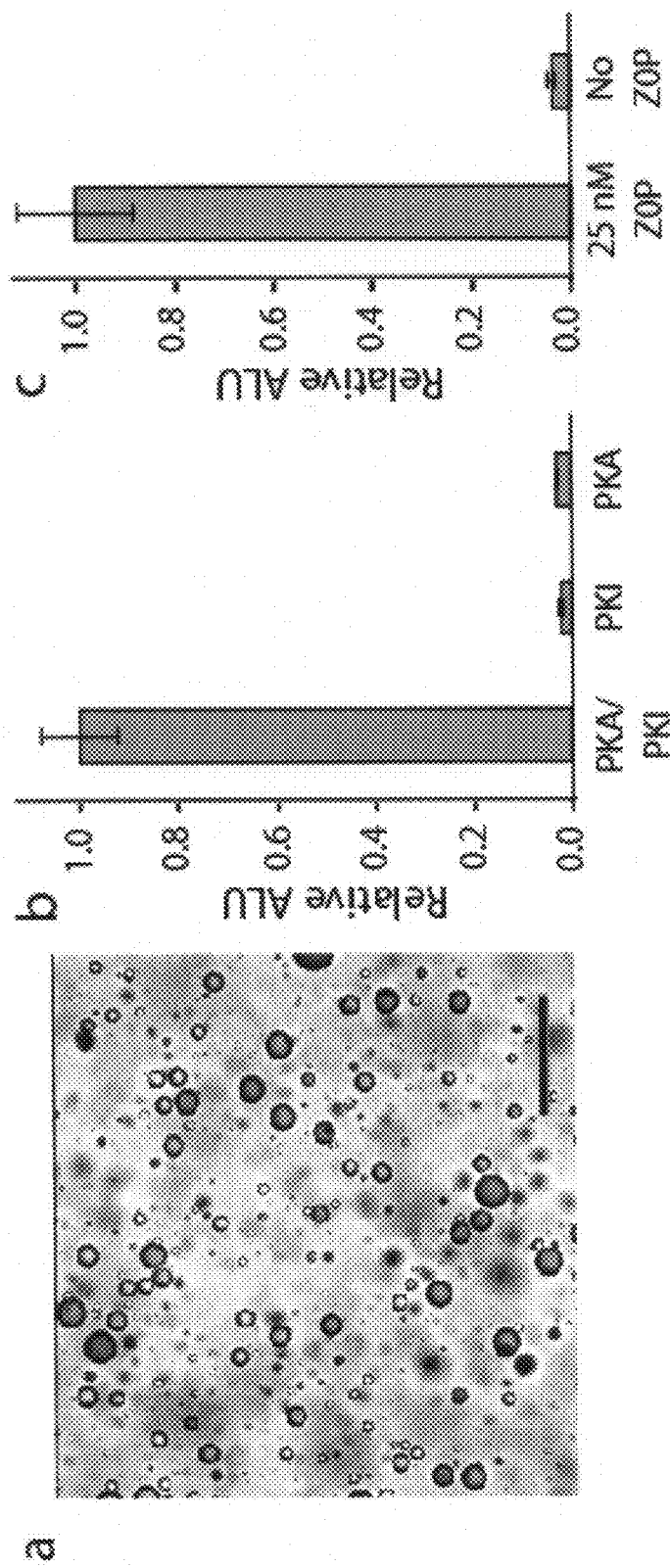
FIG. 6. Protein-protein and protein-DNA interactions in artificial cells interrogated by split-luciferase dependent bioluminescence. (a) White light microscope image of a water-in-oil emulsion containing a PKI-NFluc/CFluc-PKA translation in wheat germ extracts. Scale bar is equal to 75 µm. (b) Protein-protein association (PKI-NFluc/CFluc-PKA) dependent split-luciferase reassembly and bioluminescence within water-in-oil emulsion. (c) Protein-DNA interaction dependent firefly luciferase reassembly within water-in-oil emulsion.

Elegant experiments by Tawfik and Griffiths have recently established that water-in-oil emulsions of in vitro translation reactions can function as "artificial cells" or "man-made" cells, and they have been used for linking genotype with phenotype in protein evolution experiments (51). To demonstrate that our cell-free split luciferase assay is compatible with in vitro compartmentalization, translations containing mRNA encoding PKI-NFluc and CFluc-PKA; or PBSII-NFluc, CFluc-Zif268 and target DNA; were performed in wheat germ extract encapsulated in water-in-oil emulsions (FIG. 6a) and subjected to luminescence analysis (FIGS. 6b and 6c). These experiments clearly demonstrate that the cell-free split-firefly luciferase system can be adapted in screens for protein-protein and protein-nucleic acid interactions in artificial cell based methodologies and may also find applications in studying proteins incorporating unnatural amino acids where significantly greater control over translational machinery components is often desirable (52-55).

Previous cell based and in vitro strategies, though powerful, depend on cumbersome steps which can include transfection, cell culture, purification, washing steps, and/or covalent modification, yielding overall experimental times in excess of 12-48 hours starting from appropriate clones. By contrast this present methods provide a general platform for interrogating biomolecular interaction in homogeneous assays based on cell-free split-protein systems, and results are available within two hours. This cell-free assay can employ a variety of split protein reporters to provide fluorescent (β-lactamase) or bioluminescent (luciferase) signal outputs. One drawback of the previous methods, also found in ELISA and in vivo approaches, is that only relative affinities and $IC_{50}$ values can be determined, as compared to methods such as FP and SPR. However, the speed and ease of implementation of the present methods, which does not require cell culture, protein purification, or chemical derivatization, can be used to rapidly address biological and chemical questions with appropriate controls, as we have demonstrated with either dominant negative inhibition or known small molecule ligand.

We have demonstrated the ability to detect a wide variety of protein-ligand interactions, including the well studied heterodimerization of the leucine zippers Fos and Jun, the interaction between the protein kinase PKA and its inhibitor PKI, and the small molecule-dependent interaction between FKBP and FRB. Additionally, we provide the first example for a rapid method for interrogating the interaction between HIF-1α and p300, an emerging protein-protein target implicated in cancer progression. Furthermore, we detail the first examples of sensitive split-luciferase-mediated detection of a wide range of protein-nucleic acid interactions, including zinc finger domains with specific dsDNA, a methyl CpG-binding domain with specific methylated DNA, and RNA binding pumilio domains with target RNA. We have also shown that this methodology can be used to interrogate the relative binding affinities of nucleic-acid binding proteins for their target sites and the evaluation of small molecule, peptide and nucleic acid modulators of protein-protein interactions. In addition to using purified lysates and wheat germ extracts cell-free translation systems, we have demonstrated the detection of protein-protein and protein-nucleic acid using a system composed entirely of purified components that minimize non-specific interactions from cellular components and allow control over the translational machinery, for example in applications including, but not limited to, unnatural amino acid incorporation (52-55). Finally, we have demonstrated that the split-protein reporters are functional in water-in-oil emulsions providing artificial cell systems for studying protein-protein and protein-nucleic acid interactions that can potentially be utilized in screening methodologies (51).

This cell-free format can be used in a wide-variety of applications that include, without limitation, screening of DNA or RNA target sites for nucleic acid-binding proteins and the determination of target site preference. Importantly, this approach can also be used for screening small molecules, nucleic acids, peptides or proteins for inhibition of specific protein-protein or protein-nucleic acid or protein-small molecule interactions (1,2) Moreover, since the split-protein approaches have been widely utilized in a cellular context, the initial hits from the rapid cell-free system can be rapidly applied in a cellular context (10,19). This rapid, sensitive, and homogeneous assay system can be widely utilized for interrogating user-defined natural and unnatural biomolecular interactions and for evaluating agonists and antagonists of these interactions.

The invention may be further understood by the following non-limiting examples and information provided in the present Specification.

General Materials and Methods

All materials were obtained from Sigma-Aldrich (St. Louis, Mo.) unless otherwise noted. $ZnCl_2$ was obtained from EM Sciences (Pt. Washington, Pa.). Restriction enzymes were obtained from NEB (Ipswich, Mass.) and in vitro translational products from Promega (Madison, Wis.). Oligonucleotide primers and targets were from IDT (Coralville, Iowa).

Plasmid construction and mRNA production. The fusion protein constructs used in this study are shown in Tables 6-28. Fragments coding for reporter protein fragments (GFP, Beta-Lactamase, and three luciferases) were generated by PCR with appropriate primers and subsequently cloned into either the pETDuet-1 vector (Novagen, Madison, Wash.) or the pMAL-c2x vector (NEB) using standard techniques and verified by sequencing. Fragments encoding the nucleic acid-binding proteins or associating proteins used in this study were generated by PCR starting from the specific plasmids. The fusion protein constructs were generated using standard cloning techniques and verified by sequencing. The mRNA necessary for cell-free assays was generated as follows: PCR fragments corresponding to the desired fusion constructs were generated using a forward primer containing a T7 RNA polymerase promoter and Kozak sequence and a reverse primer containing a 3' hairpin loop. The purified PCR products were subsequently used as template for in vitro transcription using the RiboMAX Large Scale RNA Production System-T7 (Promega) following the manufacturer's protocols.

Target DNA preparation. All nucleic acid targets were obtained from IDT. A dsDNA target containing a zero base pair separation between the Zif268 and PBSII zinc finger sites (Z0P) was annealed as previously described. Hairpin DNA targets were annealed in 1× BamHI buffer by heating at 95° C. for 7 minutes followed immediately by cooling on ice.

Reassembly of the GFP variant Venus. Duplicate 150 µL translations were carried out in Wheat Germ Plus extracts (Promega) according to the manufacturer's protocol using 4 pmol of each mRNA encoding for NVenus(residues 1-157)-Zif268 and PBSII-CVenus(residues 158-238), 10 µM $ZnCl_2$, 0.5 µL of RNasin™ Plus (Promega), and either 50 nM Z0P target DNA or no DNA. Translations were incubated at 25° C. for 2 hours (no fluorescence was observed) or alternatively interrogated for fluorescence followed by a 20 hour incubation at room temperature. Fluorescence spectra were acquired by exiting at 515 nm and monitoring emission at 528 nm Reassembly of split β-lactamase-zinc finger fusions. Four duplicate 25 µL translations were carried out in wheat germ plus extracts (Promega) according to the manufacturer's protocol using 0.5 pmol of each mRNA encoding for NβLac (residues 26-196)-Zif268 and PBSII-CβLac(residues 198-290), 10 µM $ZnCl_2$, 0.5 µL of RNsin™ Plus (Promega), and either 20 nM Z0P target DNA or no DNA. Translations were incubated at 25° C. for 2 hours and assayed by adding 25 µL of translation to 75 µL of PBS containing a final concentration of 10 µM Fluorocilin Green soluble β-Lactamase substrate (Invitrogen, Carlsbad, Calif.). The final concentration of DNA in the assay was 5 nM. The rate of Fluorocillin Green hydrolysis was determined by exciting at 495 nm and monitoring emission at 525 nm with a 515 nm emission cutoff using a SPECTRAMAX™ Gemini plate reader (Molecular Devices, Sunnyvale, Calif.). Emission was read every 30 seconds for 10 minutes.

Reassembly of split firefly luciferase. Duplicate 25 µL translations were carried out in Flexi-Rabbit Reticulocyte Lysates (Promega) according to the manufacturer's protocol using 2 pmol of each mRNA encoding for either PBSII-NFluc (residues 2-416) and CFluc-Zif268 (residues 398-550) or NFluc(residues 2-398)-Zif268 and PBSII-CFluc(residues 394-550), 10 µM $ZnCl_2$, 0.5 µL of RNasin™ Plus (Promega), and either 25 nM Z0P target DNA or no DNA. Translations were incubated at 30° C. for 90 minutes and assayed by adding 20 µL of translation to 80 µL of STEADY-GLO™ Luciferase Assay System (Promega). The final concentration of DNA in the assay was 5 nM. Light emission was monitored 1 minute after STEADY-GLO™ substrate addition using a Turner TD-20e luminometer (Turner Designs, Inc, Sunnyvale, Calif.) with a 3 second delay and a 10 second integration time.

Initial cell-free assays. Duplicate 25 µL translations were carried out in Flexi-Rabbit Reticulocyte Lysates (Promega) according to the manufacturer's protocol using 2 pmol of each mRNA encoding the fusion proteins being analyzed, and 0.5 µL of RNasin™ Plus (Promega). For translations containing zinc finger proteins 10 µM $ZnCl_2$ was also added to the translation mixture. Translations were incubated at 30° C. for 90 min and assayed by adding 20 µL of translation mix to 80 µL of STEADY-GLO™ Luciferase Assay System (Promega). In the case of nucleic acid-binding proteins target oligonucleotides were either present or absent during translation. For the rapamycin induced interaction between FRB and FKBP either 5 nM rapamycin or control, DMSO, was added after translation followed by a 30 minute incubation at room temperature. Light emission was monitored 1 minute after STEADY-GLO™ substrate addition using a Turner TD-20e luminometer with a 3 second delay and a 10 second integration time.

Reassembly of split firefly luciferase in a coupled transcription/translation system. Coupled transcription/translation reactions were carried out in TNT T7 Coupled Rabbit Reticulocyte Lysates (Promega) according to the manufacturer's protocol. Coupled reactions using split firefly luciferase-zinc finger fusions contained 0.5 pmols of each DNA encoding PBSII-NFluc and CFluc-Zif268, 10 µM $ZnCl_2$, 1 µL of RNasin™ Plus™ (Promega), and either 100 nM Z0P target DNA or no DNA in a total of 25 µL. Coupled reactions using split firefly luciferase-FKBP and FRBP fusions contained 0.5 pmol of DNA encoding FRB-NFluc and CFluc-FKBP, and 1 µL of RNasin™ Plus (Promega) in a total of 25 µL. Solutions were incubated at 30° C. for 90 minutes. Reactions were diluted at a 1:4 ratio into PBS containing 1% BSA (1% BSA and either 25 nM rapamycin or DMSO in the case of FRB/FKBP) and equilibrated at room temperature for 30 minutes. Samples were assayed for luciferase activity by mixing 20 µL of lysate with 80 µL of STEADY-GLO™ Luciferase Assay System (Promega). Luminescence readings were taken on a Turner TD20e luminometer using a 3 second delay and 10 second integrations, the average of replicate experiments is shown. The final concentration of Z0P or rapamycin in the assay was 5 nM.

Reassembly of split firefly luciferase in a purified transcription/translation system. Coupled transcription/translation reactions were carried out using the PURESYSTEM classic II system (Post Genome Inst. Co. Ltd., Tokyo, JP; available from NEB) according to the manufacturer's protocol. Coupled reactions using split firefly luciferase-zinc finger fusions contained 0.5 pmols of each DNA encoding PBSII-NFluc and CFluc-Zif268, 10 µM $ZnCl_2$, 1 µL of RNasin™ Plus (Promega), and either 100 nM Z0P target DNA or no DNA in a total of 25 µL. Coupled reactions using split firefly luciferase-FKBP and FRBP fusions contained 0.5 pmol of DNA encoding FRB-NFluc and CFluc-FKBP, and 1 µL of RNasin™ Plus (Promega) in a total of 25 µL. Solutions were incubated at 37° C. for 60 minutes, followed by the addition of either 25 nM rapamycin or DMSO in the case of FKBP/FRB. Samples were assayed for luciferase activity by mixing 20 µL of lysate with 80 µL of STEADY-GLO™ Luciferase Assay System (Promega). Luminescence readings were taken on a Turner TD20e luminometer using a 3 second delay and 10 second integrations, the average of replicate experiments is shown. The final concentration of Z0P or rapamycin in the assay was 5 nM.

Competition assay to identify protein-DNA target site specificity. Duplicate 25 µL translations were carried out in Rabbit Reticulocyte Lysates (Promega) according to the manufacturer's protocol using 0.05 pmols of mRNA encoding PBSII-NFluc and CFluc-Zif268, 10 µM $ZnCl_2$, and 0.5 µL of RNasin™ Plus (Promega) and allowed to incubate for 90 minutes at 30° C. in the presence of 750 pM Z0P dsDNA target. Following translation and firefly luciferase reassembly, increasing concentrations of each Zif268 hairpin DNA being tested were added followed by a 30 minute incubation at room temperature. Light emission was monitored 1 minute after STEADY-GLO™ addition using a Wallac 1420 VICTOR 3™ V luminometer with a 1 second integration time.

Dissociation of the reassembled Pum2-NFluc, CFluc-Pum1, RNA ternary complex. Duplicate 25 µL translation reactions were carried out in Rabbit Reticulocyte Lysates (Promega) according to the manufacturer's protocol using 0.1 pmols of mRNA encoding Pum2-NFluc and CFluc-Pum1 and 0.5 µL of RNasin™ Plus (Promega) and allowed to incubate for 90 minutes at 30° C. in the presence of 2.5 nM RNA oligonucleotide target. Following translation and firefly luciferase reassembly, increasing concentrations of a competitor RNA oligonucleotide were added followed by a 30 minute incubation at room temperature. Light emission was monitored 1 minute after STEADY-GLO™ addition using a Turner TD-20e luminometer with a 3 second delay and a 10 second integration time.

Detection of small-molecule and peptide modulators of protein-protein interactions. Duplicate 25 μL translation reactions were carried out in Rabbit Reticulocyte Lysates (Promega) according to the manufacturer's protocol using 2 pmols of mRNA encoding either FRB-NFluc and CFluc-FKBP, PKI-NFluc and CFluc-PKA, or p300-NFluc and CFluc-HIF-1 and 0.5 μL of RNasin™ Plus (Promega) and allowed to incubate for 90 minutes at 30° C. in. For analysis of p300/HIF-1α interaction 10 μM $ZnCl_2$ was added to the translation reaction. Following translation lysates were diluted 1:4 with PBS containing 1% BSA followed by the addition of increasing concentrations of either rapamycin in DMSO, PKI, or chetomin in DMSO followed by a 30 minute incubation at room temperature. Light emission was obtained by adding 20 μL of the translation solution to 80 μL of STEADY-GLO™ Luciferase Assay System (Promega). Light emission was monitored 1 minute after STEADY-GLO™ addition using a Wallac 1420 VICTOR 3™ V luminometer (PerkinElmer, Waltham, Mass.) with a 1 second integration time.

Reassembly of split firefly luciferase in water-in-oil emulsions. Water-in-oil emulsions were prepared in 2 mL round bottom cryogenic vials by adding 50 μL of aqueous phase, over 2 minutes, into 950 μL of mineral oil containing 4.5% Span 80 and 0.5% Tween 80 while stirring at 1,150 rpm using a 2×9 mm stir bar. Stirring was continued for one minute after the complete addition of the aqueous phase. Translations were prepared on ice using Wheat Germ Plus extracts (Promega) according the manufacturer's protocol using 4 pmol of each mRNA encoding either PKI-NFluc, CFluc-PKA, or both and 0.5 μL of RNasin™ Plus (Promega). For DNA dependent reassembly, 4 pmol of each mRNA encoding for CFluc-Zif268 and PBSII-NFluc, 10 μM $ZnCl_2$, 0.5 μL of RNasin™ Plus (Promega), and either 25 nM Z0P target DNA or no DNA in a total of 50 μL. Emulsions were prepared using the ice-cold translation as the aqueous phase. Emulsions were incubated at 25° C. for 2 hours and assayed by adding 20 μL of emulsion to 80 μL of STEADY-GLO™ (Promega). Luminescence readings were taken on a Turner TD20e luminometer using a 3 second delay and a 10 second integration time.

Antibody Enabled Cell-Free Split-Luciferase Detection Systems

The present methods provide a robust solution phase split-luciferase assay that can, directly and sensitively, detect a protein or other molecule of interest, including but not limited to clinically relevant extracellular growth factors, such as VEGF; distinguish HIV-1 clades based on gp120-antibody specificities; and, record the abundance of cell-surface markers, such as HER2, without chemical derivatization, microscopy, or FACS.

Figure 7:
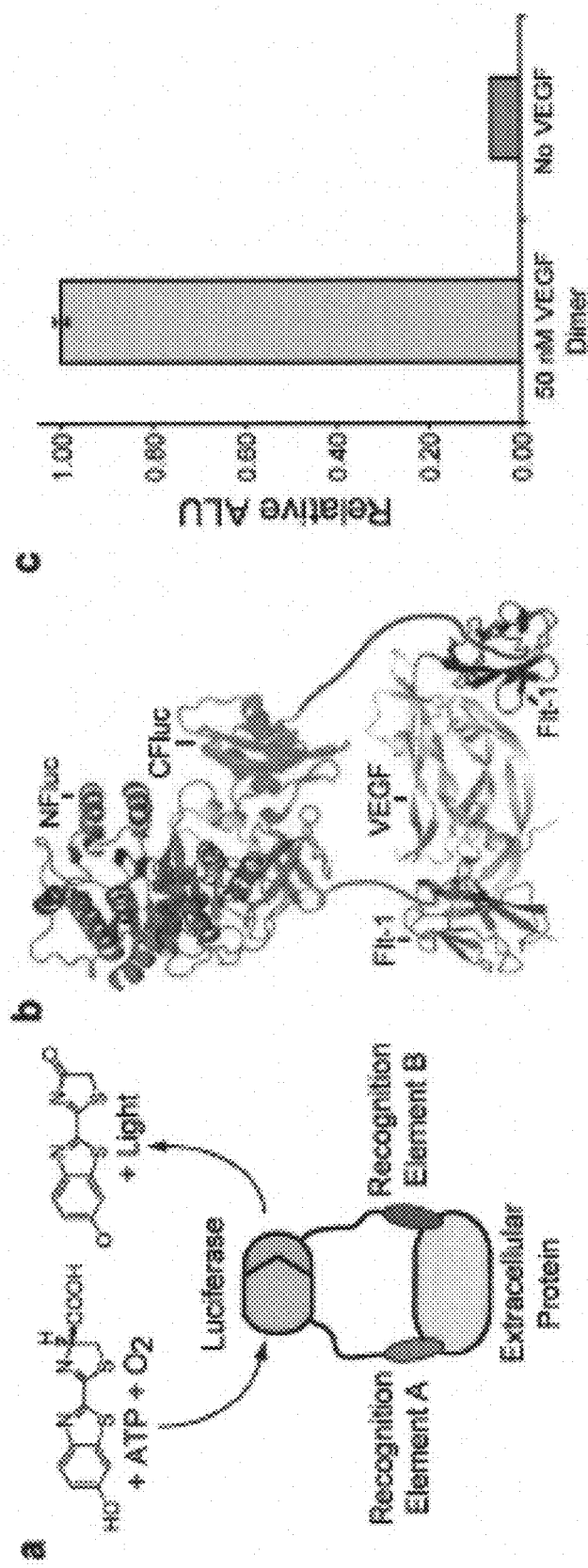
FIG. 7. A split-luciferase sandwich assay for the detection of extracellular proteins. (a) A general schematic of the designed system is shown. Specific recognition elements are used to reassemble luciferase in the presence of a target extracellular protein leading to the generation of light. (b) A schematic of the VEGF assay is shown. Flt-1 (red and blue) is attached to both the N- and C-terminal halves of luciferase and is used to directly detect the VEGF homodimer. (c) Luminescence from reassembled luciferase in the presence and absence of VEGF. In the presence of 50 nM VEGF dimer a >15-fold increase in luminescence is observed.

High-resolution methods for imaging extracellular proteins often rely on laborious transfection and/or chemical derivatization for selective labeling. (56,57) In addition analysis is generally performed using expensive microscopy or Fluorescence-Activated Cell Sorting (FACS) instrumentation employing complex deconvolution algorithms. Alternatively, the simple Enzyme-Linked Immunosorbent Assay (ELISA) can be used to detect almost any analyte, but it requires that either the antigen or antibody be captured on a solid support prior to detection followed by vigorous washing and subsequent detection by an enzyme-secondary-antibody conjugate. This limits the utility of the ELISA for the direct detection of analytes in complex heterogeneous mixtures or biological samples such as blood and lysates. Development of a one-step solution phase sandwich assay in which the activity of an attached split-luciferase reporter would be dependent on the recognition of an extracellular protein or other molecule of interest is needed (FIG. 7a). Such methodology would allow for the direct detection of any protein in complex environments without the need for immobilization, chemical derivatization or microscopy/FACS analysis.

Herein, we provide a cell-free split-luciferase assay in which the luminescence of fragmented luciferase (see also 27) fused to interacting proteins, provides a direct measure of heterodimeric protein-protein interactions (58). This rapid method takes advantage of the in situ production of signaling proteins from mRNA in in vitro translation reaction and eliminates the need for laborious cell culture or protein purification steps (10). This cell-free split-luciferase methodology provides a general solution for the rapid and direct detection of an important and previously unaddressed class of clinically relevant proteins that include growth factors, cell- and viral-surface receptors, and it is applicable to other proteins, carbohydrates, glycoproteins and other antigens or epitopes of interest.

We first confirmed that a dimeric receptor fragment could be used to detect its extracellular ligand. We chose as a model extracellular ligand Vascular Endothelial Growth Factor (VEGF), which is implicated in tumor angiogenesis and which binds its extracellular receptor Flt-1 in a 2:1 stoichiometry (59). With this in mind, we attached the N- and C-terminal halves of luciferase (residues 2-416 and 398-550, respectively) to separate Flt-1 domain 2 fragments (FIG. 7b), with the expectation that a statistical distribution of Flt-1-luciferase halves would still lead to ~50% of split-luciferase complementation. Expression of the split luciferase-Flt-1 fusion proteins in rabbit reticulocyte lysates leads to an increase in luminescence of >15-fold only in the presence of 50 nM VEGF dimmer, clearly demonstrating the ability of dimeric receptor fragments to bind their ligands and mediate split reporter reassembly in this system (FIG. 7c). Thus, this approach conceptually allows for an expedient and general method for targeting a wide-variety of dimeric growth factors and their receptors through ternary complexation. It is also understood that present methods are adaptable to virtually all epitopes or antigens of interest, especially biomolecules.

VEGF-Flt-1 Sandwich Assay

Flexi-Rabbit Reticulocyte Lysate, RNasin™, Steady-Glo™ Luciferase Assay System and the T7 Ribomax Transcription Kit were purchased from Promega. G50 ProbeQuant™ (Pharmacia Biotech AB Corporation, Uppsala, Sweden) columns were obtained from GE Healthcare. XL1-Blue™ E. coli cells were purchased from Stratagene (La Jolla, Calif.). Ni-NTA agarose resin was purchased from Qiagen (Valencia, Calif.). All other reagents were obtained through Research Products International (Mt. Prospect, Ill.).

A pQE30-VEGF expression plasmid was transformed into XL1-Blue™ E. coli by electroporation according to the manufacturer's instructions. An overnight culture of these cells was used to inoculate a 1 liter culture of 2×YT media supplemented with 100 μg/mL ampicillin at an initial $OD_{600}$ of 0.05. Protein expression was induced at an $OD_{600}$ of 0.8 with 1 mM IPTG. Protein expression was allowed to proceed overnight at 37° C. Cells were pelleted by centrifugation and resuspended in lysis buffer (Tris-HCl at pH=8 containing 8 M Urea). Resuspended cells were lysed by sonication. The lysate was cleared by centrifugation at 18,000 rcf for 30 min. His-tagged VEGF was purified under denaturing conditions using Ni-NTA resin using the manufacturer's instructions. Imidazole wash fractions were collected, pooled, and stored at −20° C. until use. Collected fractions were thawed on ice, concentrated and FPLC purified using a preparative Hi-Load 16/60 Superdex™ 75 (Pharmacia Biotech AB Corporation) column equilibrated with denaturing buffer (Tris-HCl at pH=8 containing 6 M Urea). Full length monomeric VEGF was isolated, pooled, and stored at −20° C. until required for refolding.

The pooled fractions containing full-length monomeric VEGF were diluted to 50 μg/mL with buffer containing 6M Urea, 0.1 M $Na_2HPO_4$, 10 mM Tris-HCl at pH=8.5, 1 mM EDTA, and 20 mM DTT. This solution was incubated for 3 hrs at room temperature to facilitate reduction. Reduced monomeric VEGF was then dialyzed against 100 mM Tris-HCl at pH=8.5, 5 mM cysteine, 1 mM cystine, 0.5 M Urea, and 2 mM EDTA overnight at room temperature.

To separate dimeric VEGF from monomeric and multimeric species the refolded VEGF was concentrated and purified by FPLC using a Superdex™ 75 column equilibrated with PBS. Fractions containing refolded dimeric VEGF were collected, pooled, concentrated, and reapplied to the Superdex™ 75 column. Refolded VEGF was characterized by SDS-PAGE under reducing and non-reducing conditions to visualize the monomeric versus dimeric form. Protein concentrations were calculated based by UV absorbance.

To produce Flt-1 Luciferase Fusion mRNA, open reading frames encoding domain 2 of the Flt-1 receptor were cloned into bacterial vectors containing either the N- or C-terminal portions of firefly luciferase, residues 2-416 and 398-550 respectively (27), separated by a flexible amino acid linker. These plasmid sequences were confirmed by the sequencing. These constructs were PCR amplified using a 5' primer encoding a T7 promoter and Kozak sequence and 3' primer containing a stem loop. mRNA was generated using the T7 Ribomax Transcription Kit and purified using a G50 ProbeQuant column. Concentrations of each mRNA were determined from UV absorbance.

To perform the VEGF-Flt-1 sandwich assay, translations using Flexi-Rabbit Reticulocyte Lysate were carried out according to the manufactures procedure using 2 pmols of each mRNA encoding for the Flt-1 fusions, 0.5 μL RNasin™, 70 mM KCl, 200 μM of each amino acid, 66% Lysate, and either 500 nM VEGF monomer or an equivalent volume of PBS in a 25 μL reaction. Reactions were incubated at 30° C. for 90 min after which luminescence was monitored on a Turner TD20e luminometer by mixing 20 μL of translation with 80 μL of Steady-Glo™ Luciferase Assay System giving a final concentration of 100 nm VEGF monomer. Luminescence was monitored 1 min after mixing with a 10 sec integration. Reactions were performed in duplicate and averaged.

Figure 8:
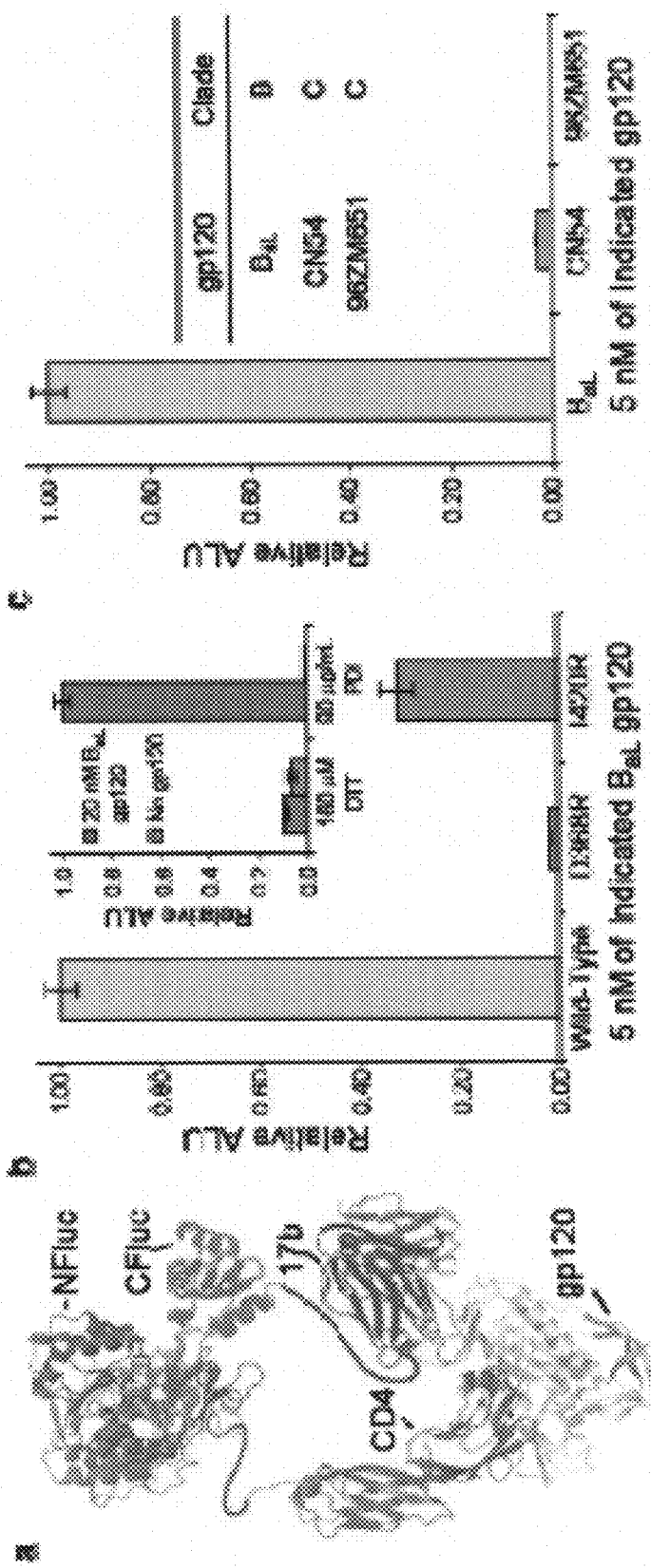
FIG. 8. An antibody enabled split-luciferase assay for gp120 detection. (a) A schematic of the solution phase detection system for gp120 is shown. (b) The specificity of the solution phase gp120 detection system is shown. Assays were performed on the indicated wild-type or mutant gp120s; D368R and I420R mutations are known to decrease CD4 and 17b binding respectively.9,10 The inset shows the luminescence signal generated from the assay when either DTT or PDI are included during translation. (c) The specificity of the gp120 detection system, as determined by luciferase reassembly, across a panel of gp120s from the indicated clades is shown. The observed luminescence highlights the ability to rapidly categorize HIV-1 clades using this assay.

We envisioned that the cell-free split-luciferase sandwich assay could rapidly and sensitively detect and categorize HIV-1 clades based on antibody specificities. Accordingly, we turned our attention towards the interaction of CD4 with the gp120 glycoprotein from HIV-1, which leads to infection of susceptible T-lymphocytes by HIV-1. The crystal structure of the complex between CD4, gp120, and the Fab portion of a neutralizing antibody 17b (60), served as a model for the development of our gp120 sandwich assay (FIG. 8a). We fused domains 1 and 2 (D1 D2, residues 1-182) of CD4, which have been shown to bind to gp120 with a $K_d$ of ~3 nM (61), to the N-terminal half of luciferase. As our second recognition element we fused the C-terminal half of luciferase to the 17b single-chain antibody (scFv), which binds a CD4-induced epitope of gp120 (FIG. 8a) (60). Initial experiments showed a negligible increase in luminescence in the presence of 20 nM $B_{aL}$ gp120. Importantly, the elimination of DTT and addition of protein disulfide isomerase (PDI) allowed for luminescence and the first functional demonstration of antibody mediated targeting in the split-luciferase system (FIG. 8b Inset). Having established conditions for favorable protein folding, we sought to verify the specificity of our gp120 assay. Accordingly, we first investigated luciferase reassembly in the presence of different $B_{aL}$ gp120s containing single amino acid mutations, D368R and I420R, known to reduce CD4 (62) or 17b (63) binding respectively. Indeed these mutant gp120s considerably reduce luminescence relative to the wild-type, confirming that both functional CD4 and 17b binding are required for luciferase reassembly (FIG. 8b). We also interrogated split-luciferase activity as a function of gp120 concentration; our assay system can reporting on the presence of as little as 12 ng/mL of $B_{aL}$ gp120, a sensitivity comparable to commercially available gp120 ELISAs. This is likely a function of antibody/D1D2 affinities. The titration experiment also indicated that ~5 nM of active complex (folding capable split-halves) is translated under our current cell-free conditions, which is sufficient for most ELISA-like applications.

To use our sandwich assay for the rapid characterization of HIV-1 clades, we investigated gp120s from isolates CN54 and 96ZM651, both of which are clade C viruses. Maximal luciferase signal was observed only in the presence of $B_{aL}$ gp120 (clade B) while a slight increase in luminescence was observed for CN54 gp120 and no detectable signal was generated for 96ZM651 gp120 (FIG. 8c). This highlights the potential utility of this rapid and inexpensive approach for rapidly distinguishing HIV-1 clades and sub-types using known antibody specificities.

gp120 Sandwich Assay

Flexi-Rabbit Reticulocyte Lysate, RNasin™, Steady-Glo™ Luciferase Assay System, and the T7 Ribomax Transcription Kit were purchased from Promega. G50 ProbeQuant™ columns were obtained from GE Healthcare. $B_{aL}$, CN54, and 96ZM651 gp120s were obtained from the NIH AIDS Reference and Reagent Program, catalog numbers 4961, 7749, and 10080 respectively. Wild-type $B_{aL}$ gp120 and the $B_{aL}$ gp120 D368R and I420R mutants used in FIG. 8, panel b (excluding the inset) were a generous gift of R. Wyatt. PDI was purchased from Sigma (St. Louis, Mo.). All other reagents were obtained through Research Products International (Mt. Prospect, Ill.).

mRNA Encoding for the split-luciferase fusions was prepared as follows. Open reading frames encoding for residues 1-182 of CD4 and the $V_H$ and $V_L$ regions of 17b separated by a $(GGGGS)_3$ linker (SEQ ID NO:91) were cloned into vectors containing the N- and C-terminal portions of luciferase respectively. These plasmid sequences were confirmed by DNA sequencing. These constructs were PCR amplified using a 5' primer encoding a T7 promoter and Kozak sequence and 3' primer containing a stem loop. mRNA was generated using the T7 Ribomax Transcription Kit and purified using a G50 ProbeQuant™ column. Concentrations of each mRNA were determined from UV absorbance.

To perform the initial gp120 sandwich assay, translations using Flexi-Rabbit Reticulocyte Lysate were carried out according to the manufactures procedure using 2 pmols of each of the mRNAs encoding the CD4-NFluc and CFluc-17b fusions, 0.5 μL RNasin™, 70 mM KCl, 200 μM of each amino acid, 66% Lysate, and either 100 nM $B_{aL}$ gp120 or an equivalent volume of PBS in a 25 μL reaction. Reactions were incubated at 30° C. for 90 min after which luminescence was monitored on a Turner TD20e luminometer by mixing 20 μL of translation with 80 μL of Steady-Glo™ Luciferase Assay System giving a final concentration of 20 nm $B_{aL}$ gp120. Reactions were performed in duplicate and averaged; significantly greater signal was generated with 20 nM gp120 than in its absence.

We sought to determine the effect of dithiothreitol (DTT) and PDI on the gp120 sandwich assay as this has previously been shown to increase scFv folding efficiency in cell-free translation systems (137). Translations using the Flexi-Rabbit Reticulocyte Lysate were carried out according to the manufactures procedure using 2 pmols of each of the mRNAs encoding the CD4-NFluc and CFluc-17b fusions, 70 mM KCl, 200 μM of each amino acid, 66% Lysate, 0.5 μL RNasin™ (160 μM DTT, from the RNasin™ storage buffer, during translation) were indicated, 90 μg/mL PDI were indicated, and either 100 nM $B_{aL}$ gp120 or an equivalent volume of PBS in a 25 μL reaction. Reactions were incubated at 30° C. for 90 min after which luminescence was monitored on a Turner TD20e luminometer by mixing 20 μL of translation with 80 μL of Steady-Glo™ Luciferase Assay System giving a final concentration of 20 nm $B_{aL}$ gp120. Luminescence was monitored 1 min after mixing with a 10 sec integration. Reactions were performed in duplicate and averaged.

gp120 Titration

Translations using Flexi-Rabbit Reticulocyte Lysate were carried out according to the manufacturer's procedure using 2 pmols of each of the mRNAs encoding the CD4-NFluc and CFluc-17b fusions, 90 μg/mL PDI, 70 mM KCl, 200 μM of each amino acid, 66% Lysate, and decreasing concentrations of $B_{aL}$ gp120 or an equivalent volume of PBS in a 25 μL reaction. Reactions were incubated at 30° C. for 90 min after which luminescence was monitored on a Turner TD20e luminometer by mixing 20 μL of translation with 80 μL of Steady-Glo™ Luciferase Assay System. Luminescence was monitored 1 min after mixing with a 10 sec integration. Reactions were performed in duplicate, background subtracted (using samples containing no gp120), and averaged.

Luminescence from reassembled luciferase was monitored as a function of the concentration of gp120. Initially luciferase fusions are in excess however as the concentration of gp120 increases a maximum is reached were the concentration of luciferase fusions capable of forming a functional complex is equivalent to that of gp120. As the gp120 concentration is increased, further luminescence decreases due to localization of the luciferase fusions to different gp120s, rather than allowing reassembly of complementary fragments.

Translations and luciferase detection were carried out as described above except that 25 nM of the indicated gp120 was added during translation, giving a final concentration of 5 nM gp120.

Figure 9:
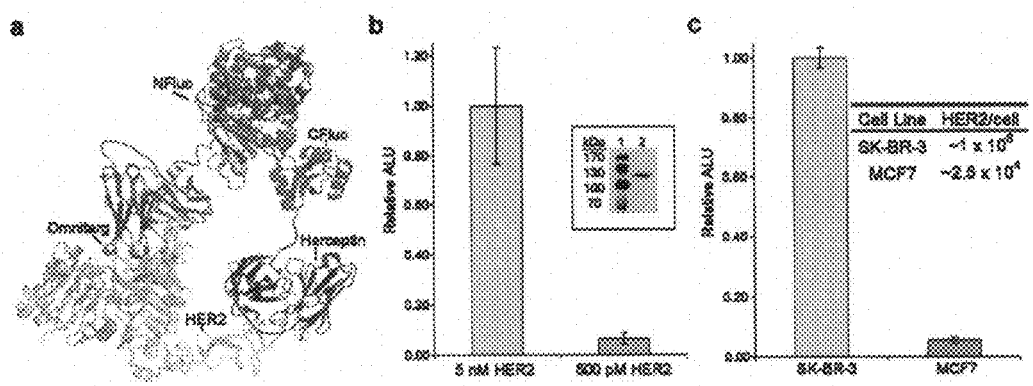
FIG. 9. A split-luciferase sandwich assay for the direct detection of HER2 on human cells. (a) An overlay of HER2 (tan and light blue) with the bound luciferase fusion proteins is shown. (b) A HER2 sandwich assay performed on purified HER2 expressed from Lec1 cells. The inset shows a western blot analysis of the purified HER2 protein, lane 1 molecular weight standards and lane 2 purified HER2 protein. (c) A HER2 sandwich assay performed on human breast cancer cells; SK-BR-3 or MCF7 cells were added after translation and luminescence was monitored after 30 min ($1 \times 10^4$ cells during luminescence assay). The inset shows the expression levels of HER2 in the indicated cell line (15).

Having identified suitable expression conditions for using scFvs in our split-luciferase system, we next established that the assay can be utilized to determine relative abundance of cell surface proteins, as specifically exemplified on human cells. For proof of concept, we chose the extracellular domain (ECD, residues 1-631) of HER2, which is over-expressed in ~30% of human breast cancers and is directly correlated with poor clinical outcomes; therefore, an expedient method to assess the relative amount of HER2 on the surface of human breast cancer cells would be of considerable utility. Two antibodies HERCEPTIN™ and Omnitarg (Genentech, South San Francisco, Calif.) bind distinct epitopes of the human HER2 ECD. Overlaying the crystal structures of these bound antibodies indicated that they are likely capable of binding HER2 simultaneously (64, 65). Moreover, the reported binding constants for a scFv version of HERCEPTIN™ and the Fab portion of Omnitarg for the HER2 ECD are 150 pM (66) and 8.5 nM (67), respectively, well within the detection limits of the present methods. Thus, we constructed mRNAs in which the scFv of Omnitarg was fused to the N-terminal portion of luciferase and the C-terminal portion of luciferase was fused to the scFv of HERCEPTIN™ (FIG. 9, panel a). As an initial test of the HER2 sandwich assay, the HER2 ECD was expressed, purified, and added at varying concentrations to the two tethered scFv fusions translated in rabbit reticulocyte lysates. A concentration dependent increase in luminescence in the presence of the HER2 ECD was observed (FIG. 9b), indicating that this new antibody enabled sandwich assay was indeed capable of reporting on the presence of HER2 at sub-nanomolar levels in a complex mixture. Preliminary experiments indicate that these cell-free translations can be stored at least 7 days at −80° C. prior to the addition of HER2, potentially allowing for the long term storage of reagents and the detection of extracellular proteins within 30 min at the point of care.

Finally, we determined that the present assay could directly detect different relative expression levels of HER2 on the surface of human breast cancer cells. We chose the SK-BR-3 and MCF7 cell lines which have been shown to produce ~$1 \times 10^6$ and ~$2.5 \times 10^4$ copies of HER2 per cell, respectively (68). Translations were conducted as above, after which cells were added and the reactions were gently shaken at room temperature for 30 min. In the presence of SK-BR-3 cells ($1 \times 10^4$ cells, theoretically ~170 pM HER2) an 18-fold increase in luminescence was observed with respect to the MCF7 cells ($1 \times 10^4$ cells, theoretically ~4 pM HER2) indicating that our sandwich assay is capable of directly reporting on the relative amount of HER2 expression on the surface of human breast cancer cell lines (FIG. 9c). Additional experiments indicate that as few as 2,600 SK-BR-3 cells can be detected using this assay format. Importantly this split-luciferase sandwich assay allowed us to specifically label and visualize the HER2 cancer-specific antigen on the surface of human breast cancer cells without the need for FACS analysis (68).

HER2 Sandwich Assay

Flexi-Rabbit Reticulocyte Lysate, Steady-Glo™ Luciferase Assay System, and the T7 Ribomax Transcription Kit were purchased from Promega. G50 ProbeQuant™ columns were obtained from GE Healthcare. SK-BR-3 cells were obtained from the American Type Culture Collection (Manassas, Va., ATCC) (HTB-30). MCF7 cells were a generous gift of the B. Olenyuk laboratory. Cell culture media and reagents were purchased from Hyclone (Logan, Utah). Plasmids encoding the $V_H$ and $V_L$ regions of both Herceptin (138) and Omnitarg (67) separated by a $(GGGGS)_3$ linker (SEQ ID NO:91) were purchased from Bio Basic (Markham, Ontario, Calif.). G418 and methotrexate were purchased from Research Products International. PDI, the Ala-Gln dipeptide, and Trypan Blue were purchased from Sigma. Ni-NTA agarose resin was purchased from Qiagen. All other reagents were obtained through Research Products International.

To produce mRNA Encoding for the split-luciferase fusions, open reading frames encoding for the $V_H$ and $V_L$ regions of Omnitarg and Herceptin separated by a $(GGGGS)_3$ linker (SEQ ID NO:91) were cloned into vectors containing the N- and C-terminal portions of luciferase respectively. These plasmid sequences were confirmed by DNA sequencing. These constructs were PCR amplified using a 5' primer encoding a T7 promoter and Kozak sequence and 3' primer containing a stem loop. mRNA was generated using the T7 Ribomax Transcription Kit and purified using a G50

ProbeQuant™ column. Concentrations of each mRNA were determined based on UV absorbance.

Expression, purification, and western blot analysis of the HER2 ECD were carried out as follows. Lec1 cells stably expressing a human growth hormone-histidine tagged-HER2 ECD protein (139) were grown in αMEM (without nucleotides or L-Gln) 95% and FBS 5% supplemented with 100 nM methotrexate, 0.5 mg/mL G418, 584 mg/L Ala-Gln, 100 units/mL penicillin, and 100 μg/mL streptomycin. Cell cultures were allowed to grow for three days, after which protein was purified from 50 mLs of culture media using Ni-NTA affinity chromatography. Protein was eluted with 10 mM Tris-HCl at pH=7.5, 50 mM NaCl, and 500 mM Imidazole. This solution was used directly for the experiments described below.

Western blot analyses were performed using a rabbit anti-His-tag polyclonal primary antibody (QED Biosciences, San Diego, Calif., 18814) and an IR dye conjugated anti-rabbit secondary goat antibody (Li-Cor Biosciences, Lincoln, Nebr., IgG IRDye 800CW, 926-32211). A Li-Cor Biosciences Odyssey scanner was used for imaging. HER2 ECD concentration was estimated from SDS-PAGE analysis.

The HER2 sandwich assay using purified HER2 ECD was carried out as follows. Translations using Flexi-Rabbit Reticulocyte Lysate were carried out according to the manufacturer's procedure using 2 pmols of each of the mRNAs encoding the Omnitarg-NFluc and CFluc-Herceptin fusions, 70 mM KCl, 200 μM of each amino acid, 66% Lysate, and 90 μg/mL PDI in a 25 μL reaction. Reactions were incubated at 30° C. for 90 min after which purified HER2 ECD or an equivalent volume of storage buffer (10 mM Tris-HCl at pH=7.5, 50 mM NaCl, and 500 mM Imidazole) was added to the translation. These solutions were allowed to equilibrate at room temperature for 30 min. Luminescence was monitored on a Turner TD20e luminometer by mixing 20 μL of translation with 80 μL of Steady-Glo™ Luciferase Assay System. Luminescence was monitored 1 min after mixing with a 10 sec integration. Reactions were performed in duplicate, background subtracted (using samples containing no HER2 ECD), and averaged. HER2 ECD concentrations after rapid dilution are shown in FIG. 9, panel b.

The HER2 sandwich assay was carried out after storage at −80° C. as follows. Two 25 μL translations were carried out as described above. Reactions were incubated at 30° C. for 90 min, flash frozen, and stored at −80° C. for 7 days. Solutions were thawed and purified HER2 ECD or an equivalent volume of storage buffer (10 mM Tris-HCl at pH=7.5, 50 mM NaCl, and 500 mM Imidazole) was added to the vials. These solutions were allowed to equilibrate at room temperature for 30 min. Luminescence was monitored on a Turner 20/20″ luminometer by mixing 20 μL of translation with 80 μL of Steady-Glo™ Luciferase Assay System. Luminescence was monitored 1 min after mixing with a 10 sec integration.

Cell-free translations of the HER2 sandwich assay were flash frozen and stored at −80° C. for 7 days; after which purified HER2 ECD was added and luminescence was monitored. HER2-dependent luciferase activity is still observed after storage for 7 days at −80° C.

The HER2 sandwich assay using human breast cancer cells was carried out as follows. SK-BR-3 and MCF7 cells were grown in RPMI 1640 90% and FBS 10% supplemented with 100 units/mL penicillin and 100 μg/mL streptomycin. Cells were detached using PBS containing 25 mM EDTA, washed, and resuspended in PBS; after which they were counted by Trypan Blue exclusion.

Luminescence as observed from the HER2 sandwich assay performed on 2,600 cells from the indicated human breast cancer cell lines. The relative luminescence was 1 for the SK-BR-3 cells, while the same number of MCF7 cells resulted in less a relative luminescence of less than 0.05.

Translations using Flexi-Rabbit Reticulocyte Lysate were carried out as above. Reactions were incubated at 30° C. for 90 min after which cells or an equivalent volume of PBS was added. These solutions were allowed to equilibrate at room temperature for 30 min with gentle shaking. Luminescence was monitored on a Turner 20/20″ or TD20e luminometer by mixing 20 μL of translation with 80 μL of Steady-Glo™ Luciferase Assay System. Luminescence was monitored 1 min after mixing with a 10 sec integration. Reactions were performed in duplicate, background subtracted (using samples containing no cells), and averaged. The number of cells in the luminescence assay is reported.

Herein we have described a split-luciferase sandwich ELISA-like assay for the rapid analysis of proteins and receptors in complex mixtures. (70,71,68). The simplicity of generating reagents, low cost of instrumentation, sensitive bioluminescent read-out, and most importantly, the generality of scFv mediated targeting allow this method to rapidly detect virtually any target protein in complex heterogeneous systems, and thus, have utility in point of care diagnostics.

Figure 11:
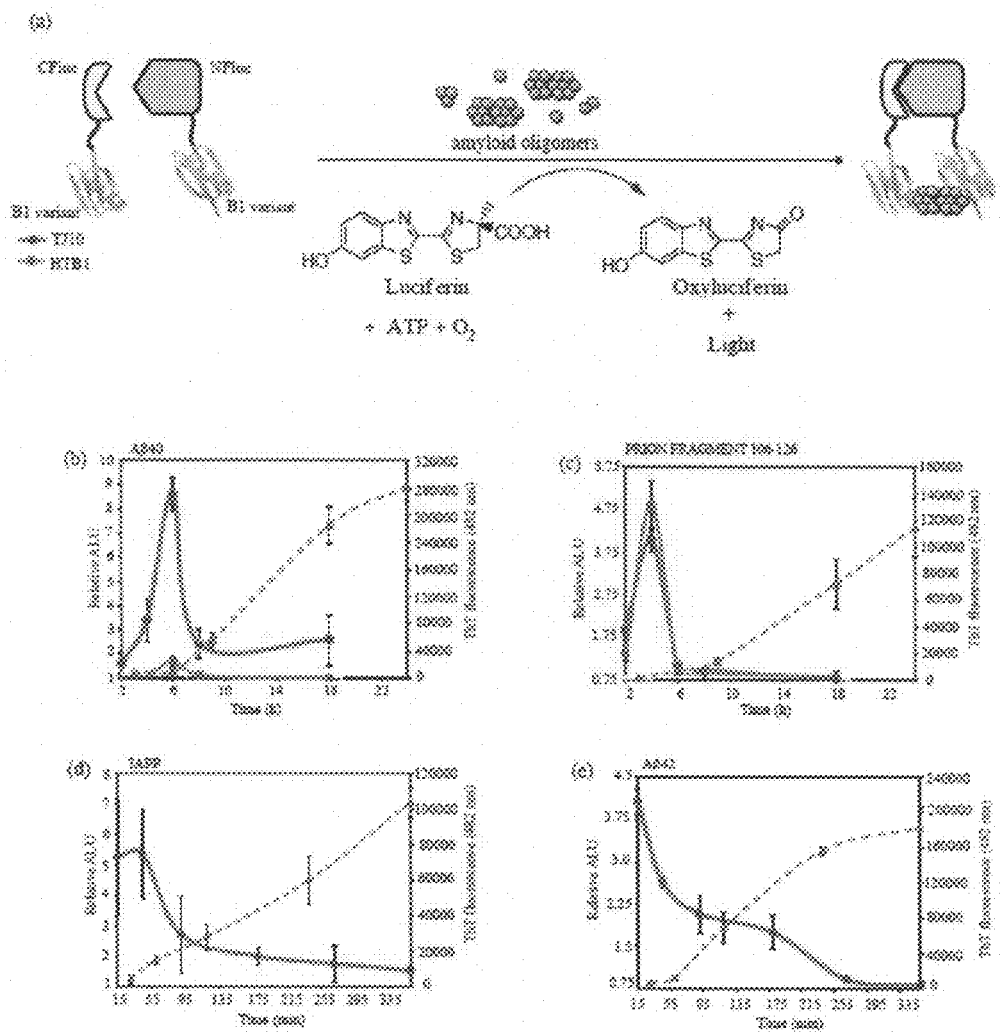
FIG. 11. Panel a summarizes the association reaction and the licferase reaction catalyzed by the reassembled luciferase fragments when amyloid aggregation mediates the generation of a functional luciferase from its split fragments. Panels b-d show a time course results for the detection of early aggregation intermediates of Aβ40, prion fragment 106-126, IAPP and $A^242$ using TJ10 fusiton constructions blue or HTB1 fusion constructs (red). Notably, there is little signal generated for the Aβ40 with the HTB1 construct, while the signal is greater for HTB1 than TJ10 with the prion fragment. In Panels c and d only the TJ10 fusion proteins were used (solid lines, blue). Fluorescence is marked by the dotted lines.
Figure 12:
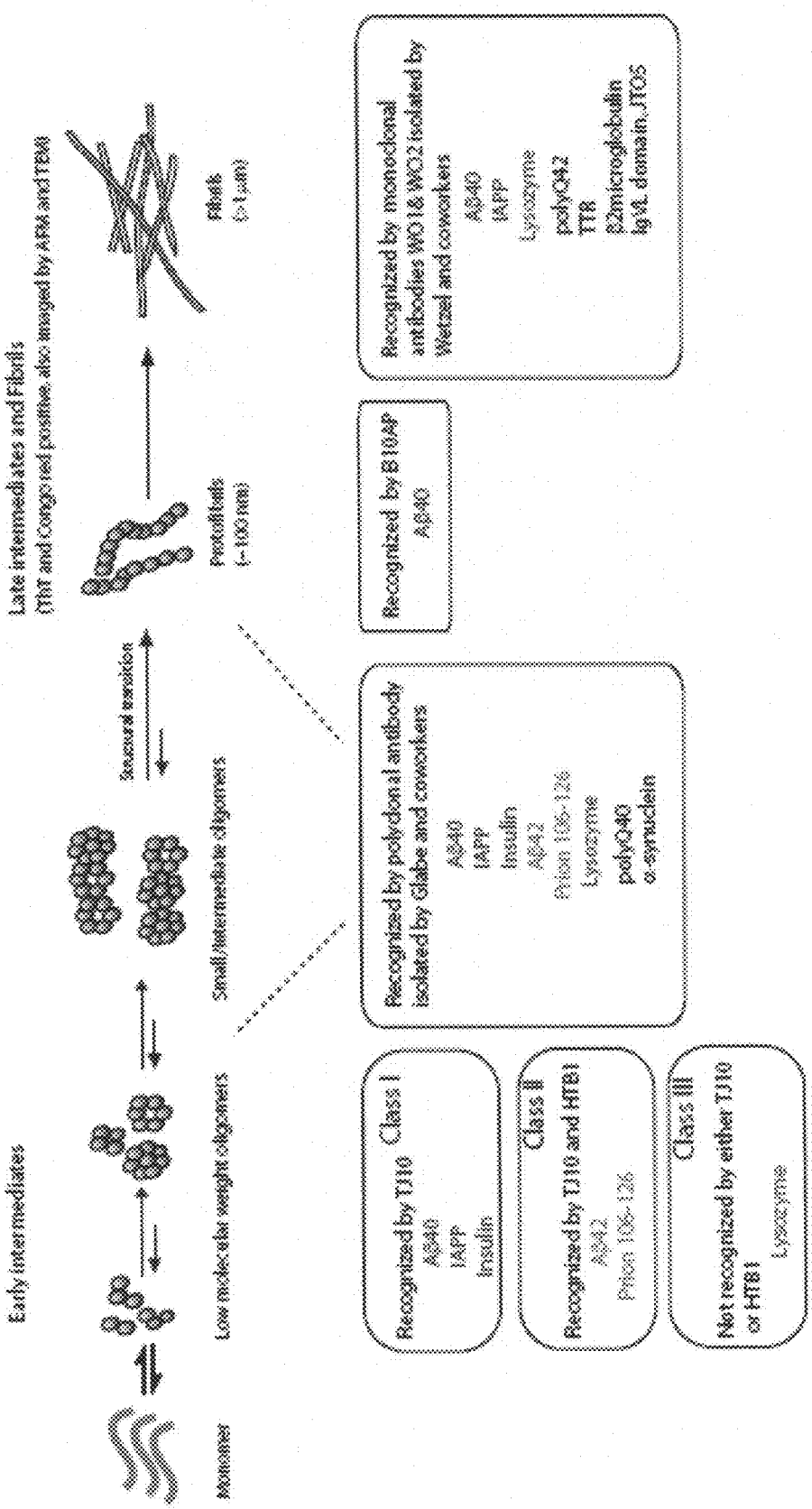
FIG. 12. Summary of the progressive association, assembly stages and conformational changes for Class I, Class II snf VClass III proteins.

Amyloid β-peptide and related assemblies have been studied with new probes and split-protein reporters. The amyloid hypothesis is that specific proteins and peptides misfold and aggregate in a nucleation dependent manner to form fibrils with a characteristic cross-β pattern. Though much insight has been gained regarding the final fibrillar state of amyloidogenic peptides and proteins from both NMR and X-ray crystallography, far less is known regarding the multistep process involving the transition of monomers to metastable oligomers and their further assembly into mature fibrils (FIG. 11, panel a and FIG. 12). We have focused our attention on the amyloid β-peptide (Ab) implicated in Alzheimer's disease, perhaps the most studied among over 30 known protein misfolding disorders, which include Parkinson's, dialysis related amyloidosis (β2-microglobulin), Huntington's disease, and prion diseases.

Ligands identified to block the Aβ aggregation process include certain aromatic small molecules, antibodies, chaperones and synthetic peptides and peptidomimetics derived from the amyloidogenic core of the parent protein. Synthetic peptides used to block fibrillization have been further modified by incorporation of proline residues, α-α disubstitution and N-methylation of amino acids and addition of charged residues at the N and C termini to increase their potency by either disrupting H-bonding or sterically hinder the self assembly process.

Inhibitors of aggregation have emerged as structural and mechanistic probes to explore two issues that provide useful insight into the aggregation mechanism of amyloid proteins. Recent studies have shown these ligands to bind and stabilize transient intermediates that can be useful in therapeutic and/or preventative strategies. For example, affibody $Z_{A\beta3}$ binds to Aβ40 with nanomolar affinity and was shown by 2DNMR studies to fold and stabilize Aβ in a beta-hairpin structure, while transthyretin, a 55 kD homotetramer present in the cerebral fluid, prevented Aβ40 fibrillization by suppressing the growth of pre-existing aggregates. Chaperones (Hsp 70/40 and Hsp90), in a similar study, appeared to bind early spheroid like intermediates of Aβ42 to prevent its further self-assembly. Recently, Glabe and coworkers detected a dodecameric intermediate of Aβ isolated from transgenic mice using the polyclonal antibody A11. Secondly, the common pathological features shared by fibrils of different proteins and the detection of common soluble oligomers by the polyclonal antibody A11 (generated against micellar Aβ by Glabe and co-workers) have led to hypothesis that different proteins follow common fibril formation pathways. However, photo-crosslinking of Aβ40 and Aβ42 by Bitan et al entrapped distinct early intermediates for these two proteins.

Drawing in part from these strategies, we designed (by directed evolution) a beta-sheet mini protein (TJ10), which inhibits the aggregation of Aβ40. The β-sheet scaffold chosen for this purpose was a 56-residue hyperthermophilic IgG binding protein redesigned by Malakauskas and Mayo, termed HTB1. Eight positions on adjacent strands of HTB1 were randomized to yield a β-sheet presenting phage display library. After five rounds of panning, only two specific HTB1 library members were preferentially selected. Of these, TJ10, which contains a large number of aromatic residues (2 Trp and 2 Tyr, postulated to be important motifs in amyloid inhibitors), was selected and found to effectively inhibit Aβ40 aggregation (FIG. 11).

The interaction of TJ0 was evaluated by designing constructs of TJ10 fused to fragmented halves of firefly luciferase. The binding of TJ10 to Aβ40 led to the reassembly of luciferase enzyme which was monitored by an increase in luminescence. This assay provides a rapid, sensitive and non-invasive method of studying the interaction between a ligand and its target amyloid protein under physiological conditions.

Because of conflicting reports, we evaluated whether different amyloid proteins assemble into common early oligomers that proceed to form fibrils or whether different early intermediates are formed by different proteins which during the aggregation process undergo structural transition to form intermediates with generic features that over a period of time mature into characteristic long fibrils. To address this question, we studied the influence of TJ10 and its parent scaffold protein, HTB1, on the aggregation properties of several unrelated amyloid proteins. TJ10 and HTB1 share a common beta-sheet epitope but vary in 8 amino acid residues displayed on the surface of two adjacent beta-strands. This subtle difference in their structure resulted in differences in their interaction with different amyloidogenic proteins. Without wishing to be bound by any particular theory, it is believed that the results obtained with TJ10 and HTB1 indicate that the early steps in fibrillization pathway are distinct processes for different proteins.

Effect of TJ10 and HTB1 on Inhibition of Aβ40

Figure 10:
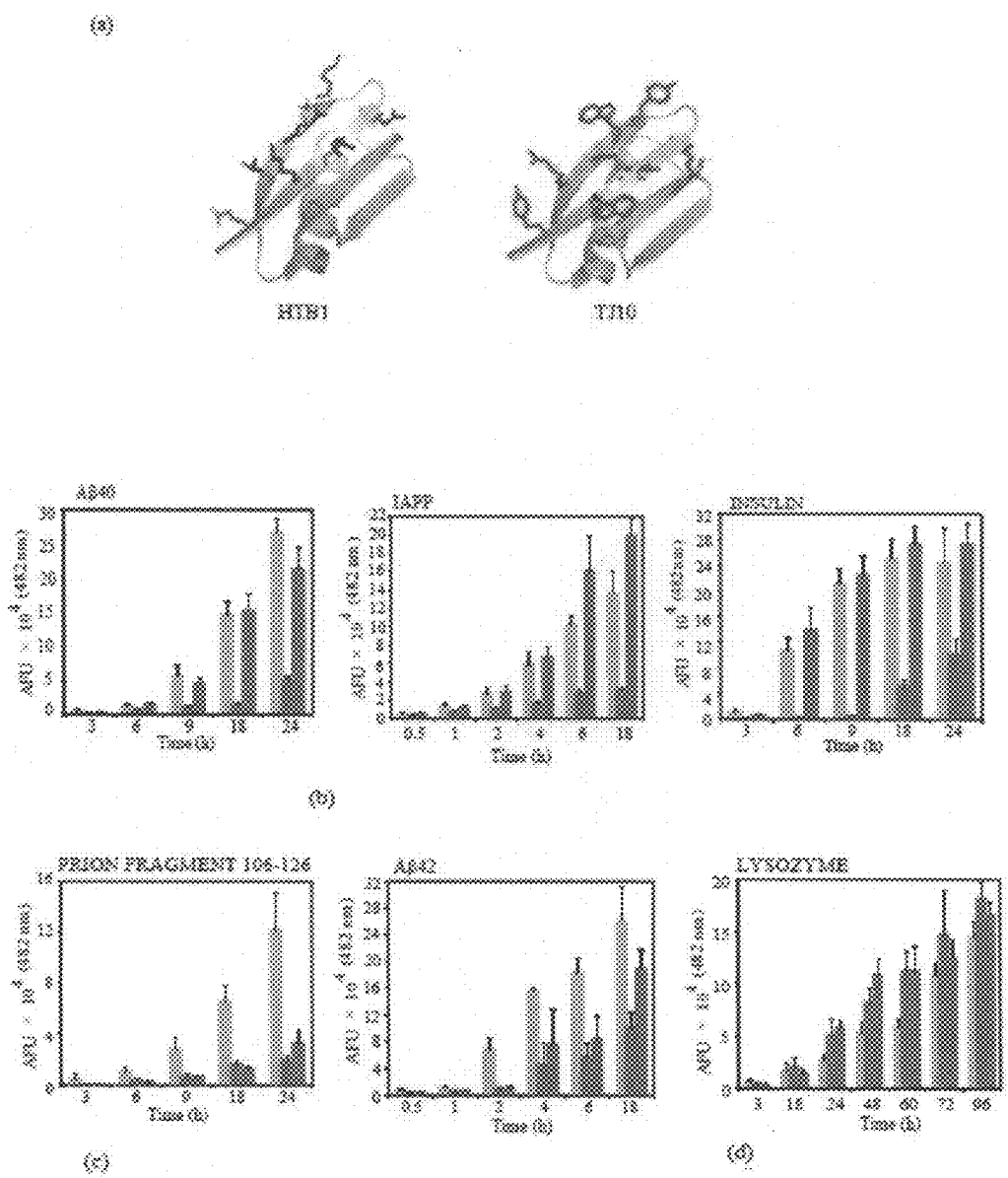
FIG. 10. Panel a shows the ribbon models of HTB1 and TJ10, displaying the site of the 8 mutations in TJ10 relative to the patent HTB1 protein. Panel b shows that class 1 molecules are inhibited by TJ10 (blue, central bars) but not HTB1 (red bars, right bars). Panel c shows that Class II aggregation of various protein interactions are inhibited by both TJ10 (blue, central) and HTB1 (red, rightmost). Panel d shows that Class III aggregation interactions are inhibited by neither both TJ10 (blue, center bars) nor HTB1 (red, rightmost).

We have recently described a beta-sheet mini protein (TJ10) (FIG. 10, panel a) which was selected by phage display screening and was found to effectively inhibit aggregation of Aβ40 for over 2 weeks. This experiment was repeated with a fresh Aβ40 sample and monitored by ThT fluorescence for 24 h. Along with TJ10, the effect of the parent scaffold, HTB1 (FIG. 10, panel b), on the aggregation kinetics of Aβ40 was also evaluated. Surprisingly, while TJ10 showed effective inhibition in a 1:1 molar ratio, HTB1 did not influence the aggregation of Aβ40 under the same conditions. As controls, TJ10 and HTB1 solutions (50 μM each) were also incubated under aggregating condition of Aβ40 but did not show any ThT positive aggregates over a period of 3 days. Even at sub-stoichiometric concentrations, TJ10 appear to inhibit Aβ40 effectively. After 18 h, while 80% of 50 μM Aβ40 aggregated under shaking conditions, in presence of 5 μM TJ10 (TJ10:Aβ40 ratio of 1:10), only 38% Aβ40 had aggregated (FIGS. 10-11).

The interaction of TJ10 with Aβ40 was further interrogated by CD and photo-induced crosslinking (PICUP) experiments. The CD spectrum of the mixture of Aβ40 with TJ10 (after incubation at 37° C. for only 3 h) was different from the simple arithmetic sum of the spectra of Aβ40 and TJ10 alone, suggesting an early interaction between the two proteins.

Photo-induced crosslinking of Aβ40, TJ10 and their mixture (1:1) was carried out after 0.5 and 10 h of incubation at 37° C. and 250 rpm. Crosslinking of Aβ40 at 0 h resulted in formation of dimers and trimers as reported before, however after 5 and 10 h of incubation, crosslinking resulted in formation of aggregates of Aβ40 of molecular weight >200 kD that could not enter the pores of the acrylamide gel and got stained in wells above the separating gel. TJ10, due to the presence of Tyr and Trp residues on its surface (which are more susceptible to free radical formation) underwent random association upon crosslinking and showed a ladder of bands on SDS/PAGE. Crosslinking of Aβ40/TJ10 mixture after incubation at 0, 5 and 10 h showed a pattern of bands similar to that of crosslinked TJ10, however it is noteworthy that the bands representing crosslinked aggregates of Aβ40 were not observed for the mixture, indicating that TJ10 prevented the self-assembly of Aβ40 into large prefibrillar species.

The interaction of TJ10 with Aβ40 was examined using cell-free split luciferase based assay. While CD and crosslinking experiments indicated binding of TJ10 to early intermediates of Aβ40, more direct evidence of this interaction was demonstrated using reassembly of split firefly luciferase in the cell-free assay. In extending this method to the interaction of TJ10 with Aβ40, fusion constructs of TJ10 with each half of fragmented firefly luciferase were prepared (TJ10-NFluc and CFluc-TJ10) and transcribed into respective mRNAs as described herein. Aβ40 solution (50 μM) was incubated under its aggregation conditions and 5 μL aliquots were taken out at different time periods and added to the translation mix along with the mRNAs to initiate the translation of the proteins (NFluc-TJ10 and CFluc-TJ10). As the proteins were synthesized over 90 minutes, the binding of TJ10 to Aβ40 oligomers (at 2, 4, 6, 8 h time points) or to Aβ40 fibrils (at 18 h timepoint) was monitored by measuring the luminescence resulting from the activity of reassembled luciferase (FIG. 10). As a control, at each time point, reassembly of the fragmented luciferase in absence of Aβ40 was also measured. A sharp increase in luminescence from 2 fold (over control, at 2 and 4 h timepoints) to 7 fold (over control) at 6 h timepoint shows preferential binding of TJ10 to Aβ40 oligomers (FIG. 10, panel b). The subsequent decrease in signal at 8 and 18 h shows that TJ10 did not bind substantially to either late intermediates (at 9 h some ThT positive aggregates are formed, FIG. 12) or fibrillar Aβ40 respectively. To ensure that the decrease in signal at 8 and 18 h timepoints were due to reduced binding of TJ10 to prefibrillar and fibrillar species of Aβ40 and not due to deleterious effect of Aβ40 on the translation system, a second control assay was simultaneously carried out. Constructs of two heterodimerizing leucine zippers (acidic and basic zippers) with each half of fragmented firefly luciferase were also prepared (RR-NFluc and CFluc-EE), transcribed and translated in a similar fashion. The two leucine zippers, once formed, dimerized spontaneously, resulting in reassembly of luciferase and a high luminescence signal. Aβ40 aliquots (5 μL) at different time points of aggregation were added to this translation mix and the luminescence monitored after 90 minutes. Similar signal for samples with and without Aβ40 proved that Aβ40 intermediates or fibrils did not affect the translation machinery or the dimerization of the leucine zippers. Hence, the changes in luminescence at various time-points can be correlated to the interaction of TJ10 with Aβ40. We would also like to mention here that in the present assay, the final concentration of Aβ40, at the time of detection, is 2.5 μM. The detection of Aβ40 oligomers at such low concentrations indicate low nM binding affinity between Aβ40 and TJ10 while other data collected suggest low μM binding between the two proteins. Hence, the correct stoichiometry of binding of TJ10 with Aβ40 could not be concluded.

The interaction of TJ10 and HTB1 with other amyloid proteins was also studied using the cell-free split reporter system. The effect of TJ10 and HTB1 on the aggregation kinetics of Aβ40 showed that although they share a common beta-sheet template (FIG. 10, panel a), the presence of aromatic residues on the surface of this beta-sheet template of TJ10 was necessary to disrupt the further association of Aβ40 into fibrils (FIG. 12). Based on this observation, the effect of TJ10 and HTB1 on the rate of aggregation of other amyloid proteins (Aβ42, IAPP, prion fragment 106-126, insulin and lysozyme) was also monitored (by ThT fluorescence) (FIG. 11). Three distinct trends were observed based on which these proteins were classified into three classes: class I consisted of Aβ40, IAPP and insulin. For these proteins, TJ10 effectively inhibited their aggregation while HTB1 had no influence on their rate of fibrillization, indicating that aromatic-aromatic and aromatic-hydrophobic interactions between the surface residues of TJ10 and early oligomers of these proteins probably played a significant role in preventing their further self-assembly. Rayleigh and co-workers in a recent publication showed that substituting the aromatic residues in IAPP sequence with leucine significantly delayed its aggregation kinetics, thus concluding that aromatic interactions did influence fibril formation of IAPP. Our data indicate that this may also be true for Aβ40 and insulin. Class II consisted of prion fragment 106-126 and Aβ42, which were inhibited equally by both TJ10 and HTB1. It is likely that the beta-sheet epitope common to TJ10 and HTB1 was also involved in stabilizing the early intermediates of prion fragment and Aβ42. This result is interesting because prion protein deposits are also found in Aβ senile plaques. A recent review discusses the similarities in post-translational modifications and metal binding domains of prion protein and Aβ (7). AChE which promotes Aβ aggregation, has also been shown to trigger fibrillization of prion 106-126 (8). Hence, the present methods can be useful for simultaneous targeting of Aβ42 and prion protein.

Finally, Class III consists of lysozyme, which aggregates in 3 days under the certain conditions without being affected by either TJ10 or HTB1. Previous studies on human lysozyme and its variants have shown that aggregation of lysozyme proceeds by cooperative unfolding of the beta-domain of the enzyme, followed by self association of this species to form beta-sheet rich fibrils. This transient intermediate does not appear to interact with either TJ10 or HTB1 and aggregates in 3 days at 37° C. with shaking (FIG. 10, panel d).

Much recent work has been carried out to identify conditions for isolation and characterization of amyloid protein aggregation intermediates that are now considered the true toxic species. These intermediates have been examined using techniques including CD, FRET, fluorescence polarization and 2D NMR, analytical ultracentrifugation, pulse-labeling hydrogen/deuterium exchange coupled with mass spectrometry, immunological detection, TEM and atomic force microscopy. Most of these techniques are elaborate, some requiring chemical derivatization, while others analyze the amyloid samples under non-physiological conditions and most utilize expensive, specialized instruments for measurements.

In the present work, we attempted to define the stage of the aggregation reaction at which TJ10 binds Aβ40, by fusing TJ10 to fragmented halves of a reporter protein, firefly luciferase and monitoring its reassembly mediated by aggregated Aβ40 via an increase in luminescence. It was evident that TJ1 did not interact with low molecular weight Aβ40, late intermediates or fibrils of Aβ40 (FIG. 10, panel b). Instead, TJ10 showed higher affinity for oligomers formed after 6 h of incubating Aβ40 under aggregation condition (FIG. 11, panel b), a time period when no significant ThT fluorescence was detected in FIG. 10, panel b.

Reporter proteins, most commonly GFP, have been used in in vivo studies to directly monitor the aggregation of Aβ, polyglutamine and prion. Cell-based luciferase systems have been used to study the effect of presenilin proteins on Notch signaling (Am 1) and in screening for chemical compounds that inhibit APP processing (Am2, Am3). GFP fused to Aβ42 in E. coli has also been reported for screening for small molecule inhibitors of Aβ42 aggregation (Am4). However, to our knowledge, this is the first report utilizing reassembly of split reporter protein for detecting soluble oligomers of amyloid proteins.

It is advantageous that the transcription product encoding one or both of the binding region-split reporter portion comprises a stabilizing element such as a 5' stem-loop, including but not limited to a 5' stem-loop derived in sequence from bacteriophage T7 and advantageously a 3' stem-loop such as that derived in sequence from bacteriophage T3 (see, e.g., 134, 135); and also advantageously a Kozak sequence 5' to the translation start site (see, e.g., 133) and a polyadenylated 3' end (see, e.g., 136) when the cell-free translation system is a eukaryotic system or a Shine-Delgarno sequence when the cell-free translation system is a bacterial translation system. Exemplary Shine Delgarno sequences include UAAGGAG-GUGA (SEQ ID NO:3), AGGAG or variants as well known in the art. Examples of Kozak sequences are GCCACCATGG (SEQ ID NO:4), CCACCATG and variants thereof, also as well known in the art. Useful examples of T7 and T3 promoter sequences are TAATACGACTCACTATA (SEQ ID NO:5) and AATTAACCCTCACTAAA (SEQ ID NO:6), respectively. Escherichia coli transcription initiation signals are widely known in the art; typically they are identified by TTGACA, followed by 15-19nucleotides, and TATAAT 5' to the start site. The SP6 promoter signal is ATTTAGGTGA-CACTATA (SEQ ID NO:7), or a functional variant thereof. RNAPII polymerases can be used with the appropriate choice of promoter and in the appropriate eukaryotic system, for example, a coupled transcription-translation system.

When RNA or DNA is expressed as proteins in the assay, the first and second fragments of the reporter associate to five a detectable signal (above background) when the two fragments associate in a manner which is mediated by the interacting protein portions fused to those reporter fragments, either directly or via a ligand or other molecule which binds to each of the interacting proteins. That is, the two reporter fragments are brought in sufficiently close proximity to allow their reassociation to form a functional protein that provides, directly or indirectly, a detectable signal.

It is understood that the direct interaction of the interacting proteins to form a reassociated, functional reporter can be disrupted by an antagonist of the interaction, which can be a small or a large molecule. In other choices of interacting protein fragments (ligand binding) there can be association of the reporter fragments mediated by an additional molecule which brings the two interacting proteins together. Again, an antagonist of the interaction of the molecule which binds to both interaction proteins can be identified by a decrease in signal resulting from decreased reassociation of the two fragments of the split reporter. Similarly, agonists can be identified where the signal is greater in the presence of the agonist than in its absence. It is understood that compositions tested for antagonist or agonist activity can be pure or relatively pure compounds, or libraries of compounds.

The present method is relatively rapid (requires about 90 minutes), does not require specialized skills or expensive instrumentation and is sensitive enough to detect low concentrations of transient oligomers formed during the lag phase of the aggregation process that are not detected in the ThT fluorescence assay. This assay can also be extended to create fusion constructs of other inhibitors with amyloid proteins.

TJ10 and its parent protein HTB1 were also used to delineate similarities and differences in the aggregation pathway of unrelated amyloid proteins. Despite much work in this area, there is still no clear understanding of the mechanism of aggregation and the related cytotoxicity. The detection of spherical oligomers and pore-like annular assemblies for α-synuclein and polyglutamine, that had previously been observed for Aβ and increased membrane permeability by soluble oligomers of these proteins, implied a common aggregation pathway. This theory was further advanced by detecting common soluble amyloid oligomers using polyclonal antibodies generated against micellar Aβ by Glabe and coworkers. However, about the same time, crosslinking experiments on Aβ40 and Aβ42 by Bitan et al showed that these two proteins oligomerized through distinct pathways. Also, chaperones Hsp70 and Hsp40 were shown to reduce the density of spherical and annular assemblies of polyglutamine by increasing the density of fibrils, and these chaperones prevented fibrillization of Aβ42 by stabilizing spheroid like intermediates. Pruisner and coworkers have reported a preamyloid state for prion protein which they propose forms a steady-state trimeric complex that can be stacked to form fibrils (Am5).

In view of inconsistent reports in the art, we evaluated the aggregation pathway of different amyloidogenic proteins based on their interaction with HTB1 and its aromatic rich variant, TJ10. Three trends were observed: Class I proteins, including of Aβ40, IAPP and insulin, were inhibited from fibrillization by TJ10 but were not influenced by the presence of HTB1 (FIG. 10, panels b and c). TJ10, selected to inhibit Aβ40 aggregation, also prevented IAPP aggregation for 18 h, since, both these proteins share more than 70% sequence similarity, and a recent study showed the suppression of Aβ aggregation by an IAPP mimic block. It is probable that the mode of inhibition of IAPP by TJ10 is similar to its inhibition of Aβ40. To test this possibility, the split-luciferase assay was carried out with IAPP samples at different time periods. A 5 fold increase in luminescence (over control) was observed within 15 and 45 min of incubating IAPP under its aggregation conditions, which decreased to 2.5 fold in 1.5 h and further to 1.5 fold (over control) at 4.5 and 6 h. IAPP is highly prone to aggregation and shows significant ThT fluorescence at 4 and 6 h (FIG. 10b). Hence, the split-luciferase assay with IAPP showed that as in the case of Aβ40, TJ10 interacts with early intermediates of IAPP. These results indicate that the early intermediates of Aβ40 and IAPP may share some features that are recognized by TJ10. Class II includes Aβ42 and prion fragment 106-126, which were inhibited equally by TJ10 and HTB1; and Class III includes lysozyme which did not interact with either TJ10 or HTB1. It is noteworthy that the interaction of TJ10 and HTB1 with Aβ40 is different from their interaction with Aβ42, thus our data seem to correlate with the crosslinking experiments by Bitan et al.

Comparing these results with results obtained with polyclonal antibody isolated by Glabe and coworkers and also with monoclonal antibodies, WO1 and WO2 isolated by ONualin and Wetzel, it is believed that the initial misfolding and association into low molecular weight assemblies may be distinct processes for different proteins. Hence, the early intermediates of Class I proteins ($I_1$) are different from those of Class II proteins ($I_2$) and Class III protein, lysozyme ($I_3$) (FIG. 12). However, as aggregation proceeds, these initial intermediates self associate and undergo conformational transition to form generic late intermediates such as protofibrils ($I_4$) which further mature into long fibrils that have been detected by monoclonal antibodies WO1 and WO2. The polyclonal antibody isolated by Glabe and coworkers is a heterogenous mixture of antibodies that bind a broad spectrum of soluble oligomers ranging from octamers and dodecamers to large spheroids and protofibrils of Aβ. The split-luciferase assay showed TJ10 to interact only with early intermediates of Aβ40 and IAPP.

Figure 13:
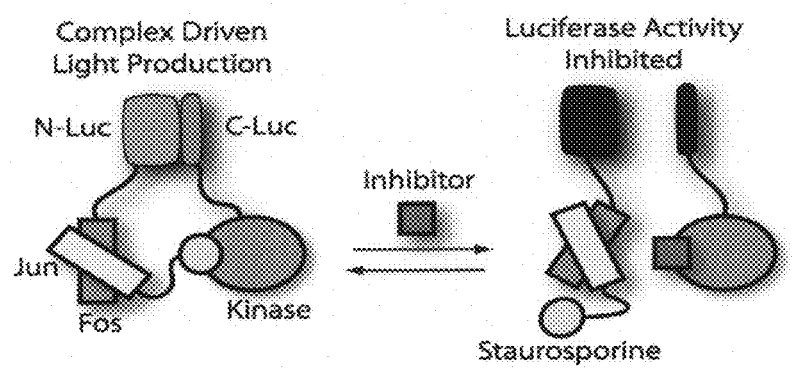
FIG. 13. Ternary complex formation driven by Jun-staurosporine. Small molecule inhibitors induce loss of activity.
Figure 16:
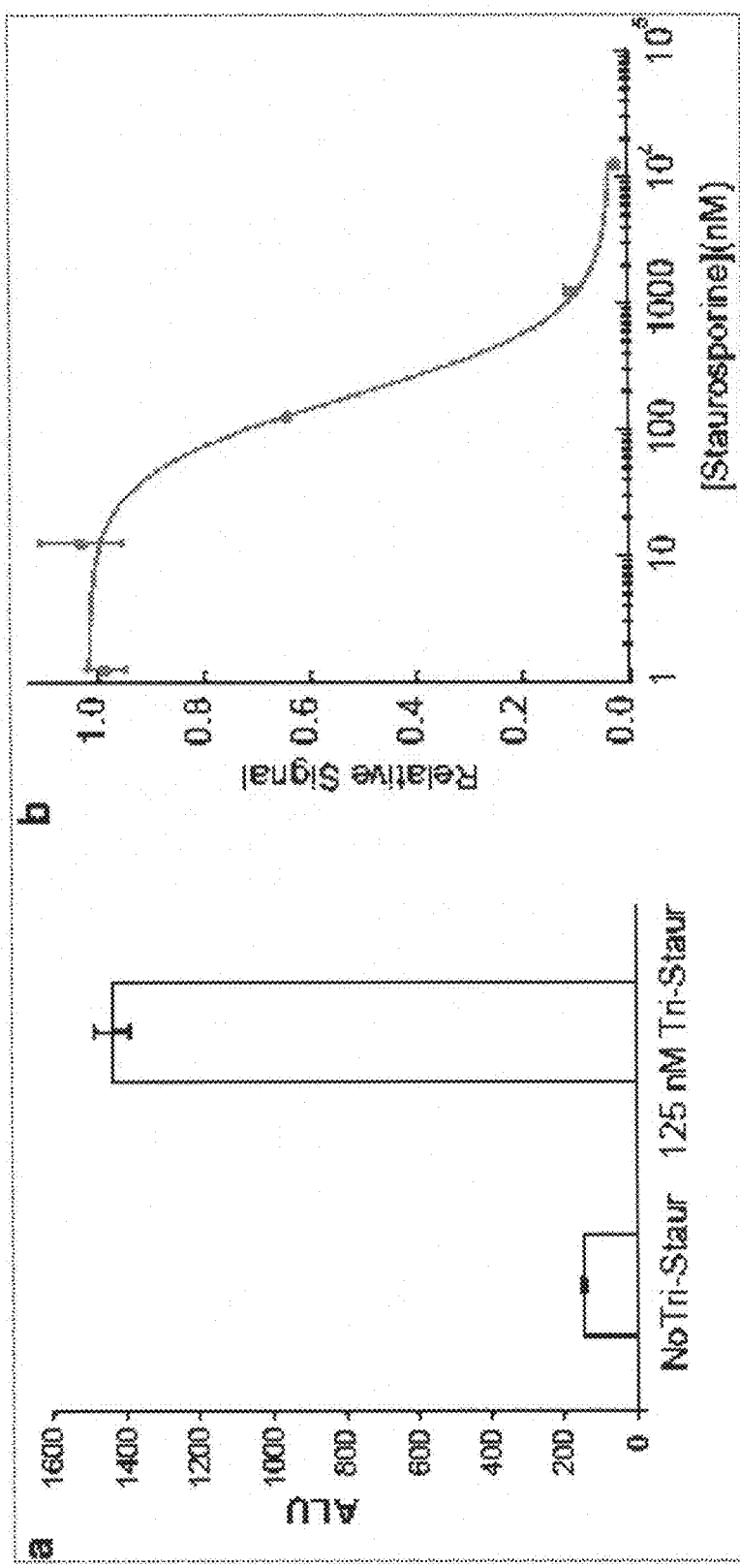
FIG. 16. (a) Tri-Staur mediated luciferase activity. (b) Dissociation of the Tri-Staur, DHFR-NFluc, and CFluc-PKA ternary complex by the addition of free staurosporine.

Cell-Free Split Luciferase Enabled Assays for Small Molecule Inhibitors of Kinases Protein fusion constructs of Fos-NLuc(residues 2-416) and CLuc(residues 398-550)-Kinase form a ternary complex and generate active luciferase upon addition of the peptide-inhibitor conjugate Jun-staurosporine (FIG. 13). Complex formation is driven by specific interactions between staurosporine and kinase active-site as well as Fos and Jun. RNA encoding each fusion construct (0.5 pmol Fos-NLuc and 0.2 pmol CLuc-Kinase) was added to duplicate 25 μl rabbit reticulocyte lysate translation reactions and incubated at 30° C. for 1.5 hrs. Water (negative control) or Jun-staurosporine (positive control) was subsequently added to the lysate reaction to a final concentration of 125 nM and incubated for 1 hr at room temperature in the dark to equilibrate. Luminescence measurements were taken by adding 80 μl STEADY-GLO™ Luciferase Assay Reagent to 20 μl of translation mix followed by one minute incubation at room temperature. Luminescence was measured using a single tube luminometer with a 10 second integration (FIG. 16, panel a).

Complex formation is reversible and the addition of small molecules competitive with staurosporine for kinase active-site binding can be added into the mixture to induce dissociation of the complex, resulting in a commensurate loss in luciferase activity (FIG. 13). This allows one to screen a kinase against a library of potential or known kinase inhibitors. By adding individual inhibitors to separate lysate reactions also containing Jun-staurosporine, one can directly compare the loss in activity to the positive control which contains only Jun-staurosporine and no inhibitor.

Because of the conserved nature of protein kinase active sites and staurosporine's ability to bind to many kinases, this system can additionally be applied to any kinase exhibiting sufficiently high affinity for staurosporine. Alternatively, staurosporine can be replaced in the peptide conjugate with an inhibitor which has high affinity for kinases that staurosporine does not bind. A diverse library of kinase active domains fused to the C-terminal fragment of luciferase can then be screened against multiple inhibitors that act competitively with staurosporine.

A panel of three inhibitors was assayed against four CLuc-fusions containing unique kinase domains (FIG. 15). Translations were prepared as above, in duplicate. Separate reactions were prepared for CLuc-PKA, CLuc-PDGFRB, CLuc-DK2, and CLuc-Fyn to contain 0.2 pmol of each RNA with 0.5 pmol Fos-NLuc RNA per 25 μl reaction. Each mixture was incubated at 30° C. for 1.5 hrs. From stock lysate mixtures, several reactions were prepared. For the negative control, 1 μl water was mixed with 24 μl lysate, followed by adding 1 μl dimethylsulfoxide (DMSO) to 24 μl of this mixture. For all inhibitor reactions and the positive control, jun-staurosporine was added to lysate translations to a final concentration of 125 nM. This mixture was then divided into aliquots containing DMSO or inhibitor dissolved in DMSO to create mixtures containing inhibitor at a final concentration of 50 μM and a positive control (DMSO only). The inhibitors tested were Sunitinib (LC Laboratories, Woburn, Mass.), PP1 (A.G. Scientific, Inc., San Diego, Calif.), and Roscovitine (LC Laboratories). Upon mixing all reactions were incubated for an hour at room temperature in the dark. Luminescence readings were taken as described above.

Similarly, a designed small molecule can be used in place of the peptide-inhibitor conjugate described above to facilitate complex formation and signal generation. The N-terminal (residues 2-416) portion of firefly luciferase is tethered to dihydrofolate reductase (DHFR) while the C-terminal (residues 398-550) portion is tethered to the protein kinase PKA. The designed small molecule consists of the small molecule trimethoprim, which is a known inhibitor of the E. coli DHFR conjugated through a tetraethylene glycol linker to the broad spectrum kinase inhibitor staurosporine creating the molecule Tri-Staur (FIG. 14). Simultaneous binding of trimethoprim by DHFR and Staurosporine to the kinase (PKA) active site results in ternary complex formation and reassembly of active firefly luciferase. Addition of staurosporine competitive small molecules results in the dissociation of the kinase-staurosporine complex and subsequent loss of luciferase activity (FIG. 15-16).

Duplicate translations were initiated by the addition of in vitro transcribed RNA encoding each fusion construct (0.5 pmol DHFR-NLuc and 0.2 pmol CLuc-PKA) to 25 μl rabbit reticulocyte lysate and incubated at 30 μC for 1.5 hrs. DMSO (negative control) or Tri-Staur (positive control) was subsequently added to the lysate reaction to a final concentration of 125 nM and incubated for 0.5 hr at room temperature in the dark to equilibrate. Luminescence measurements were taken by adding 80 μl STEADY-GLO™ Luciferase Assay Reagent to 20 μl of translation mix followed by a one minute incubation at room temperature. Luminescence was measured using a single tube luminometer with a 10 second integration (FIG. 16).

To evaluate the ability of Tri-Staur to identify kinase active site binding small-molecules duplicate translation were initiated as described above and used to assay the kinase inhibitor, staurosporine. From a stock lysate mixture, several reactions were prepared. For the negative control, 2 μl of DMSO was mixed with 23 μl of lysate. For all inhibitor reactions and the positive control, Tri-Staur was added to all translations to a final concentration of 125 nM. 24 μl of this mixture was then added to 1 μl of staurosporine dissolved in DMSO (final concentrations of 1.25 nM-12.5 μM) or DMSO only. Upon mixing all reactions were incubated for 0.5 hours at room temperature in the dark. Luminescence readings were taken as stated above. Luminescence measurements revealed a concentration dependent decrease in luciferase activity upon the addition of free staurosporine (FIG. 16b), demonstrating the use of this methodology for the identification of kinase active site binding small molecules.

Figure 17:
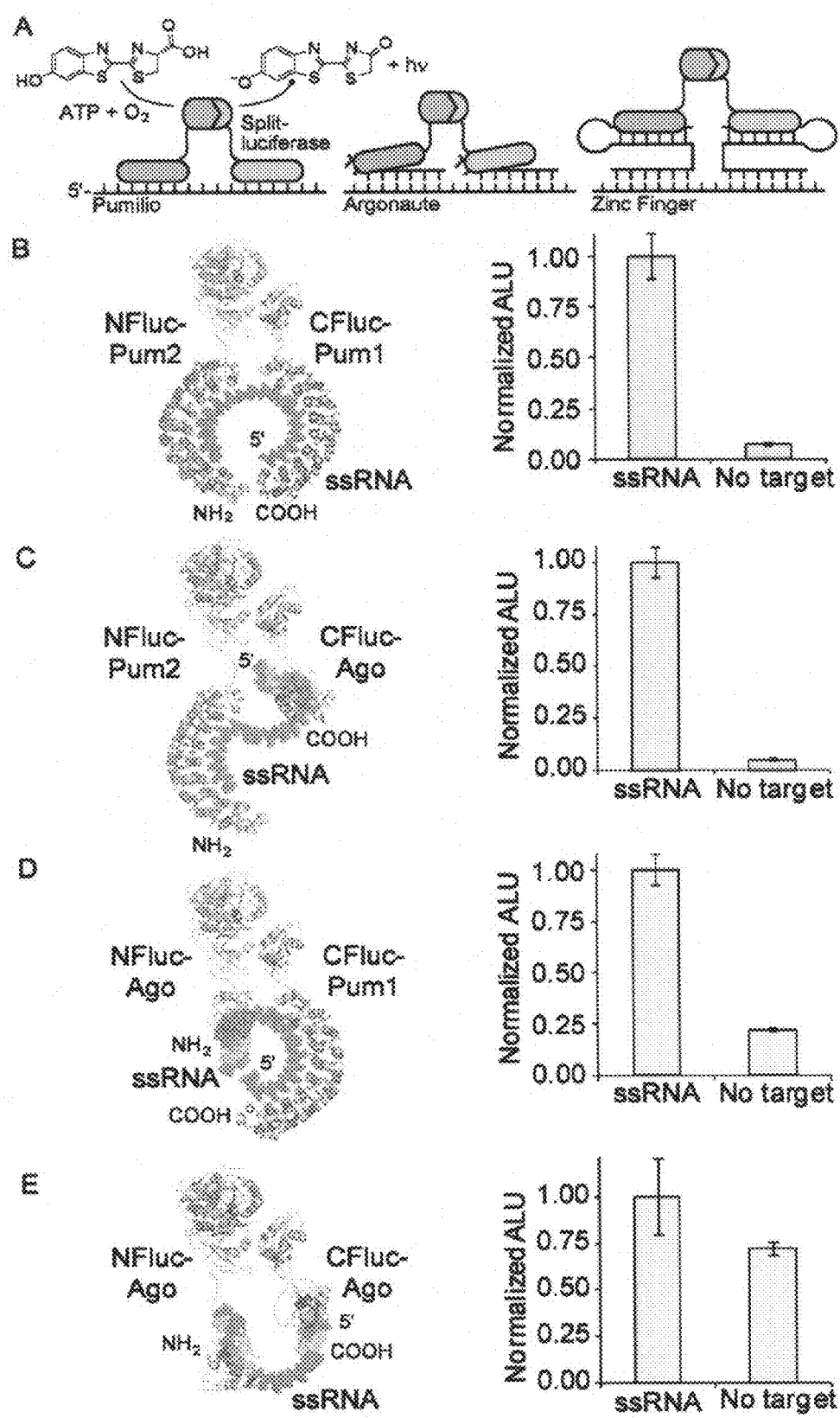
FIG. 17. ssRNA detection strategies using various polynucleotide binding domains. (A) Cartoon representations of pumilio, argonaute, and zinc finger binding domains attached to split-luciferase. The presence of target ssRNA results in luciferase reassembly and a luminescent signal. (B) NFluc-Pum2 and CFluc-Pum1 detect 10 nM cognate RNA. (C) 10 nM RNA annealed to the Pum2 guide (tan) allows for Ago and Pum1 binding. (D) NFluc-Pum2 and CFluc-Ago detect 10 nM RNA with an annealed Pum1 guide. (E) Employing both Ago constructs, NFluc-Ago and CFluc-Ago, along with guides for the Pum1 and Pum2 binding sites results in modest signal over background in the presence of target (10 nM).

We set out to develop a general approach for the sensitive, sequence-specific targeting of ssRNA by building on our cell-free split-firefly luciferase (Fluc) system (FIG. 17) (19, 27,58). We have recently shown that the use of native and designed pumilio domains7 attached to split-Fluc (FIG. 17, panel B) results in ssRNA target-dependent protein reassembly and luminescence.6c Though useful, this approach is inherently limited by the need to design pumilio domains with tailored specificity for each new ssRNA target. Thus, as a first step we amended our earlier design by replacing each pumilio domain with a ssRNA binding protein, the PAZ domain of argonaute 2 (residues 219-363) (76,77). Argonaute (Ago), which is central to the dicer complex formed in RNA interference (RNAi), binds with high affinity to the 2-nucleotide, 3' overhangs of short dsRNA. We postulated that by replacing the sequence-specific pumilio domains with the Ago PAZ domain, we would be able to direct our split-proteins toward any user-defined sequence of RNA by providing short, complementary guide oligonucleotides similar to those used in RNAi. Thus, we attached an Ago domain to each half of split-Fluc to generate NFluc-Ago and CFluc-Ago. We initially tested this approach by using NFluc-Pum2 and CFluc-Ago to detect a specific target RNA. The Pum1 ssRNA guide (Table 1), designed for directing CFluc-Ago to its binding site, was pre-hybridized to the target. Following incubation of the split-Fluc constructs with 10 nM of the guide-target complex, a significant signal over background was observed (FIG. 17, panel C). To our knowledge this is the first example of Ago being employed as a detection domain, providing a general module in protein-based nucleic acid detection. In a complimentary set of experiments, NFluc-Ago and CFluc-Pum1 were successfully used to detect 10 nM of target (FIG. 17, panels B-E). Finally, we attempted to provide a general solution to ssRNA detection by hybridizing both the Pum2 and Pum1 guides to the target (FIG. 17, panel E). However, upon incubation with NFluc-Ago and CFluc-Ago, less than a two-fold signal increase was observed in the presence of the ternary guide-target complex. This may be attributable to the affinity of Ago for its target as well as to the statistical distribution of guides in the presence of excess RNA present in our translational systems. Thus, these experiments suggest that Ago may be employed successfully in conjunction with other available sequence-specific RNA binding domains, and its use allows one to access a larger detectable sequence space than pumilio domains alone.

Cloning of NFluc-Ago and CFluc-Ago and Argonaute Refolding Experiments

Restriction enzymes, dNTPs, Antarctic phosphatase, and T4 DNA ligase were purchased from New England Biolabs (NEB, Ispwich, Mass.). Pfu Ultra polymerase was obtained from Stratagene. All DNA and RNA oligonucleotides were purchased from Integrated DNA Technologies (IDT). RNasin® Plus RNase Inhibitor, T7 RiboMAX™ Large Scale RNA Production kit, Flexi® Rabbit Reticulocyte Lysate, and Steady-Glo® Luciferase Assay System were acquired from Promega.

TABLE 1

Cloning Primers.
DNA and RNA oligonucleotides used in Ago cloning and RNA detection.

NFluc-Ago Primers (5'→3')

Ago XmaI FWD  GGGATACCCGGGGCACAGCCAGTAATCGAG
              (SEQ ID NO: 46)
Ago XhoI REV  CCCTATCTCGAGCGACCTAGCAGTCGCTCT
              (SEQ ID NO: 47)

TABLE 1-continued

Cloning Primers.
DNA and RNA oligonucleotides used in Ago cloning and RNA detection.

CFluc-Ago Primers (5'→3')

Ago BamHI FWD  GGGATAGGATCCGGCACAGCCAGTAATCGAG
               (SEQ ID NO: 48)
Ago AgeI REV   CCCTATACCGGTCGACCTAGCAGTCGCTCT
               (SEQ ID NO: 49)

RNA Target

RNA target     5'-CAUGGUGUAUAUAGUCUU*UUGAUAUAGCGGC*
               (SEQ ID NO: 50)

RNA guides

Pum1 guide     5'-CUAUAUACACCAUGUU
               (SEQ ID NO: 51)
Pum2 guide     5'-GCCGCUAUAUCAAUU
               (SEQ ID NO: 52)

in vitro transcription primers

NFluc-Ago FWD  5'GCAGC*TAATACGACTCACTATAGG*AACAGACCACCATGCGGCCTTCTCTCTGGAAAATGAT
               GCTGAATATTGATGTGTCA
               (SEQ ID NO: 53)
NFluc-Ago REV  5'<u>CCGCACACCAGTAAGGTGTGCGGT</u>TATCATCCATCCTTGTCAATCAAGGCGTT
               (SEQ ID NO: 56)
CFluc-Ago FWD  5'GCAGC*TAATACGACTCACTATAGG*AACAGACCACCATGTCCGGTTATGTAAACAATCCG
               GAAGCGACC
               (SEQ ID NO: 55)
CFluc-Ago REV  5'<u>CCGCACACCAGTAAGGTGTGCGGT</u>TCATTAAGCTGCGCTAGTAGACGAGTCCATGTGCTG
               (SEQ ID NO: 56)

The restriction sites in the primers are shown in bold. The Pum1 and Pum2 binding sites in the RNA target are shown in bold and blues, respectively. The regions complementary to the RNA target are shown in bold for the RNA guides. For the in vitro transcription primers, T7 promoters are shown in italicized, KOZAK sequences in bold, and 3' stem-loops underlined.

The RNA binding PAZ domain of *Homo sapiens* argonaute-2 (Ago) was PCR amplified from pIRESneo-FLAG/HA Ago2 corrected (Addgene plasmid 10822; Ref 9b of main text), which encoded residues 1-856 of hsAgo-2, using primers indicated in Table 1 under the heading "Cloning Primers". Only the RNA binding domain (residues 219-363) was amplified, since adjacent domains have endonuclease activity.[1] Plasmids containing NFluc-PBSII and CFluc-Zif268 were digested at XmaI/XhoI and BamHI/AgeI, respectively. The digested plasmids were phosphatased, then ligated to the Ago inserts generated by PCR. Sequences were confirmed by dideoxynucleotide sequencing. All methods concerning cloning of NFluc-Pum2 and CFluc-Pum1 have been described elsewhere (58).

We also amplified the same sequence, with 20 additional residues on the N- and C-terminus to simulate flexible linkers. Although no data are shown herein, these constructs functioned essentially the same as the PAZ domain-only constructs in all cases tested.

Annealing of guides to RNA target was carried out as follows. Guides (Table 1, RNA Guides), containing regions of complementarity to the pumilio target followed by two 3'-rU's to facilitate Ago binding, were annealed to the pumilio target using the following procedure: heating of target (Table 1, RNA Target) and guide in NEBuffer 4 (20 mM Tris-acetate, pH 7.9, 50 mM potassium acetate, 10 mM magnesium acetate, 1 mM dithiothreitol) supplemented with RNasin™ to 90° C. for 1 minute, followed by cooling to 37° C. over one hour. Samples were stored at −80° C.

Genes encoding NFluc-Ago and CFluc-Ago were PCR amplified using in vitro transcription primers (Table 1, in vitro transcription primers) containing a T7 promoter and a KOZAK sequence in the forward primer and a stem-loop sequence in the reverse primer. These primers were designed so that the complementary regions had melting temperatures greater than or equal to 70° C. A typical PCR amplification included an initial heat denaturation of 95° C. for 5 min, followed by 40 cycles of heating to 95° C., cooling at a rate of 6° C./min to an annealing temperature of 53° C. Elongation at 72° C. for 6 minutes completed the cycle. The PCR products were then used as templates for in vitro transcription using a T7 Ribomax RNA production kit according to the manufacturer's suggestions. Generally, 3 µg of amplified DNA template was incubated at 37° C. for 3 hours in the presence of 1×T7 transcription buffer, 7.5 mM rNTPs, and T7 enzyme mix. The mRNA generated was purified over illustra ProbeQuant™ G-50 Micro Columns (GE Healthcare) and analyzed by agarose gel electrophoresis. The mRNA was then introduced into the Flexi Rabbit Reticulocyte Lysate System for in vitro translation to yield the protein constructs. 25 µL reactions were set up in duplicate according to the manufacturer's instructions. A typical reaction was performed at 30° C. for 1.5 hours and consisted of the following components: 0.5 µL amino acid mix, 70 mM KCl, 1 mM DTT, 0.8 U/µL RNasin™, 0.1-2 pmol each mRNA transcript, and Nuclease-free $H_2O$ (NEB) to final volume. Specific mRNA and target conditions used in each of the experiment types (NFluc-Pum2/CFluc-Pum1, NFluc-Pum2/CFluc-Ago, NFluc-Ago/CFluc-Pum1, and NFluc-Ago/CFluc-Ago) are given in Table 2.

TABLE 2

Reaction Translation Conditions for Pum and Ago Experiments

| mRNA 1 | mRNA 2 | Final target concentration |
| --- | --- | --- |
| 2 pmol NFluc-Pum2 | 2 pmol CFluc-Pum1 | 10 nM target |
| 0.1 pmol NFluc-Pum2 | 0.1 pmol CFluc-Ago | 10 nM Pum1 guide + 10 nM target |
| 1 pmol NFluc-Ago | 1 pmol CFluc-Pum1 | 10 nM Pum2 guide + 10 nM target |
| 2 pmol NFluc-Ago | 2 pmol CFluc-Ago | 10 nM Pum1 guide + 10 nM Pum2 guide + 10 nM target |

In the case of NFluc-Pum2 and CFluc-Pum1, the ssRNA target was added at the beginning of the translation reaction. In all other cases the target with annealed guide(s) or a buffer blank (NEBuffer4) was added after completion of translation, and binding was allowed to occur for 1 hour at 4° C. The presence of target with annealed guide(s) should provide a binding site for the domains attached to each of the luciferase halves, resulting in formation of a functional enzyme. Activity was monitored as a luminescent signal produced upon addition of Steady-Glo™ Luciferase Assay system. 20 µL of each translation reaction equilibrated with target (or buffer) was added to 80 µL of Steady-Glo reagent and allowed to equilibrate at room temperature for 1 minute. Luminescence readings were acquired using a Turner TD-20e Luminometer with a 10 second integration time. Two duplicate translation reactions were performed simultaneously. Luminescence readings were averaged and normalized to one. The data summarized are results for two sets of duplicate translation reactions performed on separate days. The results from each day were averaged and normalized to one, then averaged together. The standard deviation presented for the sample in the presence of target is that of the set of translations with the greatest variation.

Additional control experiments were used to solidify the experimental results: The following results demonstrate selectivity of the Ago detection domain. 2 pmol of NFluc-Pum2 and CFluc-Ago mRNA were translated as described above, except the targets were present during translation. Luminescence readings demonstrated that both target and guide must be present for Fluc reassembly to occur. The signal generated with the combination of Pum1 guide (3'-UUGUACCACAUAUAUC, SEQ ID NO:57) and Target RNA (5'-CAUGGUGUAUAUAGUCU-UUUGAUAUAGCGGC, SEQ ID NO:58) was approximately threefold that obtained with either Target RNA or no Target RNA or Guide and ½ site Target RNA (5'-CCGAGAAUUGUAUAUAUUCG, SEQ ID NO:59). Additionally the Pum1 guide annealed to a ½-site target site, in which no Pum2 binding site exists, resulted in only background luminescence (compare bars 1, 3, and 4). Signal is lower than that in certain earlier experiments since this experiment was performed using non-optimized mRNA amounts (2 pmols as compared to 0.1 pmol each. mRNA).

Figure 18:
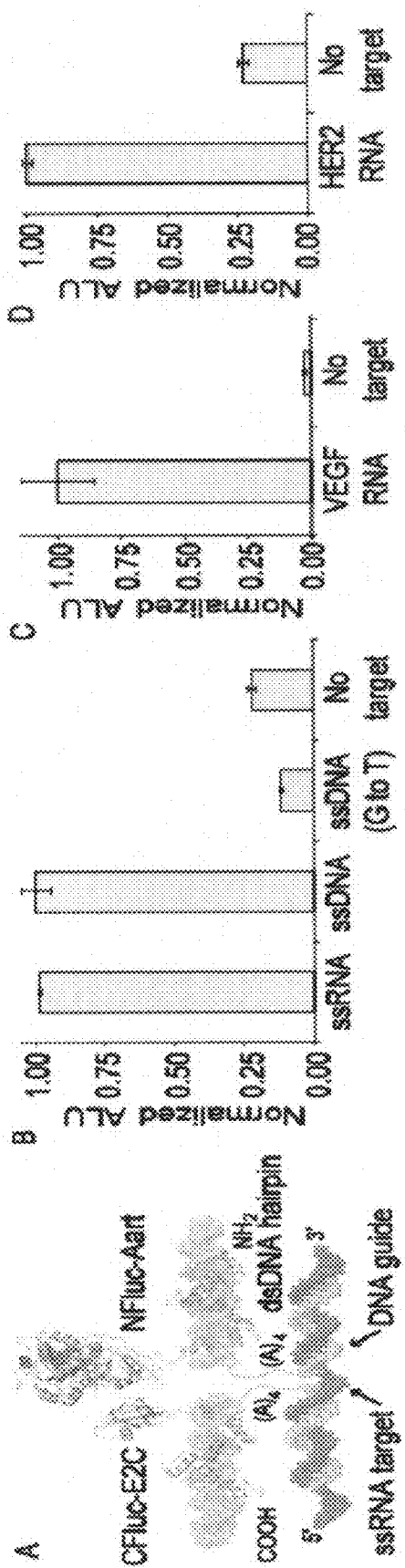
FIG. 18. Zinc finger-mediated single-stranded nucleic acid detection. (A) The designed hairpin-guides target a cognate single-stranded nucleic acid, allowing zinc finger mediated split-luciferase reassembly. (B) Hairpin-guides were designed to target 1 nM ssRNA and ssDNA, resulting in a 4.5-fold relative signal over background for each. A single G to T mutation in the ssDNA target knocked signal down to background levels. (C) Hairpin-guides were designed to detect a 295 nucleotide VEGF transcript (1 nM), resulting in a relative signal of 39-fold. (D) Hairpin-guides were designed to bind to a 201 nucleotide HER2 transcript (1 nM), resulting in a 4.3-fold relative signal.
Figure 19:
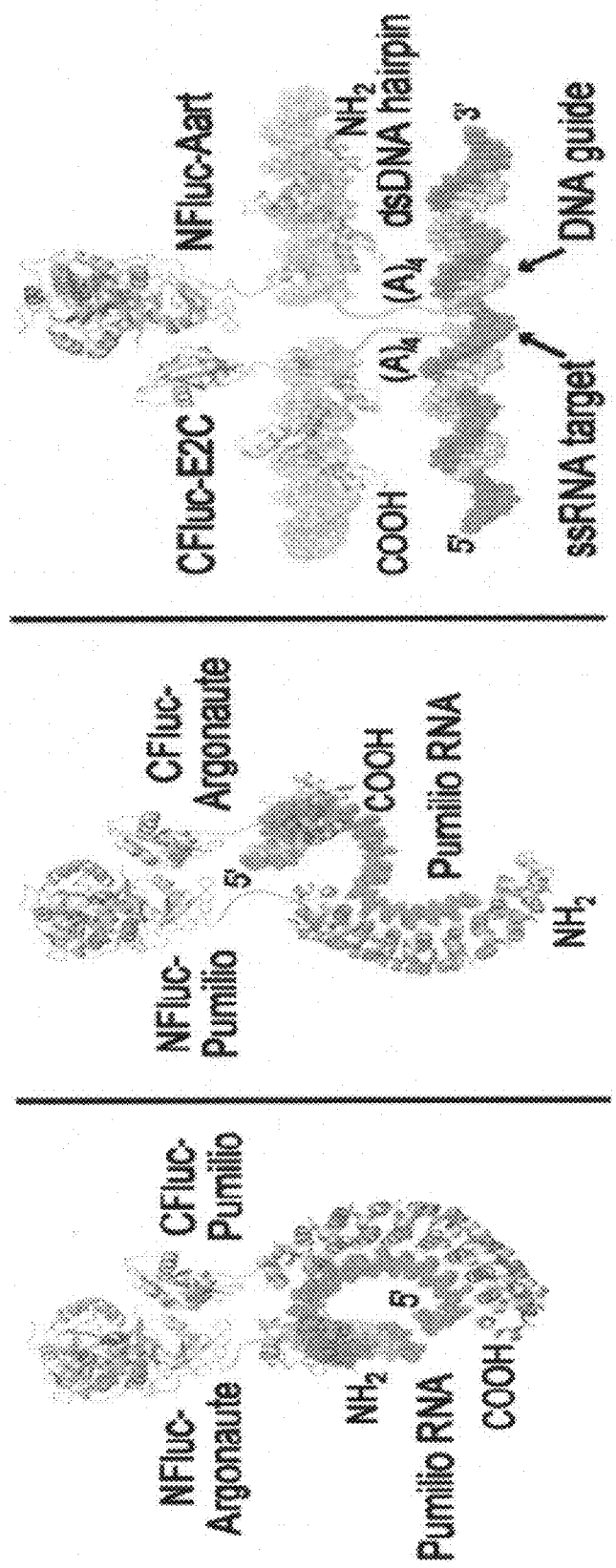
FIG. 19. Cartoons showing NFluc-Argonaute and CFluc-Pumilio, NFluc-Pumilio and CFluc-Argonature and CFluc-E2C and NFluc-Aart associations.

We created a general sequence-specific ssRNA detection strategy without the need for programming nucleic acid binding proteins for each new ssRNA target. Learning from the Ago-guide strategy, we envisioned that attachment of high affinity (Kd ~low pM), sequence-specific zinc fingers (ZFs) (22,25,78,79) to our split-proteins could serve as a motif for displaying any user-defined ssDNA guide when appended to a ZF hairpin (hp) binding site, providing a hp-guide (FIG. 18, panel a). These hp-guides would allow ZF-mediated split-Fluc reassembly only in the presence of a targeted ssRNA or ssDNA sequence. Towards this goal, we designed DNA hps as binding sites for two well-characterized and high affinity six-finger ZFs (E2C and Aart) (80,81,82) and to these we attached guide sequences of ssDNA complementary to the ssRNA target (Table 3). Addition of our designed ZF-modified split-Fluc constructs to 1 nM target (ssRNA or ssDNA) hybridized to complementary hp-guides resulted in luciferase reassembly and a signal of 4.5-fold as compared to background (FIG. 18). To directly interrogate sequence selectivity, a single G to T mutation was introduced in the ssDNA, which reduced signal to background levels.

To probe the generality of our ssRNA detection approach, we selected two disease relevant targets, vascular endothelial growth factor (VEGF) and human epidermal growth factor receptor 2 (HER2) mRNA1 (83,84). By judicious exchange of the guide portion of the existing hp-guides to designed ssDNA oligonucleotides complementary to two adjacent 19 nt sequences in the 295 nt VEGF mRNA transcript (Table 3), we observed a 39-fold signal in the presence of 1 nM target (FIG. 18, panel C) and as low as 1 pM (100 attomoles) VEGF mRNA was detectable. Finally, hp-guides were designed (Table 3) for detecting two adjacent 19 nt sequences present in a 201 nt HER2 mRNA sequence, where a 4.3-fold signal over the presence of hp-guides alone was achieved (FIG. 18D), further confirming the general applicability of this nucleic acid detection system.

In conclusion, we have developed a general ssRNA and ssDNA detection methodology utilizing split-protein reassembly, which allows for distinguishing single base substitutions and detecting attomoles of a user-defined target. Thus this new bioluminescence based methodology complements existing ssRNA and ssDNA detection methods (70,71,75) and future studies demonstrate that this methodology is applicable to in vivo imaging.

Rapid Interrogation of Transcription Factor Binding, DNA Methylation, and poly(ADP-ribosyl)ation The sequencing of the human genome revealed that transcription factors comprise the largest single group of proteins, which is perhaps not surprising since the ability to accurately recognize, bind, regulate specific DNA sequences is central to the regulation of almost all cellular processes. DNA activity is not only regulated by protein factors but also by the reversible chemical modification of both DNA and associated proteins, impacting cellular biology at multiple levels. Accordingly, the study of native DNA, its associated proteins, and their chemical regulation is of profound importance to the study of biology. Thus, there is a need for new, generally applicable methodologies for detecting and studying DNA and its associated proteins, which in turn aid in the development of designed transcription factors (85-88), and allow for the development of small molecules that modulate transcription (89-92) DNA methylation (93,94), and poly(ADP-ribose) metabolism (95,96).

General approaches for the direct detection of native dsDNA include the use of triplex forming oligonucleotides (TFOs) as well as sequence specific polyamides. Though powerful, these techniques also have associated limitations.

TFOs bind the major groove of dsDNA through Hoogsteen or reverse Hoogsteen base pairing and are thus restricted to detecting sequences comprised of purines on one strand (97). Additionally, TFOs composed of polypyrimidines require cytosine protonation in order to bind, imposing a pH regime outside of physiological conditions. On the other hand, sequence specific polyamides, which are comprised of designed N-methylpyrrole and N-methylimidazole heterocycles, are capable of recognizing all four base pairs with affinities that rival naturally occurring DNA-binding proteins (98,99). Polyamides have proven to be extremely useful for the direct in vitro detection of dsDNA when modified with environmentally sensitive fluorophores, however this approach has yet to be tested against dsDNA sequences beyond 9 bp (100,101). Furthermore the aforementioned methods are currently not capable of recognizing and reporting on chemical modifications to dsDNA such as cytosine methylation. This DNA methylation dependent epigenetic regulation is mediated by the action of methyltransferases at CpG dinucleotide sites and is currently of particular interest due to its link to transcriptional repression and cancer (102). Though distributed throughout the genome, CpG methylation is primarily excluded from promoter-associated CG-rich regions of sequence known as CpG islands. The aberrant hypermethylation of these promoters, particularly those associated with tumor-supressor genes, has been shown to occur in a sequence specific and tumor-type specific manner, leading to the elucidation of gene hypermethylation profiles for a number of cancer types (103). Additionally, overall genome wide hypomethylation has also been associated with tumor cells (104,105), making the determination of DNA methylation a potential biomarker for cellular states, particularly tumorigenesis. Moreover, tools for the measurement of methylation and demethylation can also be potentially utilized for measuring the activities of associated DNA modifying enzymes.

In addition to modifications to dsDNA, modifications to proteins associated with DNA are also of much interest, for example, proteins associated with DNA may be modified by poly(ADP-ribosyl)ation (PAR), which usually occurs in response to DNA damage (106). Poly(ADP-ribosyl)ation is catalyzed by poly(ADP-ribose) polymerases (PARPs), while deribosylation is catalyzed by polyADP-glycohydrolysases (PARGs) (107). This modification is implicated in transcriptional regulation (108,109), apoptosis (110,111), and tumorigenesis (112,113). The ability to directly measure the presence and extent of protein poly(ADP-ribosyl)ation using designed reagents has yet to be realized and could provide a potent marker for DNA damage as well as a method for interrogating the activity of enzymes such as PARP and PARG. As described herein, we have demonstrated the application of the split-protein reassembly approach to interrogate the aforementioned targets.

Figure 20:
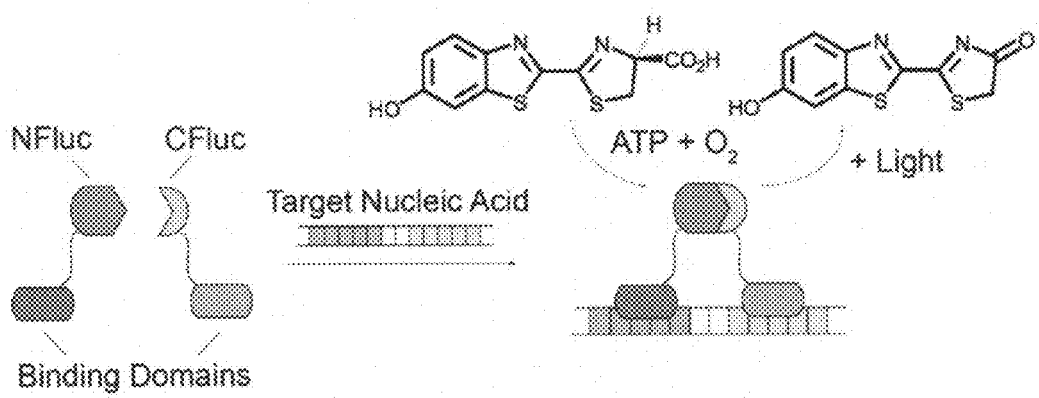
FIG. 20. Split luciferase detection of a target nucleic acid (chemically modified or sequence specific). Inactive luciferase fragments are tethered to target binding domains which form a ternary complex upon nucleic acid target binding results in split-luciferase reassembly and luminescence.

Generally, split-protein reassembly or protein complementation utilizes a protein reporter dissected into two inactive fragments, each of which when appended to a member of an interacting protein/peptide pair results in reassembly of the dissected protein reporter whose activity can be measured. This approach beginning with ubiquitin has been utilized for the in vivo detection of a wide variety of biomolecular interactions utilizing monomeric split-reporters such as beta-lactamase, green fluorescent protein, and luciferase (12-19,27). Recently, designed split-protein reassembly methods have also been applied towards the study of protein-DNA interactions (22,23,25,58), as well as the determination of DNA methylation and protein phosphorylation (23,27,37). Additionally, Varshavsky has proposed how DNA sequence enabled split-protein reassembly may be utilized as an enabling therapeutic strategy (115), while Barbas and coworkers have elegantly utilized this method for directed methylation of a dsDNA target (116). In each of these cases two nucleic acid-binding domains direct the formation of a ternary complex in the presence of a target dsDNA providing a sensitive "turn on" sensor (FIG. 20), which is conceptually similar to a yeast-three hybrid (17) or chemical dimerizer approach (118,119). Herein we demonstrate the utility of the fragmented firefly luciferase system in constructing extremely rapid and sensitive reporters capable of the direct detection of a) specific 36-basepair DNA sequences; b) sequence specific as well as overall DNA methylation; c) dimeric DNA-binding transcription factors; and d) the direct determination of poly(ADP-ribosyl)ation.

Direct and Sensitive Detection of 36-mer dsDNA Sequences.

We have previously shown that 3-finger zinc finger proteins can be utilized to directly detect an 18 bp dsDNA molecule using split-GFP, beta-lactamase, and luciferase while polyamide based approaches have been shown to detect dsDNA molecules shorter than 9 bp. We then tested if it is possible to detect shorter and longer dsDNA molecules and examine whether sequence specific 6-finger zinc fingers (ZFs) offer a means for greater affinity and selectivity than their 3-fingered counterparts and whether it is possible to recognize and directly detect 36 bp of dsDNA. Beyond the diagnostic capabilities of such a reagent, the ability to design both specific as well as high affinity ZFs is of particular relevance for ZF mediated gene therapy approaches.

Figure 21:
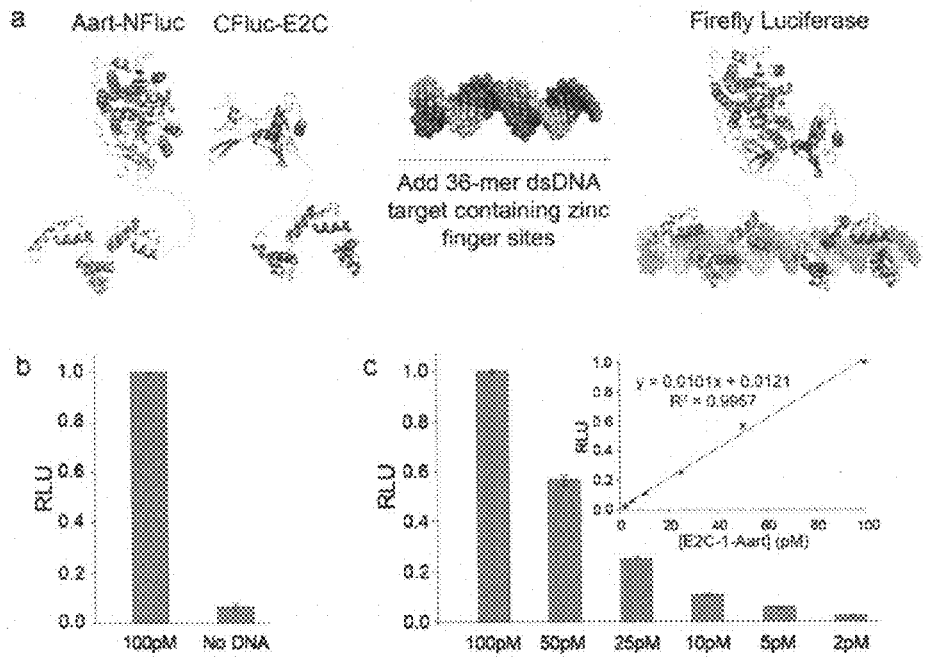
FIG. 21. Sequence specific reassembly of split-firefly luciferase. a) Cartoon representation of the detection of a 36-mer dsDNA sequence utilizing two 6-finger zinc fingers. b) Luciferase reassembly utilizing the 3-finger zinc finger Zif268 and the 6-finger zinc finger Aart in the presence or absence of the dsDNA target Zif268-1-Aart. c) Luciferase reassembly utilizing the 6-finger zinc fingers E2C and Aart in the presence of decreasing amounts of the target dsDNA E2C-1-Aart. (inset) Linear fit from 100 to 2 pM E2C-1-Aart.

As an initial test we chose the well characterized 6-finger ZF Aart, a designed finger which binds the 18 base pair sequence 5'-ATGTAGGGAAAAGCCCGG-3' (SEQ ID NO:1) with a reported $K_d$ of 50 pM (81,82). To create a platform capable of dsDNA dependent luciferase reassembly (our most sensitive reporter), the N-terminal fragment of luciferase was fused to Aart creating Aart-NFluc(residues 2-416) while the C-terminal fragment of luciferase was fused to the 3-finger ZF Zif268 creating CFLuc(residues 398-550)-Zif268. Cell-free translations were initiated by adding in vitro transcribed mRNA corresponding to the fragmented luciferase-ZF fusions in either the presence or absence of the dsDNA target Zif268-2-Aart. A 15-fold increase in luminescence was observed in the presence of 100 pM (10 fmols) Zif268-1-Aart, demonstrating the ability of a 6-finger ZF to facilitate split-luciferase reassembly in a dsDNA templated fashion (FIG. 21, panel b). Having demonstrated the ability of Aart to direct the reassembly of fragmented luciferase, we next designed a DNA sensor in which both fragments of luciferase were attached to 6-finger ZFs, where we chose another designed 6-finger ZF, E2C, which was designed to bind the 18 base pair sequence 5'-GGGGCCGGAGCCG-CAGTG-3' (SEQ ID NO:2) with a $K_d$ of 500 pM (53). To recognize 36 bp of dsDNA, the 3-finger ZF Zif268 was replaced by E2C, creating the fusion CFluc-E2C (FIG. 21, panel a). Initial experiments demonstrated a 70-fold increase in luminescence over background in the presence of 100 pM (10 fmols) of the dsDNA target E2C-1-Aart). Importantly, minimal signal was generated in the presence of 100-fold excess genomic herring sperm DNA, suggesting low non-specific binding for these 6-finger ZFs. Furthermore, titrations with decreasing amounts of E2C-1-Aart in the presence of the two 6-finger proteins attached to split-luciferase (FIG. 21, panel c) show that as low as 2 pM (200 amols) of target dsDNA is clearly detectable above background (2.7-fold). In comparison, an analogous system utilizing the 3-finger ZFs Zif268 and PBSII allowed for the detection of 10 pM (1 fmol) of target dsDNA with a 1.3-fold signal above background.

These results demonstrated the possibility of improving the detection limit associated with the use of 6-finger ZFs, presumably due to their higher affinity as compared to 3-finger ZFs. Next we wanted to directly address whether the split-luciferase approach provides a method for directly interrogating the ZF specificity of these 18 bp binders.

Selectivity of the Designed 6-Finger Zinc Finger Aart.

Figure 22:
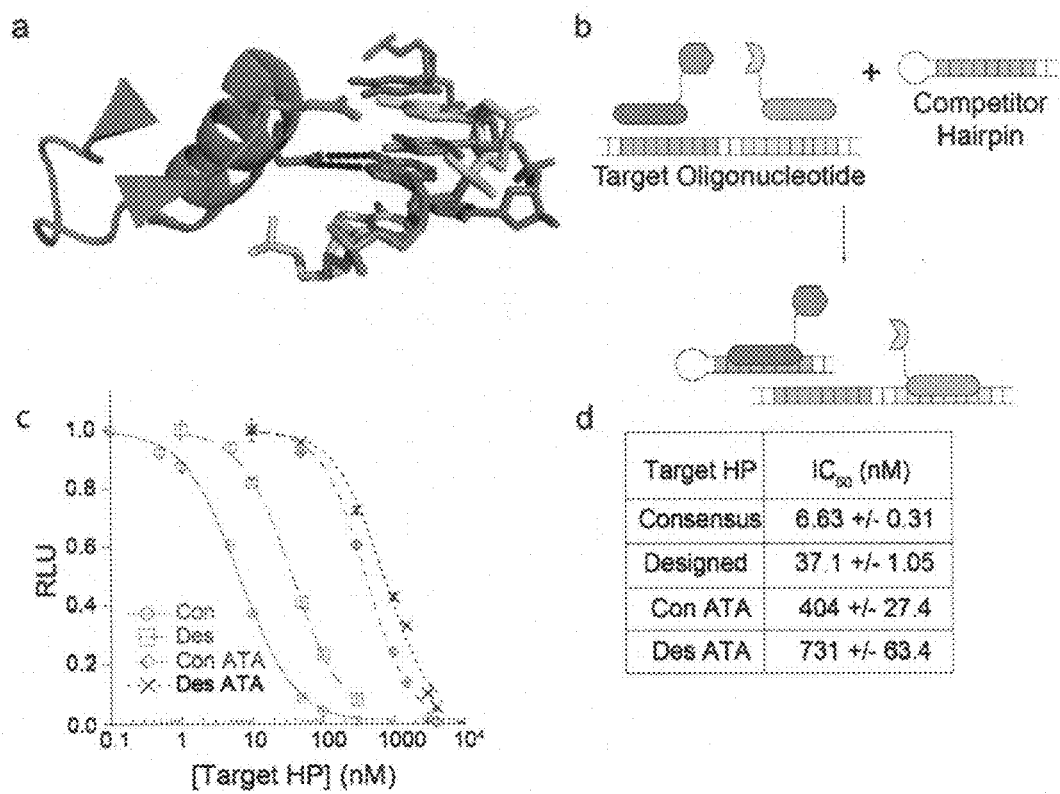
FIG. 22. Interrogation of 6-finger zinc finger, Aart, specificity. a) X-ray crystal structure of finger 3 of Aart in complex with target DNA 5'-AAA-3'. Specific hydrogen bond contacts are shown between residue N92 and the DNA position of interrogation. b) Cartoon showing approach for the interrogation of Aart specificity, where the addition of a competitor hairpin DNA containing a zinc finger binding site results in the disruption of dsDNA-firefly luciferase ternary complex formation and a loss in signal. c) Competition experiments in the presence of increasing concentrations of the competitor Aart hairpin DNA containing the consensus (con) and designed (des) recognition sequences and the 3rd finger 5'-AAA-3' to 5'-ATA-3' mutations of both the consensus (Con ATA) and designed (Des ATA) recognition sequences. d) Tabulated IC¬50 values of Aart for the respective hairpin DNA targets.

Interestingly Aart, which was designed to bind the aforementioned A-rich DNA sequence, was found, through cyclic amplification and selection of targets (CAST) assays, to prefer an alternate and more G-rich consensus sequence 5'-ATGTAGGGAAAAGCCCGG-3' (SEQ ID NO:1) (120). Of particular interest is finger 3, which shows a very strong preference for the DNA triplet 5'-AAA-3' (underlined) in both the consensus and the designed sequences. A recently available co-crystal structure suggests that the origin of the observed specificity likely arises from the specific hydrogen bond contacts provided by residues Q89 and N92 (FIG. 21, panel a) (82). To functionally interrogate the specificity of Aart for this triplet in the context of the consensus and designed targets, cell-free translations of the split-proteins, Aart-NFluc and CFluc-E2C, were initiated in the presence of the target (consensus) oligonucleotide E2C-1-Aart, and a series of competitor hairpin DNAs (hpDNAs) (FIG. 22, panel b). The hpDNAs contained either the designed or consensus Aart recognition sequences or the designed or consensus sequence containing the mutated $3^{rd}$ triplet 5'-ATA-3', which should lack the possibility of the N92 hydrogen bond to adenine. In all cases a competitor hairpin concentration dependent decrease in luminescence was observed, facilitating the determination of $IC_{50}$ values for each competitor hpDNA (FIG. 22, panels c and d). The observed 6-fold difference in $IC_{50}$ between the designed and consensus hpDNAs confirms the previously reported preference of Aart for the consensus target. More interestingly, competitor hpDNAs with single A to T bp substitutions in the consensus and designed binding sites reduced the signal intensity by 60- and 20-fold when compared to the parent hpDNA targets, speaking to the surprising specificity of these 6-finger proteins. Thus this approach allows for a rapid method for evaluating ZF specificity, an application of great interest to investigators engaged in designing ZFs for use in gene therapy. Having established that 6-finger proteins are amenable for targeting dsDNA in the context of split-protein assays, we turned to demonstrating their utility in specifically targeting sites of DNA methylation. The 18 bp ZF targeting domains offer the potential for the unique recognition of specific sites of methylation in genomic DNA, which was not possible with our previous designs incorporating three-finger ZFs.

Interrogation of dsDNA Methylation

As previously discussed cytosine methylation at CpG dinucleotides is dependent on the transfer of a methyl group from S-adenosylmethionine to the C5-position of cytosines within these CpG dinucleotides (FIG. 23, panel a), a mechanism regulated by DNA methyltransferases (121). Previously, split-protein reassembly systems for GFP and β-lactamase have been used to directly detect site-specific determination of dsDNA methylation utilizing a mCpG targeting domain, MBD2, attached to one half and a three-finger ZF attached to the other half (FIG. 23, panel b) (37,58). These studies had demonstrated a geometric/length dependence on GFP and β-lactamase reassembly, thus before evaluating our new 6-finger targeting domains, we evaluated the effect of both distance and geometry on split-luciferase reassembly.

TABLE 4

Protein fusions, nucleic acid binding domains, and nucleic acid targets used.

| Reassembly Pairs | Nucleic Acid Binding Domains | Nucleic Acid Target | |
|---|---|---|---|
| Aart-NFluc CFluc-Zif268 | Aart Zif268 | GCGTAGCGTGGGCGAGATGTAGGGAAAAGCCCGGTACCG | (SEQ ID NO: 72) |
| Aart-NFluc CFluc-E2C | Aart E2C | GCGTAGGGGCCGGAGCCGCAGTGGATGTAGGGAAAAGCCCGGTACCG | (SEQ ID NO: 73) |
| MBD2-NFluc CFluc-Zif268 | MBD2 (147-215) Zif268 | GCGTA$_m$CG(N)CGCCCACGCCACCG | (SEQ ID NO: 74) |
| MBD2-NFluc CFluc-E2C | MBD2 (147-215) E2C | GCGTA$_m$CGTACACTGCGGCTCCGGCCCCTACCG | (SEQ ID NO: 75) |
| MBD2-NFluc CFluc-λCro | MBD2 (147-215) λ-Cro (1-66) | GCCTA$_m$CGACTATCACCGCGGGTGATACAGCC GCCTACGACTATCACCGCGGGTGATACAGCC | (SEQ ID NO: 76) (SEQ ID NO: 77) |
| MBD2-NFluc CFluc-MBD2 | MBD2 (147-215) MBD2 (147-215) | GATCA$_m$CGATGGTA$_m$CGACTAG GCCTA$_m$CGACTATCACCGCGGGTGATAGT$_m$CGTAGGC | (SEQ ID NO: 78) (SEQ ID NO: 79) |
| APLF-NFluc CFluc-APLF | APLF (376-441) APLF (376-441) | poly(ADP-ribose) | |
| PBSII-NFluc CFluc-Zif268 | PBSII Zif268 | GCGTAGCGTGGGCGGTGTGGAAACACCG | (SEQ ID NO: 80) |

TABLE 5

Methylated dsDNA targets and Aart competitive hairpins used

Methylated dsDNA Targets mCpG-0-Zif268
GCGTA$_m$CGCGCCCACGCCACCG
(SEQ ID NO: 81)

mCpG-1-Zif268
GCGTA$_m$CGTCGCCCACGCCACCG
(SEQ ID NO: 82)

mCpG-2-Zif268
GCGTA$_m$CGTACGCCCACGCCACCG
(SEQ ID NO: 83)

mCpG-3-Zif268
GCGTA$_m$CGTAGCGCCCACGCCACCG
(SEQ ID NO: 84)

mCpG-6-Zif268
GCGTA$_m$CGTAGGACCGCCCACGCCACCG
(SEQ ID NO: 85)

mCpG-10-Zif268
GCGTA$_m$CGTAGGACGATACGCCCACGCCACCG
(SEQ ID NO: 86)

Aart Campetative Hairpins

Consensus
GCATGTAGGGAAAAGCCCGGCGTCCTCGCCGGGCTTTTCCCTACATGC    (SEQ ID NO: 87)

Consensus ATA
GCATGTAGGGAATAGCCCGGCGTCCTCGCCGGGCTATTCCCTACATGC    (SEQ ID NO: 86)

Designed
GCATGTAGAGAAAAACCAGGCGTCCTCGCCTGGTTTTTCTCTACATGC    (SEQ ID NO: 89)

Designed ATA
GCATGTAGAGAATAACCAGGCGTCCTCGCCTGGTTATTCTCTACATGC    (SEQ ID NO: 90)

Aart and E2C mediated firefly luciferase reassembly. Duplicate 25 µL reactions were carried out in Flexi-Rabbit Reticulocyte according to manufacturer's protocol using 0.2 pmols of Aart-NFluc(residue 2-416) and 0.1 pmols of CFluc (398-550)-E2C, 10 µM ZnCl$_2$, 0.5 µL RNasin Plus (Promega), and 1.25 µL of either 10 nM E2C-1-Aart target or water. Translations were incubated for 90 minutes at 30° C. and assayed by adding 80 µL of Steady-Glo™ Luciferase Assay System (Promega) to 20 µL of translated lysate. Light emission was monitored 1 minute after substrate addition using a Turner TD-20e luminometer with a 3 sec. delay and a 10 sec. integration time.

Experiments were carried out to confirm that reassembly of the split luciferase was sequence specific. There was essentially no signal generated in response to the inclusion of sheared herring sperm DNA rather than target, and supplementation of the assay containing target DNA did not result in increase reporter reassembly.

PBSII and Zif268 mediated firefly luciferase reassembly. Duplicate 25 µL reactions were carried out in Flexi-Rabbit Reticulocyte according to manufacturer's protocol using 0.2 pmols of PBSII-NFluc(residue 2-416) and 0.2 pmols of CFluc(398-550)-Zif268, 10 µM ZnCl$_2$, 0.5 µL RNasin™ Plus (Promega), and 1.25 µL of decreasing concentrations of Zif268-0-PBSII target dsDNA (100 nM-1 nM) or water. Translations were incubated for 90 minutes at 30° C. and assayed by adding 80 µL of Steady-Glo™ Luciferase Assay System (Promega) to 20 µL of translated lysate. Light emission was monitored 1 minute after substrate addition using a Turner TD-20e luminometer with a 3 sec. delay and a 10 sec. integration time.

Aart and E2C mediated firefly luciferase reassembly in the presence of sheared Herring Sperm (HS) DNA. Duplicate 25 µL reactions were carried out in Flexi-Rabbit Reticulocyte according to manufacturer's protocol using 0.2 pmols of Aart-NFluc(residue 2-416) and 0.4 pmols of CFluc(398-550)-E2C, 10 µM ZnCl$_2$, 0.5 µL RNasin™ Plus (Promega), and either 1.25 µL of 30 nM E2C-1-Aart (Target), Target plus 1.25 µL of 91.65 ng/µL HS-DNA, 1.25 of 91.65 ng/µL HS-DNA, or water. Translations were incubated for 90 minutes at 30° C. and assayed by adding 80 µL of Steady-Glo™ Luciferase Assay System (Promega) to 20 µL of translated lysate. Light emission was monitored 1 minute after substrate addition using a Turner TD-20e luminometer with a 3 sec. delay and a 10 sec. integration time.

Methylation mediated luciferase reassembly. For initial MBD2 and E2C mediated luciferase reassembly duplicate 25 µL reactions were carried out in Flexi-Rabbit Reticulocyte according to manufacturer's protocol using 0.2 pmols of MBD2-NFluc(residue 2-416) and of CFluc(398-550)-E2C, 10 µM ZnCl$_2$, 0.5 µL RNasin™ Plus (Promega), and 1.25 µL of either 1 µM mCpG-2-E2C target or water. For MBD2 and Zif268 duplicate 25 µL reactions were carried out in Flexi-Rabbit Reticulocyte according to manufacturer's protocol using 0.2 pmols of MBD2-NFluc(residue 2-416) and of CFluc(398-550)-Zif268, 10 µM ZnCl$_2$, 0.5 µL RNasin™ Plus (Promega), and 1.25 µL of decreasing concentrations of mCpG-2-Zif268 target (100 nM-1 nM) or water. Translations were incubated for 90 minutes at 30° C. and assayed by adding 80 µL of Steady-Glo™ Luciferase Assay System (Promega) to 20 µL of translated lysate. Light emission was monitored 1 minute after substrate addition using a Turner TD-20e luminometer with a 3 sec. delay and a 10 sec. integration time.

Figure 23:
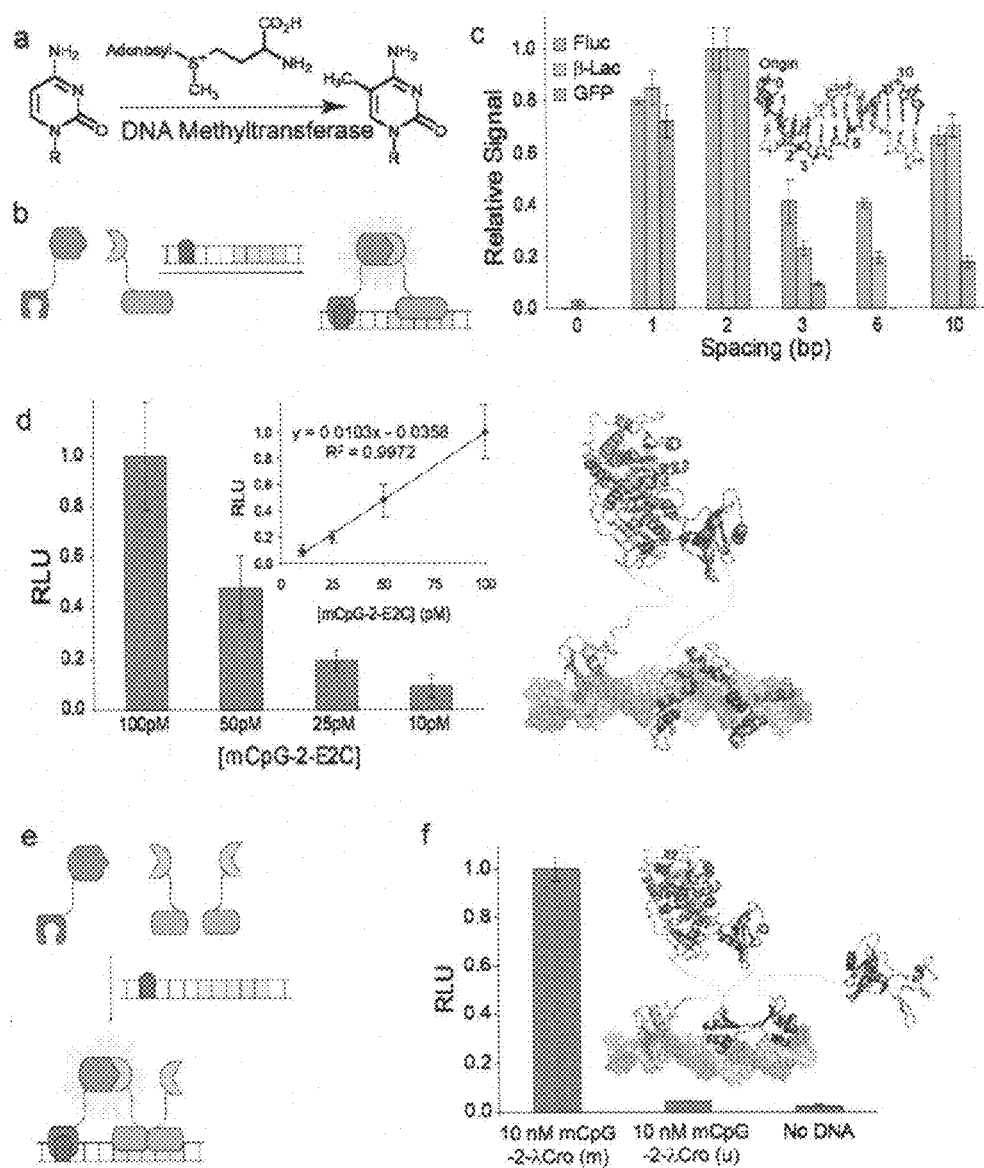
FIG. 23. Detection of DNA Methylation and Dimeric Transcription Factor Binding. a) C5-Cytosine methylation by DNA methyltransferase; b) Cartoon showing the site-specific determination of dsDNA methylation utilizing MBD2 and a sequence-specific zinc finger. c) Profile of different split-protein reporters tethered to MBD2 and Zif268 in the presence of a dsDNA target as a function of increasing number of base pairs between the mCpG and Zif268 sites. d) Luminescence of split-firefly luciferase tethered to MBD2 and the 6-finger zinc finger E2C in the presence of decreasing concentrations of the methylated dsDNA target mCpG-2-E2C. (inset) Linear fit from 100 pM to 10 pM mCpG-2-E2C. e) Cartoon showing the detection of dsDNA by split-luciferase utilizing MBD2 and the dimeric transcription factor λ-Cro. f) Luminescence in the presence of methylated (m) and non-methylated (u) target mCpG-2-λ-Cro containing the dimeric λ-Cro recognition site (10 nM).

Translations with MBD2-NFluc(2-416) (SEQ ID NO: 32-33) and CFluc(398-550)-Zif268 (SEQ ID NO: 26-27) in the presence of a series of methylated dsDNA targets incorporating increasing distances between the mCpG and Zif268 binding sites was tested and showed a profile similar to split-lactamase but distinct from split-GFP (FIG. 23, panel c). Essentially no activity is observed when the DNA binding domains are directly adjacent to each other (0 bp separation), a likely result of the inability of MBD2 and Zif268 to simultaneously bind their DNA targets. Beyond 1 bp the pattern, likely recapitulate the helical nature of dsDNA, as also observed when fragmented beta-lactamase or GFP are used as signaling domains in place of luciferase (FIG. 23, panel c, center and righthand bars in each trio of bars, respectively).

The manner in which these 3 fragmented systems are assembled provides some insight with respect to the differences in signal generation observed. Both split-GFP and split-β-lactamase were rationally designed, such that the point of dissection and new-protein attachment sites lie between loops. GFP is perhaps the most sensitive to geometrical constraints as the secondary structural elements adjacent to the dissected loop are beta-strands whereas the region adjacent to the dissection site in β-lactamase is less structured (15,16). In contrast the firefly luciferase fragments, selected from a library, have the interacting proteins fused to the native wild type termini (27) that are separated by ~40 Å as seen in the crystal structure. This inherent separation between protein attachment sites likely allows split-firefly luciferase to tolerate targets at larger separation distance compared to GFP and β-lactamase though surprisingly still showing highest signal at a 1 bp separation distance. These initial results suggest that the direct detection of sites of specific promoter methylation will likely be primarily dictated by the specificity of the sequence specific dsDNA binding domain, with the site of adjacent methylation lying anywhere between 2-10 base pairs away. Thus, this lack of stringency may be a boon, allowing for greater latitude in choosing sites for targeting given that the design/selection of zinc fingers, though very powerful, is still not capable of providing ZFs capable of targeting any dsDNA sequences with high selectivity. Noting that a 6-finger ZF targeting domain (18 bp) ensures unique targeting within the genome we next tested if new domains could function in the site-specific determination of dsDNA methylation.

Given the enhancement in dsDNA detection gained by the use of 6-finger ZFs discussed above, we next utilized the 6-finger ZF E2C for the site-specific determination of dsDNA methylation. Initial experiments demonstrated the methylated dsDNA dependent reassembly of fragmented firefly luciferase-MBD2/E2C fusions (not shown). To determine the minimal amount of methylated dsDNA needed to generate an observable signal over background, cell-free translations were initiated using 0.2 pmols of mRNA corresponding to MBD2-NFluc (SEQ ID NO: 32-33) and CFluc-E2C (SEQ ID NO: 28-29) in the presence of decreasing amounts of the methylated dsDNA target mCpG-2-E2C (100 pM-10 pM) (FIG. 23, panel d). These experiments clearly show that 5 pM (500 amols) of mCpG-2-E2C is detectable above background and that activity scales linearly across the range of concentrations tested. When compared to the analogous platform utilizing the 3-finger ZF Zif268 that is capable of detecting 10 fmols of methylated dsDNA (not shown), these results demonstrate a 20-fold improvement in the minimal amount of dsDNA needed to generate signal above background. Importantly, this demonstrates that the use of a single 6-finger ZF capable of specifically recognizing 18 contiguous base pairs potentially allows for the detection of an unique promoter within the human genome, a feature not available using a single 3-finger ZF.

DNA-Mediated RNA Detection Experiments

Note: The cloning and initial characterization of the 6-fingers, E2C and Aart with NFluc and CFluc, are in the accompanying manuscript that focuses upon a different topic.

TABLE 3 in vitro transcription primers and DNA oligonucleotides used in the zinc finger-mediated RNA detection method.

| Name | Sequence |
|---|---|
| VEGF FWD | 5' GCAGC*TAATACGACTCACTATAGG*CATCACGAAGTGGTGAAGTTCATGGATGTCTATCAGC (SEQ ID NO: 60) |
| VEGF REV | 5'CTTTCTTTGGTCTGCATTCACATTTGTTGTGCTGTAGGAAGC (SEQ ID NO: 61) |
| HER2 FWD | 5'GCAGC*TAATACGACTCACTATAGG*CTGATAGACACCAACCGCTCTCGGGC (SEQ ID NO: 62) |
| HER2 REV | 5'GTGCTTGGGGCCCGTGCAGC (SEQ ID NO: 63) |
| Hairpin-guides | |
| Pum1-E2C | 5'GAGGGGCCGGAGCCGCAGTGCGTCCTCGCACTGCGGCTCCGGCCCCTCAAAACTAT*ATACACCATG* (SEQ ID NO: 64) |
| Pum2-Aart | 5'*GCCGCTATATCAAAAAAC*TCCGGGCTTTTCCCTACATGCTCCTGCATGTAGGGAAAAGCCCGGAG (SEQ ID NO: 65) |
| VEGF60-78-E2C | 5'GAGGGGCCGGAGCCGCAGTGCGTCCTCGCACTGCGGCTCCGGCCCCTCAAAAGAA*GATGTCCACCAGGGTC* (SEQ ID NO: 66) |
| VEGF81-99-Aart | 5'*GATCTCATCAGGGTACTCCAAAAC*TCCGGGCTTTTCCCTACATGCTCCTGCATGTAGGGAAAAGCCCGGAG (SEQ ID NO: 67) |
| E2C-HER2 100-118 | 5'GAGGGGCCGGAGCCGCAGTGCGTCCTCGCACTGCGGCTCCGGCCCCTCAAAACGG*CACAGACAGTGCGCGT* (SEQ ID NO: 68) |
| HER2 122-140-Aart | 5'*CCCTTGCAGCGGGCACAGCAAAAC*TCCGGGCTTTTCCCTACATGCTCCTGCATGTAGGGAAAAGCCCGGAG (SEQ ID NO: 69) |

TABLE 3-continued in vitro transcription primers and DNA oligonucleotides used in the zinc finger-mediated RNA detection method.

Additional targets

| | |
|---|---|
| DNA target | 5'-CATGGTGTATATAGTCTTTTGATATAGCGGC (SEQ ID NO: 70) |
| DNA (G to T) | 5'-CATGG<u>T</u>TTATATAGTCTTTTGATATAGCGGC (SEQ ID NO: 71) |

Hairpin-guides are colored according to the following regions: sequences forming zinc finger binding site hairpins are bold, the hairpin loop region is underlined, and the region complementary to the target is italicized. Numbering in the names of the VEGF and HER2 hairpin-guides is based on the first base of the transcribed mRNA target being considered as position one. The T7 promoter present in the in vitro transcription primersis blue. The single base mutation in the ssDNA G to T target is underlined.

Generation of Target mRNA

VEGF dsDNA was PCR amplified from an existing plasmid, pQE30-VEGF, which contained nucleotides 109403 of VEGF cDNA, isoform 165. This 295 nucleotide region was amplified using the primers indicated in Table 3 under the heading in vitro transcription primers. Note the exclusion of a KOZAK sequence and start codon in the FWD primer and a stem-loop structure in the REV primer, as the VEGF mRNA is not meant to be subsequently translated. in vitro transcription was carried out according to the manufacturer's instructions (using 2-3 μg dsDNA template, as limited by PCR yields), and purity was assessed with agarose gel electrophoresis. To select a VEGF mRNA region to target, the following considerations were made: 1) High melting temperature (thermodynamic stability) between guide and target, 2) no tetraglycine motif, 3) no secondary structure in guide region, 4) no (or minimal) complementarity to other sites in the target, 5) presence of a suitable adjacent binding site (currently we have only employed 14 nucleotide separations, and the use of more distal sites has not been investigated), 6) site accessibility based on secondary structure prediction (mfold, internet address frontend.bioinfo.rpi.edu/applications/mfold/cgi-bin/rna-form1.cgi) of VEGF transcript. Based on these considerations, the following regions were chosen: 60-78 and 81-99 of the 295 nucleotide VEGF transcript.

HER2 mRNA was generated essentially as described above. HER2 dsDNA (nucleotides 480-681) was PCR amplified from an existing plasmid, pSGHV0-HER2, which contained nucleotides 1-1983 of the HER2 extracellular domain, using primers indicated in Table 3. Due to the presence of contaminating PCR products, a gel extraction was performed using a QIAquick PCR purification kit (Qiagen), resulting in isolation of a pure product, as visualized by agarose gel electrophoresis. Considerations regarding targetable areas were as described above, although difficulty was encountered in finding guides without secondary structure. The following regions were chosen: 100-118 and 122-140 of the 201 nucleotide HER2 transcript.

Annealing of ternary complex was achieved as follows. DNA hairpins (Table S3, Hairpin-guides) were pre-formed in NEBuffer SalI (10 mM Tris-HCl, pH 7.9, 150 mM NaCl, 10 mM MgCl$_2$, 1 mM dithiothreitol) by an annealing procedure consisting of heating to 95° C. for 7 minutes, cooling at a rate of 1° C./min to 56° C. for 5 minutes, followed by cooling at a rate of 1° C./min to 25° C. for 10 minutes, followed by storage at −20° C. Targets (RNA, DNA, or DNA (G to T) targets; VEGF mRNA; HER2 mRNA; or SalI buffer blank) were heat denatured in NEBuffer SalI supplemented with 0.8 U/μL RNasin™ at 90° C. for 7 minutes, followed by cooling at a rate of 6° C./min to 37° C. for 10 minutes. Heat denaturation was followed directly by dilution of the target (or buffer blank) into the corresponding set of pre-formed hairpins, which was then held at 37° C. for 3 hours. We have since reduced the holding time to 30 minutes, with no adverse effects. The annealed ternary complex stock was stored and held at all times at 4° C.

Protein reassembly was accomplished according to the following protocol. NFluc-Aart was generated by PCR amplification of Aart from an existing plasmid, followed by ligation into a plasmid containing NFluc. CFluc-E2C was generated by ligating an E2C dsDNA insert into a plasmid containing CFluc. Details regarding these cloning procedures are available (58).

Translation experiments occurred as described above with the addition of 10 μM ZnCl$_2$. Optimal conditions required 0.2 pmol of each mRNA, NFluc-Aart and CFluc-E2C, and annealed ternary targets or a "background" were added after completion of the translation reaction. Background consisted of buffer only and of the hairpin-guides without target RNA. The presence of non-cognate nucleic acids (i.e. hairpin-guides) consistently resulted in a reduction of background as compared to buffer alone. This may be attributable to prevention of non-specific interactions between the split-Fluc constructs. Luminescence readings were taken following 30 minutes of incubation with the ternary target or background at 4° C. 80 μL of Steady-Glo™ reagent was added to 20 μL of each reaction (final target concentration=1 nM) and allowed to incubate at room temperature for 1 minute prior to acquiring luminescence readings on a Turner TD-20e Luminometer with a 10 second integration time, except in the case of HER2 readings, which were collected on a Turner Biosystems 20/20" luminometer. Two duplicate translation reactions performed simultaneously. Luminescence readings were averaged and normalized to one.

VEGF Detection

The lower limits of VEGF mRNA detection were determined according to protocols indicated above, using target concentrations of 10 nM, 1 nM, 100 pM, 10 pM, 1 pM, or buffer. Background in this case is buffer only. The buffer luminescence was subtracted from each reading in the presence of decreasing concentrations of target mRNA, followed by normalization of the signal to one. The presence of 10 pM (1 fmol) VEGF mRNA definitively produces signal over background, while the 1 pM (100 amol) sample is very close to background levels.

Direct Detection of DNA Binding by Dimeric DNA Binding Domains.

Having validated the use of monomeric DNA binding domains (DBDs), including ZFs and MBD, we next attempted the development of a platform utilizing dimeric sequence specific DBDs. This would not only serve to augment the available DBDs, but also potentially allow for detecting any dsDNA sequence that can be targeted by a known natural DBD, whether monomeric or dimeric. As an initial test we interrogated DNA binding by the bacteriophage Lambda Cro repressor protein (λ-Cro). This prototypical helix-turn-helix DBD recognizes a 17 base pair dsDNA sequence (two copies of a 7-mer palindromic half-site separated by 3 unrecognized base pairs) through the formation of an obligate DNA binding homodimer, in which each monomer binds to the half-site 5'-TATCACC-3'. To test the use of this dimeric DNA binder, the mCpG dinucleotide recognized by MBD2 was placed upstream of the 17 base pair λ-Cro recognition site separated by a 2 base pair spacer, generating the dsDNA target mCpG-2-λCro. Molecular modeling suggested that attaching CFluc to the N-terminus of %-Cro and attaching MBD2 to the N-terminus of NFluc would result in a viable protein-DNA complex positioned for reassembly of fragmented firefly luciferase (FIG. 23, panel e). It is noted that studies with split-GFP utilizing similar targeting domains were unsuccessful in generating fluorescence.

To assess the ability of split-luciferase to report on λ-Cro binding its cognate dsDNA, translations with mRNA corresponding to MBD2-NFluc and CFluc-λCro in the presence of the methylated (m), non-methylated dsDNA target CpG-2-λCro, or no DNA (FIG. 23, panel f) were tested. A reproducible 22-fold increase in luminescence signal was observed in the presence of 10 nM mCpG-2-λCro compared to the non-methylated target. These results demonstrate for the first time that dimeric DBD domains can be utilized in split-luciferase reassembly to potentially allow for targeting sites of methylation not easily amenable to ZFs. Additionally, this approach provides the possibility for interrogating the interaction between dimeric transcription factors and their target DNA sequences.

Determination of Global DNA Methylation.

Figure 24:
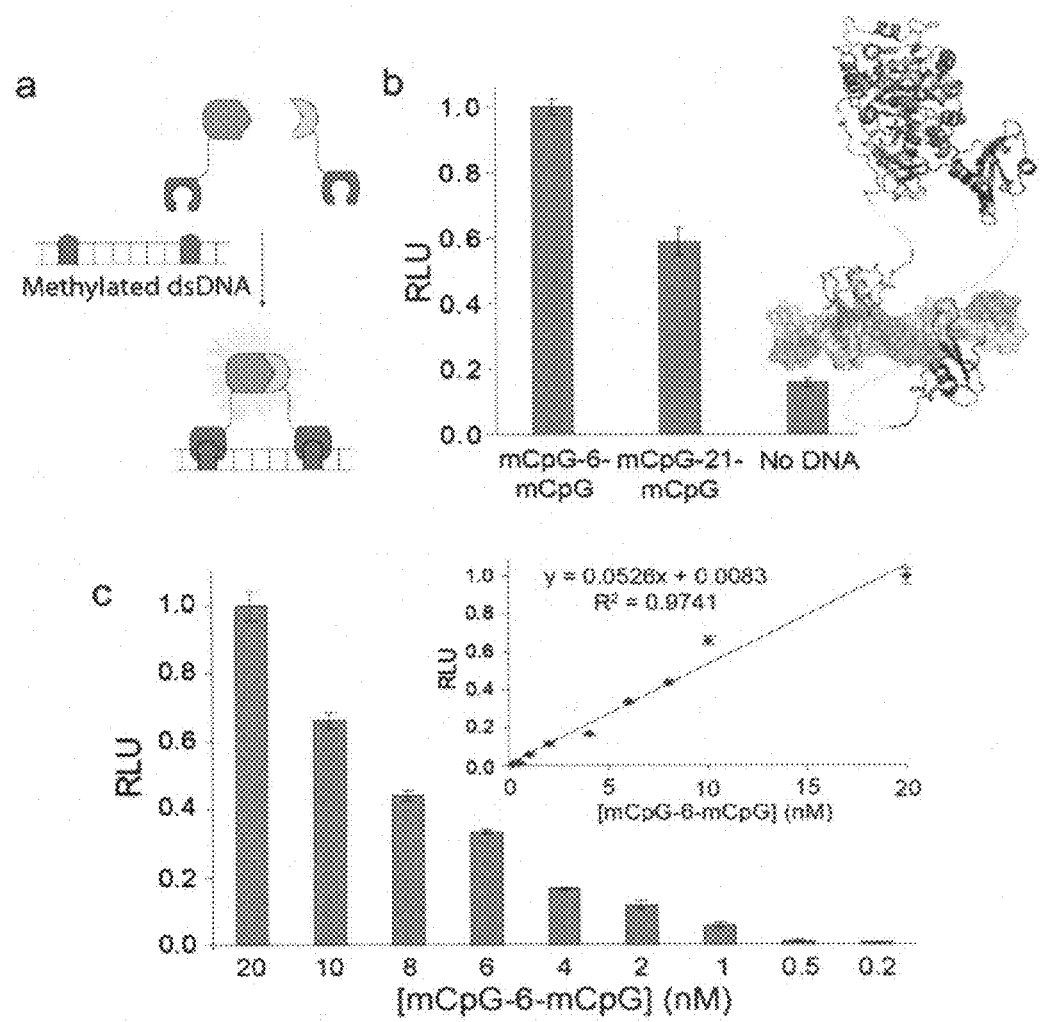
FIG. 24. Determination of total methylation at two sites. a) Cartoon showing the detection of di-methylated dsDNA utilizing fragmented luciferase tethered to MBD2. Addition of a di-methylated dsDNA target results in ternary complex formation and luminescence. b) Luminescence above background in the presence of dsDNA targets containing either 6 or 21 base pairs between mCpG sites. c) Split-luciferase signal generation in the presence of decreasing amounts of the methylated target mCpG-6-mCpG. (inset) Linear fit from 20 to 0.2 nM mCpG-6-mCpG.

These approaches towards the determination of site-specific methylation status are useful as diagnostic and research tools, however they do not provide a means to determine global changes in genomic methylation, which have been observed in both disease progression (102) and aging (122). Furthermore, a global methylation sensor would provide a convenient means for interrogating the activity of methyltransferases and demethylating enzymes, as well as allow for a new method for determining the activity of small molecules that perturb their activity. Thus, we asked whether a sensor containing MBD2 to both the N-terminal and C-terminal fragments of firefly luciferase creating the fusions MBD2-NFluc and CFluc-MBD2 would allow for the detection of any dsDNA target containing multiple methylation sites (FIG. 24, panel a) with the caveat that we would statistically expect to see 50% of the total possible signal. As our first test, cell-free translations of MBD2-NFluc and CFluc-MBD2 were carried out in the presence of dimethylated dsDNA targets containing either a short separation distance of 6 bp or a long separation distance of 21 bp (our maximum calculated distance for split-luciferase assembly is ~140 Å) between methylated CpG sites. Both the 6 and 21 bp dimethylated targets allowed for reproducible increase in luminescence as compared to no DNA (FIG. 24, panel b). Titrations were carried out to determine the minimal amount of methylated dsDNA needed to generate an observable signal for the 6 bp site, (FIG. 24, panel c). These experiments show that 0.2 nM (20 fmols) mCpG-6-mCpG is detectable above background. Thus this a conceptually new approach, that is utilizing the same targeting domain, for detecting DNA modification and may find utility in detecting global levels of methylation as well as the activity of associated enzymes and their inhibitors.

Direct Detection of poly(ADP-ribose) Using a poly(ADP-ribose)-Binding Zinc Finger.

Figure 25:
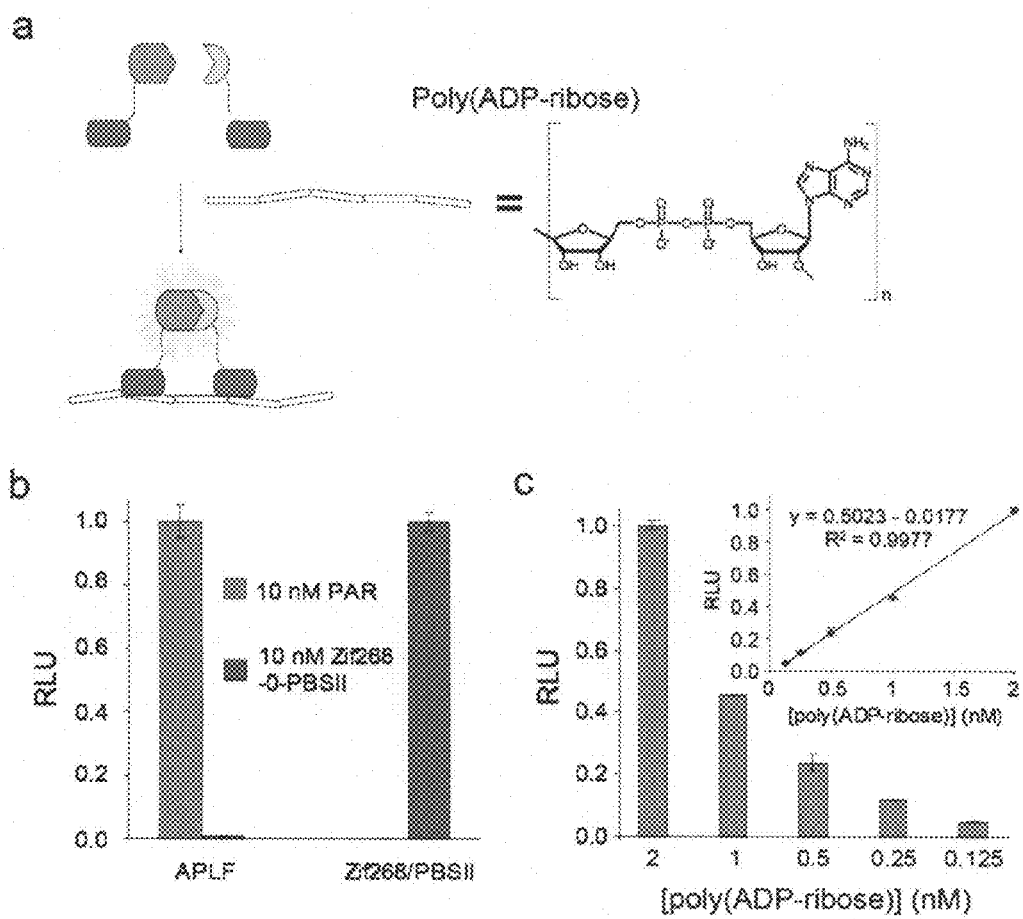
FIG. 25. Direct detection of poly(ADP-ribose). a) Cartoon showing the detection of poly(ADP-ribose) utilizing split-luciferase tethered to the poly(ADP-ribose) binding zinc finger APLF. b) Ternary complex formation of APLF-NFluc/CFluc-APLF and PBSII-NFLuc/CFluc-Zif268 in the presence of either 10 nM poly(ADP-ribose) (PAR) or 10 nM of the dsDNA target Zif-0-PBS. c) Luminescence as a function of PAR concentration. (inset) Linear fit from 2 to 0.125 nM PAR.

Building on our success in using a single domain to detect multiple sites of modification, we next used this strategy for interrogating poly(ADP-ribosyl)ation. This ubiquitous post-translational modification has been linked to carcinogenesis and is considered a possible marker for cancer detection (123). We chose the poly(ADP-ribose) (PAR) binding domain from aprataxin PNK-like factor (APLF) for the detection of PAR. APLF is a protein involved in the cellular response to DNA damage (124-126) and contains two putative $Cys_2His_2$ ZF domains capable of binding PAR with high affinity (127). Our designed sensor incorporated the zinc finger domain of APLF (residues 376-441) to both the N-terminal and C-terminal fragments of firefly luciferase to create APLF-NFluc and CFluc-APLF. We envisioned that the simultaneous binding of each APLF-luciferase fusion to poly(ADP-ribose) would result in firefly luciferase reassembly (FIG. 25, panel a). Translations with mRNA for APLF-NFluc and CFluc-APLF in presence of poly(ADP-ribose), non-cognate Zif268-0-PBSII dsDNA, and no added target. Additional complementary controls were also carried out where mRNA corresponding to the ZF PBSII-NFluc and CFluc-Zif268 were carried out with added poly(ADP-ribose) or Zif268-0-PBSII (FIG. 25, panel b). A 25-fold increase in luminescence was observed for APLF-NFLuc/CFluc-APLF pair in the presence of 10 nM PAR, while no luminescent signal was observed in the presence of dsDNA, Zif268-0-PBSII. Conversely, translations containing the dsDNA binding ZFs PBSII-NFLuc/CFLuc-Zif268 did not generate signal in the presence of PAR. Additionally, cell-free translations in the presence of decreasing amounts of poly(ADP-ribose) showed that 0.125 pM (12.5 fmols) of PAR is detectable above background (FIG. 25, panel c). Thus, this represents the first split-luciferase sensor for sensitive detection of PAR. This method as well as variations with other split-protein sensors may provide a also provide a means for PAR detection within a cell and may also be a valuable addition to the tool-kit for interrogating of the activity and chemical perturbation of the PAR associated proteins, PARP and PARG.

Considerable effort has been focused on the development of new and enabling technologies to elucidate the function of biological macromolecules (59,128, 129). We build upon these efforts with the development of a fragmented-firefly luciferase tool-kit that allows for the rapid, sensitive, and direct interrogation of specific dsDNA sequences, site-specific and overall DNA methylation, monomeric and dimeric DNA binding domains, and the presence of poly(ADP-ribose). Specifically, tandem 6-finger ZF based sensors will potentially allow for the rapid and direct detection of attomole quantities of a specific 36-mer dsDNA sequence while the use of 6-finger ZF in conjunction with a methylation specific binding domain may allow for the sensitive characterization of unique sites of dsDNA methylation. Furthermore, the incorporation of λCro provides the first example of the use of dimeric dsDNA binding domains in split-protein systems, which not only increases the repertoire of available targeting domains but may also provide a means for directly probing DNA binding of this important class of transcription factors. Finally, we provide two conceptually new approaches utilizing split-proteins that allow for the direct and sensitive detecting global levels of dsDNA methylation and poly(ADP-ribosyl)ation. Thus, these new methods provide a valuable toolkit to examine DNA and DNA-associated chemical modifications and perhaps more importantly, provide access to rapid assays for related enzymes and their small molecule perturbants.

Plasmid construction and mRNA production. Fusion protein constructs used in this study are shown in Tables 6-28. DNA coding for firefly luciferase fragments were generated by PCR and cloned into the pETDuet-1 vector (Novagen, Madison, Wis.) using standard cloning techniques. Fragments encoding the nucleic acid-binding proteins were generated by PCR. Fusion protein constructs were generated using standard cloning techniques.

mRNA for cell-free assays was generated as follows: PCR fragments corresponding to the desired fusion constructs were generated using a forward primer containing a T7 RNA polymerase promoter and a Kozak sequence and a reverse primer containing a 3' hairpin loop. The purified PCR fragments were used as the template for in vitro transcription using the RiboMAX Large Scale RNA Production System-T7 (Promega) following the manufacturer's protocols.

Target DNA preparation. All nucleic acid targets were obtained from IDT. All dsDNA targets were annealed as previously described (23,58). Hairpin DNA targets were annealed in 1× BamHI buffer by heating at 95° C. for 7 minutes followed immediately by cooling on ice.

Reassembly of fragmented firefly luciferase-zinc finger fusion. Duplicate 25 µL translation reactions were carried out in Flexi-Rabbit Reticulocyte Lysate (Promega) according to the manufacturer's protocol using 0.2 pmols of Aart-NFluc (residues 2-416) and CFluc(residues 398-550)-Zif268 mRNA, 10 µM $ZnCl_2$, 0.5 µL of RNasin Plus (Promega), and either 1.25 µL 10 nM Zif268-2-Aart target dsDNA or no dsDNA. For the case where two 6-finger zinc fingers were used, duplicate translations were carried out in Flexi-Rabbit Reticulocyte Lysate using 0.2 pmols of Aart-NFluc (residues 2-416) and 0.1 pmols of CFluc(residues 398-550)-E2C mRNA, 10 µM $ZnCl_2$, 0.5 µL of RNasin™ Plus (Promega), and the concentrations of E2C-1-Aart target dsDNA indicated. Translations were incubated at 30° C. for 90 minutes and assayed by adding 80 µL of Steady-Glo™ Luciferase Assay System (Promega) to 20 µL of translated lysate. Light-emission was monitored 1 minute after STEADY-GLO™ addition using a Turner TD-20e luminometer with a 3 second delay and a 10 second integration time.

Interrogation of Aart specificity. Duplicate 25 µL translations were carried out in Rabbit Reticulocyte Lysate according to the manufacturer's protocol using 0.2 pmols of Aart-NFluc(residues 2-416) and 0.4 pmols of CFluc(residues 398-550)-E2C mRNA, 10 µM $ZnCl_2$, and 0.5 µL of RNasin Plus (Promega) and allowed to incubate for 90 minutes at 30° C. in the presence of 300 pM Aart-1-E2C dsDNA target and increasing concentrations of hairpin DNA. Samples were assayed for luciferase activity as described above.

The effects of distance and proximity of fragmented luciferase reassembly were explored as discussed below. Duplicate 25 µL translations were carried out in rabbit reticulocyte lysates (Promega) according to the manufacturer's protocol using 2 pmols of mRNA corresponding to MBD2-NFluc(residues 2-416) and CFluc(residues 398-550)-Zif268, 10 µM $ZnCl_2$, and 0.5 µL of RNasin™ Plus (Promega) and allowed to incubate for 90 minutes at 30° C. in the presence of 1.25 µL of 500 nM methylated target dsDNA containing either 0, 1, 2, 3, 6, or 10 basepairs between the mCpG and Zif268 binding sites. Samples were assayed for luciferase activity as described above.

Reassembly of fragmented luciferase utilizing MBD2 and E2C was performed as follows. Duplicate 25 µL translations were carried out in rabbit reticulocyte lysate according to the manufacturer's protocol using 0.1 pmols of mRNA corresponding to MBD2-NFluc(residues 2-416) and CFluc(residues 398-550)-E2C, 10 µM $ZnCl_2$, and 0.5 µL of RNasin™ Plus (Promega) and allowed to incubate for 90 minutes at 30° C. in the presence of 1.25 µL of decreasing concentrations of the dsDNA target mCpG-2-E2C. Samples were assayed for luciferase activity as described above.

Reassembly of fragmented luciferase utilizing MBD2 and λ-Cro was examined using the following protocol. Duplicate 25 µL translations were carried out in rabbit reticulocyte lysates according to the manufacturer's protocol using 2 pmols of MBD2-NFluc(residues 2-416) and CFluc(residues 398-550)-λ-Cro mRNA, and 0.5 µL of RNasin™ Plus (Promega) and allowed to incubate for 90 minutes at 30° C. in the presence of 1.25 µL of 1 µM of the dsDNA target mCpG-2-λ-Cro(m), mCpG-2-λ-Cro(u), or water. Samples were assayed for luciferase activity as described above.

Reassembly of fragmented luciferase utilizing two MBD2s was carried out as follows. Duplicate 25 µL translations were carried out in rabbit reticulocyte lysates according to the manufacturer's protocol using 2 pmols of MBD2-NFluc (residues 2-416) and CFluc (residues 398-550)-MBD2 mRNA, and 0.5 µL of RNasin™ Plus (Promega) and allowed to incubate for 90 minutes at 30° C. in the presence of 1.25 µL of 1 µM of the dsDNA targets mCpG-6-mCpG, mCpG-21-mCpG, or water. Samples were assayed for luciferase activity as described above.

Reassembly of fragmented luciferase utilizing two poly (ADP-ribose) binding zinc finger domains was examined as follows. Duplicate 25 µL translations were carried out in rabbit reticulocyte lysates according to the manufacturer's protocol using 1.3 pmols of APLF-NFluc(residues 2-416) and CFluc(residues 398-550)-APLF, or 2 pmols of PBSII-NFluc(residues 2-416) (SEQ ID NO: 24-25) and CFluc(residues 398-550)-Zif268 mRNA (SEQ ID NO: 26-27), 10 µM $ZnCl_2$ and 0.5 µL of RNasin™ Plus (Promega) and allowed to incubate for 90 minutes at 30° C. in the presence of 1.25 µL of 1 µM poly(ADP-ribose) (BioMol International, Plymouth Meeting, Pa.), 1 µM Zif268-0-PBSII, or water. Samples were assayed for luciferase activity as described above.

Regulation at the level of DNA is controlled by protein binding factors as well as chemical modifications such as DNA methylation, histone acetylation, and protein poly (ADP-ribosyl)ation. Alterations to "normal" DNA and its associated factors, which include mutations and chromosomal translocations, aberrant methylation, and deregulated poly(ADP-ribosyl)ation, can provide diagnostic signatures for the status of a cell and are often disease markers. Thus, there is much interest in developing new reagents for the direct detection of dsDNA, interrogation of transcription factor/DNA binding, monitoring DNA-methylation, and measuring poly(ADP-ribosyl)ation. Towards this goal we have developed a simple and general cell-free split-luciferase system that can be decorated with user-defined protein targeting modules allowing for the detection of unique dsDNA sequences at the attomolar level, site-specific and overall DNA methylation levels, dimeric transcription factor DNA binding events, and the direct measurement of poly(ADP-ribose). These new reagents are not only useful for chemical diagnostics, but they also provide a tool-kit for discovering specific small molecules that can perturb DNA regulation.

We have systematically designed a class of split-firefly luciferase sensors for ssRNA detection, each utilizing different detection domains. The first class comprises sequence-specific pumilio domains, which although successful in detecting ssRNA, are limited by the necessity of designing new domains for each ssRNA target of interest. Thus, our second class of sensors incorporated the RNA binding domain of argonaute, which specifically recognizes 2-nucleotide, 3' overhangs of dsRNA. By introducing short guide sequences of user-defined ssRNA, we successfully detected cognate ssRNA target when using argonaute in conjunction with pumilio domains. However, the use of two argonaute domains, which would allow one to recognize any ssRNA of interest did not provide sufficient signal. Building on these designs our third and most general design provides a convenient method of both ssRNA and ssDNA detection through the use of ssDNA guides tethered to high affinity zinc finger DNA binding hairpin guides. When a target contains adjacent sequences complementary to the guides, the hairpins are brought into proximity, allowing for zinc finger binding and luciferase reassembly. This general approach has been used to sensitively (~100 amol) and specifically detect physiologically relevant targets, including VEGF and HER2 mRNA.

In the following tables, bold type represents residues derived from luciferase, and italic type represents sequences derived from an attached protein.

Sequences of split reporter fusions useful in the detection of gp120 and her2 with protein and antibody conjugated to luciferase halves are shown in Tables 6-9.

TABLE 6

CFluc-17b (see also SEQ ID NOs: 8-9).

```
atgatgtccggttatgtaaacaatccggaagcgaccaacgccttgattgacaaggatgga
 M  M  S  G  Y  V  N  N  P  E  A  T  N  A  L  I  D  K  D  G tggctacattctggagacatagcttactgggacgaagacgaacacttcttcatagttgac
 W  L  H  S  G  D  I  A  Y  W  D  E  D  H  F  F  I  V  D cgcttgaagtctttaattaaatacaaaggatatcaggtggccccgctgaattggaatcg
 R  L  K  S  L  I  K  Y  K  G  Y  Q  V  A  P  A  E  L  E  S atattgttacaacaccccaacatcttcgacgcgggcgtggcaggtcttcccgacgatgac
 I  L  L  Q  H  P  N  I  F  D  A  G  V  A  G  L  P  D  D  D gccggtgaacttcccgccgccgttgttgttttggagcacggaaagacgatgacggaaaaa
 A  G  E  L  P  A  A  V  V  V  L  E  H  G  K  T  M  T  E  K gagatcgtggattacgtcgccagtcaagtaacaaccgcgaaaaagttgcgcggaggagtt
 E  I  V  D  Y  V  A  S  Q  V  T  T  A  K  K  L  R  G  G  V gtgtttgtggacgaagtaccgaaaggtcttaccggaaaactcgacgcaagaaaaatcaga
 V  F  V  D  E  V  P  K  G  L  T  G  K  L  D  A  R  K  I  R gagatcctcataaaggccaagaagggcggaaagtccaaattgggcctgcagggcggttca
 E  I  L  I  K  A  K  K  G  G  K  S  K  L  G  L  Q  G  G  S ggcggtgggggttctggcgggggtgggagcccc gggcaggtgcagctgctcgagtctggg
 G  G  G  S  G  G  G  G  S  P  G  Q  V  Q  L  L  E  S  G gctgaggtgaagaagcctgggtcctcggtgaaggtctcctgcaaggcctctggagacacc
 A  E  V  K  K  P  G  S  S  V  K  V  S  C  K  A  S  G  D  T ttcatcagatatagttttacctgggtgcgacaggcccctggacaaggccttgagtggatg
 F  I  R  Y  S  F  T  W  V  R  Q  A  P  G  Q  G  L  E  W  M ggaaggatcatcactatccttgatgtagcacactacgcaccgcacctccagggcagagtc
 G  R  I  I  T  I  L  D  V  A  H  Y  A  P  H  L  Q  G  R  V acgattaccgcggacaagtccacgagcacagtctacctggagctgcggaatctaagatct
 T  I  T  A  D  K  S  T  S  T  V  Y  L  E  L  R  N  L  R  S gacgatacggccgtatatttctgtgcgggagtgtacgagggagaggcggacgaggggaa
 D  D  T  A  V  Y  F  C  A  G  V  Y  E  G  E  A  D  E  G  E tatgataataatgggtttctgaaacattggggccagggaaccctggtcacggtcacctca
 Y  D  N  N  G  F  L  K  H  W  G  Q  G  T  L  V  T  V  S ggtggcggtggctccggaggtggtgggagcggtggcggcggatctgagctcgagttgacg
 G  G  G  G  S  G  G  G  G  S  G  G  G  G  S  E  L  E  L  T cagtctccagccaccctgtctgtgtctccaggggaaagagccaccctctcctgcagggcc
 Q  S  P  A  T  L  S  V  S  P  G  E  R  A  T  L  S  C  R  A agtgagagtgttagtagcgacttagcctggtaccagcagaaacctggccaggctcccagg
 S  E  S  V  S  S  D  L  A  W  Y  Q  Q  K  P  G  Q  A  P  R ctcctcatatatggtgcatccaccagggccaccggtgtcccagccaggttcagtggcagt
 L  L  I  Y  G  A  S  T  R  A  T  G  V  P  A  R  F  S  G  S gggtctggggcagaattcactctcaccatcagcagcctgcagtctgaagattttgcagtt
 G  S  G  A  E  F  T  L  T  I  S  S  L  Q  S  E  D  F  A  V tattactgtcagcagtacaataactggcctccgaggtacacttttggccaggggaccagg
 Y  Y  C  Q  Q  Y  N  N  W  P  P  R  Y  T  F  G  Q  G  T  R
```

TABLE 6-continued

CFluc-17b (see also SEQ ID NOs: 8-9).

ctggagatcaaagtcgagtctggtaaagaaaccgctgctgcgaaatttgaacgccagcac
L  E  I  K  V  E  S  G  K  E  T  A  A  A  K  F  E  R  Q  H atggactcgtctactagcgcagcttaa
M  D  S  S  T  S  A  A  -

TABLE 7

CD4-NFluc (see also SEQ ID NOs: 10-11).

atgggcagcagccatcaccatcatcaccacagccaggatccgaaagtggtgctgggcaaa
M  G  S  S  H  H  H  H  H  H  S  Q  D  P  K  V  V  L  G  K aaaggggatacagtggaactgacctgtacagcttcccagaagaagagcatacaattccac
K  G  D  T  V  E  L  T  C  T  A  S  Q  K  K  S  I  Q  F  H tggaaaaactccaaccagataaagattctgggaaatcagggctcctttcttaactaaaggt
W  K  N  S  N  Q  I  K  I  L  G  N  Q  G  S  F  L  T  K  G ccatccaagctgaatgatcgcgctgactcaagaagaagcctttgggaccaaggaaacttc
P  S  K  L  N  D  R  A  D  S  R  R  S  L  W  D  Q  G  N  F cccctgatcatcaagaatcttaagatagaagactcagatacttacatctgtgaagtggag
P  L  I  I  K  N  L  K  I  E  D  S  D  T  Y  I  C  E  V  E gaccagaaggaggaggtgcaattgctagtgttcggattgactgccaactctgacacccac
D  Q  K  E  E  V  Q  L  L  V  F  G  L  T  A  N  S  D  T  H ctgcttcagggcagagcctgaccctgaccttggagagccccctggtagtagcccctca
L  L  Q  G  Q  S  L  T  L  T  L  E  S  P  P  G  S  S  P  S gtgcaatgtaggagtccaaggggtaaaaacatacaggggggaagaccctctccgtgtct
V  Q  C  R  S  P  R  G  K  N  I  Q  G  G  K  T  L  S  V  S cagctggagctccaggatagtggcacctggacatgcactgtcttgcagaaccagaagaag
Q  L  E  L  Q  D  S  G  T  W  T  C  T  V  L  Q  N  Q  K  K gtggagttcaaaatagacatcgtggtgctagcttttccagaaggcctccaccggtgggggt
V  E  F  K  I  D  I  V  V  L  A  F  Q  K  A  S  T  G  G  G ggcggttcaggcggtgggggttctggtgggggtggtaccgaagacgccaaaaacataaag
G  G  S  G  G  G  G  S  G  G  G  G  T  E  D  A  K  N  I  K aaaggcccggcgccattctatcctctagaggatggaaccgctggagagcaactgcataag
K  G  P  A  P  F  Y  P  L  E  D  G  T  A  G  E  Q  L  H  K gctatgaagagatacgccctggttcctggaacaattgcttttacagatgcacatatcgag
A  M  K  R  Y  A  L  V  P  G  T  I  A  F  T  D  A  H  I  E gtgaacatcacgtacgcggaatacttcgaaatgtccgttcggttggcagaagctatgaaa
V  N  I  T  Y  A  E  Y  F  E  M  S  V  R  L  A  E  A  M  K cgatatgggctgaatacaaatcacagaatcgtcgtatgcagtgaaaactctcttcaattc
R  Y  G  L  N  T  N  H  R  I  V  V  C  S  E  N  S  L  Q  F tttatgccggtgttgggcgcgttatttatcggagttgcagttgcgcccgcgaacgacatt
F  M  P  V  L  G  A  L  F  I  G  V  A  V  A  P  A  N  D  I tataatgaacgtgaattgctcaacagtatgaacatttcgcagcctaccgtagtgtttgtt
Y  N  E  R  E  L  L  N  S  M  N  I  S  Q  P  T  V  V  F  V tccaaaaaggggttgcaaaaaattttgaacgtgcaaaaaaaattaccaataatcccagaaa
S  K  K  G  L  Q  K  I  L  N  V  Q  K  K  L  P  I  I  Q  K attattatcatggattctaaaacggattaccagggatttcagtcgatgtacacgttcgtc
I  I  I  M  D  S  K  T  D  Y  Q  G  F  Q  S  M  Y  T  F  V acatctcatctacctcccggttttaatgaatacgattttgtaccagagtcctttgatcgt
T  S  H  L  P  P  G  F  N  E  Y  D  F  V  P  E  S  F  D  R gacaaaacaattgcactgataatgaattcctctggatctactgggttacctaagggtgtg
D  K  T  I  A  L  I  M  N  S  S  G  S  T  G  L  P  K  G  V gcccttccgcatagaactgcctgcgtcagattctcgcatgccagagatcctattttggc
A  L  P  H  R  T  A  C  V  R  F  S  H  A  R  D  P  I  F  G

TABLE 7-continued

CD4-NFluc (see also SEQ ID NOs: 10-11).

```
aatcaaatcattccggatactgcgattttaagtgttgttccattccatcacggttttgga
 N  Q  I  I  P  D  T  A  I  L  S  V  V  P  F  H  H  G  F  G atgtttactacactcggatatttgatatgtggatttcgagtcgtcttaatgtatagattt
 M  F  T  T  L  G  Y  L  I  C  G  F  R  V  V  L  M  Y  R  F gaagaagagctgtttttacgatcccttcaggattacaaaattcaaagtgcgttgctagta
 E  E  E  L  F  L  R  S  L  Q  D  Y  K  I  Q  S  A  L  L  V ccaaccctattttcattcttcgccaaaagcactctgattgacaaatacgatttatctaat
 P  T  L  F  S  F  F  A  K  S  T  L  I  D  K  Y  D  L  S  N ttacacgaaattgcttctgggggcgcacctctttcgaaagaagtcggggaagcggttgca
 L  H  E  I  A  S  G  G  A  P  L  S  K  E  V  G  E  A  V  A aaacgcttccatcttccagggatacgacaaggatatgggctcactgagactacatcagct
 K  R  F  H  L  P  G  I  R  Q  G  Y  G  L  T  E  T  T  S  A attctgattacacccgaggggatgataaaccgggcgcggtcggtaaagttgttccattt
 I  L  I  T  P  E  G  D  D  K  P  G  A  V  G  K  V  V  P  F tttgaagcgaaggttgtggatctggataccgggaaaacgctgggcgttaatcagagaggc
 F  E  A  K  V  V  D  L  D  T  G  K  T  L  G  V  N  Q  R  G gaattatgtgtcagaggacctatgattatgtccggttatgtaaacaatccggaagcgacc
 E  L  C  V  R  G  P  M  I  M  S  G  Y  V  N  N  P  E  A  T aacgccttgattgacaaggatggatga
 N  A  L  I  D  K  D  G  -
```

TABLE 8

CFluc-4D5 (see also SEQ ID NOs: 12-13).

```
atgatgtccggttatgtaaacaatccggaagcgaccaacgccttgattgacaaggatgga
 M  M  S  G  Y  V  N  N  P  E  A  T  N  A  L  I  D  K  D  G tggctacattctggagacatagcttactgggacgaagacgaacacttcttcatagttgac
 W  L  H  S  G  D  I  A  Y  W  D  E  D  E  H  F  F  I  V  D cgcttgaagtctttaattaaatacaaaggatatcaggtggcccccgctgaattggaatcg
 R  L  K  S  L  I  K  Y  K  G  Y  Q  V  A  P  A  E  L  E  S atattgttacaacaccccaacatcttcgacgcgggcgtggcaggtcttcccgacgatgac
 I  L  L  Q  H  P  N  I  F  D  A  G  V  A  G  L  P  D  D  D gccggtgaacttccggccgccgttgttgttttggagcacggaaagacgatgacggaaaaa
 A  G  E  L  P  A  A  V  V  V  L  E  H  G  K  T  M  T  E  K gagatcgtggattacgtcgccagtcaagtaacaaccgcgaaaaagttgcgcggaggagtt
 E  I  V  D  Y  V  A  S  Q  V  T  T  A  K  K  L  R  G  G  V gtgtttgtggacgaagtaccgaaaggtcttaccggaaaactcgacgcaagaaaaatcaga
 V  F  V  D  E  V  P  K  G  L  T  G  K  L  D  A  R  K  I  R gagatcctcataaaggccaagaagggcggaaagtccaaattgggcctgcagggcggttca
 E  I  L  I  K  A  K  K  G  G  K  S  K  L  G  L  Q  G  G  S ggcggtgggggttctggcggggtgggagccccggggaggtgcagctggtggagagcggc
 G  G  G  G  S  G  G  G  S  P  G  E  V  Q  L  V  E  S  G ggcggcctggtgcagcccggcggcagcctgaggctgagctgcgccgccagcggcttcaac
 G  G  L  V  Q  P  G  G  S  L  R  L  S  C  A  A  S  G  F  N atcaaggacacctacatccactgggtgaggcaggccccggcaagggcctggagtgggtg
 I  K  D  T  Y  I  H  W  V  R  Q  A  P  G  K  G  L  E  W  V gccaggatctaccccaccaacggctacaccaggtacgccgacagcgtgaagggcaggttc
 A  R  I  Y  P  T  N  G  Y  T  R  Y  A  D  S  V  K  G  R  F accatcagcgccgacaccagcaagaacaccgcctacctccagatgaacagcctgagggcc
 T  I  S  A  D  T  S  K  N  T  A  Y  L  Q  M  N  S  L  R  A
```

TABLE 8-continued

CFluc-4D5 (see also SEQ ID NOs: 12-13).

```
gaggacaccgccgtgtactactgtagcaggtggggcggcgacggcttctacgccatggac
 E  D  T  A  V  Y  Y  C  S  R  W  G  G  D  G  F  Y  A  M  D tactggggccagggcaccctggtgaccgtgagcagcacgcgtggtggaggcggttcaggc
 Y  W  G  Q  G  T  L  V  T  V  S  S  T  R  G  G  G  S  G ggaggtggctctggcggtggcggatcggctagcgacatccagatgacccagagccccagc
 G  G  G  S  G  G  G  S  A  S  D  I  Q  M  T  Q  S  P  S agcctgagcgccagcgtgggcgacagggtgaccatcacctgtagggccagccaggacgtg
 S  L  S  A  S  V  G  D  R  V  T  I  T  C  R  A  S  Q  D  V aacaccgccgtggcctggtatcagcagaagcccggcaaggcccccaagctgctgatctac
 N  T  A  V  A  W  Y  Q  Q  K  P  G  K  A  P  K  L  L  I  Y agcgccagcttcctgtacagcggcgtgcccagcaggttcagcggcagcaggagcggcacc
 S  A  S  F  L  Y  S  G  V  P  S  R  F  S  G  S  R  S  G  T gacttcacccctgaccatcagcagcctccagcccgaggacttcgccacctactactgccag
 D  F  T  L  T  I  S  S  L  Q  P  E  D  F  A  T  Y  Y  C  Q cagcactacaccacccctcccaccttcggccagggcaccaaggtggagatcaaggtcgag
 Q  H  Y  T  T  P  P  T  F  G  Q  G  T  K  V  E  I  K  V  E tctggtaaagaaaccgctgctgcgaaatttgaacgccagcacatggactcgtctactagc
 S  G  K  E  T  A  A  A  K  F  E  R  Q  H  M  D  S  S  T  S gcagcttaa
 A  A  -
```

TABLE 9

2C4-NFluc (see also SEQ ID NOs: 14-15)

```
atgggcagcagccatcaccatcatcaccacagccaggatccggaggtgcagctggtggag
 M  G  S  S  H  H  H  H  H  H  S  Q  D  P  E  V  Q  L  V  E agcggcggaggcctggtgcagcccggaggcagcctgaggctgagctgcgccgccagcggc
 S  G  G  G  L  V  Q  P  G  G  S  L  R  L  S  C  A  A  S  G ttcaccttcaccgactacaccatggactgggtgaggcaggccccggcaagggcctggag
 F  T  F  T  D  Y  T  M  D  W  V  R  Q  A  P  G  K  G  L  E tgggtggccgacgtgaaccccaacagcggcggcagcatctacaaccagaggttcaagggc
 W  V  A  D  V  N  P  N  S  G  G  S  I  Y  N  Q  R  F  K  G aggttcacccctgagcgtggacaggagcaagaacaccctgtacctccagatgaacagcctg
 R  F  T  L  S  V  D  R  S  K  N  T  L  Y  L  Q  M  N  S  L agggccgaggacaccgccgtgtactactgcgccaggaacctgggccccagcttctacttc
 R  A  E  D  T  A  V  Y  Y  C  A  R  N  L  G  P  S  F  Y  F gactactggggccagggcaccctggtgaccgtgagctccacgcgtggtggaggcggttca
 D  Y  W  G  Q  G  T  L  V  T  V  S  S  T  R  G  G  G  S ggcggaggtggctctggcggtggcggatcggctagcgacatccagatgacccagagcccc
 G  G  G  G  S  G  G  G  S  A  S  D  I  Q  M  T  Q  S  P agctccctgagcgccagcgtgggcgacagggtgaccatcacctgcaaggccagccaggac
 S  S  L  S  A  S  V  G  D  R  V  T  I  T  C  K  A  S  Q  D gtgagcatcggcgtggcctggtatcagcagaagcccggcaaggcccccaagctgctgatc
 V  S  I  G  V  A  W  Y  Q  Q  K  P  G  K  A  P  K  L  L  I tacagcgccagctacaggtacaccggcgtgcccagcaggttcagcggcagcggcagcggc
 Y  S  A  S  Y  R  Y  T  G  V  P  S  R  F  S  G  S  G  S  G accgacttcacccctgaccatcagctccctccagcccgaggacttcgccacctactactgc
 T  D  F  T  L  T  I  S  S  L  Q  P  E  D  F  A  T  Y  Y  C cagcagtactatatctaccccctacaccttcggccagggcaccaaggtggagatcaagacc
 Q  Q  Y  Y  I  Y  P  Y  T  F  G  Q  G  T  K  V  E  I  K  T ggtgggggtggcggttcaggcggtgggggttctggtgggggtggtaccgaagacgccaaa
 G  G  G  G  S  G  G  G  G  S  G  G  G  G  T  E  D  A  K
```

TABLE 9-continued

2C4-NFluc (see also SEQ ID NOs: 14-15)

```
aacataaagaaaggcccggcgccattctatcctctagaggatggaaccgctggagagcaa
 N   I   K   K   G   P   A   P   F   Y   P   L   E   D   G   T   A   G   E   Q ctgcataaggctatgaagagatacgccctggttcctggaacaattgcttttacagatgca
 L   H   K   A   M   K   R   Y   A   L   V   P   G   T   I   A   F   T   D   A catatcgaggtgaacatcacgtacgcggaatacttcgaaatgtccgttcggttggcagaa
 H   I   E   V   N   I   T   Y   A   E   Y   F   E   M   S   V   R   L   A   E gctatgaaacgatatgggctgaatacaaatcacagaatcgtcgtatgcagtgaaaactct
 A   M   K   R   Y   G   L   N   T   N   H   R   I   V   V   C   S   E   N   S cttcaattctttatgccggtgttgggcgcgttatttatcggagttgcagttgcgcccgcg
 L   Q   F   F   M   P   V   L   G   A   L   F   I   G   V   A   V   A   P   A aacgacatttataatgaacgtgaattgctcaacagtatgaacatttcgcagcctaccgta
 N   D   I   Y   N   E   R   E   L   L   N   S   M   N   I   S   Q   P   T   V gtgtttgtttccaaaaaggggttgcaaaaaattttgaacgtgcaaaaaaaattaccaata
 V   F   V   S   K   K   G   L   Q   K   I   L   N   V   Q   K   K   L   P   I atccagaaaattattatcatggattctaaaacggattaccagggatttcagtcgatgtac
 I   Q   K   I   I   I   M   D   S   K   T   D   Y   Q   G   F   Q   S   M   Y acgttcgtcacatctcatctacctcccggttttaatgaatacgatttttgtaccagagtcc
 T   F   V   T   S   H   L   P   P   G   F   N   E   Y   D   F   V   P   E   S tttgatcgtgacaaaacaattgcactgataatgaattcctctggatctactgggttacct
 F   D   R   D   K   T   I   A   L   I   M   N   S   S   G   S   T   G   L   P aagggtgtggcccttccgcatagaactgcctgcgtcagattctcgcatgccagagatcct
 K   G   V   A   L   P   H   R   T   A   C   V   R   F   S   H   A   R   D   P attttttggcaatcaaatcattccggatactgcgatttttaagtgttgttccattccatcac
 I   F   G   N   Q   I   I   P   D   T   A   I   L   S   V   V   P   F   H   H ggttttggaatgtttactacactcggatatttgatatgtggatttcgagtcgtcttaatg
 G   F   G   M   F   T   T   L   G   Y   L   I   C   G   F   R   V   V   L   M tatagatttgaagaagagctgtttttacgatcccttcaggattacaaaattcaaagtgcg
 Y   R   F   E   E   L   F   L   R   S   L   Q   D   Y   K   I   Q   S   A ttgctagtaccaaccctattttcattcttcgccaaaagcactctgattgacaaatacgat
 L   L   V   P   T   L   F   S   F   F   A   K   S   T   L   I   D   K   Y   D ttatctaatttacacgaaattgcttctggggcgcacctctttcgaaagaagtcggggaa
 L   S   N   L   H   E   I   A   S   G   G   A   P   L   S   K   E   V   G   E gcggttgcaaaacgcttccatcttccagggatacgacaaggatatgggctcactgagact
 A   V   A   K   R   F   H   L   P   G   I   R   Q   G   Y   G   L   T   E   T acatcagctattctgattacacccgaggggatgataaaccgggcgcggtcggtaaagtt
 T   S   A   I   L   I   T   P   E   G   D   D   K   P   G   A   V   G   K   V gttccatttttgaagcgaaggttgtggatctggataccgggaaaacgctgggcgttaat
 V   P   F   F   E   A   K   V   V   D   L   D   T   G   K   T   L   G   V   N cagagaggcgaattatgtgtcagaggacctatgattatgtccggttatgtaaacaatccg
 Q   R   G   E   L   C   V   R   G   P   M   I   M   S   G   Y   V   N   N   P gaagcgaccaacgccttgattgacaaggatggatga
 E   A   T   N   A   L   I   D   K   D   G   -
```

Tables 10-13 present split reporter sequences useful in the studies of protein-protein and protein-peptide interactions.

TABLE 10

PKI-NFluc(2-416) (see also SEQ ID NOs: 16-17).

```
atgggaggtactacgtatgctgactttatagcgagtggtcgaacaggaaga
 M   G   G   T   T   Y   A   D   F   I   A   S   G   R   T   G   R
```

TABLE 10-continued

PKI-NFluc(2-416) (see also SEQ ID NOs: 16-17).

```
aggaatgcaattcatgatggtggagcaggcggtgctgcaggtgggggttctggtgggggt
 R  N  A  I  H  D  G  G  A  G  G  A  A  G  G  G  S  G  G  G ggtaccgaagacgccaaaaacataaagaaaggcccggcgccattctatcctctagaggat
 G  T  E  D  A  K  N  I  K  K  G  P  A  P  F  Y  P  L  E  D ggaaccgctggagagcaactgcataaggctatgaagagatacgccctggttcctggaaca
 G  T  A  G  E  Q  L  H  K  A  M  K  R  Y  A  L  V  P  G  T attgcttttacagatgcacatatcgaggtgaacatcacgtacgcggaatacttcgaaatg
 I  A  F  T  D  A  H  I  E  V  N  I  T  Y  A  E  Y  F  E  M tccgttcggttggcagaagctatgaaacgatatgggctgaatacaaatcacagaatcgtc
 S  V  R  L  A  E  A  M  K  R  Y  G  L  N  T  N  H  R  I  V gtatgcagtgaaaactctcttcaattctttatgccggtgttgggcgcgttatttatcgga
 V  C  S  E  N  S  L  Q  F  F  M  P  V  L  G  A  L  F  I  G gttgcagttgcgcccgcgaacgacatttataatgaacgtgaattgctcaacagtatgaac
 V  A  V  A  P  A  N  D  I  Y  N  E  R  E  L  L  N  S  M  N atttcgcagcctaccgtagtgtttgtttccaaaaaggggttgcaaaaaatttttgaacgtg
 I  S  Q  P  T  V  V  F  V  S  K  K  G  L  Q  K  I  L  N  V caaaaaaaattaccaataatccagaaaattattatcatggattctaaaacggattaccag
 Q  K  K  L  P  I  I  Q  K  I  I  I  M  D  S  K  T  D  Y  Q ggatttcagtcgatgtacacgttcgtcacatctcatctacctcccggttttaatgaatac
 G  F  Q  S  M  Y  T  F  V  T  S  H  L  P  P  G  F  N  E  Y gattttgtaccagagtcctttgatcgtgacaaaacaattgcactgataatgaattcctct
 D  F  V  P  E  S  F  D  R  D  K  T  I  A  L  I  M  N  S  S ggatctactgggttacctaagggtgtggcccttccgcatagaactgcctgcgtcagattc
 G  S  T  G  L  P  K  G  V  A  L  P  H  R  T  A  C  V  R  F tcgcatgccagagatcctattttggcaatcaaatcattccggatactgcgattttaagt
 S  H  A  R  D  P  I  F  G  N  Q  I  I  P  D  T  A  I  L  S gttgttccattccatcacggttttggaatgtttactacactcggatatttgatatgtgga
 V  V  P  F  H  H  G  F  G  M  F  T  T  L  G  Y  L  I  C  G tttcgagtcgtcttaatgtatagatttgaagaagagctgttttttacgatcccttcaggat
 F  R  V  V  L  M  Y  R  F  E  E  E  L  F  L  R  S  L  Q  D tacaaaattcaaagtgcgttgctagtaccaaccctattttcattcttcgccaaaagcact
 Y  K  I  Q  S  A  L  L  V  P  T  L  F  S  F  F  A  K  S  T ctgattgacaaatacgatttatctaatttacacgaaattgcttctgggggcgcacctctt
 L  I  D  K  Y  D  L  S  N  L  H  E  I  A  S  G  G  A  P  L tcgaaagaagtcggggaagcggttgcaaaacgcttccatcttccagggatacgacaagga
 S  K  E  V  G  E  A  V  A  K  R  F  H  L  P  G  I  R  Q  G tatgggctcactgagactacatcagctattctgattacacccgagggggatgataaaccg
 Y  G  L  T  E  T  T  S  A  I  L  I  T  P  E  G  D  D  K  P ggcgcggtcggtaaagttgttccattttttgaagcgaaggttgtggatctggataccggg
 G  A  V  G  K  V  V  P  F  F  E  A  K  V  V  D  L  D  T  G aaaacgctgggcgttaatcagagaggcgaattatgtgtcagaggacctatgattatgtcc
 K  T  L  G  V  N  Q  R  G  E  L  C  V  R  G  P  M  I  M  S ggttatgtaaacaatccggaagcgaccaacgccttgattgacaaggatggatgataagcg
 G  Y  V  N  N  P  E  A  T  N  A  L  I  D  K  D  G  -
```

TABLE 11

CFluc(398-550)-PKA (see also SEQ ID NOs: 18-19).

```
atgatgtccggttatgtaaacaatccggaagcgaccaacgccttg
 M  M  S  G  Y  V  N  N  P  E  A  T  N  A  L attgacaaggatggatggctacattctggagacatagcttactgggacgaagacgaacac
 I  D  K  D  G  W  L  H  S  G  D  I  A  Y  W  D  E  D  E  H
```

TABLE 11-continued

CFluc(398-550)-PKA (see also SEQ ID NOs: 18-19).

```
ttcttcatagttgaccgcttgaagtctttaattaaatacaaaggatatcaggtggcccc
 F  F  I  V  D  R  L  K  S  L  I  K  Y  K  G  Y  Q  V  A  P gctgaattggaatcgatattgttacaacaccccaacatcttcgacgcgggcgtggcaggt
 A  E  L  E  S  I  L  L  Q  H  P  N  I  F  D  A  G  V  A  G cttcccgacgatgacgccggtgaacttcccgcgccgttgttgttttggagcacggaaag
 L  P  D  D  A  G  E  L  P  A  A  V  V  V  L  E  H  G  K acgatgacggaaaaagagatcgtggattacgtcgccagtcaagtaacaaccgcgaaaaag
 T  M  T  E  K  E  I  V  D  Y  V  A  S  Q  V  T  T  A  K  K ttgcgcggaggagttgtgtttgtggacgaagtaccgaaaggtcttaccggaaaactcgac
 L  R  G  G  V  V  F  V  D  E  V  P  K  G  L  T  G  K  L  D gcaagaaaaatcagagagatcctcataaaggccaagaagggcggaaagtccaaattgggc
 A  R  K  I  R  E  I  L  I  K  A  K  K  G  G  K  S  K  L  G ctgcagggcggttcaggcggtgggggttctggcggggtgggagccccgggaacgccgcc
 L  Q  G  G  S  G  G  G  G  S  G  G  G  G  S  P  G  N  A  A gccgccaagaagggcagcgagcaggagagcgtgaaagagttcctagccaaagccaaggaa
 A  A  K  K  G  S  E  Q  E  S  V  K  E  F  L  A  K  A  K  E gatttcctgaaaaaatgggagacccccttctcagaatacagcccagttggatcagtttgat
 D  F  L  K  K  W  E  T  P  S  Q  N  T  A  Q  L  D  Q  F  D agaatcaagacccttggcaccggctcctttgggcgagtgatgctggtgaagcacaaggag
 R  I  K  T  L  G  T  G  S  F  G  R  V  M  L  V  K  H  K  E agtgggaaccactacgccatgaagatcttagacaagcagaaggtggtgaagctaaagcag
 S  G  N  H  Y  A  M  K  I  L  D  K  Q  K  V  V  K  L  K  Q atcgagcacactctgaatgagaagcgcatcctgcaggccgtcaacttcccgttcctggtc
 I  E  H  T  L  N  E  K  R  I  L  Q  A  V  N  F  P  F  L  V aaacttgaattctccttcaaggacaactcaaacctgtacatggtcatggagtatgtagct
 K  L  E  F  S  F  K  D  N  S  N  L  Y  M  V  M  E  Y  V  A ggtggcgagatgttctcccacctacggcggattggaaggttcagcgagccccatgcccgt
 G  G  E  M  F  S  H  L  R  R  I  G  R  F  S  E  P  H  A  R ttctacgcggcgcagatcgtcctgacctttgagtatctgcactccctggacctcatctac
 F  Y  A  A  Q  I  V  L  T  F  E  Y  L  H  S  L  D  L  I  Y cgggacctgaagcccgagaatcttctcatcgaccagcagggctatattcaggtgacagac
 R  D  L  K  P  E  N  L  L  I  D  Q  Q  G  Y  I  Q  V  T  D ttcggttttgccaagcgtgtgaaaggccgtacttggaccttgtgtgggaccctgagtac
 F  G  F  A  K  R  V  K  G  R  T  W  T  L  C  G  T  P  E  Y ttggcccccgagattatcctgagcaaaggctacaacaaggctgtggactggtgggctctc
 L  A  P  E  I  I  L  S  K  G  Y  N  K  A  V  D  W  W  A  L ggagtcctcatctacgagatggctgctggttacccacccttcttcgctgaccagcctatc
 G  V  L  I  Y  E  M  A  A  G  Y  P  P  F  F  A  D  Q  P  I cagatctatgagaaaatcgtctctgggaaggtgcggttcccatcccacttcagctctgac
 Q  I  Y  E  K  I  V  S  G  K  V  R  F  P  S  H  F  S  S  D ttgaaggacctgctgcggaaccttctgcaagtggatctcaccaagcgctttgggaacctc
 L  K  D  L  L  R  N  L  L  Q  V  D  L  T  K  R  F  G  N  L aagaacggggtcaatgacatcaagaaccacaagtggtttgccacgactgactggattgcc
 K  N  G  V  N  D  I  K  N  H  K  W  F  A  T  T  D  W  I  A atctatcagagaaaggtggaagctccttcataccaaagtttaaaggcctggggacacg
 I  Y  Q  R  K  V  E  A  P  F  I  P  K  F  K  G  P  G  D  T agtaactttgacgactatgaggaggaagagatccgggtctccatcaatgagaagtgtggc
 S  N  F  D  D  Y  E  E  E  E  I  R  V  S  I  N  E  K  C  G aaggagtttactgagttttaggggctcgagtctggtaaa
 K  E  F  T  E  F  -
```

TABLE 12 p300-NFluc(2-416) (see also SEQ ID NOs: 20-21).

```
atgggcagcggcgcgcataccgccgatccggaaaaacgtaaactgattcag
 M  G  S  G  A  H  T  A  D  P  E  K  R  K  L  I  Q cagcagctggtgctgctgctgcatgcgcataaatgccagcgccgtgaacaggcgaatggc
 Q  Q  L  V  L  L  L  H  A  H  K  C  Q  R  R  E  Q  A  N  G gaagttcgtcagtgcaatctgccgcattgccgcaccatgaaaaacgtgctgaaccatatg
 E  V  R  Q  C  N  L  P  H  C  R  T  M  K  N  V  L  N  H  M acccattgtcagagcggtaaaagctgccaggttgcccattgcgcgagcagccgccagatt
 T  H  C  Q  S  G  K  S  C  Q  V  A  H  C  A  S  S  R  Q  I attagccactggaaaaactgcacccgccatgattgccggtgtgcctgccgctgaaaaac
 I  S  H  W  K  N  C  T  R  H  D  C  P  V  C  L  P  L  K  N gcgggcgataaaaccggtgggggtggcggttcaggcggtgggggttctggtggggtggt
 A  G  D  K  T  G  G  G  G  S  G  G  G  G  S  G  G  G  G accgaagacgccaaaaacataaagaaaggcccggcgccattctatcctctagaggatgga
 T  E  D  A  K  N  I  K  K  G  P  A  P  F  Y  P  L  E  D  G accgctggagagcaactgcataaggctatgaagagatacgccctggttcctggaacaatt
 T  A  G  E  Q  L  H  K  A  M  K  R  Y  A  L  V  P  G  T  I gcttttacagatgcacatatcgaggtaacatcacgtacgcggaatacttcgaaatgtcc
 A  F  T  D  A  H  I  E  V  N  I  T  Y  A  E  Y  F  E  M  S gttcggttggcagaagctatgaaacgatatgggctgaatacaaatcacagaatcgtcgta
 V  R  L  A  E  A  M  K  R  Y  G  L  N  T  N  H  R  I  V  V tgcagtgaaaactctcttcaattctttatgccggtgttgggcgcgttatttatcggagtt
 C  S  E  N  S  L  Q  F  F  M  P  V  L  G  A  L  F  I  G  V gcagttgcgccgcgaacgacatttataatgaacgtgaattgctcaacagtatgaacatt
 A  V  A  P  A  N  D  I  Y  N  E  R  E  L  L  N  S  M  N  I tcgcagcctaccgtagtgtttgtttccaaaaaggggttgcaaaaaattttgaacgtgcaa
 S  Q  P  T  V  V  F  V  S  K  K  G  L  Q  K  I  L  N  V  Q aaaaaattaccaataatccagaaaattattatcatggattctaaaacggattaccaggga
 K  K  L  P  I  I  Q  K  I  I  I  M  D  S  K  T  D  Y  Q  G tttcagtcgatgtacacgttcgtcacatctcatctacctcccggttttaatgaatacgat
 F  Q  S  M  Y  T  F  V  T  S  H  L  P  P  G  F  N  E  Y  D tttgtaccagagtcctttgatcgtgacaaaacaattgcactgataatgaattcctctgga
 F  V  P  E  S  F  D  R  D  K  T  I  A  L  I  M  N  S  S  G tctactgggttacctaagggtgtggcccttccgcatagaactgcctgcgtcagattctcg
 S  T  G  L  P  K  G  V  A  L  P  H  R  T  A  C  V  R  F  S catgccagagatcctatttttggcaatcaaatcattccggatactgcgattttaagtgtt
 H  A  R  D  P  I  F  G  N  Q  I  I  P  D  T  A  I  L  S  V gttccattccatcacggttttggaatgtttactacactcggatatttgatatgtggattt
 V  P  F  H  H  G  F  G  M  F  T  T  L  G  Y  L  I  C  G  F cgagtcgtcttaatgtatagatttgaagaagagctgttttttacgatcccttcaggattac
 R  V  V  L  M  Y  R  F  E  E  E  L  F  L  R  S  L  Q  D  Y aaaattcaaagtgcgttgctagtaccaaccctattttcattcttcgccaaaagcactctg
 K  I  Q  S  A  L  L  V  P  T  L  F  S  F  F  A  K  S  T  L attgacaaatacgatttatctaatttacacgaaattgcttctggggggcgcacctctttcg
 I  D  K  Y  D  L  S  N  L  H  E  I  A  S  G  G  A  P  L  S aaagaagtcggggaagcggttgcaaaacgcttccatcttccagggatacgacaaggatat
 K  E  V  G  E  A  V  A  K  R  F  H  L  P  G  I  R  Q  G  Y gggctcactgagactacatcagctattctgattacacccgagggggatgataaaccgggc
 G  L  T  E  T  T  S  A  I  L  I  T  P  E  G  D  D  K  P  G gcggtcggtaaagttgttccatttttttgaagcgaaggttgtggatctggataccgggaaa
 A  V  G  K  V  V  P  F  F  E  A  K  V  V  D  L  D  T  G  K
```

TABLE 12-continued p300-NFluc(2-416) (see also SEQ ID NOs: 20-21).

```
acgctgggcgttaatcagagaggcgaattatgtgtcagaggacctatgattatgtccggt
 T   L   G   V   N   Q   R   G   E   L   C   V   R   G   P   M   I   M   S   G Tatgtaaacaatccggaagcgaccaacgccttgattgacaaggatggatgataagcggcc
 G   Y   V   N   N   P   E   A   T   N   A   L   I   D   K   D   G
```

TABLE 13

CFluc(398-550)-Hif-1α (see also SEQ ID NOs: 22-23).

```
atgatgtccggttatgtaaacaatccggaagcgaccaacgccttgattgacaag
 M   M   S   G   Y   V   N   N   P   E   A   T   N   A   L   I   D   K gatggatggctacattctggagacatagcttactgggacgaagacgaacacttcttcata
 D   G   W   L   H   S   G   D   I   A   Y   W   D   E   D   E   H   F   F   I gttgaccgcttgaagtctttaattaaatacaaaggatatcaggtggcccccgctgaattg
 V   D   R   L   K   S   L   I   K   Y   K   G   Y   Q   V   A   P   A   E   L gaatcgatattgttacaacaccccaacatcttcgacgcgggcgtggcaggtcttcccgac
 E   S   I   L   L   Q   H   P   N   I   F   D   A   G   V   A   G   L   P   D gatgacgccggtgaacttcccgccgccgttgttgttttggagcacggaaagacgatgacg
 D   D   A   G   E   L   P   A   A   V   V   L   E   H   G   K   T   M   T gaaaaagagatcgtggattacgtcgccagtcaagtaacaaccgcgaaaaagttgcgcgga
 E   K   E   I   V   D   Y   V   A   S   Q   V   T   T   A   K   K   L   R   G ggagttgtgtttgtggacgaagtaccgaaaggtcttaccggaaaactcgacgcaagaaa
 G   V   V   F   V   D   E   V   P   K   G   L   T   G   K   L   D   A   R   K atcagagagatcctcataaaggccaagaagggcggaaagtccaaattgggcctgcagggc
 I   R   E   I   L   I   K   A   K   K   G   G   K   S   K   L   G   L   Q   G ggttcaggcggtgggggttctggcggggggtgggagccccgggagcgatctggcgtgccgc
 G   S   G   G   G   G   S   G   G   G   G   S   P   G   S   D   L   A   C   R ctgctgggccagagcatggatgaaagcggcctgccgcagctgaccagctatgattgcgaa
 L   L   G   Q   S   M   D   E   S   G   L   P   Q   L   T   S   Y   D   C   E gtgaacgcgccgattcagggcagccgcaacctgctgcagggcgaagaactgctgcgcgcg
 V   N   A   P   I   Q   G   S   R   N   L   L   Q   G   E   E   L   L   R   A ctggatcaggtgaactgactcgagtctggtaaagaaaccgctgctgcgaaatttgaacgc
 L   D   Q   V   N   -
```

Tables 14-18 present constructs for DNA, methylated DNA detection, and RNA detection studies carried out with the cell free split reporter methods of the present invention.

TABLE 14

PBSII-NFluc(2-416) (see also SEQ ID NOs: 24-25).

```
atgggcagcagccatcaccatcatcaccacagccaggatccgaattcggag
 M   G   S   S   H   H   H   H   H   H   S   Q   D   P   N   S   E aagccctatgcttgtccggaatgtggtaagtccttcagccagcgcgcaaacctgcgcgcc
 K   P   Y   A   C   P   E   C   G   K   S   F   S   Q   R   A   N   L   R   A caccagcgtacccacacgggtgaaaaaccgtataagtgcccagagtgcggcaaatctttt
 H   Q   R   T   H   T   G   E   K   P   Y   K   C   P   E   C   G   K   S   F agccgcagcgatcacctgactacccatcaacgcactcatactggcgagaagccatacaaa
 S   R   S   D   H   L   T   T   H   Q   R   T   H   T   G   E   K   P   Y   K tgtccagaatgtggcaagtctttcagtcgcagcgatgtgctggtgcgccaccaacgtact
 C   P   E   C   G   K   S   F   S   R   S   D   V   L   V   R   H   Q   R   T cacaccggtgggggtggcggttcaggcggtgggggttctggtgggggtggtaccgaagac
 H   T   G   G   G   G   S   G   G   G   G   S   G   G   G   G   T   E   D
```

TABLE 14-continued

PBSII-NFluc(2-416) (see also SEQ ID NOs: 24-25).

```
gccaaaaacataaagaaaggcccggcgccattctatcctctagaggatggaaccgctgga
 A  K  N  I  K  K  G  P  A  P  F  Y  P  L  E  D  G  T  A  G gagcaactgcataaggctatgaagagatacgccctggttcctggaacaattgcttttaca
 E  Q  L  H  K  A  M  K  R  Y  A  L  V  P  G  T  I  A  F  T gatgcacatatcgaggtgaacatcacgtacgcggaatacttcgaaatgtccgttcggttg
 D  A  H  I  E  V  N  I  T  Y  A  E  Y  F  E  M  S  V  R  L gcagaagctatgaaacgatatgggctgaatacaaatcacagaatcgtcgtatgcagtgaa
 A  E  A  M  K  R  Y  G  L  N  T  N  H  R  I  V  V  C  S  E aactctcttcaattctttatgccggtgttgggcgcgttatttatcggagttgcagttgcg
 N  S  L  Q  F  F  M  P  V  L  G  A  L  F  I  G  V  A  V  A cccgcgaacgacatttataatgaacgtgaattgctcaacagtatgaacatttcgcagcct
 P  A  N  D  I  Y  N  E  R  E  L  L  N  S  M  N  I  S  Q  P accgtagtgtttgtttccaaaaaggggttgcaaaaaattttgaacgtgcaaaaaaaatta
 T  V  V  F  V  S  K  K  G  L  Q  K  I  L  N  V  Q  K  K  L ccaataatccagaaaattattatcatggattctaaaacggattaccaggGattTcagtcg
 P  I  I  Q  K  I  I  I  M  D  S  K  T  D  Y  Q  G  F  Q  S atgtacacgttcgtcacatctcatctacctcccggttttaatgaatacgattttgtacca
 M  Y  T  F  V  T  S  H  L  P  P  G  F  N  E  Y  D  F  V  P gagtcctttgatcgtgacaaaacaattgcactgataatgaattcctctggatctactggg
 E  S  F  D  R  D  K  T  I  A  L  I  M  N  S  S  G  S  T  G ttacctaagggtgtggcccttccgcatagaactgcctgcgtcagattctcgcatgccaga
 L  P  K  G  V  A  L  P  H  R  T  A  C  V  R  F  S  H  A  R gatcctattttggcaatcaaatcattccggatactgcgattttaagtgttgttccattc
 D  P  I  F  G  N  Q  I  I  P  D  T  A  I  L  S  V  V  P  F catcacggttttggaatgtttactacactcggatatttgatatgtggatttcgagtcgtc
 H  H  G  F  G  M  F  T  T  L  G  Y  L  I  C  G  F  R  V  V ttaatgtatagatttgaagaagagctgtttttacgatcccttcaggattacaaaattcaa
 L  M  Y  R  F  E  E  E  L  F  L  R  S  L  Q  D  Y  K  I  Q agtgcgttgctagtaccaaccctatttcattcttcgccaaaagcactctgattgacaaa
 S  A  L  L  V  P  T  L  F  S  F  F  A  K  S  T  L  I  D  K tacgattatctaatttacacgaaattgcttctgggggcgcacctctttcgaaagaagtc
 Y  D  L  S  N  L  H  E  I  A  S  G  G  A  P  L  S  K  E  V ggggaagcggttgcaaaacgcttccatcttccagggatacgacaaggatatgggctcact
 G  E  A  V  A  K  R  F  H  L  P  G  I  R  Q  G  Y  G  L  T gagactacatcagctattctgattacacccgaggggatgataaaccgggcgcggtcggt
 E  T  T  S  A  I  L  I  T  P  E  G  D  D  K  P  G  A  V  G aaagttgttccattttttgaagcgaaggttgtggatctggataccgggaaaacgctgggc
 K  V  V  P  F  F  E  A  K  V  V  D  L  D  T  G  K  T  L  G gttaatcagagaggcgaattatgtgtcagaggacctatgattatgtccggttatgtaaac
 V  N  Q  R  G  E  L  C  V  R  G  P  M  I  N  S  G  Y  V  N aatccggaagcgaccaacgccttgattgacaaggatggtgataagcggccgcataatgc
 N  P  E  A  T  N  A  L  I  D  K  D  G  -
```

TABLE 15

CFluc(398-550)-Zif268 (see also SEQ ID NOs: 26-27).

```
atgatgtccggttatgtaaacaatccggaagcgaccaacgccttgattgacaag
 M  M  S  G  Y  V  N  N  P  E  A  T  N  A  L  I  D  K gatggatggctacattctggagacatagcttactgggacgaagacgaacacttcttcata
 D  G  W  L  H  S  G  D  I  A  Y  W  D  E  D  E  H  F  F  I gttgaccgcttgaagtctttaattaaatacaaaggatatcaggtggccccCGctgaattg
 V  D  R  L  K  S  L  I  K  Y  K  G  Y  Q  V  A  P  A  E  L
```

TABLE 15-continued

CFluc(398-550)-Zif268 (see also SEQ ID NOs: 26-27).

```
gaatcgatattgttacaacaccccaacatcttcgacgcgggcgtggcaggtcttcccgac
 E  S  I  L  L  Q  H  P  N  I  F  D  A  G  V  A  G  L  P  D gatgacgccggtgaacttcccgccgccgttgttgttttggagcacggaaagacgatgacg
 D  D  A  G  E  L  P  A  A  V  V  V  L  E  H  G  K  T  M  T gaaaaagagatcgtggattacgtcgccagtcaagtaacaaccgcgaaaaagttgcgcgga
 E  K  E  I  V  D  Y  V  A  S  Q  V  T  T  A  K  K  L  R  G ggagttgtgtttgtggacgaagtaccgaaaggtcttaccggaaaactcgacgcaagaaaa
 G  V  V  F  V  D  I  V  P  K  G  L  T  G  K  L  D  A  R  K atcagagagatcctcataaaggccaagaagggcggaaagtccaaattgggcctgcagggc
 I  R  E  I  L  I  K  A  K  K  G  G  K  S  K  L  G  L  Q  G ggttcaggcggtgggggttctggcggggtgggagcccggggaacgcccttacgcttgc
 G  S  G  G  G  G  S  G  G  G  G  S  P  G  E  R  P  Y  A  C ccagtggagtcctgtgatcgccgcttctcccgctccgacgagctcacccgccacatccgc
 P  V  E  S  C  D  R  R  F  S  R  S  D  E  L  T  R  H  I  R atccacacaggccagaagcccttccagtgccgcatctgcatgcgcaacttcagccgcagc
 I  H  T  G  Q  K  P  F  Q  C  R  I  C  M  R  N  F  S  R  S gaccacctcaccacccacatccgcacccacacaggcgaaaagccctttgcctgcgacatc
 D  H  L  T  T  H  I  R  T  H  T  G  E  K  P  F  A  C  D  I tgtggaagaaagtttgccaggagcgatgaacgcaagaggcataccaagatccacttgcgg
 C  G  R  K  F  A  R  S  D  E  R  K  R  H  T  K  I  H  L  R cagaaggacctcgagtctggtaaagaaaccgctgctgcgaaatttgaacgccagcacatg
 Q  K  D  L  E  S  G  K  E  T  A  A  A  K  F  E  R  Q  H  M gactcgtctactagcgcagcttaattaacctaggctgctgccaccgctgagcaataacta
 D  S  S  T  S  A  A  -
```

TABLE 16

CFluc-E2C (see also SEQ ID NOs: 28-29).

```
atgatgtccggttatgtaaacaatccggaagcgaccaacgccttgattgacaaggatgga
 M  M  S  G  Y  V  N  N  P  E  A  T  N  A  L  I  D  K  D  G tggctacattctggagacatagcttactgggacgaagacgaacacttcttcatagttgac
 W  L  H  S  G  D  I  A  Y  W  D  E  D  E  H  F  F  I  V  D cgcttgaagtctttaattaaatacaaaggatatcaggtggccccccgctgaattggaatcg
 R  L  K  S  L  I  K  Y  K  G  Y  Q  V  A  P  A  E  L  E  S atattgttacaacaccccaacatcttcgacgcgggcgtggcaggtcttcccgacgatgac
 I  L  L  Q  H  P  N  I  F  D  A  G  V  A  G  L  P  D  D  D gccggtgaacttcccgccgccgttgttgttttggagcacggaaagacgatgacgaaaaa
 A  G  E  L  P  A  A  V  V  V  L  E  H  G  K  T  M  T  E  K gagatcgtggattacgtcgccagtcaagtaacaaccgcgaaaaagttgcgcggaggagtt
 E  I  V  D  Y  V  A  S  Q  V  T  T  A  K  K  L  R  G  G  V gtgtttgtggacgaagtaccgaaaggtcttaccggaaaactcgacgcaagaaaaatcaga
 V  F  V  D  E  V  P  K  G  L  T  G  K  L  D  A  R  K  I  R gagatcctcataaaggccaagaagggcggaaagtccaaattgggcctgcagggcggttca
 E  I  L  I  K  A  K  K  G  G  K  S  K  L  G  L  Q  G  G  S ggcggtgggggttctggcggggtgggagcccggggagaagcctatgcttgtccggaa
 G  G  G  G  S  G  G  G  G  S  P  G  E  K  P  Y  A  C  P  E tgtggtaagtccttcagtaggaaggattcgcttgtgaggcaccagcgtacccacacgggt
 C  G  K  S  F  S  R  K  D  S  L  V  R  H  Q  R  T  H  T  G gaaaaaccgtataaatgcccagagtgcggcaaatctttagtcagtcggggatcttagg
 E  K  P  Y  K  C  P  E  C  G  K  S  F  S  Q  S  G  D  L  R
```

TABLE 16-continued

CFluc-E2C (see also SEQ ID NOs: 28-29).

```
cgtcatcaacgcactcatactggcgagaagccatacaaatgtccagaatgtggcaagtct
 R   H   Q   R   T   H   T   G   E   K   P   Y   K   C   P   E   C   G   K   S ttcagtgattgtcgtgatcttgcgaggcaccaacgtactcacaccggggagaagccctat
 F   S   D   C   R   D   L   A   R   H   Q   R   T   H   T   G   E   K   P   Y gcttgtccggaatgtggtaagtccttctctcagagctctcacctggtgcgccaccagcgt
 A   C   P   E   C   G   K   S   F   S   Q   S   S   H   L   V   R   H   Q   R acccacacgggtgaaaaaccgtataaatgcccagagtgcggcaaatcttttagtgactgc
 T   H   T   G   E   K   P   Y   K   C   P   E   C   G   K   S   F   S   D   C cgcgaccttgctcgccatcaacgcactcatactggcgagaagccatacaaatgtccagaa
 R   D   L   A   R   H   Q   R   T   H   T   G   E   K   P   Y   K   C   P   E tgtggcaagtctttcagccgctctgacaagctggtgcgtcaccaacgtactcacaccggt
 C   G   K   S   F   S   R   S   D   K   L   V   R   H   Q   R   T   H   T   G aaaaaaactagttaa
 K   K   T   S   -
```

TABLE 17

Aart-NFluc (see also SEQ ID NOs: 30-31).

```
atgggcagcagccatcaccatcatcaccacagccaggatccccccggggagaagccctat
 M   G   S   S   H   H   H   H   H   H   S   Q   D   P   P   G   E   K   P   Y gcttgtccggaatgtggtaagtccttcagccgcagcgatcacctggccgaacaccagcgt
 A   C   P   E   C   G   K   S   F   S   R   S   D   H   L   A   E   H   Q   R acccacacgggtgaaaaaccgtataaatgcccagagtgcggcaaatcttttagcgataag
 T   H   T   G   E   K   P   Y   K   C   P   E   C   G   K   S   F   S   D   K aaagatctgacccggcatcaacgcactcatactggcgagaagccatacaaatgtccagaa
 K   D   L   T   R   H   Q   R   T   H   T   G   E   K   P   Y   K   C   P   E tgtggcaagtctttcagccagcgcgcaaacctgcgcgcccaccaacgtactcacaccggg
 C   G   K   S   F   S   Q   R   A   N   L   R   A   H   Q   R   T   H   T   G gagaagccttatgcttgtccggaatgtggtaagtccttctctcagctggcccacctgcgc
 E   K   P   Y   A   C   P   E   C   G   K   S   F   S   Q   L   A   H   L   R gccaccagcgtacccacacgggtgaaaaaccgtataaatgcccagagtgcggcaaatct
 A   H   Q   R   T   H   T   G   E   K   P   Y   K   C   P   E   C   G   K   S tttagccgcgaggataacctgcacacccatcaacgtactcatactggcgagaagccatac
 F   S   R   E   D   N   L   H   T   H   Q   R   T   H   T   G   E   K   P   Y aaatgtccagaatgtggcaagtctttctcccgccgcgatgctctgaacgtgcaccaacgt
 K   C   P   E   C   G   K   S   F   S   R   R   D   A   L   N   V   H   Q   R actcacaccggcaaaaaaactagcaccggtgggggtggcggttcaggcggtgggggttct
 T   H   T   G   K   K   T   S   T   G   G   G   G   S   G   G   G   G   S ggtggggtggtaccgaagacgccaaaaacataaagaaaggcccggcgccattctatcct
 G   G   G   T   E   D   A   K   N   I   K   K   G   P   A   P   F   Y   P ctagaggatggaaccgctggagagcaactgcataaggctatgaagagatacgccctggtt
 L   E   D   G   T   A   G   E   Q   L   H   K   A   M   K   R   Y   A   L   V cctggaacaattgcttttacagatgcacatatcgaggtgaacatcacgtacgcggaatac
 P   G   T   I   A   F   T   D   A   H   I   E   V   N   I   T   Y   A   E   Y ttcgaaatgtccgttcggttggcagaagctatgaaacgatatgggctgaatacaaatcac
 F   E   M   S   V   R   L   A   E   A   M   K   R   Y   G   L   N   T   N   H agaatcgtcgtatgcagtgaaaactctcttcaattctttatgccggtgttgggcgcgtta
 R   I   V   V   C   S   E   N   S   L   Q   F   F   M   P   V   L   G   A   L tttatcggagttgcagttgcgcccgcgaacgacatttataatgaacgtgaattgctcaac
 F   I   G   V   A   V   A   P   A   N   D   I   Y   N   E   R   E   L   L   N agtatgaacatttcgcagcctaccgtagtgtttgtttccaaaaaggggttgcaaaaaatt
 S   M   N   I   S   Q   P   T   V   V   F   V   S   K   K   G   L   Q   K   I
```

TABLE 17-continued

Aart-NFluc (see also SEQ ID NOs: 30-31).

```
ttgaacgtgcaaaaaaaattaccaataatccagaaaattattatcatggattctaaaacg
 L  N  V  Q  K  K  L  P  I  I  Q  K  I  I  I  M  D  S  K  T gattaccagggatttcagtcgatgtacacgttcgtcacatctcatctacctcccggtttt
 D  Y  Q  G  F  Q  S  M  Y  T  F  V  T  S  H  L  P  P  G  F aatgaatacgattttgtaccagagtcctttgatcgtgacaaaacaattgcactgataatg
 N  E  Y  D  F  V  P  E  S  F  D  R  D  K  T  I  A  L  I  M aattcctctggatctactgggttacctaagggtgtggcccttccgcatagaactgcctgc
 N  S  S  G  S  T  G  L  P  K  G  V  A  L  P  H  R  T  A  C gtcagattctcgcatgccagagatcctattttggcaatcaaatcattccggatactgcg
 V  R  F  S  H  A  R  D  P  I  F  G  N  Q  I  I  P  D  T  A atttaagtgttgttccattccatcacggttttggaatgtttactacactcggatatttg
 I  L  S  V  V  P  F  H  H  G  F  G  M  F  T  T  L  G  Y  L atatgtggatttcgagtcgtcttaatgtatagatttgaagaagagctgttttttacgatcc
 I  C  G  F  R  V  V  L  M  Y  R  F  E  E  E  L  F  L  R  S cttcaggattacaaaattcaaagtgcgttgctagtaccaaccctatttttcattcttcgcc
 L  Q  D  Y  K  I  Q  S  A  L  L  V  P  T  L  F  S  F  F  A aaaagcactctgattgacaaatacgatttatctaatttacacgaaattgcttctgggggc
 K  S  T  L  I  D  K  Y  D  L  S  N  L  H  E  I  A  S  G  G gcacctctttcgaaagaagtcggggaagcggttgcaaaacgcttccatcttccaggata
 A  P  L  S  K  E  V  G  E  A  V  A  K  R  F  H  L  P  G  I cgacaaggatatgggctcactgagactacatcagctattctgattacacccgagggggat
 R  Q  G  Y  G  L  T  E  T  T  S  A  I  L  I  T  P  E  G  D gataaaccgggcgcggtcggtaaagttgttccatttttttgaagcgaaggttgtggatctg
 D  K  P  G  A  V  G  K  V  V  P  F  F  E  A  K  V  V  D  L gataccgggaaaacgctgggcgttaatcagagaggcgaattatgtgtcagaggacctatg
 D  T  G  K  T  L  G  V  N  Q  R  G  E  L  C  V  R  G  P  M attatgtccggttatgtaaacaatccggaagcgaccaacgccttgattgacaaggatgga
 I  M  S  G  Y  V  N  N  P  E  A  T  N  A  L  I  D  K  D  G tga
```

TABLE 18

MBD2-NFluc(2-416) (see also SEQ ID NOs: 32-33).

```
atgggcagcagccatcaccatcatcaccacagccaggatccgaattcggaaagcggcaaa
 M  G  S  S  H  H  H  H  H  H  S  Q  D  P  N  S  E  S  G  K cgcatggattgcccggcgctgccgccgggttggaaaaaagaagaagtgattcgtaaaagc
 R  M  D  C  P  A  L  P  P  G  W  K  K  E  E  V  I  R  K  S ggcctgagcgcgggcaaaagcgatgtgtattattttagcccgagcggcaaaaaatttcgt
 G  L  S  A  G  K  S  D  V  Y  Y  F  S  P  S  G  K  K  F  R agcaaaccgcagctggcgcgttatctgggcaacaccgtggatctgagcagctttgatttt
 S  K  P  Q  L  A  R  Y  L  G  N  T  V  D  L  S  S  F  D  F cgtaccggcaaaatgaccggtgggggtggcggttcaggcggtgggggttctggtggggt
 R  T  G  K  M  T  G  G  G  G  S  G  G  G  G  S  G  G  G ggtaccgaagacgccaaaaacataaagaaaggcccggcgccattctatcctctagaggat
 G  T  E  D  A  K  N  I  K  K  G  P  A  P  F  Y  P  L  E  D ggaaccgctggagagcaactgcataaggctatgaagagatacgccctggttcctggaaca
 G  T  A  G  E  Q  L  H  K  A  M  K  R  Y  A  L  V  P  G  T attgcttttacagatgcacatatcgaggtgaacatcacgtacgcggaatacttcgaaatg
 I  A  F  T  D  A  H  I  E  V  N  I  T  Y  A  E  Y  F  E  M tccgttcggttggcagaagctatgaaacgatatgggctggatacaaatcacagaatcgtc
 S  V  R  L  A  E  A  M  K  R  Y  G  L  D  T  N  H  R  I  V
```

TABLE 18-continued

MBD2-NFluc(2-416) (see also SEQ ID NOs: 32-33).

```
gtatgcagtgaaaactctcttcaattctttatgccggtgttgggcgcgttatttatcgga
 V  C  S  E  N  S  L  Q  F  F  M  P  V  L  G  A  L  F  I  G gttgcagttgcgcccgcgaacgacatttataatgaacgtgaattgctcaacagtatgaac
 V  A  V  A  P  A  N  D  I  Y  N  E  R  E  L  L  N  S  M  N atttcgcagcctaccgtagtgtttgtttccaaaaaggggttgcaaaaaattttgaacgtg
 I  S  Q  P  T  V  V  F  V  S  K  K  G  L  Q  K  I  L  N  V caaaaaaattaccaataatccagaaaattattatcatggattctaaaacggattaccag
 Q  K  K  L  P  I  I  Q  K  I  I  I  M  D  S  K  T  D  Y  Q ggatttcagtcgatgtacacgttcgtcacatctcatctacctcccggttttaatgaatac
 G  F  Q  S  M  Y  T  F  V  T  S  H  L  P  P  G  F  N  E  Y gattttgtaccagagtcctttgatcgtgacaaaacaattgcactgacaatgaattcctct
 D  F  V  P  E  S  F  D  R  D  K  T  I  A  L  T  M  N  S  S ggatctactgggttacctaagggtgtggcccttccgcatagaactgcctgcgtcagattc
 G  S  T  G  L  P  K  G  V  A  L  P  H  R  T  A  C  V  R  F tcgcatgccagagatcctattttggcaatcaaatcattccggatactgcgattttaagt
 S  H  A  R  D  P  I  F  G  N  Q  I  I  P  D  T  A  I  L  S gttgttccattccatcacggttttggaatgtttactacactcggatatttgatatgtgga
 V  V  P  F  H  H  G  F  G  M  F  T  T  L  G  Y  L  I  C  G tttcgagtcgtcttaatgtatagatttgaagaagagctgttttttacgatcccttcaggat
 F  R  V  V  L  M  Y  R  F  E  E  E  L  F  L  R  S  L  Q  D tacaaaattcaaagtgcgttgctagtaccaaccctatttcattcttcgccaaaagcact
 Y  K  I  Q  S  A  L  L  V  P  T  L  F  S  F  F  A  K  S  T ctgattgacaaatacgatttatctaatttacacgaaattgcttctgggggcgcacctctt
 L  I  D  K  Y  D  L  S  N  L  H  E  I  A  S  G  G  A  P  L tcgaaagaagtcggggaagcggttgcaaaacgcttccatcttccagggatacgacaagga
 S  K  E  V  G  E  A  V  A  K  R  F  H  L  P  G  I  R  Q  G tatgggctcactgagactacatcagctattctgattacacccgaggggatgataaaccg
 Y  G  L  T  E  T  T  S  A  I  L  I  T  P  E  G  D  D  K  P ggcgcggtcggtaaagttgttccattttttgaagcgaaggttgtggatctggataccggg
 G  A  V  G  K  V  V  P  F  F  E  A  K  V  V  D  L  D  T  G aaaacgctgggcgttaatcagagaggcgaattatgtgtcagaggacctatgattatgtcc
 K  T  L  G  V  N  Q  R  G  E  L  C  V  R  G  P  M  I  M  S ggttatgtaaacaatccggaagcgaccaacgccttgattgacaaggatggatgataagcg
 G  Y  V  N  N  P  E  A  T  N  A  L  I  D  K  D  G  -
```

Tables 19-24 provide split reporter fusion protein sequences useful in assays for the detection of small-molecule inhibitors of kinases.

TABLE 19

Cfluc-PKA_ (see also SEQ ID NOs: 34-35).

```
atgatgtccggttatgtaaacaatccggaagcgaccaacgccttgattgacaaggatgga
 M  M  S  G  Y  V  N  N  P  E  A  T  N  A  L  I  D  K  D  G tggctacattctggagacatagcttactgggacgaagacgaacacttcttcatagttgac
 W  L  H  S  G  D  I  A  Y  W  D  E  D  H  F  F  I  V  D cgcttgaagtctttaattaaatacaaaggatatcaggtggcccccgctgaattggaatcg
 R  L  K  S  L  I  K  Y  K  G  Y  Q  V  A  P  A  E  L  E  S atattgttacaacaccccaacatcttcgacgcgggcgtggcaggtcttcccgacgatgac
 I  L  L  Q  H  P  N  I  F  D  A  G  V  A  G  L  P  D  D  D gccggtgaacttcccgccgccgttgttgtttttggagcacggaaagacgatgacggaaaaa
 A  G  E  L  P  A  A  V  V  V  L  E  H  G  K  T  N  T  E  K
```

TABLE 19-continued

Cfluc-PKA_(see also SEQ ID NOs: 34-35).

gagatcgtggattacgtcgccagtcaagtaacaaccgcgaaaaagttgcgcggaggagtt
E  I  V  D  Y  V  A  S  Q  V  T  T  A  K  K  L  R  G  G  V gtgtttgtggacgaagtaccgaaaggtcttaccggaaaactcgacgcaagaaaaatcaga
V  F  V  D  E  V  P  K  G  L  T  G  K  L  D  A  R  K  I  R gagatcctcataaaggccaagaagggcggaaagtccaaattgggcctgcagggcggttca
E  I  L  I  K  A  K  K  G  G  K  S  K  L  G  L  Q  G  G  S ggcggtgggggttctggcggggtgggagccccgggaacgccgccgccgccaagaagggc
G  G  G  G  S  G  G  G  G  S  P  G  N  A  A  A  A  K  K  G agcgagcaggagagcgtgaaagagttcctagccaaagccaaggaagatttcctgaaaaaa
S  E  Q  E  S  V  K  E  F  L  A  K  A  K  E  D  F  L  K  K tgggagacccctctcagaatacagcccagttggatcagtttgatagaatcaagacccctt
W  E  T  P  S  Q  N  T  A  Q  L  D  Q  F  D  R  I  K  T  L ggcaccggctcctttgggcgagtgatgctggtgaagcacaaggagagtgggaaccactac
G  T  G  S  F  G  R  V  M  L  V  K  H  K  E  S  G  N  H  Y gccatgaagatcttagacaagcagaaggtggtgaagctaaagcagatcgagcacactctg
A  M  K  I  L  D  K  Q  K  V  V  K  L  K  Q  I  E  H  T  L aatgagaagcgcatcctgcaggccgtcaacttcccgttcctggtcaaacttgaattctcc
N  E  K  R  I  L  Q  A  V  N  F  P  F  L  V  K  L  E  F  S ttcaaggacaactcaaacctgtacatggtcatggagtatgtagctggtggcgagatgttc
F  K  D  N  S  N  L  Y  M  V  M  E  Y  V  A  G  G  E  M  F tcccacctacggcggattggaaggttcagcgagccccatgcccgtttctacgcggcgcag
S  H  L  R  R  I  G  R  F  S  E  P  H  A  R  F  Y  A  A  Q atcgtcctgacctttgagtatctgcactccctggacctcatctaccgggacctgaagccc
I  V  L  T  F  E  Y  L  H  S  L  D  L  I  Y  R  D  L  K  P gagaatcttctcatcgaccagcagggctatattcaggtgacagacttcggttttgccaag
E  N  L  L  I  D  Q  Q  G  Y  I  Q  V  T  D  F  G  F  A  K cgtgtgaaaggccgtacttggaccttgtgtgggacccctgagtacttggccccccgagatt
R  V  K  G  R  T  W  T  L  C  G  T  P  E  Y  L  A  P  E  I atcctgagcaaaggctacaacaaggctgtggactggtgggctctcggagtcctcatctac
I  L  S  K  G  Y  N  K  A  V  D  W  W  A  L  G  V  L  I  Y gagatggctgctggttacccacccttcttcgctgaccagcctatccagatctatgagaaa
E  M  A  A  G  Y  P  P  F  F  A  D  Q  P  I  Q  I  Y  E  K atcgtctctgggaaggtgcggttccccatcccacttcagctctgacttgaaggacctgctg
I  V  S  G  K  V  R  F  P  S  H  F  S  S  D  L  K  D  L  L cggaaccttctgcaagtggatctcaccaagcgctttgggaacctcaagaacggggtcaat
R  N  L  L  Q  V  D  L  T  K  R  F  G  N  L  K  N  G  V  N gacatcaagaaccacaagtggtttgccacgactgactggattgccatctatcagagaaag
D  I  K  N  H  K  W  F  A  T  T  D  W  I  A  I  Y  Q  R  K gtggaagctcccttcataccaaagtttaaaggccctggggacacgagtaactttgacgac
V  E  A  P  F  I  P  K  F  K  G  P  G  D  T  S  N  F  D  D tatgaggaggaagagatccgggtctccatcaatgagaagtgtggcaaggagtttactgag
Y  E  E  E  E  I  R  V  S  I  N  E  K  C  G  K  E  F  T  E ttttag
F  -

TABLE 20

Cfluc-PDGFRB (see also SEQ ID NOs: 36-37).

atgggtatgtccggttatgtaaacaatccggaagcgaccaacgccttgattgacaaggat
M  G  M  S  G  Y  V  N  N  P  E  A  T  N  A  L  I  D  K  D ggatggctacattctggagacatagcttactgggacgaagacgaacacttcttcatagtt
G  W  L  H  S  G  D  I  A  Y  W  D  E  D  E  H  F  F  I  V TABLE 20-continued Cfluc-PDGFRB (see also SEQ ID NOs: 36-37).

```
gaccgcttgaagtctttaattaaatacaaaggatatcaggtggccccgctgaattggaa
 D   R   L   K   S   L   I   K   Y   K   G   Y   Q   V   A   P   A   E   L   E tcgatattgttacaacaccccaacatcttcgacgcgggcgtggcaggtcttcccgacgat
 S   I   L   L   Q   H   P   N   I   F   D   A   G   V   A   G   L   P   D   D gacgccggtgaacttcccgccgccgttgttgttttggagcacggaaagacgatgacggaa
 D   A   G   E   L   P   A   A   V   V   V   L   E   H   G   K   T   M   T   E aaagagatcgtggattacgtcgccagtcaagtaacaaccgcgaaaaagttgcgcggagga
 K   E   I   V   D   Y   V   A   S   Q   V   T   T   A   K   K   L   R   G   G gttgtgtttgtggacgaagtaccgaaaggtcttaccggaaaactcgacgcaagaaaaatc
 V   V   F   V   D   E   V   P   K   G   L   T   G   K   L   D   A   R   K   I agagagatcctcataaaggccaagaagggcggaaagtccaaattgggcctgcagggcggt
 R   E   I   L   I   K   A   K   K   G   G   K   S   K   L   G   L   Q   G   G tcaggcggtgggggttctggcgggggtgggagcgtcgactccacgtgggagctgccgcgg
 S   G   G   G   G   S   G   G   G   G   S   V   D   S   T   W   E   L   P   R gaccagcttgtgctgggacgcaccctcggctctggggcctttgggcaggtggtggaggcc
 D   Q   L   V   L   G   R   T   L   G   S   G   A   F   G   Q   V   V   E   A acggctcatggcctgagccattctcaggccacgatgaaagtggccgtcaagatgcttaaa
 T   A   H   G   L   S   H   S   Q   A   T   M   K   V   A   V   K   M   L   K tccacagcccgcagcagtgagaagcaagcccttatgtcggagctgaagatcatgagtcac
 S   T   A   R   S   S   E   K   Q   A   L   M   S   E   L   K   I   M   S   H cttgggccccacctgaacgtggtcaacctgttgggggcctgcaccaaaggaggacccatc
 L   G   P   H   L   N   V   V   N   L   L   G   A   C   T   K   G   G   P   I tatatcatcactgagtactgccgctacggagacctggtggactacctgcaccgcaacaaa
 Y   I   I   T   E   Y   C   R   Y   G   D   L   V   D   Y   L   H   R   N   K cacaccttcctgcagcaccactccgacaagcgccgccgccagcgcggagctctacagc
 H   T   F   L   Q   H   H   S   D   K   R   R   P   P   S   A   E   L   Y   S aatgctctgcccgttgggctcccccctgcccagccatgtgtccttgaccggggagagcgac
 N   A   L   P   V   G   L   P   L   P   S   H   V   S   L   T   G   E   S   D ggtggctacatggacatgagcaaggacgagtcggtggactatgtgcccatgctggacatg
 G   G   Y   M   D   M   S   K   D   E   S   V   D   Y   V   P   M   L   D   M aaaggagacgtcaaatatgcagacatcgagtcctccaactacatggccccttacgataac
 K   G   D   V   K   Y   A   D   I   E   S   S   N   Y   M   A   P   Y   D   N tacgttccctctgcccctgagaggacctgccgagcaactttgatcaacgagtctccagtg
 Y   V   P   S   A   P   E   R   T   C   R   A   T   L   I   N   E   S   P   V ctaagctacatggacctcgtgggcttcagctaccaggtggccaatggcatggagtttctg
 L   S   Y   M   D   L   V   G   F   S   Y   Q   V   A   N   G   M   E   F   L gcctccaagaactgcgtccacagagacctggcggctaggaacgtgctcatctgtgaaggc
 A   S   K   N   C   V   H   R   D   L   A   A   R   N   V   L   I   C   E   G aagctggtcaagatctgtgactttggcctggctcgagacatcatgcgggactcgaattac
 K   L   V   K   I   C   D   F   G   L   A   R   D   I   M   R   D   S   N   Y atctccaaaggcagcaccttttttgcctttaaagtggatggctccggagagcatcttcaac
 I   S   K   G   S   T   F   L   P   L   K   W   M   A   P   E   S   I   F   N agcctctacaccaccctgagcgacgtgtggtccttcgggatcctgctctgggagatcttc
 S   L   Y   T   T   L   S   D   V   W   S   F   G   I   L   L   W   E   I   F acccttgggtggcaccccttacccagagctgcccatgaacgagcagttctacaatgccatc
 T   L   G   G   T   P   Y   P   E   L   P   M   N   E   Q   F   Y   N   A   I aaacggggttaccgcatggcccagcctgcccatgcctccgacgagatctatgagatcatg
 K   R   G   Y   R   M   A   Q   P   A   H   A   S   D   E   I   Y   E   I   M
```

TABLE 20-continued

Cfluc-PDGFRB (see also SEQ ID NOs: 36-37).

```
cagaagtgctgggaagagaagtttgagattcggccccccttctcccagctggtgctgctt
 Q   K   C   W   E   E   K   F   E   I   R   P   P   F   S   Q   L   V   L   L ctcgagagactgttgtga
 L   E   R   L   L   -
```

TABLE 21

Cfluc-CDK2 (see also SEQ ID NOs: 38-39).

```
atgggtatgtccggttatgtaaacaatccggaagcgaccaacgccttgattgacaaggat
 M   G   M   S   G   Y   V   N   N   P   E   A   T   N   A   L   I   D   K   D ggatggctacattctggagacatagcttactggacgaagacgaacacttcttcatagtt
 G   W   L   H   S   G   D   I   A   Y   W   D   E   D   E   H   F   F   I   V gaccgcttgaagtctttaattaaatacaaaggatatcaggtggccccgctgaattggaa
 D   R   L   K   S   L   I   K   Y   K   G   Y   Q   V   A   P   A   E   L   E tcgatattgttacaacaccccaacatcttcgacgcgggcgtggcaggtcttccgacgat
 S   I   L   L   Q   H   P   N   I   F   D   A   G   V   A   G   L   P   D   D gacgccggtgaacttccgccgccgttgttgttttggagcacggaaagacgatgacggaa
 D   A   G   E   L   P   A   A   V   V   V   L   E   H   G   K   T   M   T   E aaagagatcgtggattacgtcgccagtcaagtaacaaccgcgaaaaagttgcgcggagga
 K   E   I   V   D   Y   V   A   S   Q   V   T   T   A   K   K   L   R   G   G gttgtgtttgtggacgaagtaccgaaaggtcttaccggaaaactcgacgcaagaaaaatc
 V   V   F   V   D   E   V   P   K   G   L   T   G   K   L   D   A   R   K   I agagagatcctcataaaggccaagaagggcggaaagtccaaattgggcctgcagggcggt
 R   E   I   L   I   K   A   K   K   G   G   K   S   K   L   G   L   Q   G   G tcaggcggtggggttctggcgggggtgggagcgtcgacatggagaacttccaaaaggtg
 S   G   G   G   G   S   G   G   G   S   V   D   M   E   N   F   Q   K   V gaaaagatcggagagggcacgtacggagttgtgtacaaagccagaaacaagttgacggga
 E   K   I   G   E   G   T   Y   G   V   V   Y   K   A   R   N   K   L   T   G gaggtggtggcgcttaagaaaatccgcctggacactgagactgagggtgtgcccagtact
 E   V   V   A   L   K   K   I   R   L   D   T   E   T   E   G   V   P   S   T gccatccgagagatctctctgcttaaggagcttaaccatcctaatattgtcaagctgctg
 A   I   R   E   I   S   L   L   K   E   L   N   H   P   N   I   V   K   L   L gatgtcattcacacagaaaataaaactctacctggttttttgaatttctgcaccaagatctc
 D   V   I   H   T   E   N   K   L   Y   L   V   F   E   F   L   H   Q   D   L aagaaattcatggatgcctctgctctcactggcattcctcttcccctcatcaagagctat
 K   K   F   M   D   A   S   A   L   T   G   I   P   L   P   L   I   K   S   Y ctgttccagctgctccagggcctagctttctgccattctcatcgggtcctccaccgagac
 L   F   Q   L   L   Q   G   L   A   F   C   H   S   H   R   V   L   H   R   D cttaaacctcagaatctgcttattaacacagaggggccatcaagctagcagactttgga
 L   K   P   Q   N   L   L   I   N   T   E   G   A   I   K   L   A   D   F   G ctagccagagcttttggagtccctgttcgtacttacacccatgaggtggtgaccctgtgg
 L   A   R   A   F   G   V   P   V   R   T   Y   T   H   E   V   V   T   L   W taccgagctcctgaaatcctcctgggctgcaaatattattccacagctgtggacatctgg
 Y   R   A   P   E   I   L   L   G   C   K   Y   Y   S   T   A   V   D   I   W agcctgggctgcatctttgctgagatggtgactcgccggccctattccctggagattct
 S   L   G   C   I   F   A   E   M   V   T   R   R   A   L   F   P   G   D   S gagattgaccagctcttccggatctttcggactctgggaccccagatgaggtggtgtgg
 E   I   D   Q   L   F   R   I   F   R   T   L   G   T   P   D   E   V   V   W ccaggagttacttctatgcctgattacaagccaagtttcccaagtgggccggcaagat
 P   G   V   T   S   M   P   D   Y   K   P   S   F   P   K   W   A   R   Q   D tttagtaaagttgtacctcccctggatgaagatggacggagcttgttatcgcaaatgctg
 F   S   K   V   V   P   P   L   D   E   D   G   R   S   L   L   S   Q   M   L
```

TABLE 21-continued

Cfluc-CDK2 (see also SEQ ID NOs: 38-39).

```
cactacgaccctaacaagcggatttcggccaaggcagccctggctcacccttcttccag
 H   Y   D   P   N   K   R   I   S   A   K   A   A   L   A   H   P   F   F   Q gatgtgaccaagccagtaccccatcttcgactctga
 D   V   T   K   P   V   P   H   L   R   L   -
```

TABLE 22

Cfluc-FYN (see also SEQ ID NOs: 40-41).

```
atgggtatgtccggttatgtaaacaatccggaagcgaccaacgccttgattgacaaggat
 M   G   M   S   G   Y   V   N   N   P   E   A   T   N   A   L   I   D   K   D ggatggctacattctggagacatagcttactgggacgaagacgaacacttcttcatagtt
 G   W   L   H   S   G   D   I   A   Y   W   D   E   D   E   H   F   F   I   V gaccgcttgaagtctttaattaaatacaaaggatatcaggtggccccgctgaattggaa
 D   R   L   K   S   L   I   K   Y   K   G   Y   Q   V   A   P   A   E   L   E tcgatattgttacaacaccccaacatcttcgacgcgggcgtggcaggtcttcccgacgat
 S   I   L   L   Q   H   P   N   I   F   D   A   G   V   A   G   L   P   D   D gacgccggtgaacttcccgccgccgttgttgttttggagcacggaaagacgatgacggaa
 D   A   G   E   L   P   A   A   V   V   V   L   E   H   G   K   T   M   T   E aaagagatcgtggattacgtcgccagtcaagtaacaaccgcgaaaaagttgcgcggagga
 K   E   I   V   D   Y   V   A   S   Q   V   T   T   A   K   K   L   R   G   G gttgtgtttgtggacgaagtaccgaaaggtcttaccggaaaactcgacgcaagaaaaatc
 V   V   F   V   D   E   V   P   K   G   L   T   G   K   L   D   A   R   K   I agagagatcctcataaaggccaagaagggcggaaagtccaaattggggcctgcagggcggt
 R   E   I   L   I   K   A   K   K   G   G   K   S   K   L   G   L   Q   G   G tcaggcggtgggggttctggcgggggtgggagcgtcgacgctgcaggtctctgctgccgc
 S   G   G   G   G   S   G   G   G   G   S   V   D   A   A   G   L   C   C   R ctagtagttccctgtcacaaagggatgccaaggcttaccgatctgtctgtcaaaaccaaa
 L   V   V   P   C   H   K   G   M   P   R   L   T   D   L   S   V   K   T   K gatgtctgggaaatccctcgagaatccctgcagttgatcaagagactgggaaatgggcag
 D   V   W   E   I   P   R   E   S   L   Q   L   I   K   R   L   G   N   G   Q tttggggaagtatggatgggtacctggaatggaaacacaaaagtagccataaagactctt
 F   G   E   V   W   M   G   T   W   N   G   N   T   K   V   A   I   K   T   L aaaccaggcacaatgtcccccgaatcattccttgaggaagcgcagatcatgaagaagctg
 K   P   G   T   M   S   P   E   S   F   L   E   E   A   Q   I   M   K   K   L aagcacgacaagctggtccagctctatgcagtggtgtctgaggagcccatctacatcgtc
 K   H   D   K   L   V   Q   L   Y   A   V   V   S   E   E   P   I   Y   I   V accgagtatatgaacaaggaagtttactggatttcttaaaagatggagaaggaagagct
 T   E   Y   M   N   K   G   S   L   L   D   F   L   K   D   G   E   G   R   A ctgaaattaccaaatcttgtggacatggcagcacaggtggctgcaggaatggcttacatc
 L   K   L   P   N   L   V   D   M   A   A   Q   V   A   A   G   M   A   Y   I gagcgcatgaattatatccatagagatctgcgatcagcaaacattctagtggggaatgga
 E   R   M   N   Y   I   H   R   D   L   R   S   A   N   I   L   V   G   N   G ctcatatgcaagattgctgacttcggattggcccgattgatagaagacaatgagtacaca
 L   I   C   K   I   A   D   F   G   L   A   R   L   I   E   D   N   E   Y   T gcaagacaaggtgcaaagttccccatcaagtggacggccccgaggcagccctgtacggg
 A   R   Q   G   A   K   F   P   I   K   W   T   A   P   E   A   A   L   Y   G aggttcacaatcaagtctgacgtgtggtctttggaatcttactcacagagctggtcacc
 R   F   T   I   K   S   D   V   W   S   F   G   I   L   L   T   E   L   V   T aaaggaagagtgccataccaggcatgaacaaccggggaggtgctggagcaggtggagcga
 K   G   R   V   P   Y   P   G   M   N   N   R   E   V   L   E   Q   V   E   R
```

TABLE 22-continued

Cfluc-FYN (see also SEQ ID NOs: 40-41).

```
ggctacaggatgccctgcccgcaggactgccccatctctctgcatgagctcatgatccac
 G   Y   R   M   P   C   P   Q   D   C   P   I   S   L   H   E   L   M   I   H tgctggaaaaaggaccctgaagaacgccccacttttgagtacttgcagagcttcctggaa
 C   W   K   K   D   P   E   E   R   P   T   F   E   Y   L   Q   S   F   L   E gactactttaccgcgacagagccccagtaccaacctggtgaaaacctgtaa
 D   Y   F   T   A   T   E   P   Q   Y   Q   P   G   E   N   L   -
```

TABLE 23

DHFR-NFluc(2-416) (see also SEQ ID NOs: 42-43).

```
atgggcagcagccatcaccatcatcaccacagccaggatccgatcagtctgattgcggcg
 M   G   S   S   H   H   H   H   H   H   S   Q   D   P   I   S   L   I   A   A ttagcggtagatcgcgttatcggcatggaaaacgccatgccgtggaacctgcctgccgat
 L   A   V   D   R   V   I   G   M   E   N   A   M   P   W   N   L   P   A   D ctcgcctggtttaaacgcaacaccttaaataaacccgtgattatgggccgccatacctgg
 L   A   W   F   K   R   N   T   L   N   K   P   V   I   M   G   R   H   T   W gaatcaatcggtcgtccgttgccaggacgcaaaaatattatcctcagcagtcaaccgggt
 E   S   I   G   R   P   L   P   G   R   K   N   I   I   L   S   S   Q   P   G acggacgatcgcgtaacgtgggtgaagtcggtggatgaagccatcgcggcgtgtggtgac
 T   D   D   R   V   T   W   V   K   S   V   D   E   A   I   A   A   C   G   D gtaccagaaatcatggtgattggcggcggtcgcgtttatgaacagttcttgccaaaagcg
 V   P   E   I   M   V   I   G   G   G   R   V   Y   E   Q   F   L   P   K   A caaaaactgtatctgacgcatatcgacgcagaagtggaaggcgacacccatttcccggat
 Q   K   L   Y   L   T   H   I   D   A   E   V   E   G   D   T   H   F   P   D tacgagccggatgactgggaatcggtattcagcgaattccacgatgctgatgcgcagaac
 Y   E   P   D   D   W   E   S   V   F   S   E   F   H   D   A   D   A   Q   N tctcacagctattgctttgagattctggagcggcggaccggtggggggtggcggttcaggc
 S   H   S   Y   C   F   E   I   L   E   R   R   T   G   G   G   G   S   G ggtgggggttctggtgggggtggtaccgaagacgccaaaaacataaagaaaggcccggcg
 G   G   G   S   G   G   G   G   T   E   D   A   K   N   I   K   K   G   P   A ccattctatcctctagaggatggaaccgctggagagcaactgcataaggctatgaagaga
 P   F   Y   P   L   E   D   G   T   A   G   E   Q   L   H   K   A   M   K   R tacgccctggttcctggaacaattgcttttacagatgcacatatcgaggtgaacatcacg
 Y   A   L   V   P   G   T   I   A   F   T   D   A   H   I   E   V   N   I   T tacgcggaatacttcgaaatgtccgttcggttggcagaagctatgaaacgatatgggctg
 Y   A   E   Y   F   E   M   S   V   R   L   A   E   A   M   K   R   Y   G   L gatacaaatcacagaatcgtcgtatgcagtgaaaactctcttcaattctttatgccggtg
 D   T   N   H   R   I   V   V   C   S   E   N   S   L   Q   F   F   M   P   V ttgggcgcgttatttatcggagttgcagttgcgcccgcgaacgacatttataatgaacgt
 L   G   A   L   F   I   G   V   A   V   A   P   A   N   D   I   Y   N   E   R gaattgctcaacagtatgaacatttcgcagcctaccgtagtgtttgtttccaaaaagggg
 E   L   L   N   S   M   N   I   S   Q   P   T   V   V   F   V   S   K   K   G ttgcaaaaaattttgaacgtgcaaaaaaaattaccaataatccagaaaattattatcatg
 L   Q   K   I   L   N   V   Q   K   K   L   P   I   I   Q   K   I   I   I   M gattctaaaacggattaccagggatttcagtcgatgtacacgttcgtcacatctcatcta
 D   S   K   T   D   Y   Q   G   F   Q   S   M   Y   T   F   V   T   S   H   L cctcccggttttaatgaatacgattttgtaccagagtcctttgatcgtgacaaaacaatt
 P   P   G   F   N   E   Y   D   F   V   P   E   S   F   D   R   D   K   T   I gcactgacaatgaattcctctggatctactgggttacctaagggtgtggcccttccgcat
 A   L   T   M   N   S   S   G   S   T   G   L   P   K   G   V   A   L   P   H agaactgcctgcgtcagattctcgcatgccagagatcctatttttggcaatcaaatcatt
 R   T   A   C   V   R   F   S   H   A   R   D   P   I   F   G   N   Q   I   I
```

TABLE 23-continued

DHFR-NFluc(2-416) (see also SEQ ID NOs: 42-43).

```
ccggatactgcgatttttaagtgttgttccattccatcacggttttggaatgtttactaca
 P  D  T  A  I  L  S  V  V  P  F  H  H  G  F  G  M  F  T  T ctcggatatttgatatgtggatttcgagtcgtcttaatgtatagatttgaagaagagctg
 L  G  Y  L  I  C  G  F  R  V  V  L  M  Y  R  F  E  E  L tttttacgatcccttcaggattacaaaattcaaagtgcgttgctagtaccaaccctatt
 F  L  R  S  L  Q  D  Y  K  I  Q  S  A  L  L  V  P  T  L  F tcattcttcgccaaaagcactctgattgacaaatacgatttatctaatttacacgtaatt
 S  F  F  A  K  S  T  L  I  D  K  Y  D  L  S  N  L  H  E  I gcttctgggggcgcacctctttcgaaagaagtcggggaagcggttgcaaaacgcttccat
 A  S  G  G  A  P  L  S  K  E  V  G  E  A  V  A  K  R  F  H cttccagggatacgacaaggatatgggctcactgagactacatcagctattctgattaca
 L  P  G  I  R  Q  G  Y  G  L  T  E  T  T  S  A  I  L  I  T cccgaggggatgataaaccgggcgcggtcggtaaagttgttccattttttgaagcgaag
 P  E  G  D  D  K  P  G  A  V  G  K  V  V  P  F  F  E  A  K gttgtggatctggataccgggaaaacgctgggcgttaatcagagaggcgaattatgtgtc
 V  V  D  L  D  T  G  K  T  L  G  V  N  Q  R  G  E  L  C  V agaggacctatgattatgtccggttatgtaaacaatccggaagcgaccaacgccttgatt
 R  G  P  M  I  M  S  G  Y  V  N  N  P  E  A  T  N  A  L  I gacaaggatggatgataagcg
 D  K  D  G  -
```

TABLE 24

Fos-Nfluc (see also SEQ ID NOs: 44-45).

```
atgggcagcagccatcaccatcatcaccacagccaggatccgaattcgagctcgcttact
 M  G  S  S  H  H  H  H  H  H  S  Q  D  P  N  S  S  S  L  T gatactcttcaagctgaaactgatcaacttgaagatgaaaaaagtgctcttcaaactgaa
 D  T  L  Q  A  E  T  D  Q  L  E  D  E  K  S  A  L  Q  T  E attgctaatcttcttaaagaaaaagaaaaacttgaatttattcttgctggtggtggttct
 I  A  N  L  L  K  E  K  E  K  L  E  F  I  L  A  G  G  G  S ggtggtggtggttctggtggtggtggtaagcttgaagacgccaaaaacataaagaaaggc
 G  G  G  S  G  G  G  G  K  L  E  D  A  K  N  I  K  K  G ccggcgccattctatcctctagaggatggaaccgctggagagcaactgcataaggctatg
 P  A  P  F  Y  P  L  E  D  G  T  A  G  E  Q  L  H  K  A  M aagagatacgccctggttcctggaacaattgcttttacagatgcacatatcgaggtgaac
 K  R  Y  A  L  V  P  G  T  I  A  F  T  D  A  H  I  E  V  N atcacgtacgcggaatacttcgaaatgtccgttcggttggcagaagctatgaaacgatat
 I  T  Y  A  E  Y  F  E  M  S  V  R  L  A  E  A  M  K  R  Y gggctgaatacaaatcacagaatcgtcgtatgcagtgaaaactctcttcaattctttatg
 G  L  N  T  N  H  R  I  V  V  C  S  E  N  S  L  Q  F  F  M ccggtgttgggcgcgttatttatcggagttgcagttgcgcccgcgaacgacatttataat
 P  V  L  G  A  L  F  I  G  V  A  V  A  P  A  N  D  I  Y  N gaacgtgaattgctcaacagtatgaacatttcgcagcctaccgtagtgtttgtttccaaa
 E  R  E  L  L  N  S  M  N  I  S  Q  P  T  V  V  F  V  S  K aaggggttgcaaaaaatttttgaacgtgcaaaaaaaattaccaataatccagaaaattatt
 K  G  L  Q  K  I  L  N  V  Q  K  K  L  P  I  I  Q  K  I  I atcatggattctaaaacggattaccagggatttcagtcgatgtacacgttcgtcacatct
 I  M  D  S  K  T  D  Y  Q  G  F  Q  S  M  Y  T  F  V  T  S catctacctcccggttttaatgaatacgatttttgtaccagagtcctttgatcgtgacaaa
 H  L  P  P  G  F  N  E  Y  D  F  V  P  E  S  F  D  R  D  K
```

TABLE 24-continued

Fos-Nfluc (see also SEQ ID NOs: 44-45).

```
acaattgcactgataatgaattcctctggatctactgggttacctaagggtgtggcctt
 T   I   A   L   I   M   N   S   S   G   S   T   G   L   P   K   G   V   A   L ccgcatagaactgcctgcgtcagattctcgcatgccagagatcctattttggcaatcaa
 P   H   R   T   A   C   V   R   F   S   H   A   R   D   P   I   F   G   N   Q atcattccggatactgcgattttaagtgttgttccattccatcacggttttggaatgttt
 I   I   P   D   T   A   I   L   S   V   V   P   F   H   H   G   F   G   M   F actacactcggatatttgatatgtggatttcgagtcgtcttaatgtatagatttgaagaa
 T   T   L   G   Y   L   I   C   G   F   R   V   V   L   M   Y   R   F   E   E gagctgttttacgatcccttcaggattacaaaattcaaagtgcgttgctagtaccaacc
 E   L   F   L   R   S   L   Q   D   Y   K   I   Q   S   A   L   L   V   P   T ctattttcattcttcgccaaaagcactctgattgacaaatacgatttatctaatttacac
 L   F   S   F   F   A   K   S   T   L   I   D   K   Y   D   L   S   N   L   H gaaattgcttctggggcgcacctctttcgaaagaagtcggggaagcggttgcaaaacgc
 E   I   A   S   G   G   A   P   L   S   K   E   V   G   E   A   V   A   K   R ttccatcttccagggatacgacaaggatatgggctcactgagactacatcagctattctg
 F   H   L   P   G   I   R   Q   G   Y   G   L   T   E   T   T   S   A   I   L attacaccgaggggatgataaaccgggcgcggtcggtaaagttgttccattttttgaa
 I   T   P   E   G   D   D   K   P   G   A   V   G   K   V   V   P   F   F   E gcgaaggttgtggatctggataccgggaaaacgctgggcgttaatcagagaggcgaatta
 A   K   V   V   D   L   D   T   G   K   T   L   G   V   N   Q   R   G   E   L tgtgtcagaggacctatgattatgtccggttatgtaaacaatccggaagcgaccaacgcc
 C   V   R   G   P   M   I   M   S   G   Y   V   N   N   P   E   A   T   N   A ttgattgacaaggatggatga
 L   I   D   K   D   G
```

Proteins useful for the detection of amyloid oligomers with designed protein conjugated to luciferase halves are given in Tables 25-28.

TABLE 25

CFluc-TJ10. See also SEQ ID NO: 92-93.

```
atgatgtccggttatgtaaacaatccggaagcgaccaacgccttgattgacaaggatgga
 M   M   S   G   Y   V   N   N   P   E   A   T   N   A   L   I   D   K   D   G tggctacattctggagacatagcttactgggacgaagacgaacacttcttcatagttgac
 W   L   H   S   Q   D   I   A   Y   W   D   E   D   E   H   F   F   I   V   D cgcttgaagtctttaattaaatacaaaggatatcaggtggcccccgctgaattggaatcg
 R   L   K   S   L   I   K   Y   K   G   Y   Q   V   A   P   A   E   L   E   S atattgttacaacaccccaacatcttcgacgcgggcgtggcaggtcttcccgacgatgac
 I   L   L   Q   H   P   N   I   F   D   A   G   V   A   G   L   P   D   D   D gccggtgaacttcccgccgcgttgttgttttggagcacggaaagacgatgacggaaaaa
 A   G   E   L   P   A   A   V   V   V   L   E   H   G   K   T   M   T   E   K gagatcgtggattacgtcgccagtcaagtaacaaccgcgaaaaagttgcgcggaggagtt
 E   I   V   D   Y   V   A   S   Q   V   T   T   A   K   K   L   R   G   G   V gtgtttgtggacgaagtaccgaaaggtcttaccggaaaactcgacgcaagaaaaatcaga
 V   F   V   D   E   V   P   K   G   L   T   G   K   L   D   A   R   K   I   R gagatcctcataaaggccaagaagggcggaaagtccaaattgggcctgcagggcggttca
 E   I   L   I   K   A   K   K   G   G   K   S   K   L   G   L   Q   G   G   S ggcggtggggttctggcgggggtgggagccccggg
 G   G   G   S   G   G   G   S   P   G atggcccagaccttctggcttagtatacagggtaaa
 M   A   Q   T   F   W   L   S   I   Q   G   K
```

TABLE 25-continued

CFluc-TJ10. See also SEQ ID NO: 92-93.

accctgtattggcagatcaggatctatgctattgacgctgcagaagctgaaaaaatcttc
T  L  Y  W  Q  I  R  I  Y  A  I  D  A  A  E  A  E  K  I  F aaacagtacgctaacgacaacggtatcgacggtgaatggacctacgacgacgctaccaaa
K  Q  Y  A  N  D  N  G  I  D  G  E  W  T  Y  D  D  A  T  K accttcaccgttaccgaa
T  F  T  V  T  E

TABLE 26

TJ10-NFluc. See also SEQ ID NO: 94-95.

catcacggatccgcagctcattatatggcccagaccttctggcttagtatacagggtaaa
H  H  G  S  A  A  H  Y  M  A  Q  T  F  W  L  S  I  Q  G  K accctgtattggcagatcaggatctatgctattgacgctgcagaagctgaaaaaatcttc
T  L  Y  W  Q  I  R  I  Y  A  I  D  A  A  E  A  E  K  I  F aaacagtacgctaacgacaacggtatcgacggtgaatggacctacgacgacgctaccaaa
K  Q  Y  A  N  D  N  G  I  D  G  E  W  T  Y  D  D  A  T  K accttcaccgttaccgaa
T  F  T  V  T  E accggtggggt
T  G  G ggcggttcaggcggtgggggttctggtggggtggtaccgaagacgccaaaaacataaag
G  G  S  G  G  G  G  S  G  G  G  G  T  E  D  A  K  N  I  K aaaggcccggcgccattctatcctctagaggatggaaccgctggagagcaactgcataag
K  G  P  A  P  F  Y  P  L  E  D  G  T  A  G  E  Q  L  H  K gctatgaagagatacgccctggttcctggaacaattgcttttacagatgcacatatcgag
A  M  K  R  Y  A  L  V  P  G  T  I  A  F  T  D  A  H  I  E gtgaacatcacgtacgcggaatacttcgaaatgtccgttcggttggcagaagctatgaaa
V  N  I  T  Y  A  E  Y  F  E  M  S  V  R  L  A  E  A  M  K cgatatgggctgaatacaaatcacagaatcgtcgtatgcagtgaaaactctcttcaattc
R  Y  G  L  N  T  N  H  R  I  V  V  C  S  E  N  S  L  Q  F tttatgccggtgttgggcgcgttatttatcggagttgcagttgcgcccgcgaacgacatt
F  M  P  V  L  G  A  L  F  I  G  V  A  V  A  P  A  N  D  I tataatgaacgtgaattgctcaacagtatgaacatttcgcagcctaccgtagtgtttgtt
Y  N  E  R  E  L  L  N  S  M  N  I  S  Q  P  T  V  V  F  V tccaaaaaggggttgcaaaaaattttgaacgtgcaaaaaaaattaccaataatccagaaa
S  K  K  G  L  Q  K  I  L  N  V  Q  K  K  L  P  I  I  Q  K attattatcatggattctaaaacggattaccagggatttcagtcgatgtacacgttcgtc
I  I  I  M  D  S  K  T  D  Y  Q  G  F  Q  S  M  Y  T  F  V acatctcatctacctcccggttttaatgaatacgattttgtaccagagtcctttgatcgt
T  S  H  L  P  P  G  F  N  E  Y  D  F  V  P  E  S  F  D  R gacaaaacaattgcactgataatgaattcctctggatctactgggttacctaagggtgtg
D  K  T  I  A  L  I  M  N  S  S  G  S  T  G  L  P  K  G  V gcccttccgcatagaactgcctgcgtcagattctcgcatgccagagatcctattttggc
A  L  P  H  R  T  A  C  V  R  F  S  H  A  R  D  P  I  F  G aatcaaatcattccggatactgcgattttaagtgttgttccattccatcacggttttgga
N  Q  I  I  P  D  T  A  I  L  S  V  V  P  F  H  H  G  F  G atgtttactacactcggatatttgatatgtggatttcgagtcgtcttaatgtatagattt
M  F  T  T  L  G  Y  L  I  C  G  F  R  V  V  L  M  Y  R  F gaagaagagctgttttttacgatccttcaggattacaaaattcaaagtgcgttgctagta
E  E  E  L  F  L  R  S  L  Q  D  Y  K  I  Q  S  A  L  L  V ccaacccctattttcattcttcgccaaaagcactctgattgacaaatacgatttatctaat
P  T  L  F  S  F  F  A  K  S  T  L  I  D  K  Y  D  L  S  N

TABLE 26-continued

TJ10-NFluc. See also SEQ ID NO: 94-95.

```
ttacacgaaattgcttctgggggcgcacctctttcgaaagaagtcggggaagcggttgca
 L   H   E   I   A   S   G   G   A   P   L   S   K   E   V   G   E   A   V   A aaacgcttccatcttccagggatacgacaaggatatgggctcactgagactacatcagct
 K   R   F   H   L   P   G   I   R   Q   G   Y   G   L   T   E   T   T   S   A attctgattacacccgagggggatgataaaccgggcgcggtcggtaaagttgttccattt
 I   L   I   T   P   E   G   D   D   K   P   G   A   V   G   K   V   V   P   F tttgaagcgaaggttgtggatctggataccgggaaaacgctgggcgttaatcagagaggc
 F   E   A   K   V   V   D   L   D   T   G   K   T   L   G   V   N   Q   R   G gaattatgtgtcagaggacctatgattatgtccggttatgtaaacaatccggaagcgacc
 E   L   C   V   R   G   P   M   I   M   S   G   Y   V   N   N   P   E   A   T aacgccttgattgacaaggatggatga
 N   A   L   I   D   K   D   G   -
```

TABLE 27

CFluc-HTB1. See also SEQ ID NO: 96-97.

```
catatgatgtccggttatgtaaacaatccggaa
   M   M   S   G   Y   V   N   N   P   E gcgaccaacgccttgattgacaaggatggatggctacattctggagacatagcttactgg
 A   T   N   A   L   I   D   K   D   G   W   L   H   S   G   D   I   A   Y   W gacgaagacgaacacttcttcatagttgaccgcttgaagtctttaattaaatacaaagga
 D   E   D   E   H   F   F   I   V   D   R   L   K   S   L   I   K   Y   K   G tatcaggtggcccccgctgaattggaatcgatattgttacaacaccccaacatcttcgac
 Y   Q   V   A   P   A   E   L   E   S   I   L   L   Q   H   P   N   I   F   D gcgggcgtggcaggtcttcccgacgatgacgccggtgaacttccgccgccgttgttgtt
 A   G   V   A   G   L   P   D   D   D   A   G   E   L   P   A   A   V   V   V ttggagcacggaaagacgatgacggaaaaagagatcgtggattacgtcgccagtcaagta
 L   E   H   G   K   T   N   T   E   K   E   I   V   D   Y   V   A   S   Q   V acaaccgcgaaaaagttgcgcggaggagttgtgtttgtggacgaagtaccgaaaggtctt
 T   T   A   K   K   L   R   G   G   V   V   F   V   D   E   V   P   K   G   L accggaaaactcgacgcaagaaaaatcagagagatcctcataaaggccaagaagggcgga
 T   G   K   L   D   A   R   K   I   R   E   I   L   I   K   A   K   K   G   G aagtccaaattgggcctgcagggcggttcaggcggtggggttctggcggggtgggagc
 K   S   K   L   G   L   Q   G   G   S   G   G   G   G   S   G   G   G   S cccgggatggcccagaccttcaaacttatcatcaacggtaaaaaccctgaaaggtgaaatc
 P   G   M   A   Q   T   F   K   L   I   I   N   G   K   T   L   K   G   E   I accatcgaagctgttgacgctgcagaagctgaaaaaatcttcaaacagtacgctaacgac
 T   I   E   A   V   D   A   A   E   A   E   K   I   F   K   Q   Y   A   N   D aacggtatcgacggtgaatggacctacgacgacgctaccaaaaaccttcaccgttaccgaa
 N   G   I   D   G   E   W   T   Y   D   D   A   T   K   P   F   T   V   T   E ctcgagtctggtaaagaaaccgctgctgcgaaatttgaacgccagcacatg
 L   E   S   G   K   E   T   A   A   A   K   F   E   R   Q   H   M
```

TABLE 28

HTB1-NFluc. See also SEQ ID NO: 98-99.

```
atgggcggatcgcatcaccatcac
 M  G  G  S  H  H  H  H catcacggatccgcagctcattatatggcccagaccttcaagcttatcatcaacggtaaa
 H  H  G  S  A  A  H  Y  M  A  Q  T  F  K  L  I  I  N  G  K accctgaaaggtgaaatcaccatcgaagctgttgacgctgcagaagctgaaaaaatcttc
 T  L  K  G  E  I  T  I  E  A  V  D  A  A  E  A  E  K  I  F aaacagtacgctaacgacaacggtatcgacggtgaatggacctacgacgacgctaccaaa
 K  Q  Y  A  N  D  N  G  I  D  G  E  W  T  Y  D  D  A  T  K accttcaccgttaccgaaacc
 T  F  T  V  T  E  T ggtggggggtggcggttcaggcggtgggggttctggtgggggtggtaccgaagacgccaaa
 G  G  G  G  S  G  G  G  G  S  G  G  G  G  T  E  D  A  K aacataaagaaaggcccggcgccattctatcctctagaggatggaaccgctggagagcaa
 N  I  K  K  G  P  A  P  F  Y  P  L  E  D  G  T  A  G  E  Q ctgcataaggctatgaagagatacgccctggttcctggaacaattgcttttacagatgca
 L  H  K  A  M  K  R  Y  A  L  V  P  G  T  I  A  F  T  D  A catatcgaggtgaacatcacgtacgcggaatacttcgaaatgtccgttcggttggcagaa
 H  I  E  V  N  I  T  Y  A  E  Y  F  E  M  S  V  R  L  A  E gctatgaaacgatatgggctgaatacaaatcacagaatcgtcgtatgcagtgaaaactct
 A  M  K  R  Y  G  L  N  T  N  H  R  I  V  V  C  S  E  N  S cttcaattctttatgccggtgttgggcgcgttatttatcggagttgcagttgcgcccgcg
 L  Q  F  F  M  P  V  L  G  A  L  F  I  G  V  A  V  A  P  A aacgacatttataatgaacgtgaattgctcaacagtatgaacatttcgcagcctaccgta
 N  D  I  Y  N  E  R  E  L  L  N  S  M  N  I  S  Q  P  T  V gtgtttgtttccaaaaaggggttgcaaaaaatttttgaacgtgcaaaaaaaattaccaata
 V  F  V  S  K  K  G  L  Q  K  I  L  N  V  Q  K  K  L  P  I atccagaaaattattatcatggattctaaaacggattaccagggatttcagtcgatgtac
 I  Q  K  I  I  I  M  D  S  K  T  D  Y  Q  G  F  Q  S  M  Y acgttcgtcacatctcatctacctcccggttttaatgaatacgattttgtaccagagtcc
 T  F  V  T  S  H  L  P  P  G  F  N  E  Y  D  F  V  P  E  S tttgatcgtgacaaaacaattgcactgataatgaattcctctggatctactgggttacct
 F  D  R  D  K  T  I  A  L  I  M  N  S  S  G  S  T  G  L  P aagggtgtggcccttccgcatagaactgcctgcgtcagattctcgcatgccagagatcct
 K  G  V  A  L  P  H  R  T  A  C  V  R  F  S  H  A  R  D  P attttggcaatcaaatcattccggatactgcgattttaagtgttgttccattccatcac
 I  F  G  N  Q  I  I  P  D  T  A  I  L  S  V  V  P  F  H  H ggttttggaatgtttactacactcggatatttgatatgtggatttcgagtcgtcttaatg
 G  F  G  M  F  T  T  L  G  Y  L  I  C  G  F  R  V  V  L  M tatagatttgaagaagagctgttttttacgatcccttcaggattacaaaattcaaagtgcg
 Y  R  F  E  E  E  L  F  L  R  S  L  Q  D  Y  K  I  Q  S  A ttgctagtaccaaccctatttcattcttcgccaaaagcactctgattgacaaatacgat
 L  L  V  P  T  L  F  S  F  F  A  K  S  T  L  I  D  K  Y  D ttatctaatttacacgaaattgcttctgggggcgcacctctttcgaaagaagtcggggaa
 L  S  N  L  H  E  I  A  S  G  G  A  P  L  S  K  E  V  G  E gcggttgcaaaacgcttccatcttccagggatacgacaaggatatgggctcactgagact
 A  V  A  K  R  F  H  L  P  G  I  R  Q  G  Y  G  L  T  E  T acatcagctattctgattacacccgagggggatgataaaccgggcgcggtcggtaaagtt
 T  S  A  I  L  I  T  P  E  G  D  D  K  P  G  A  V  G  K  V gttccattttttgaagcgaaggttgtggatctggataccgggaaaacgctgggcgttaat
 V  P  F  F  E  A  K  V  V  D  L  D  T  G  K  T  L  G  V  N
```

TABLE 28-continued

HTB1-NFluc. See also SEQ ID NO: 98-99.

```
cagagaggcgaattatgtgtcagaggacctatgattatgtccggttatgtaaacaatccg
 Q  R  G  E  L  C  V  R  G  P  M  I  M  S  G  Y  V  N  N  P gaagcgaccaacgccttgattgacaaggatggatga
 E  A  T  N  A  L  I  D  K  D  G  -
```

Examples of methods employing living cells or transgenic organisms are provided in US Patent Publications 2005/0144661, 2004/0235064; 2007/0161067; 2006/0224331; and U.S. Pat. Nos. 6,897,017; 6,872,871; 7,166,424; 7,160,691; 6,828,099; 6,428,951; 6,929,916; 7,062,219; and 7,176,287. See also Kim et al. (130); Porter et al. (23); Porter et al. (58); Paulmurugan et al. (131). These references provide numerous examples of split reporters useful in the practice of the present invention in addition to those particular examples taught herein, although certain split reporters may be preferred over others.

All references throughout this application, for example patent documents including issued or granted patents or equivalents; patent application publications; and non-patent literature documents or other source material; are hereby incorporated by reference herein in their entireties, including any Supporting Information, addenda, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains and these references cited herein reflect the state of the art as of their filing and publication dates, it is intended that this information can be employed herein, if needed, to exclude (or disclaim) specific embodiments that are in the prior art. For example, when a compound is claimed, it should be understood that compounds known in the prior art, including certain compounds disclosed in the references cited herein (for example, in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individually or in any combination. One of ordinary skill in the art will appreciate that methods, device elements, starting materials, synthetic methods, and amino acid and protein sequences other than those specifically exemplified but functionally equivalent to those specifically disclosed herein can be employed in the practice of the invention without resort to undue experimentation. All art-known functional equivalents, of any such methods, device elements, starting materials, synthetic methods, and sequences with equivalent function to those specifically disclosed are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as for description and not for limitation, and there is no intention in the use of such terms and expressions to exclude any equivalents of the features or portions thereof shown and described, but it is recognized that various modifications are possible within the scope of the invention claimed. Thus, it should be understood that although the present invention has been specifically disclosed by certain embodiments and optional features, modification and variation of the concepts disclosed herein may be made by those skilled in the art, and that such modifications and variations are considered to be within the scope of this invention as defined by the appended claims.

In general the terms and phrases used herein have their art-recognized meanings which can be found by reference to standard texts, journal publication and contexts known to those skilled in the art.

Although the description herein contains certain specific information and examples, these should not be construed as limiting the scope of the invention but as merely providing illustrations of some of the presently preferred embodiments of the invention. For example, thus the scope of the invention should be determined by the appended claims and their equivalents, rather than by the examples given.

An active reporter protein is one for which activity can be detected directly or indirectly upon reassembly of the first and second fragments. In the case of a fluorescent protein, fluorescence can be detected at the relevant wavelength. In the case of a reassembled enzyme, the enzymatic activity is detected via generation of a signal upon action of a substrate to generate a product which can be measured spectrophotometrically at a particular wavelength of light, for example. In the case of luciferase, generation of light is measured using a luminometer, for example.

BIBLIOGRAPHY

1. Wells, J. A.; McClendon, C. L. *Nature* 2007, 450, 1001-1009.
2. Hurley, L. H. *Nature Reviews Cancer* 2002, 2, 188-200.
3. Braisted, A. C.; Oslob, J. D.; Delano, W. L.; Hyde, J.; McDowell, R. S.; Waal, N.; Yu, C.; Arkin, M. R.; Raimundo, B. C. *J Am Chem Soc* 2003, 125, 3714-3715.
4. Chin, J. W.; Schepartz, A. *Angew Chem Int Ed* 2001, 40, 3806-+.
5. Ding, K.; Lu, Y.; Nikolovska-Coleska, Z.; Qiu, S.; Ding, Y. S.; Gao, W.; Stuckey, J.; Krajewski, K.; Roller, P. P.; Tomita, Y.; Parrish, D. A.; Deschamps, J. R.; Wang, S. M. *J Am Chem Soc* 2005, 127, 10130-10131.
6. Orner, B. P.; Ernst, J. T.; Hamilton, A. D. *J Am Chem Soc* 2001, 123, 5382-5383.
7. Rajagopal, S.; Meyer, S. C.; Goldman, A.; Zhou, M.; Ghosh, I. *J Am Chem Soc* 2006, 128, 14356-14363.
8. Fields, S.; Song, O. *Nature* 1989, 340, 245-6.
9. Fields, S. *FEBS J* 2005, 272, 5391-9.
10. Michnick, S. W.; Ear, P. H.; Manderson, E. N.; Remy, I.; Stefan, E. *Nat Rev Drug Discov* 2007, 6, 569-82.
11. Richards, F. M.; Vithayathil, P. J. *J Biol Chem* 1959, 234, 1459-65.
12. Johnsson, N.; Varshavsky, A. *Proc Natl Acad Sci USA* 1994, 91, 10340-4.
13. Rossi, F.; Charlton, C. A.; Blau, H. M. *Proc Natl Acad Sci USA* 1997, 94, 8405-10.
14. Pelletier, J. N.; Campbell-Valois, F. X.; Michnick, S. W. *Proc Natl Acad Sci USA* 1998, 95, 12141-6.
15. Galarneau, A.; Primeau, M.; Trudeau, L. E.; Michnick, S. W. *Nat Biotechnol* 2002, 20, 619-22.
16. Ghosh, I.; Hamilton, A. D.; Regan, L. *J. Am. Chem. Soc.* 2000, 122, 5658-5659.
17. MacDonald, M. L.; Lamerdin, J.; Owens, S.; Keon, B. H.; Bilter, G. K.; Shang, Z.; Huang, Z.; Yu, H.; Dias, J.; Minami, T.; Michnick, S. W.; Westwick, J. K. *Nat Chem Biol* 2006, 2, 329-337.
18. Hu, C. D.; Kerppola, T. K. *Nat Biotechnol* 2003, 21, 539-45.
19. Paulmurugan, R.; Umezawa, Y.; Gambhir, S. S. *Proc Natl Acad Sci USA* 2002, 99, 15608-13.
20. Remy, I.; Michnick, S. W. *Nat Methods* 2006, 3, 977-9.
21. Ghosh, I.; Stains, C. I.; Ooi, A. T.; Segal, D. J. *Molecular Biosystems* 2006, 2, 551-560.
22. Stains, C. I.; Porter, J. R.; Ooi, A. T.; Segal, D. J.; Ghosh, I. *J Am Chem Soc* 2005, 127, 10782-10783.
23. Porter, J. R.; Stains, C. I.; Segal, D. J.; Ghosh, I. *Anal Chem* 2007, 79, 6702-6708.
24. Ozawa, T.; Natori, Y.; Sato, M.; Umezawa, Y. *Nat Methods* 2007, 4, 413-419.
25. Ooi, A. T.; Stains, C. I.; Ghosh, I.; Segal, D. J. *Biochemistry* 2006, 45, 3620-3625.
26. Remy, I.; Campbell-Valois, F. X.; Michnick, S. W. *Nat. Protocols* 2007, 2, 2120-2125.
27. Luker, K. E.; Smith, M. C. P.; Luker, G. D.; Gammon, S. T.; Piwnica-Worms, H.; Piwnica-Worms, D. *Proc Natl Acad Sci USA* 2004, 101, 12288-12293.
28. Paulmurugan, R.; Gambhir, S. S. *Anal Chem* 2007, 79, 2346-53.
29. Knighton, D. R.; Zheng, J. H.; Ten Eyck, L. F.; Xuong, N. H.; Taylor, S. S.; Sowadski, J. M. *Science* 1991, 253, 414-20.
30. Narayana, N.; Cox, S.; Shaltiel, S.; Taylor, S. S.; Xuong, N. H. *Biochemistry* 1997, 36, 4438-4448.
31. Taylor, S. S.; Buechler, J. A.; Yonemoto, W. *Annu Rev Biochem* 1990, 59, 971-1005.
32. Chen, J.; Zheng, X. F.; Brown, E. J.; Schreiber, S. L. *Proc Natl Acad Sci USA* 1995, 92, 4947-4951.
33. Brown, E. J.; Albers, M. W.; Shin, T. B.; Ichikawa, K.; Keith, C. T.; Lane, W. S.; Schreiber, S. L. *Nature* 1994, 369, 756-758.
34. Vanduyne, G. D.; Standaert, R. F.; Schreiber, S. L.; Clardy, J. *J Am Chem Soc* 1991, 113, 7433-7434.
35. Vidal, M.; Legrain, P. *Nuc Acids Res* 1999, 27, 919-29.
36. Wolfe, S. A.; Nekludova, L.; Pabo, C. O. *Ann Rev Biophys Biomol Struct* 2000, 29, 183-212.
37. Stains, C. I.; Furman, J. L.; Segal, D. J.; Ghosh, I. *J Am Chem Soc* 2006, 128, 9761-9765.
38. Esteller, M.; Corn, P. G.; Baylin, S. B.; Herman, J. G. *Cancer Research* 2001, 61, 3225-3229.
39. Fraga, M. F.; Ballestar, E.; Montoya, G.; Taysavang, P.; Wade, P. A.; Esteller, M. *Nuc Acids Res* 2003, 31, 1765-1774.
40. Ohki, I.; Shimotake, N.; Fujita, N.; Jee, J. G.; Ikegami, T.; Nakao, M.; Shirakawa, M. *Cell* 2001, 105, 487-497.
41. Cheong, C. G.; Hall, T. M. *Proc Natl Acad Sci USA* 2006, 103, 13635-9.
42. O'Shea, E. K.; Rutkowski, R.; Kim, P. S. *Cell* 1992, 68, 699-708.
43. O'Shea, E. K.; Rutkowski, R.; Stafford, W. F., 3rd; Kim, P. S. *Science* 1989, 245, 646-8.
44. Meyer, S. C.; Shomin, C. D.; Gaj, T.; Ghosh, I. *J Am Chem Soc* 2007, 129, 13812-3.
45. Freedman, S. J.; Sun, Z. Y.; Poy, F.; Kung, A. L.; Livingston, D. M.; Wagner, G.; Eck, M. J. *Proc Natl Acad Sci USA* 2002, 99, 5367-72.
46. Kung, A. L.; Zabludoff, S. D.; France, D. S.; Freedman, S. J.; Tanner, E. A.; Vieira, A.; Cornell-Kennon, S.; Lee, J.; Wang, B. Q.; Wang, J. M.; Memmert, K.; Naegeli, H. U.; Petersen, F.; Eck, M. J.; Bair, K. W.; Wood, A. W.; Livingston, D. M. *Cancer Cell* 2004, 6, 33-43.
47. Shimizu, Y.; Inoue, A.; Tomari, Y.; Suzuki, T.; Yokogawa, T.; Nishikawa, K.; Ueda, T. *Nat Biotech* 2001, 19, 751-755.
48. Berger, M. F.; Philippakis, A. A.; Qureshi, A. M.; He, F. S.; Estep, P. W., 3rd; Bulyk, M. L. *Nat Biotech* 2006, 24, 1429-35.
49. Bulyk, M. L.; Huang, X. H.; Choo, Y.; Church, G. M. *Proc Natl Acad Sci USA* 2001, 98, 7158-7163.
50. Kung, A. L.; Wang, S.; Klco, J. M.; Kaelin, W. G.; Livingston, D. M. *Nat Med* 2000, 6, 1335-40.
51. Tawfik, D. S.; Griffiths, A. D. *Nat Biotech* 1998, 16, 652-656.
52. Forster, A. C.; Tan, Z. P.; Nalam, M. N. L.; Lin, H. N.; Qu, H.; Cornish, V. W.; Blacklow, S. C. *Proc Natl Acad Sci USA* 2003, 100, 6353-6357.
53. Mendel, D.; Cornish, V. W.; Schultz, P. G. *Ann Rev Biophys Biomol Struct* 1995, 24, 435-462.
54. Rackham, O.; Chin, J. W. *Nat Chem Biol* 2005, 1, 159-166.
55. Seebeck, F. P.; Szostak, J. W. *J Am Chem Soc* 2006, 128, 7150-7151.
56. Howarth, M. et al.
57. Maurel, D. et al. Nat. Methods 5, 561-567 (2008).
58. Porter, J. R., Stains, C. I., Jester, B. W. & Ghosh, I. J. Am. Chem. Soc. 130, 6488-6497 (2008).
59. Wiesmann, C. et al. Cell 91, 695-704 (1997).

60. Kwong, P. D. et al. Nature 393, 648-659 (1998).
61. Ryu, S. E. et al. Nature 348, 419-426 (1990).
62. Olshevsky, U. et al. J. Virol. 64, 5701-5707 (1990).
63. Thali, M. et al. J. Virol. 67, 3978-3988 (1993).
64. Cho, H. S. et al. Nature 421, 756-760 (2003).
65. Franklin, M. C. et al. Cancer Cell 5, 317-328 (2004).
66. Kubetzko, S. et al. J. Biol. Chem. 281, 35186-35201 (2006).
67. Adams, C. W. et al. Cancer Immunol. Immunother. 55, 717-727 (2006).
68. Prang, N. et al. Br. J. Cancer 92, 342-349 (2005).
69. Michnick, S. W. (2003) Curr. Opin. Biotechnol. 14, 610-617
70. Levsky, J. M.; Singer, R. H. J. Cell Sci. 2003, 116, 2833-2838.
71. Tan, W.; Wang, K.; Drake, T. Curr. Opin. Chem. Biol. 2004, 8, 547-553.
72. Chenoweth, D. M.; Viger, A.; Dervan, P. B. J. Am. Chem. Soc. 2007, 129, 2216-2217.
73. Takeda, S.; Tsukiji, S.; Ueda, H.; Nagamune, T. Org. Biomol. Chem. 2008, 10.1039/b720013g.
74. Demidov, V. V.; Dokholyan, N. V.; Witte-Hoffman, C.; Chalasani, P.; Yiu, H.-W.; Ding, F.; Yu, Y.; Cantor, C. R.; Broude, N. E. Proc. Natl. Acad. Sci., U.S.A. 2006, 103, 2052-2056.
75. Kolpashchikov, D. M. J. Am. Chem. Soc. 2008, 130, 2934-2935.
76. Ma, J.-B.; Ye, K.; Patel, D. J. Nature 2004, 429, 318-322.
77. Meister, G.; Landthaler, M.; Patkaniowska, A.; Dorsett, Y.; Teng, G.; Tuschl, T. Mol. Cell 2004, 15, 185-197.
78. Segal, D. J.; Barbas III, C. F. Curr. Opin. Biotechnol. 2001, 12, 632-637.
79. Blancafort, P.; Segal, D. J.; Barbas III, C. F. Mol. Pharmacol. 2004, 66, 1361-1371.
80. Beerli, R. R.; Segal, D. J.; Dreier, B.; Barbas III, C. F. Proc. Natl. Acad. Sci., U.S.A. 1998, 95, 14628-14633.
81. Dreier, B.; Beerli, R. R.; Segal, D. J.; Flippin, J. D.; Barbas III, C. F. J. Biol. Chem. 2001, 276, 29466-29478.
82. Segal, D. J.; Crotty, J. W.; Bhakta, M. S.; Barbas III, C. F.; Horton, N. C. J. Mol. Biol. 2006, 363, 405-421.
83. Plate, K. H.; Breier, G.; Weich, H. A.; Risau, W. Nature 1992, 359, 845-848.
84. Slamon, D. J.; Clark, G. M.; Wong, S. G.; Levin, W. J.; Urlich, A.; McGuire, W. L. Science 1987, 235, 177-182.
85. Kwon, Y., Arndt, H. D., Mao, Q., Choi, Y., Kawazoe, Y., Dervan, P. B., and Uesugi, M. (2004) J. Am. Chem. Soc. 126, 15940-15941.
86. Liu, B., Han, Y., Corey, D. R., and Kodadek, T. (2002) T J. Am. Chem. Soc. 124, 1838-1839.
87. Lum, J. K., Majmudar, C. Y., Ansari, A. Z., and Mapp, A. K. (2006) ACS Chem. Biol. 1, 639-643.
88. Lin, Q., Barbas, C. F., 3rd, and Schultz, P. G. (2003) J. Am. Chem. Soc. 125, 612-613.
89. Daugherty, D. L., and Gellman, S. H. (1999) J. Am. Chem. Soc. 121, 4325-4333.
90. Berg, T., Cohen, S. B., Desharnais, J., Sonderegger, C., Maslyar, D. J., Goldberg, J., Boger, D. L., and Vogt, P. K. (2002) Proc. Natl. Acad. Sci. U.S.A. 99, 3830-3835.
91. Arndt, H. D. (2006) Angew. Chem. Int. Ed. 45, 4552-4560.
92. Nickols, N. G., Jacobs, C. S., Farkas, M. E., and Dervan, P. B. (2007) Modulating hypoxia-inducible transcription by disrupting the HIF-1-DNA interface, ACS Chem. Biol. 2, 561-571.
93. Kiziltepe, T., Hideshima, T., Catley, L., Raje, N., Yasui, H., Shiraishi, N., Okawa, Y., Ikeda, H., Vallet, S., Pozzi, S., Ishitsuka, K., Ocio, E. M., Chauhan, D., and Anderson, K. C. (2007) Mol. Cancer Ther. 6, 1718-1727.
94. Gore, S. D. (2005) Nat. Clin. Pract. Oncol. 2 Suppl. 1, S30-35.
95. Putt, K. S., and Hergenrother, P. J. (2004) Anal. Biochem. 326, 78-86.
96. Putt, K. S., and Hergenrother, P. J. (2004) Anal. Biochem. 333, 256-264.
97. Chan, P. P., and Glazer, P. M. (1997) J. Mol. Med. 75, 267-282.
98. Dervan, P. B. (2001) Bioorg. Med. Chem. 9, 2215-2235.
99. White, S., Szewczyk, J. W., Turner, J. M., Baird, E. E., and Dervan, P. B. (1998) Nature 391, 468-471.
100. Rucker, V. C., Foister, S., Melander, C., and Dervan, P. B. (2003) J. Am. Chem. Soc. 125, 1195-1202.
101. Fechter, E. J., Olenyuk, B., and Dervan, P. B. (2005) J. Am. Chem. Soc. 127, 16685-16691.
102. Jones, P. A., and Baylin, S. B. (2002) Nat. Rev. Genet. 3, 415-428.
103. Esteller, M., et al. (2001) Cancer Res. 61, 3225-3229.
104. Feinberg, A. P., and Vogelstein, B. (1983) Nature 301, 89-92.
105. Feinberg, A. P., Gehrke, C. W., Kuo, K. C., and Ehrlich, M. (1988) Cancer Res. 48, 1159-1161.
106. Lindahl, T., Satoh, M. S., Poirier, G. G., and Klungland, A. (1995) Trends Biochem. Sci. 20, 405-411.
107. Hatakeyama, K., Nemoto, Y., Ueda, K., and Hayaishi, O. (1986) J. Biol. Chem. 261, 14902-14911.
108. Hassa, P. O., Buerki, C., Lombardi, C., Imhof, R., and Hottiger, M. O. (2003) J. Biol. Chem. 278, 45145-45153.
109. Hassa, P. O., and Hottiger, M. O. (2002) Cell. Mol. Life Sci. 59, 1534-1553.
110. Cregan, S. P., Dawson, V. L., and Slack, R. S. (2004) Oncogene 23, 2785-2796.
111. Yu, S. W., Wang, H., Poitras, M. F., Coombs, C., Bowers, W. J., Federoff, H. J., Poirier, G. G., Dawson, T. M., and Dawson, V. L. (2002) Science 297, 259-263.
112. Boulikas, T. (1991) Anticancer Res. 11, 489-527.
113. Herceg, Z., and Wang, Z. Q. (2001) Mutat. Res. 477, 97-110.
114. Kerppola, T. K. (2006) Visualization of molecular interactions by fluorescence complementation, Nat. Rev. Mol. Cell. Biol. 7, 449-456.
115. Varshavsky, A. (2007) Proc. Natl. Acad. Sci. U.S.A. 104, 14935-14940.
116. Nomura, W., and Barbas, C. F., 3rd. (2007) J. Am. Chem. Soc. 129, 8676-8677.
117. Vidal, M., and Legrain, P. (1999) Nucleic Acids Res. 27, 919-929.
118. Spencer, D. M., Wandless, T. J., Schreiber, S. L., and Crabtree, G. R. (1993) Science 262, 1019-1024.
119. Gallagher, S. S., Miller, L. W., and Cornish, V. W. (2007) Anal. Biochem. 363, 160-162.
120. Segal, D. J., Beerli, R. R., Blancafort, P., Dreier, B., Effertz, K., Huber, A., Koksch, B., Lund, C. V., Magnenat, L., Valente, D., and Barbas, C. F., 3rd. (2003) Biochemistry 42, 2137-2148.
121. Bird, A. (2002) Genes Dev. 16, 6-21.
122. Richardson, B. (2003) Ageing Res. Rev. 2, 245-261.
123. Devi, B. J., Schneeweiss, F. H., and Sharan, R. N. (2005) Cancer Detect. Prev. 29, 66-71.
124. Iles, N., Rulten, S., El-Khamisy, S. F., and Caldecott, K. W. (2007) Mol. Cell. Biol. 27, 3793-3803.
125. Kanno, S., Kuzuoka, H., Sasao, S., Hong, Z., Lan, L., Nakajima, S., and Yasui, A. (2007) EMBO J. 26, 2094-2103.

126. Bekker-Jensen, S., Fugger, K., Danielsen, J. R., Gromova, I., Sehested, M., Celis, J., Bartek, J., Lukas, J., and Mailand, N. (2007) J. Biol. Chem. 282, 19638-19643.
127. Ahel, I., Ahel, D., Matsusaka, T., Clark, A. J., Pines, J., Boulton, S. J., and West, S. C. (2008) Nature 451, 81-85.
128. Johnsson, N., and Johnsson, K. (2007) ACS Chem. Biol. 2, 31-38.
129. Kim, W., Kim, Y., Min, J., Kim, D. J., Chang, Y. T., and Hecht, M. H. (2006) ACS Chem. Biol. 1, 461-469.
130. Kim, S. B., Otani, Y., Umezawa, Y. and Tao, H. (2007) Anal. Chem. 79:4820-4826.
131. Paulmurugan, R and Gambhir, S. S. (2006) PNAS 103: 15883-15888.
132. Paulmurugan, R and Gambhir, S. S. (2003) Anal. Chem. 75:1584-1589.
133. Kozak, M. (1986) Cell 44:283.
134. Belasco, J. G. and Brawerman, G. (1993) Control of Messenger RNA Stability, Academic Press, Sand Diego, Calif.
135. Reynolds, R., Bermudez-Cruz, R. M. and Chamberlin, J. M. (1992) J. Mol. Biol. 224:31.
136. Gerstel, B, Tuite, M. F., and McCarthy, J. E. G. (1992) Mol. Microbiol. 6:2339.
137. Ryabova, L. A., Desplancq, D., Spirin, A. S. & Pluckthun, A. *Nat. Biotechnol.* 15, 79-84 (1997).
138. Carter, P. et al. *Proc. Natl. Acad. Sci. USA* 89, 4285-4289 (1992).
139. Cho, H. S. et al. *Nature* 421, 756-760 (2003).

We claim:

1. A method for detecting interactions of a ligand molecule with an interacting protein having a binding site for said ligand, using a split monomeric reporter protein system in a cell-free assay, said method comprising the steps of:
   (a) providing (i) a cell-free system comprising coupled or uncoupled transcription and translational machinery; (ii) a first nucleic acid molecule comprising at least one stabilizing element region and encoding a first interacting fusion protein, said first interacting fusion protein comprising a first fragment of a reporter protein covalently linked to a first interacting domain of the interacting protein, said first interacting domain comprising a binding site for said ligand, and (iii) a second interacting fusion protein, said second interacting fusion protein comprising a second fragment of a reporter protein covalently linked to a second interacting domain of the second interacting protein, wherein neither the first nor second fragment of the reporter protein are active alone but are active when reassembled to form an active reporter protein;
   (b) allowing the expression of the first nucleic acid molecule in the cell-free system in step (a) to produce the first fusion interacting protein and providing a second interacting fusion protein;
   (c) contacting the first and second interacting fusion proteins either (i) with a composition where the second interacting fusion protein comprises a ligand of the first interacting fusion protein such that when the ligand and the first interacting fusion protein are present, the first and second fragments of the reporter reassemble to form an active reporter protein; or (ii) with a composition that contains a ligand of both interacting fusion proteins such that when a ligand to both of the first and second interacting fusion proteins is present, the ligand binds to the first and second fusion interacting proteins and the first and second fragments of the reporter located within the first and second interacting fusion proteins reassemble to form an active reporter protein;
   (d) detecting the active reporter protein when the ligand is present in the composition and the first and second reporter fragments have reassembled to form an active reporter protein.

2. The method of claim 1 wherein the monomeric reporter protein is a fluorescent protein, a β-lactamase or a luciferase.

3. The method of claim 1 wherein the fluorescent protein is a green, blue, yellow, red or enhanced green fluorescent protein.

4. The method of claim 1, wherein the stabilizing element region is a stem-loop structure.

5. The method of claim 4, wherein the stem and loop structure is a 5' stem-loop structure and/or a 3' stem-loop structure.

6. The method of claim 4, wherein the stem-loop structure is a 3' stem-loop structure of bacteriophage T3 and/or is a 5' stem-loop structure of bacteriophage T7.

7. The method of claim 1, wherein the first interacting fusion protein and the second interacting fusion protein comprise antibody (Ab), single chain Ab, an antigen-binding fragment of an Ab, or an antigen-binding fragment of a single chain Ab.

8. The method of claim 1, wherein the ligand is a double stranded DNA molecule, a single stranded DNA molecule, an RNA molecule, a methylated DNA molecule, a peptide, a protein, an antigen, an amyloid protein, or a small molecule ligand.

9. The method of claim 8, wherein the small molecule ligand is an enzyme binding molecule, the enzyme selected from a group consisting of transferases, hydrolases, ligases, oxidoreductases, lyases and isomerases.

10. The method of claim 9, wherein the enzyme is a kinase.

11. The method of claim 8, wherein the ligand is an RNA molecule and the interacting protein is a pumilio domain, a KH domain, a RRM domain, Argonaut, bacteriophage MS2 coat protein, or eukaryotic initiation factor 4a.

12. The method of claim 1, wherein the second interacting fusion protein is translated in the cell-free system from a second nucleic acid molecule encoding the second fragment of reporter protein covalently linked in frame to the nucleic acid encoding the second interacting domain.

13. The method of claim 1, wherein the ligand molecule and the interacting protein are p53 protein and HDM2; Bcl and Bak; FKBP and FRAP; BAD and BCL-XL; p38a MAPK and MAPK activated protein kinase 2; cMyc and Max; HIF1α and p300; Fos and Jun; PIN1 and Jun; PKA and PKI, or JT10 and HTB10.

14. The method of claim 8, wherein the ligand is a double stranded DNA molecule, a single stranded DNA molecule, an RNA molecule or a methylated DNA molecule, DNA or RNA of a pathogen or a diseased cell, whereby assessment of disease markers, diagnosis and prognosis is achieved.

15. The method of claim 14, wherein the ligand is a double stranded DNA molecule, a single stranded DNA molecule, an RNA molecule or a methylated DNA molecule, DNA or RNA of a pathogen or an amyloid protein, whereby confirmation of presence or absence of the pathogen in a biological, environmental, food, beverage, meat, poultry, fish or water sample is achieved.

16. The method of claim 8, wherein the ligand is a peptide or protein derived from a pathogen or diseased cell, whereby disease markers are measured with that result that prediction, diagnosis or assessment of therapeutic success is achieved.

17. The method of claim 8, wherein the ligand is a protein of a pathogen, whereby confirmation of presence or absence of the pathogen in a biological, environmental, pharmaceutical, commercial, food or water sample is achieved.

18. The method of claim 1 for detecting an agonist or an antagonist of an interaction of a ligand molecule with a biomolecule using a split monomeric reporter protein system in a cell-free assay, said method further comprising after step (b):
   (c) contacting the first and second fragments of the reporter protein produced in step (b) with either (i) with a composition where the second interacting protein comprises a ligand of the first interacting protein such that when the ligand and the first interacting protein are present, the first and second fragments of the reporter reassemble to form an active reporter protein; or (ii) with a composition that comprises a ligand of both interacting proteins such that when a ligand to both of the first and second interacting proteins is present, the ligand binds to the first and second interacting proteins and the first and second fragments of the reporter reassemble to form an active reporter protein;
   (d) simultaneously or subsequently with respect to step (c) contacting with a composition which may or may not contain an antagonist or an agonist of ligand binding; and
   (e) detecting the signal generated by the active reporter protein when the ligand is present in the composition and comparing the signal in the presence and absence of the composition, whereby an antagonist of ligand binding is identified or detected when the signal is less in the presence of the composition than in the absence of the composition or an agonist of ligand binding is detected or identified when the signal is greater in the presence of the compositions than in the absence of the composition.

19. The method of claim 18, wherein the ligand molecule and the biomolecule comprise but are not limited to, p53 protein and HDM2; Bcl and Bak; FKBP and FRAP; BAD and BCL-XL; p38a MAPK and MAPK activated protein kinase 2; cMyc and Max; HIF1α and p300; Fos and Jun; PIN1 and Jun; or PKA and PKI.

20. The method of claim 18, wherein the ligand binding protein is an enzyme selected from a group consisting of transferases, hydrolases, ligases, oxidoreductases, lyases and isomerases.

21. The method of claim 20, wherein the enzyme is a protein kinase.

22. The method of claim 18, wherein the first interacting protein and the second interacting protein comprise (i) antibody (Ab), (ii) single chain Ab, (iii) antigen-binding fragment of an Ab or antigen-binding fragment of a single chain Ab.

23. The method of claim 8, wherein the ligand is an amyloidogenic protein comprising beta-amyloid(1-40, 1-41, 1-42, 1-43), prion protein, alpha-synuclein, tau, immunoglobulin, islet amyloid polypeptide or huntington protein.

24. The method of claim 23, wherein the amyloidogenic protein is in a sample extracted from or is present in a biological sample, whereby assessment of disease markers, diagnosis and prognosis is achieved.

* * * * *